US012441798B2

(12) United States Patent
Hernandez-Hoyos et al.

(10) Patent No.: US 12,441,798 B2
(45) **Date of Patent: *Oct. 14, 2025**

(54) CD123 BINDING PROTEINS AND RELATED COMPOSITIONS AND METHODS

(71) Applicant: APTEVO RESEARCH AND DEVELOPMENT LLC, Seattle, WA (US)

(72) Inventors: Gabriela Hernandez-Hoyos, Seattle, WA (US); Elaine T. Sewell, Seattle, WA (US); Catherine J. McMahan, Seattle, WA (US); David Bienvenue, Seattle, WA (US); John W. Blankenship, Seattle, WA (US); Danielle Mitchell, Seattle, WA (US); Peter Pavlik, Seattle, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/442,779

(22) Filed: Feb. 15, 2024

(65) Prior Publication Data

US 2024/0343801 A1 Oct. 17, 2024

Related U.S. Application Data

(63) Continuation of application No. 17/557,440, filed on Dec. 21, 2021, now Pat. No. 11,939,392, which is a continuation of application No. 16/335,561, filed as application No. PCT/US2017/052808 on Sep. 21, 2017, now Pat. No. 11,242,400.

(60) Provisional application No. 62/466,192, filed on Mar. 2, 2017, provisional application No. 62/397,736, filed on Sep. 21, 2016.

(51) Int. Cl.

| | |
|---|---|
| ***C07K 16/28*** | (2006.01) |
| ***A61P 35/00*** | (2006.01) |
| ***A61P 35/02*** | (2006.01) |
| ***C07K 16/30*** | (2006.01) |
| ***C12N 15/62*** | (2006.01) |
| *A61K 39/00* | (2006.01) |
| *C07K 16/00* | (2006.01) |

(52) U.S. Cl.

CPC .......... *C07K 16/2809* (2013.01); *A61P 35/00* (2018.01); *A61P 35/02* (2018.01); *C07K 16/2866* (2013.01); *C07K 16/2896* (2013.01); *C07K 16/3061* (2013.01); *C12N 15/62* (2013.01); *A61K 2039/505* (2013.01); *A61K 2039/545* (2013.01); *C07K 16/005* (2013.01); *C07K 2317/24* (2013.01); *C07K 2317/31* (2013.01); *C07K 2317/33* (2013.01); *C07K 2317/524* (2013.01); *C07K 2317/526* (2013.01); *C07K 2317/53* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/75* (2013.01); *C07K 2317/90* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 5,731,168 | A | 3/1998 | Carter et al. | |
| 5,821,337 | A | 10/1998 | Carter et al. | |
| 5,834,597 | A | 11/1998 | Tso et al. | |
| 6,180,370 | B1 * | 1/2001 | Queen | A61P 19/02 435/69.6 |
| 6,551,592 | B2 | 4/2003 | Lindhofer et al. | |
| 7,612,181 | B2 | 11/2009 | Wu et al. | |
| 9,745,381 | B2 | 8/2017 | Liu et al. | |
| 9,856,327 | B2 * | 1/2018 | Bernett | C07K 16/468 |
| 10,676,533 | B2 | 6/2020 | Hernandez-Hoyos et al. | |
| 11,242,400 | B2 | 2/2022 | Hernandez-Hoyos et al. | |
| 11,939,392 | B2 | 3/2024 | Hernandez-Hoyos et al. | |
| 2005/0009743 | A1 | 1/2005 | Sundquist et al. | |

(Continued)

FOREIGN PATENT DOCUMENTS

| | | | |
|---|---|---|---|
| WO | WO-2006124784 | A2 | 11/2006 |
| WO | WO-2007146948 | A2 | 12/2007 |

(Continued)

OTHER PUBLICATIONS

Liu, Keqiang, et al. Life sciences 122 (2015): 59-64 (Year: 2015).*

(Continued)

*Primary Examiner* — Zachariah Lucas
*Assistant Examiner* — Lia E Taylor
(74) *Attorney, Agent, or Firm* — COOLEY LLP

(57) ABSTRACT

The present disclosure relates to protein molecules that specifically bind to CD123, which may have at least one humanized or human CD123-binding domain. Such molecules are useful for the treatment of cancer. The protein molecule binding to CD123 may have a second binding domain that binds to another target. In one embodiment, multi-specific polypeptide molecules bind both CD123-expressing cells and the T-cell receptor complex on T-cells to induce target-dependent T-cell cytotoxicity, activation, and proliferation. The disclosure also provides pharmaceutical compositions comprising the CD123-binding polypeptide molecules, nucleic acid molecules encoding these polypeptides and methods of making these molecules.

15 Claims, 23 Drawing Sheets

Specification includes a Sequence Listing.

(56) References Cited

U.S. PATENT DOCUMENTS

| | | | |
|---|---|---|---|
| 2005/0163782 A1 | 7/2005 | Glaser et al. | |
| 2005/0208048 A1 | 9/2005 | McMahan et al. | |
| 2006/0035320 A1 | 2/2006 | Tissot et al. | |
| 2006/0234302 A1 | 10/2006 | Hoet et al. | |
| 2007/0077246 A1 | 4/2007 | Koenig et al. | |
| 2011/0293619 A1 | 12/2011 | Kufer et al. | |
| 2012/0082670 A1 | 4/2012 | Konopitzky et al. | |
| 2013/0266569 A1 | 10/2013 | Gurney et al. | |
| 2015/0110789 A1 | 4/2015 | Liu et al. | |
| 2015/0232557 A1 | 8/2015 | Tan et al. | |
| 2016/0068605 A1* | 3/2016 | Nemeth | C07K 16/2866 435/254.2 |
| 2016/0176953 A1 | 6/2016 | Purcell Ngambo et al. | |
| 2017/0349660 A1 | 12/2017 | Saville et al. | |
| 2018/0273622 A1 | 9/2018 | Tan et al. | |
| 2019/0071513 A1 | 3/2019 | Hernandez-Hoyos et al. | |
| 2020/0165346 A1 | 5/2020 | Hernandez-Hoyos et al. | |
| 2023/0151102 A1 | 5/2023 | Clapper et al. | |
| 2023/0303720 A1 | 9/2023 | Clapper et al. | |

FOREIGN PATENT DOCUMENTS

| | | |
|---|---|---|
| WO | WO-2009017823 A2 | 2/2009 |
| WO | WO-2011034969 A1 | 3/2011 |
| WO | WO-2011090761 A1 | 7/2011 |
| WO | WO-2012021934 A1 | 2/2012 |
| WO | WO-2012065161 A2 | 5/2012 |
| WO | WO-2013173820 A2 | 11/2013 |
| WO | WO-2014143807 A2 | 9/2014 |
| WO | WO-2016116626 A1 | 7/2016 |
| WO | WO-2016130819 A2 | 8/2016 |
| WO | WO-2017053469 A2 | 3/2017 |
| WO | WO-2018057802 A1 | 3/2018 |

OTHER PUBLICATIONS

Buss, Nicholas APS, et al. Current opinion in pharmacology 12.5 (2012): 615-622 (Year: 2012).*
Dechant, Michael, et al. Blood, The Journal of the American Society of Hematology 100.13 (2002): 4574-4580 (Year: 2002).*
Hezareh, M et al. Journal of virology vol. 75,24 (2001): 12161-8 (Year: 2001).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Baeuerle et al., "Bispecific T-Cell Engaging Antibodies for Cancer Therapy," Cancer Research, 69(12): 4941-4944 (2009).
Bargou et al., "Tumor Regression in Cancer Patients by Very Low Doses of a T Cell-Engaging Antibody," Science, 321 (5891): 974-977 (2008).
Bortoletto et al., "Optimizing Anti-CD3 Affinity for Effective Targeting Against Tumor Cells," European Journal of Immunology, 32(11): 3102-3107 (2002).
Buss et al., "Monoclonal antibody therapeutics: history and future," Current Opinion in Pharmacology, 12: 615-622 (2012).
Chichili et al., "A CD3xCD123 bispecific DART for redirecting host T cells to myelogenous leukemia: Preclinical activity and safety in nonhuman primates," Science Translational Medicine, 7(289): 289ra82-289ra82 (2015).
Chu et al., "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia," Blood, 124(21): 2316, 2014.
ClinicalTrials.gov, History of Changes for Study: NCT00635596: Phase I Study MT110-101 in CDC; GI and Lung Cancer, first published Mar. 7, 2008, retrieved from https://clinicaltrials.gov/ct2/history/NCT00635596?A=1&B=1&C=merged#StudyPageTop, 7 pages.
Croasdale et al., "Development of Tetravalent IgG1 Dual Targeting IGF-1R-EGFR Antibodies with Potent Tumor Inhibition," Archives of Biochemistry and Biophysics, 526: 206-218 (2012).
Dechant et al., "Chimeric IgA antibodies against HLA class II effectively trigger lymphoma cell killing," Blood, 100(13): 4574-4580 (2002).
Dong et al., "A Stable IgG-Like Bispecific Antibody Targeting the Epidermal Growth Factor Receptor and the Type I Insulin-like Growth Factor Receptor Demonstrates Superior Anti-Tumor Activity," mAbs, 3(3): 373-288 (2011).
Dreier et al., "Extremely Potent, Rapid, and Costimulation-Independent Cytotoxic T-Cell Response Against Lymphoma Cells Catalyzed by a Single-Chain Bispecific Antibody," International Journal of Cancer, 100(6): 690-692 (2002).
Enver et al., "Next generation immunotherapeutics—honing the magic bullet," Current Opinion in Biotechnology, 20:405-411 (2009).
Extended European Search Report for European Application No. 17853936.7 dated Aug. 19, 2020, 14 pages.
Extended European Search Report for European Application No. 13790217.7 dated Mar. 21, 2016, 12 pages.
Fiedler et al., "A Phase I Study of EpCAM/CD3-Bispecific Antibody (MT110) in Patients with Advanced Solid Tumors," Abstract, Journal of Clinical Oncology, 30(15) Suppl. 2504, 2012, 1 page.
Genbank Accession No. AEV43323.1, "Fe IgG1 Heavy Chain Constant Region, Partial [*Homo sapiens*]", Jul. 25, 2016, 1 page.
Henn et al., "Preclinical characterization of MT114, a novel CD33/CD3-bispecific BiTE antibody for the treatment of acute myeloid leukemia (AML)", Cancer Research, Apr. 15, 2012, XP055251939, Retrieved from the internet: URL: http://cancerres.aacrjournals.org/content/72/8_Supplement/3523 [retrieved on Feb. 22, 2016], 2 pages, Abstract only.
Hezareh et al., "Effector Function Activities of a Panel of Mutants of a Broadly Neutralizing Antibody against Human Immunodeficiency Virus Type 1," Journal of Virology, Dec. 2001, vol. 75, No. 24, pp. 12161-12168.
International Search Report and Written Opinion for International Application No. PCT/US2017/052808, dated Jan. 23, 2018, 14 pages.
Janeway, C. A. et al., "Immunobiology: the Immune System in Health and Disease," Current Biology, 1997, 14 pages.
Janeway et al., "The interaction of the antibody molecule with specific antigen," Immunobiology: The Immune System in Health and Disease, 5th Edition, Garland Science, 2001, 5 pages.
Kiewe et al., "Phase I trial of the trifunctional anti HER2x anti CD3 antibody ertumaxomab in metastatic breast cancer," Clinical Cancer Research, 12:3085-3091 (2006).
Kipriyanov et al., "Generation and Production of Engineered Antibodies," Molecular Biotechnology, 26:39-60 (2004).
Kontermann, "Dual targeting strategies with bispecific antibodies," mAbs, 4(2):182-197(2012).
Kugler et al., "A recombinant trispecific single-chain Fv derivative directed against CD123 and CD33 mediates effective elimination of acute myeloid leukaemia cells by dual targeting", British Journal of Haematology 150; 574-586 (2010), published on Jul. 16, 2010.
Kuo et al., "Antibody Internalization After Cell Surface Antigen Binding is Critical for Immunotoxin Development," Bioconjugate Chemistry, 20(10): 1975-1982 (2009).
Kuo, et al., "Engineering a CD123xCD3 bispecific scFv immunofusion for the treatment of leukemia and elimination of leukemia stem cells." Protein Engineering, Design and Selection (2012); 25 (10): 561-570.
Liu et al., "CD123 and its potential clinical application in leukemias," Life Sciences (2015) 122: 59-64.
Müller et al., "Bispecific Antibodies for Cancer Immunotherapy Current Perspectives", Biodrugs, 24(2): 89-98, 2010.
Moore et al., "A novel bispecific antibody format enables simultaneous bivalent and monovalent co-engagement of distinct target antigens", mAbs, 3(6): 546-557, 2011.
Naujokat, "Targeting Human Cancer Stem Cells with Monoclonal Antibodies," Journal of Clinical & Cellular Immunology, S5: 007 (2012), 15 pages.
Niranjana et al. "AEV43323.1. Fe IgG1 Heavy Chain Constant Region, partial [*Homo sapiens*]", Genbank, Jul. 6, 2011, 1 page.

(56) References Cited

OTHER PUBLICATIONS

Non-Final Office Action mailed Jul. 16, 2021 for U.S. Application No. 16,335,561, filed on Mar. 21, 2019, 25 pages.
Pohl et al., "A Cassette Vector System for the Rapid Cloning and Production of Bispecific Tetravalent Antibodies", Antibodies, 1: 19-38 (2012).
Radcliff et al., "Mobilization of dendritic cells in cancer patients treated with granulocyte colony-stimulating factor and chemotherapy", British Journal of Haematology 119; 204-11 (2002).
Ramos, et al., "Current Approaches in the Treatment of Relapsed and Refractory Acute Myeloid Leukemia." J. Clin. Med., 4(4): 665-695 (2015).
Request for Ex Parte Reexamination filed Jul. 13, 2018 in U.S. Pat. No. 9,745,381, 57 pages.
Request for Ex Parte Reexamination filed May 3, 2019 in U.S. Pat. No. 9,745,381, 67 pages.
Robinson, W.H., "Sequencing the functional antibody repertoire-diagnostic and therapeutic discovery," Nature Reviews Rheumatology (2015) 11: 171-182.
Roopenian and Akilesh, "FcRn: the neonatal Fc receptor comes of age," Nature Reviews Immunology, 2007, vol. 7, pp. 715-725.
Rudikoff, S. et al., "Singel amino acid substitution altering antigen-binding specificity," proc. Natl. Acad. Sci. USA, 79:1979-1983 (1982).
Schlereth et al., "Eradication of tumors from a Human Colon Cancer Cell Line and from Ovarian Cancer Metastases in Immunodeficient Mice by a Single-Chain-Ep-CAM-/CD3- Bispecific Antibody Construct," Cancer Research, 65(7):2882-2889 (2005).
Sievers and Senter, "Antibody-Drug Conjugates in Cancer Therapy," Annual Review of Medicine, 64: 15-29 (2013).
Stamova et al., "Simultaneous engagement of the activatory receptors NKG2D and CD3 for retargeting of effector cells to CD33-positive malignant cells", Leukemia 25; 1053-1056 (2011), published on Mar. 18, 2011.
Stein et al., "Novel conjugates of single-chain Fv antibody fragments specific for stem cell antigen CD123 mediate potent death of acute myeloid leukaemia cells," British Journal of Haematology (2010) 148, 879-889.
Testa, et al., "CD 123 is a membrane biomarker and a therapeutic target in hematologic malignancies." Biomarker Research (2014); 2: 4, 11 pages.
Third Party Observations Issued in Corresponding European Application No. 13790217.7, dated Apr. 11, 2019, 12 pages.
Third Party Observations Issued in Corresponding European Application No. 13790217.7, dated Apr. 25, 2019, 31 pages.
Wang et al., "Monoclonal antibodies with identical Fe sequences can bind to FcRn differentially with pharmacokinetic consequences," Drug Metabolism and Disposition, 2011, vol. 39, No. 9, pp. 1469-1477, 2011.
Wolf et al.,"'BiTEs' Bispecific Antibody Constructs with Unique Anti-Tumor Activity," Drug Discovery Today, 10(18): 1237-1244 (2005).
Yalcintepe et al., "Expression of interleukin-3 receptor subunits on defined subpopulations of acute myeloid leukemia blasts predicts the cytotoxicity of diptheria toxin interleukin-3 fusion protein against malignant progenitors that engraft in immunodeficient mice," Blood, 2006, vol. 108, pp. 3530-3537.
U.S. Appl. No. 17/802,927, filed Aug. 26, 2022.
U.S. Appl. No. 17/802,920, filed Aug. 26, 2022.
U.S. Appl. No. 18/562,725, filed Oct. 10, 2023.

* cited by examiner

| | TRI125 |
|---|---|
| EC50 (nM) | 3.14 |

| | TRI129 | TRI130 |
|---|---|---|
| EC50 (nM) | 5.33 | 4.31 |

| | TRI139 |
|---|---|
| EC50 (nM) | 2.33 |

| | TRI129 | TRI130 | TRI139 |
|---|---|---|---|
| EC50 (nM) | 9.69 | 4.65 | 2.81 |

| | TRI123 | TRI126 |
|---|---|---|
| EC50 (nM) | 7.38 | 37.18 |

| | TRI129 | TRI130 | TRI132 |
|---|---|---|---|
| EC50 (nM) | 8.77 | 12.12 | 4.23 |

| | TRI137 | TRI139 |
|---|---|---|
| EC50 (nM) | 4.79 | 3.64 |

| | TRI123 | TRI125 | TRI126 | TRI127 | TRI128 | TRI129 | TRI130 | TRI131 | TRI132 | TRI134 |
|---|---|---|---|---|---|---|---|---|---|---|
| EC50 (pM) | 19.70 | 4.99 | 7.96 | 10.94 | 3.54 | 10.4 | 3.66 | 22.80 | 6.74 | 22.69 |

| | TRI137 | TRI138 | TRI139 |
|---|---|---|---|
| EC50 (pM) | 36.39 | 15.17 | 7.96 |

Proliferation of $CD4^+$ T cells in the Presence of Bispecific anti-CD123 x anti-CD3ε Molecules and Molm-13 Target Cells

| CD4 | TRI129 | TRI130 | TRI139 |
|---|---|---|---|
| EC50 (pM) | 1.65 | 1.53 | 1.54 |

Proliferation of $CD8^+$ T cells in the Presence of Bispecific anti-CD123 x anti-CD3ε Molecules and Molm-13 Target Cells

| CD8 | TRI129 | TRI130 | TRI139 |
|---|---|---|---|
| EC50 (pM) | 2.29 | 1.46 | 2.06 |

Activation of CD4⁺ T cells in the Presence of Bispecific anti-CD123 x anti-CD3ε Molecules and Molm-13 Target Cells

| CD4 | TRI129 | TRI130 | TRI139 |
|---|---|---|---|
| EC50 (pM) | 2.63 | 3.40 | 2.71 |

Activation of CD8⁺ T cells in the Presence of Bispecific anti-CD123 x anti-CD3ε Molecules and Molm-13 Target Cells

| CD8 | TRI129 | TRI130 | TRI139 |
|---|---|---|---|
| EC50 (pM) | 5.79 | 6.50 | 6.36 |

| Curve | ka (1/Ms) | kd (1/s) | KD (M) | Rmax (RU) | Conc (M) | tc | Flow (ul/min) | kt (RU/Ms |
|---|---|---|---|---|---|---|---|---|
| | 1.720E+5 | 4.717E-4 | 2.743E-9 | 131.2 | | 8.534E+8 | | |
| Cycle: 9 3 nM | | | | | 3.000E-9 | | 30.00 | 2.652E |
| Cycle: 10 48 nM | | | | | 4.800E-8 | | 30.00 | 2.652E |
| Cycle: 11 6 nM | | | | | 6.000E-9 | | 30.00 | 2.652E |
| Cycle: 12 24 nM | | | | | 2.400E-8 | | 30.00 | 2.652E |
| Cycle: 13 12 nM | | | | | 1.200E-8 | | 30.00 | 2.652E |

*Tumor volumes are plotted as the mean + SEM of tumor volume measurement
*Last recorded volume carried forward after endpoint reached
*Groups plotted until all mice in group reached endpoint, or until study terminiated

*Tumor volumes are plotted as the mean + SEM of tumor volume measurement
*Last recorded volume carried forward after endpoint reached
*Groups plotted until all mice in group reached endpoint, or until study terminiated FIG. 13 WinNonlin NCA Estimates and Fit of Half-life for Treatment Groups FIG. 14 Change in Lymphocyte Population Over Time in Cynomolgus Monkeys
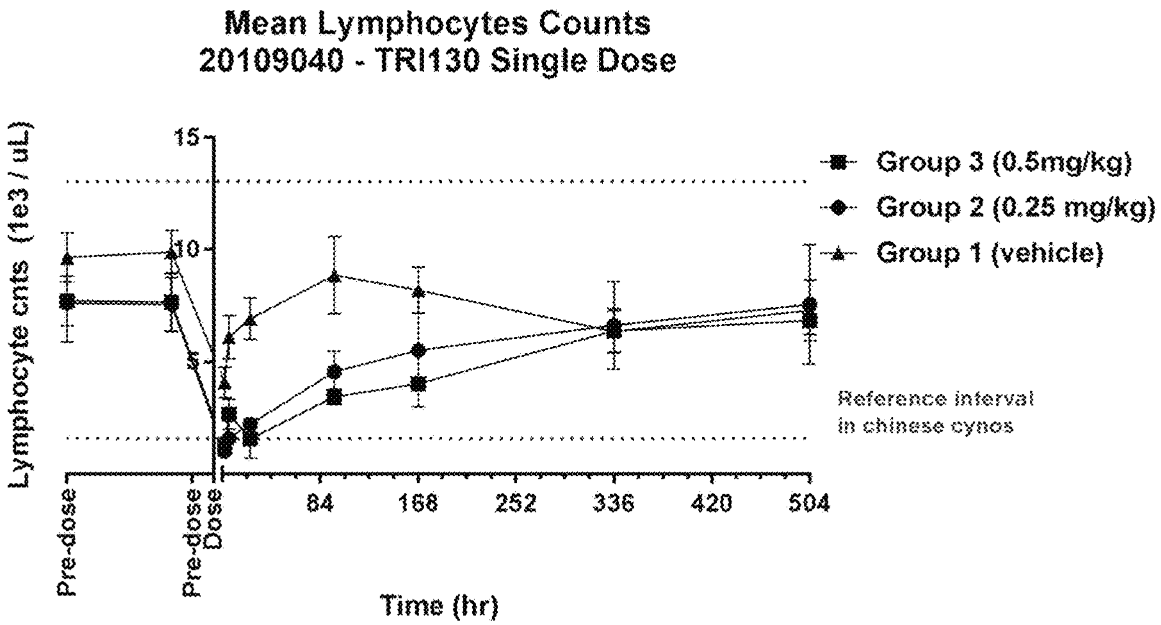
FIG. 15 Change in Basophil Population Over Time in Cynomolgus Monkeys
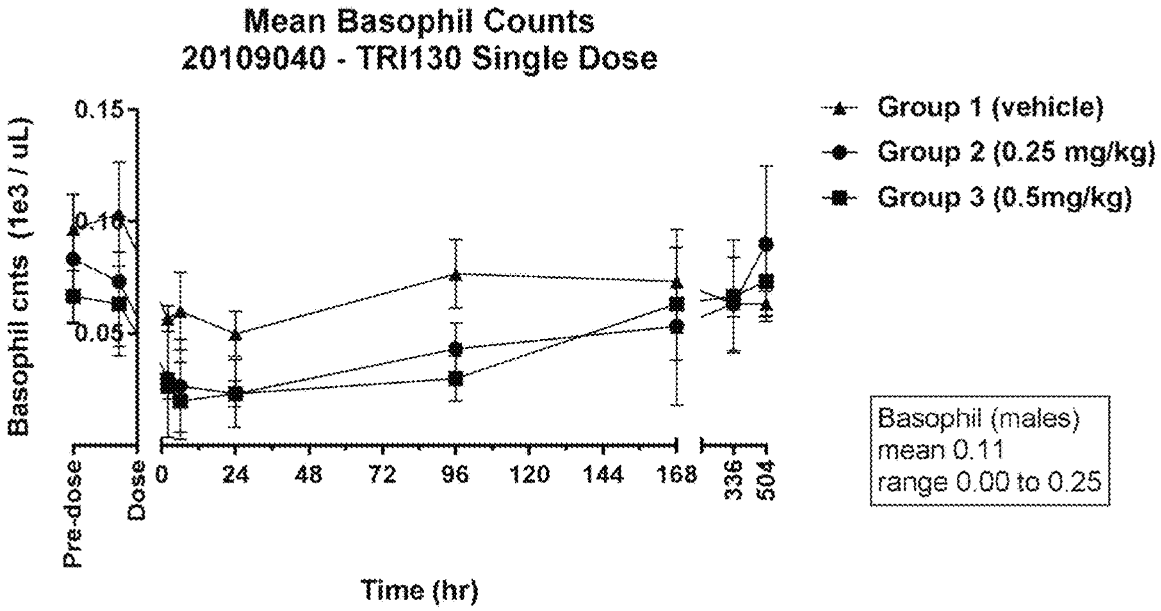

FIG. 16 Bioluminescent Tumor Burden of MOLM-13 Disseminated Xenograft Study
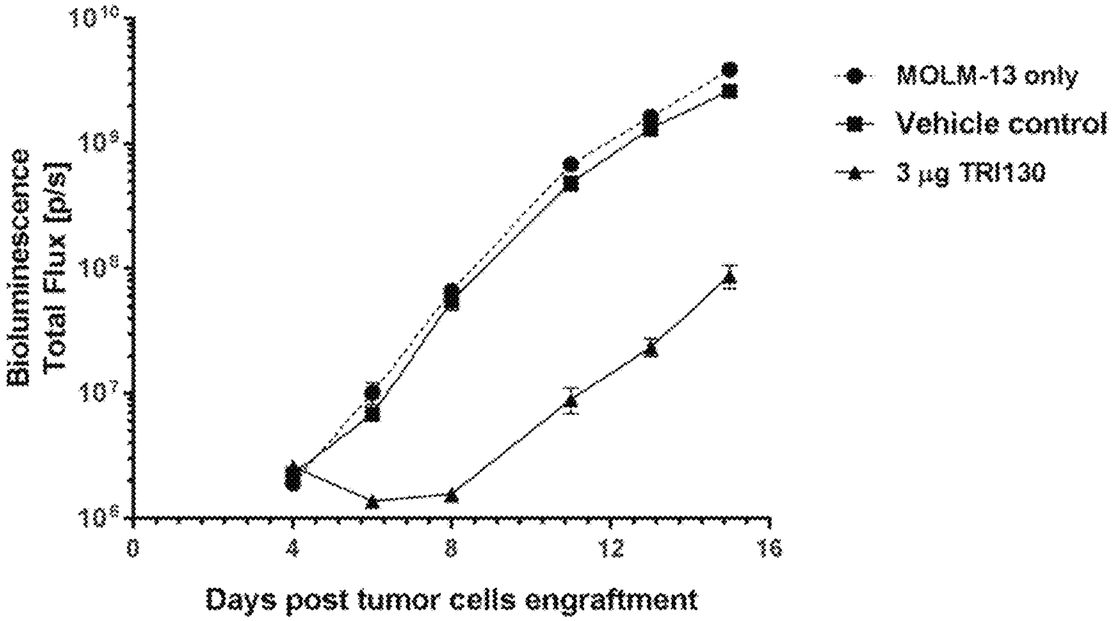
FIG. 17 Bioluminescent Images of Day 14 Tumor Burden
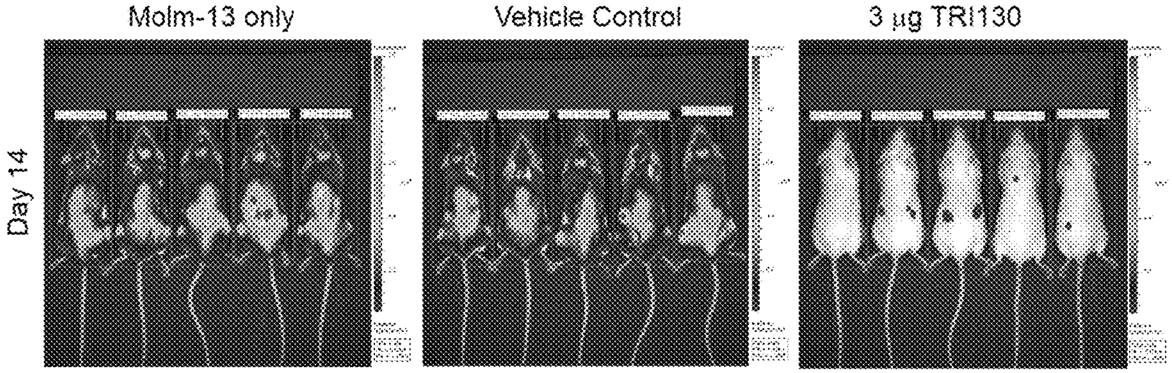

FIG. 18 TRI130 and TRI168 Induced T-cell Activation with Molm-13 Target Cells
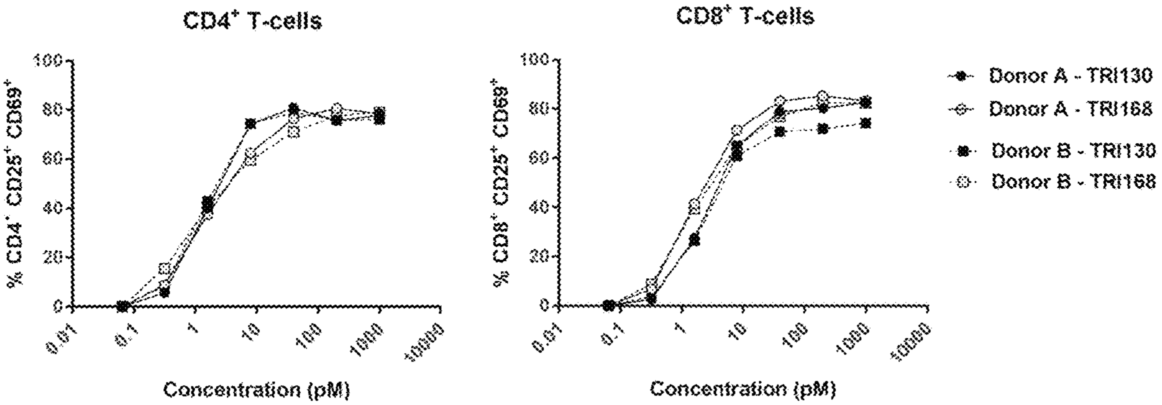
| EC50 (pM) | TRI130 | TRI168 |
|---|---|---|
| Donor A | 1.5 | 1.7 |
| Donor B | 1.4 | 1.0 |
| EC50 (pM) | TRI130 | TRI168 |
|---|---|---|
| Donor A | 2.6 | 1.6 |
| Donor B | 2.4 | 1.7 |
FIG. 19 TRI130 and TRI168 Induced T-cell Cytotoxicity of CD123$^+$ Molm-13 Target Cells
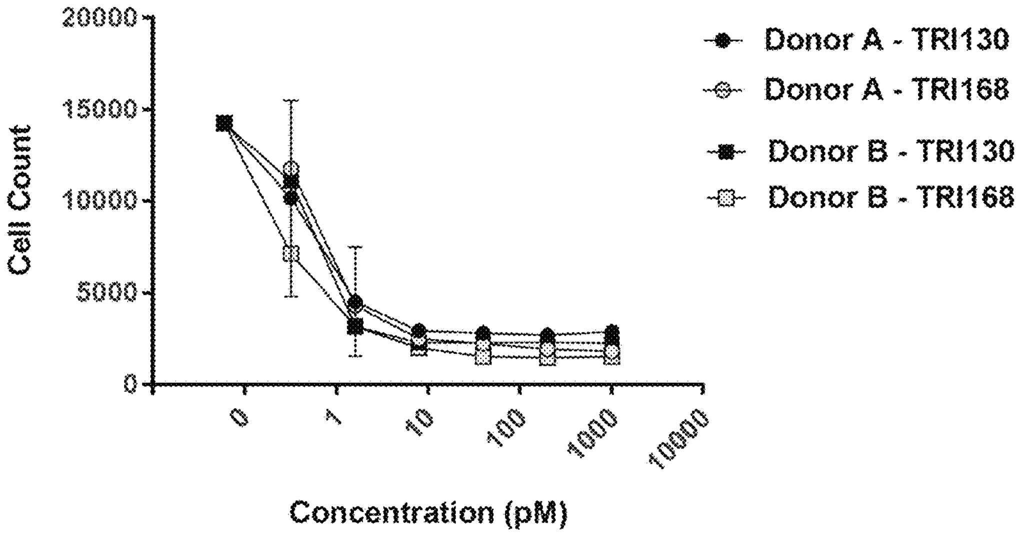

FIG. 20 TRI130 and TRI168 Induced T-cell Cytokine Release with Molm-13 Target Cells
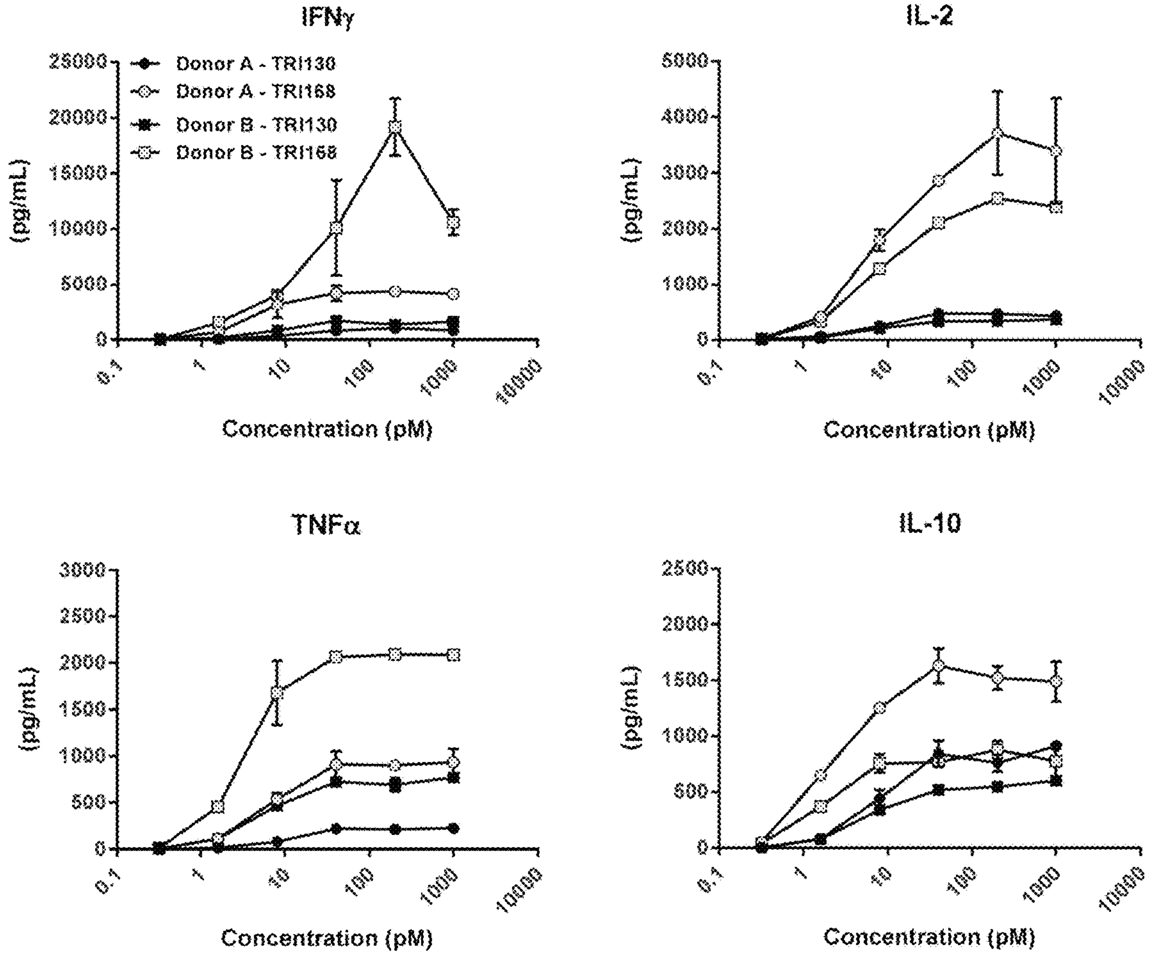

FIG. 21 TRI130 and TRI168 Induced Cytokine Release in PBMC Cultures
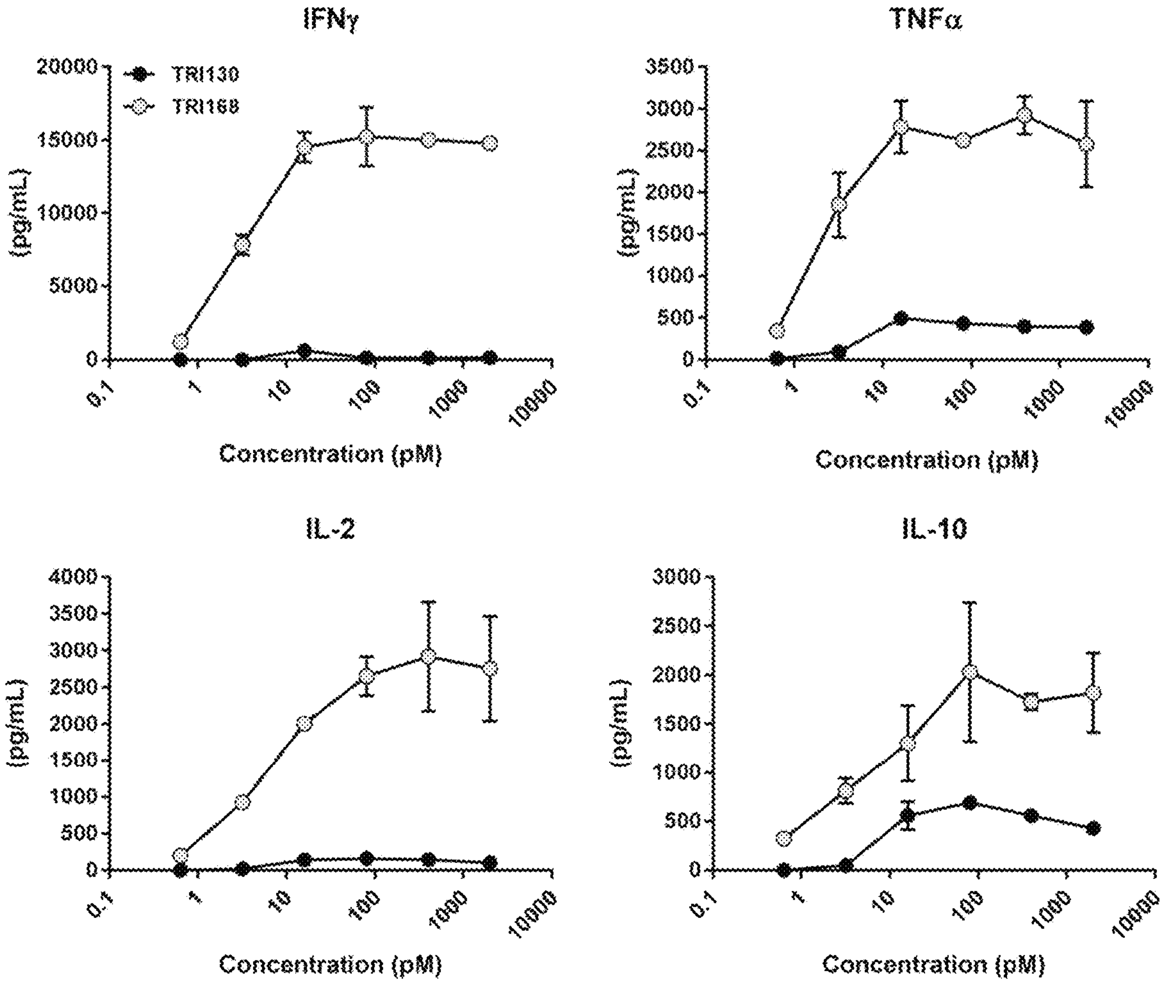

FIG. 22 Cytotoxicity of TRI130 Incubated with AML Cell Samples
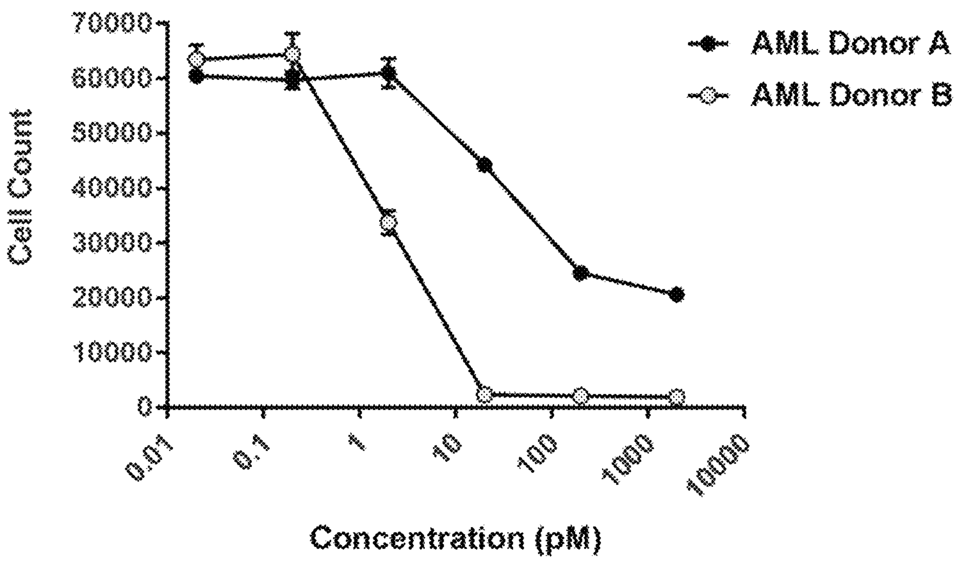

CD123 BINDING PROTEINS AND RELATED COMPOSITIONS AND METHODS

This application is a continuation application of U.S. application Ser. No. 17/557,440, filed Dec. 21, 2021, now U.S. Pat. No. 11,939,392 issued Mar. 26, 2024, which is a continuation application of U.S. application Ser. No. 16/335,561, filed Mar. 21, 2019, now U.S. Pat. No. 11,242,400 issued Feb. 8, 2022, which is a U.S. national stage application of International Application No. PCT/US2017/052808, filed Sep. 21, 2017, which claims priority to and benefit of U.S. Provisional Patent Application No. 62/397,736, filed on Sep. 21, 2016, and U.S. Provisional Patent Application No. 62/466,192, filed on Mar. 2, 2017. The contents of each of these applications are herein incorporated by reference in their entirety.

REFERENCE TO AN ELECTRONIC SEQUENCE LISTING

The contents of the electronic sequence listing (APVO_054_07US_SeqList_ST26.xml; Size: 439,447 bytes; and Date of Creation: Feb. 15, 2024) are herein incorporated by reference in its entirety.

FIELD OF THE DISCLOSURE

The present disclosure relates to molecules that specifically bind to CD123, which may have at least one humanized CD123-binding domain. These molecules are useful for the characterization or treatment of disorders characterized by overexpression of CD123, such as cancer. A protein therapeutic binding to CD123 may be a monospecific protein therapeutic or a multi-specific protein therapeutic. A multi-specific protein therapeutic may bind both CD123-expressing cells and the T-cell receptor complex on T-cells to induce target-dependent T-cell cytotoxicity, activation and proliferation.

BACKGROUND OF THE DISCLOSURE

CD123 is also known as the alpha chain of the human interleukin-3 (IL-3) receptor. CD123 is a type I transmembrane glycoprotein and is a member of the cytokine receptor superfamily. The interleukin-3 receptor is a heterodimer formed by CD123 and the beta chain (CD131). IL-3 binds to CD123, and signal transduction is provided by CD131. IL-3 regulates the function and production of hematopoietic and immune cells and stimulates endothelial cell proliferation (Testa et al., *Biomark Res.* 2:4 (2014)).

CD123 is overexpressed in many hematologic malignancies, including a subset of acute myeloid leukemia (AML), B-lymphoid leukemia, blastic plasmocytoid dendritic neoplasms (BPDCN) and hairy cell leukemia. Id. While most AML patients respond well to initial therapies, the majority of AML patients are ultimately diagnosed with relapsed or refractory disease (Ramos et al., *J. Clin. Med.* 4:665-695 (2015)). There is a need for molecules targeting CD123 with increased efficiency and potency and reduced adverse effects and that may be used to treat disorders associated with dysregulation of CD123.

SUMMARY OF THE DISCLOSURE

In some embodiments, the disclosure encompasses a recombinant polypeptide comprising a CD123-binding domain, wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises an amino acid sequence as set forth in SEQ ID NO:6 or a sequence that differs from SEQ ID NO:6 by at least one amino acid substitution; the LCDR2 comprises an amino acid sequence as set forth in WAS or a sequence that differs from WAS by at least one amino acid substitution; the LCDR3 comprises an amino acid sequence as set forth in SEQ ID NO:10 or a sequence that differs from SEQ ID NO:10 by at least one amino acid substitution; the HCDR1 comprises an amino acid sequence as set forth in SEQ ID NO:12 or a sequence that differs from SEQ ID NO:12 by at least one amino acid substitution; the HCDR2 comprises an amino acid sequence as set forth in SEQ ID NO:14 or a sequence that differs from SEQ ID NO:14 by at least one amino acid substitution; and the HCDR3 comprises an amino acid sequence as set forth in SEQ ID NO:16 or a sequence that differs from SEQ ID NO:16 by at least one amino acid substitution. For instance, the disclosure encompasses a recombinant polypeptide comprising a CD123-binding domain, wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises an amino acid sequence as set forth in SEQ ID NO:6 or a sequence that differs from SEQ ID NO:6 by one or two amino acid substitutions; the LCDR2 comprises an amino acid sequence as set forth in WAS or a sequence that differs from WAS by one or two amino acid substitutions; the LCDR3 comprises an amino acid sequence as set forth in SEQ ID NO:10 or a sequence that differs from SEQ ID NO:10 by one or two amino acid substitutions; the HCDR1 comprises an amino acid sequence as set forth in SEQ ID NO:12 or a sequence that differs from SEQ ID NO:12 by one or two amino acid substitutions; the HCDR2 comprises an amino acid sequence as set forth in SEQ ID NO:14 or a sequence that differs from SEQ ID NO:14 by one or two amino acid substitutions; and the HCDR3 comprises an amino acid sequence as set forth in SEQ ID NO:16 or a sequence that differs from SEQ ID NO:16 by one or two amino acid substitutions. The invention includes a recombinant polypeptide with a CD-123 binding domain that comprises (a) the LCDR1 amino acid sequence as set forth in SEQ ID NO:6; (b) the LCDR2 amino acid sequence as set forth in WAS; (c) the LCDR3 amino acid sequence as set forth in SEQ ID NO:10; (d) the HCDR1 amino acid sequence as set forth in SEQ ID NO:12; (e) the HCDR2 amino acid sequence as set forth in SEQ ID NO:14; and (f) the HCDR3 amino acid sequence as set forth in SEQ ID NO:16. A recombinant polypeptide that binds CD123 may comprises (i) an immunoglobulin light chain variable region comprising an amino acid sequence that is at least 88%, at least 90%, at least 92%, at least 95%, at least 97%, at least 98% or at least 99% identical to the amino acid sequence set forth in SEQ ID NO:2; and (ii) an immunoglobulin heavy chain variable region comprising an amino acid sequence that is at least 85%, at least 90%, at least 92%, at least 95%, at least 97%, at least 98% or at least 99% identical to the amino acid sequence set forth in SEQ ID NO:4. For instance, the invention includes a recombinant polypeptide of claim 1, wherein the CD123-binding domain comprises: (i) the immunoglobulin light chain variable region comprising the amino acid sequence of SEQ ID NO:2; and (ii) the immunoglobulin heavy chain variable region comprising the amino acid sequence of SEQ ID NO:4.

In another embodiment, the invention includes a recombinant CD123-binding polypeptide comprising a CD123-binding domain, wherein the binding domain comprises an immunoglobulin light chain variable region comprising LCDR1, LCDR2, LCDR3 and an immunoglobulin heavy chain variable region comprising HCDR1, HCDR2 and HCDR3, and wherein (i) (a) the HCDR1 comprises an amino acid sequence as set forth in SEQ ID NO:28 or a sequence that differs from SEQ ID NO:28 by at least one amino acid substitution; (b) the HCDR2 comprises an amino acid sequence as set forth in SEQ ID NO:30 or a sequence that differs from SEQ ID NO:30 by at least one amino acid substitution; and (c) the HCDR3 comprises an amino acid sequence as set forth in SEQ ID NO:32 or a sequence that differs from SEQ ID NO:32 by at least one amino acid substitution; or (ii) (a) the HCDR1 comprises an amino acid sequence as set forth in SEQ ID NO:36 or a sequence that differs from SEQ ID NO:36 by at least one amino acid substitution; (b) the HCDR2 comprises an amino acid sequence as set forth in SEQ ID NO:38 or a sequence that differs from SEQ ID NO:38 by at least one amino acid substitution; and (c) the HCDR3 comprises an amino acid sequence as set forth in SEQ ID NO:40 or a sequence that differs from SEQ ID NO:40 by at least one amino acid substitution; or (iii) (a) the HCDR1 comprises an amino acid sequence as set forth in SEQ ID NO:44 or a sequence that differs from SEQ ID NO:44 by at least one amino acid substitution; (b) the HCDR2 comprises an amino acid sequence as set forth in SEQ ID NO:46 or a sequence that differs from SEQ ID NO:46 by at least one amino acid substitution; and (c) the HCDR3 comprises an amino acid sequence as set forth in SEQ ID NO:48 or a sequence that differs from SEQ ID NO:48 by at least one amino acid substitution; or (iv) (a) the HCDR1 comprises an amino acid sequence as set forth in SEQ ID NO:100 or a sequence that differs from SEQ ID NO:100 by at least one amino acid substitution; (b) the HCDR2 comprises an amino acid sequence as set forth in SEQ ID NO:102 or a sequence that differs from SEQ ID NO:102 by at least one amino acid substitution; and (c) the HCDR3 comprises an amino acid sequence as set forth in SEQ ID NO:104 or a sequence that differs from SEQ ID NO:104 by at least one amino acid substitution; or (v) (a) the HCDR1 comprises an amino acid sequence as set forth in SEQ ID NO:108 or a sequence that differs from SEQ ID NO:108 by at least one amino acid substitution; (b) the HCDR2 comprises an amino acid sequence as set forth in SEQ ID NO:110 or a sequence that differs from SEQ ID NO:110 by at least one amino acid substitution; and (c) the HCDR3 comprises an amino acid sequence as set forth in SEQ ID NO:112 or a sequence that differs from SEQ ID NO:112 by at least one amino acid substitution; or (vi) (a) the HCDR1 comprises an amino acid sequence as set forth in SEQ ID NO:116 or a sequence that differs from SEQ ID NO:116 by at least one amino acid substitution; (b) the HCDR2 comprises an amino acid sequence as set forth in SEQ ID NO:118 or a sequence that differs from SEQ ID NO:118 by at least one amino acid substitution; and (c) the HCDR3 comprises an amino acid sequence as set forth in SEQ ID NO:120 or a sequence that differs from SEQ ID NO:120 by at least one amino acid substitution; or (vii) (a) the HCDR1 comprises an amino acid sequence as set forth in SEQ ID NO:124 or a sequence that differs from SEQ ID NO:124 by at least one amino acid substitution; (b) the HCDR2 comprises an amino acid sequence as set forth in SEQ ID NO:126 or a sequence that differs from SEQ ID NO:126 by at least one amino acid substitution; and (c) the HCDR3 comprises an amino acid sequence as set forth in SEQ ID NO:128 or a sequence that differs from SEQ ID NO:128 by at least one amino acid substitution. The invention includes recombinant polypeptides comprising a heavy chain variable region as defined by (i)-(vii) and a light chain variable region comprising (a) the LCDR1 comprises an amino acid sequence as set forth in SEQ ID NO:22 or a sequence that differs from SEQ ID NO:22 by at least one amino acid substitution; (b) the LCDR2 comprises an amino acid sequence as set forth in SEQ ID NO:24 or a sequence that differs from SEQ ID NO:24 by at least one amino acid substitution; and (c) the LCDR3 comprises an amino acid sequence as set forth in SEQ ID NO:26 or a sequence that differs from SEQ ID NO:26 by at least one amino acid substitution. For instance, the invention includes a recombinant polypeptide comprising a light chain variable region comprises an amino acid sequence that is at least 88%, at least 90%, at least 92%, at least 95%, at least 97%, at least 98% or at least 99% identical to the amino acid sequence set forth in SEQ ID NO:18, and a heavy chain variable region comprises an amino acid sequence that is at least 85%, at least 90%, at least 92%, at least 95%, at least 97%, at least 98% or at least 99% identical to the amino acid sequence set forth in SEQ ID NO:20, 34, 42, 98, 106, 114, or 122.

In certain embodiments, a recombinant CD123-binding polypeptide comprises (a) the LCDR 1 has an amino acid sequence set forth in SEQ ID NO:54 or a sequence that differs from SEQ ID NO:54 by at least one amino acid substitution; (b) the LCDR2 has an amino acid sequence set forth in SEQ ID NO:56 or a sequence that differs from SEQ ID NO:56 by at least one amino acid substitution; (c) the LCDR3 has an amino acid sequence set forth in SEQ ID NO:58 or a sequence that differs from SEQ ID NO:58 by at least one amino acid substitution; (d) the HCDR1 has an amino acid sequence set forth in SEQ ID NO:60 or a sequence that differs from SEQ ID NO:60 by at least one amino acid substitution; (e) the HCDR2 has an amino acid sequence set forth in SEQ ID NO:61 or a sequence that differs from SEQ ID NO:61 by at least one amino acid substitution; and (f) the HCDR3 has an amino acid sequence set forth in SEQ ID NO:62 or a sequence that differs from SEQ ID NO:62 by at least one amino acid substitution. For instance, the invention includes a recombinant polypeptide comprising a CD123-binding domain, wherein (i) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:50; and (ii) the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:52.

In another embodiment, the recombinant polypeptide comprising a CD123-binding domain, comprises (a) the LCDR1 comprises an amino acid sequence as set forth in SEQ ID NO:70 or a sequence that differs from SEQ ID NO:70 by at least one amino acid substitution; (b) the LCDR2 comprises an amino acid sequence as set forth in SEQ ID NO:72 or a sequence that differs from SEQ ID NO:72 by at least one amino acid substitution; (c) the LCDR3 comprises an amino acid sequence as set forth in SEQ ID NO:74 or a sequence that differs from SEQ ID NO:74 by at least one amino acid substitution; (d) the HCDR1 comprises an amino acid sequence as set forth in SEQ ID NO:76 or a sequence that differs from SEQ ID NO:76 by at least one amino acid substitution; (e) the HCDR2 comprises an amino acid sequence as set forth in SEQ ID NO:78 or a sequence that differs from SEQ ID NO:78 by at least one amino acid substitution; and (f) the HCDR3 comprises an amino acid sequence as set forth in SEQ ID NO:80 or a sequence that differs from SEQ ID NO:80 by at least one amino acid substitution. For instance, the invention includes a recombinant polypeptide comprising the variable regions set forth in SEQ ID Nos: 66 and 68.

In certain embodiments, the recombinant polypeptide comprises (a) the LCDR1 comprises an amino acid sequence as set forth in SEQ ID NO:86 or a sequence that differs from SEQ ID NO:86 by at least one amino acid substitution; (b) the LCDR2 comprises an amino acid sequence as set forth in SEQ ID NO:88 or a sequence that differs from SEQ ID NO:88 by at least one amino acid substitution; (c) the LCDR3 comprises an amino acid sequence as set forth in SEQ ID NO:90 or a sequence that differs from SEQ ID NO:90 by at least one amino acid substitution; (d) the HCDR1 comprises an amino acid sequence as set forth in SEQ ID NO:92 or a sequence that differs from SEQ ID NO:92 by at least one amino acid substitution; (e) the HCDR2 comprises an amino acid sequence as set forth in SEQ ID NO:94 or a sequence that differs from SEQ ID NO:94 by at least one amino acid substitution; and (f) the HCDR3 comprises an amino acid sequence as set forth in SEQ ID NO:96 or a sequence that differs from SEQ ID NO:96 by at least one amino acid substitution. For instance, the invention includes a polypeptide comprising the variable domains as set forth in SEQ ID NO:82 and 84.

(ii) the immunoglobulin heavy chain variable region comprising an amino acid sequence that is at least 85%, at least 90%, at least 92%, at least 95%, at least 97%, at least 98% or at least 99% identical to the amino acid sequence set forth in SEQ ID NO:84.

The polypeptides of the invention bind to human CD123 with specificity. In certain embodiments, the polypeptides bind to non-human primate CD123. In further embodiments, the polypeptides bind to cynomolgous monkey CD123. The invention includes a CD123-binding polypeptide comprising a human CD123-binding domain and a CD123-binding polypeptide comprising a humanized CD123-binding domain. In one embodiment, the CD123-binding domain is a single chain variable fragment (scFv).

The recombinant polypeptides of the invention include bi-specific polypeptides comprising a second binding domain. In one embodiment, the second binding domain binds a T-cell, CD3, CD3ε or a T-cell receptor (TCR) complex or a component of a T-cell receptor complex with specificity. For instance, the invention includes recombinant CD123-binding polypeptides comprising a CD3 binding scFv. The invention includes combining any one of the CD123-binding scFvs disclosed with a disclosed CD3 binding scFv. In one embodiment, the polypeptide comprises, from (i) the CD123-binding domain, (ii) a hinge region, (iii) an immunoglobulin constant region, (iv) a carboxyl-terminus linker, and (v) the second binding domain. For instance, the invention includes a recombinant polypeptide comprising, in order from amino to carboxyl terminus, (i) the CD123-binding domain, (ii) the hinge region, (iii) the immunoglobulin constant region, (iv) the carboxyl-terminus linker, and (v) the second binding domain.

In one embodiment of the invention, the bi-specific polypeptides comprising a CD123 binding domain and a CD3 binding domain comprise a modified immunoglobulin constant region engineered to exhibit no to minimal antibody-dependent cell-mediated cytotoxicity (ADCC) activity and/or complement-dependent cytotoxicity (CDC) activity. In one embodiment of the invention, the CD3 binding domain is derived from a monoclonal antibody selected from CRIS-7, HuM291 and I2C.

In certain embodiments of the invention, the CD123-binding polypeptide comprises (i) an amino acid sequence at least about 93% identical, at least about 95% identical, at least about 97% identical, at least about 98% identical or at least about 99% identical to the amino acid sequence of SEQ ID NO:130; (ii) an amino acid sequence at least about 93% identical, at least about 95% identical, at least about 97% identical, at least about 98% identical or at least about 99% identical to the amino acid sequence of SEQ ID NO:132; (iii) an amino acid sequence at least about 93% identical, at least about 95% identical, at least about 97% identical, at least about 98% identical or at least about 99% identical to the amino acid sequence of SEQ ID NO:134; (iv) an amino acid sequence at least about 93% identical, at least about 95% identical, at least about 97% identical, at least about 98% identical or at least about 99% identical to the amino acid sequence of SEQ ID NO:136; (v) an amino acid sequence at least about 93% identical, at least about 95% identical, at least about 97% identical, at least about 98% identical or at least about 99% identical to the amino acid sequence of SEQ ID NO:138; (vi) an amino acid sequence at least about 93% identical, at least about 95% identical, at least about 97% identical, at least about 98% identical or at least about 99% identical to the amino acid sequence of SEQ ID NO:140; (vii) an amino acid sequence at least about 93% identical, at least about 95% identical, at least about 97% identical, at least about 98% identical or at least about 99% identical to the amino acid sequence of SEQ ID NO:142; (viii) an amino acid sequence at least about 93% identical, at least about 95% identical, at least about 97% identical, at least about 98% identical or at least about 99% identical to the amino acid sequence of SEQ ID NO:144; (iv) an amino acid sequence at least about 93% identical, at least about 95% identical, at least about 97% identical, at least about 98% identical or at least about 99% identical to the amino acid sequence of SEQ ID NO:146; (x) amino acid sequence at least about 93% identical, at least about 95% identical, at least about 97% identical, at least about 98% identical or at least about 99% identical to the amino acid sequence of SEQ ID NO:148; (xi) an amino acid sequence at least about 93% identical, at least about 95% identical, at least about 97% identical, at least about 98% identical or at least about 99% identical to the amino acid sequence of SEQ ID NO:150; (xii) an amino acid sequence at least about 93% identical, at least about 95% identical, at least about 97% identical, at least about 98% identical or at least about 99% identical to the amino acid sequence of SEQ ID NO:152; (xiii) an amino acid sequence at least about 93% identical, at least about 95% identical, at least about 97% identical, at least about 98% identical or at least about 99% identical to the amino acid sequence of SEQ ID NO:154; or (xiv) an amino acid sequence at least about 93% identical, at least about 95% identical, at least about 97% identical, at least about 98% identical or at least about 99% identical to the amino acid sequence of SEQ ID NO:156.

In one embodiment of the invention, the recombinant polypeptide induces redirected T-cell cytotoxicity (RTCC). In certain embodiments, the recombinant polypeptide induces T-cell activation or T-cell proliferation. In certain embodiments, the polypeptide induces T-cell-dependent lysis of CD123-expressing cells.

In certain embodiments of the invention, the bi-specific polypeptide comprising a CD123-binding domain and a CD3-binding domain when bound to a CD3 protein on a T cell induces reduced cytokine release from said T cell as compared to an OKT3 antibody control. In certain embodiments of the invention, the bi-specific polypeptide comprising a CD123-binding domain and a CRIS-7 derived CD3-binding domain induces reduced cytokine release from said T cell as compared to a bi-specific comprising an CD3-binding domain derived from OKT3 or I2C. In certain embodiments of the invention, the bi-specific polypeptide comprising a CD123-binding domain (e.g., a CD123-binding domain comprising an amino acid sequence at least 93%, at least 95%, at least 96%, at least 97%, at least 98%, at least 99% or 100% identical to SEQ ID NO: 2 and/or SEQ ID NO:4) and a CRIS-7 derived CD3-binding domain and in the scFv-Fc-scFv format induces reduced cytokine release in a non-human primate or human as compared to a bi-specific polypeptide comprising a CD123-binding domain and I2C derived CD3-binding domain in an scFv-scFv or diabody format.

In certain embodiments of the invention, the bispecific polypeptide comprising a CD123-binding domain and a CD3-binding domain (for instance, a recombinant polypeptide comprising an amino acid sequence at least 93%, at least 95%, at least 96%, at least 97%, at least 98%, at least 99% or 100% identical to SEQ ID NO:130 or SEQ ID NO:132) induces reduced cytokine release in a non-human primate or human as compared to MGD006 or TRI168. In one embodiment of the invention, a recombinant polypeptide comprising an amino acid sequence at least 93%, at least 95%, at least 96%, at least 97%, at least 98%, at least 99% or 100% identical to SEQ ID NO:130 or SEQ ID NO:132 induces reduced levels of IFNγ, IL-2, TNFα and/or IL-10 as compared to MGD006 or TRI168.

The disclosure encompasses an isolated nucleic acid molecule encoding a CD123-binding polypeptide described herein or a portion of said CD123-binding polypeptide. The isolated nucleic acid molecule may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

The disclosure relates to an expression vector comprising a nucleic acid segment encoding a CD123-binding polypeptide described herein, wherein the nucleic acid segment is operatively linked to regulatory sequences suitable for expression of the nucleic acid segment in a host cell. The nucleic acid segment of the expression vector may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

The disclosure includes a recombinant host cell comprising an expression vector described herein.

The disclosure relates to a method for producing a CD123-binding polypeptide, the method comprising culturing a recombinant host cell comprising an expression vector described herein under conditions whereby the nucleic acid segment of the vector is expressed, thereby producing the CD123-binding polypeptide. The method may further comprise recovering the CD123-binding polypeptide.

In some embodiments, the disclosure relates to a pharmaceutical composition comprising a CD123-binding polypeptide described herein and a pharmaceutically acceptable carrier, diluent, or excipient. The pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The pharmaceutical composition formulated as an oral unit dosage form may be selected from the group consisting of: tablets, pills, pellets, capsules, powders, lozenges, granules, solutions, suspensions, emulsions, syrups, elixirs, sustained-release formulations, aerosols, and sprays.

The disclosure also relates to a method for inducing redirected T-cell cytotoxicity (RTCC) against a cell expressing CD123, the method comprising: contacting said CD123-expressing cell with a CD123-binding polypeptide described herein, wherein the second binding domain specifically binds a T-cell, CD3, CD3ε or a T-cell receptor (TCR) complex or a component of a T-cell receptor complex; and wherein said contacting is under conditions whereby RTCC against the CD123-expressing cell is induced.

The disclosure encompasses a method for inducing T-cell dependent lysis of a cell expressing CD123, the method comprising: contacting said CD123-expressing cell with a CD123-binding polypeptide or CD123-binding protein described herein, wherein the second binding domain specifically binds a T-cell, CD3, CD3ε or a T-cell receptor (TCR) complex or a component of a T-cell receptor complex; and wherein said contacting is under conditions whereby T-cell dependent lysis of the CD123-expressing cell is induced.

The disclosure encompasses a method for treating a disorder (e.g., cancer) in a subject, wherein said disorder is characterized by overexpression of CD123, the method comprising administering to the subject a therapeutically effective amount of a CD123-binding polypeptide described herein. The disclosure also relates to a CD123-binding polypeptide described herein for the manufacture of a medicament for treatment of a disorder (e.g., cancer) in a subject, wherein said disorder is characterized by overexpression of CD123. The disclosure includes a CD123-binding polypeptide described herein for use in treating a disorder (e.g., cancer) in a subject, wherein said disorder is characterized by overexpression of CD123. The cancer treated by the CD123-binding polypeptides described herein may be acute myeloid leukemia (AML), B-lymphoid leukemia, blastic plasmocytoid dendritic neoplasm (BPDCN), or hairy cell leukemia.

These and other embodiments and/or other aspects of the disclosure will become evident upon reference to the following detailed description of the disclosure and the attached drawings.

BRIEF DESCRIPTION OF THE DRAWINGS

FIG. 13 shows the WinNonlin® non-compartmental (NCA) estimates and fit of half-life (HL) for treatment groups of cynomolgus monkeys treated with TRI130, as described in Example 14.

FIG. 14 shows a graph depicting the change in lymphocyte population over time in cynomolgus monkeys treated with TRI130, as described in Example 14.

FIG. 15 shows a graph depicting the change in basophil population over time in cynomolgus monkeys treated with TRI130, as described in Example 14.

FIG. 16 shows a graph depicting the tumor burden as measured by bioluminescence levels over time in a disseminated xenograft mouse model of acute myeloid leukemia (AML), as described in Example 15.

FIG. 17 shows bioluminescent images of tumor burden in mice at day 14.

FIG. 18 shows the results of assays measuring TRI130- and TRI168-induced T-cell activation with $CD123^+$ Molm-13 target cells, as described in Example 17.

FIG. 19 shows the results of assays measuring TRI130- and TRI168-induced T-cell cytotoxicity of $CD123^+$ Molm-13 target cells, as described in Example 17.

FIG. 20 shows the results of assays measuring TRI130- and TRI168-induced T-cell cytokine release with $CD123^+$ Molm-13 target cells, as described in Example 17.

FIG. 21 shows the results of assays measuring TRI130- and TRI168-induced T-cell cytokine release in peripheral blood mononuclear cells (PBMC) cultures, as described in Example 17.

FIG. 22 shows the results of assays measuring cytotoxicity of TRI130 incubated with AML cell samples from AML subjects, as described in Example 18.

DETAILED DESCRIPTION OF THE DISCLOSURE

Figure 1A:
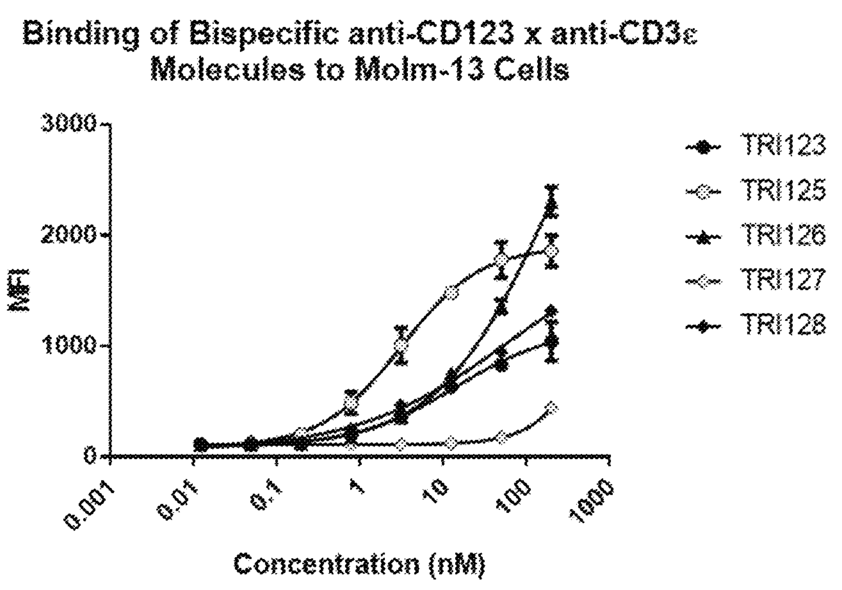
FIG. 1A-FIG. 1D show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in three independent experiments to the CD123 (+) Molm-13 human tumor cell line.
Figure 1B:
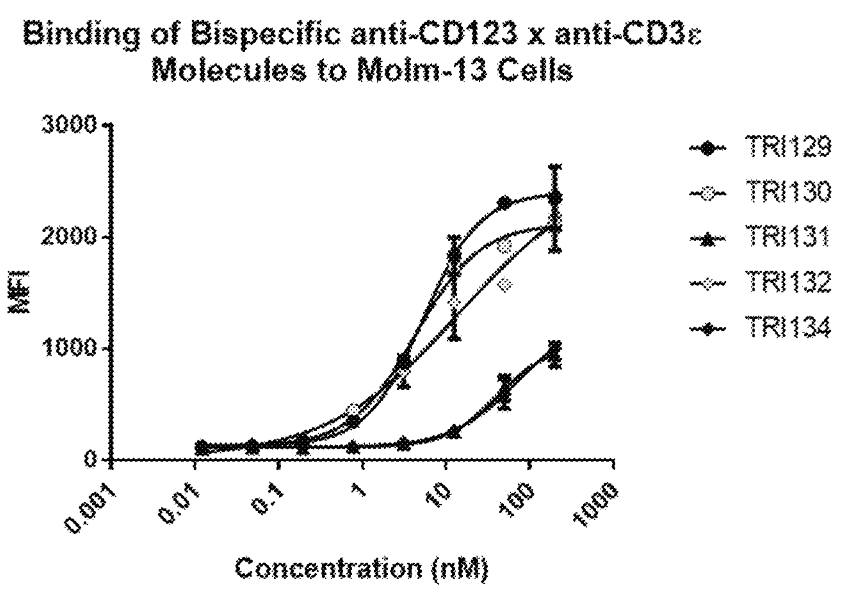
Figure 1C:
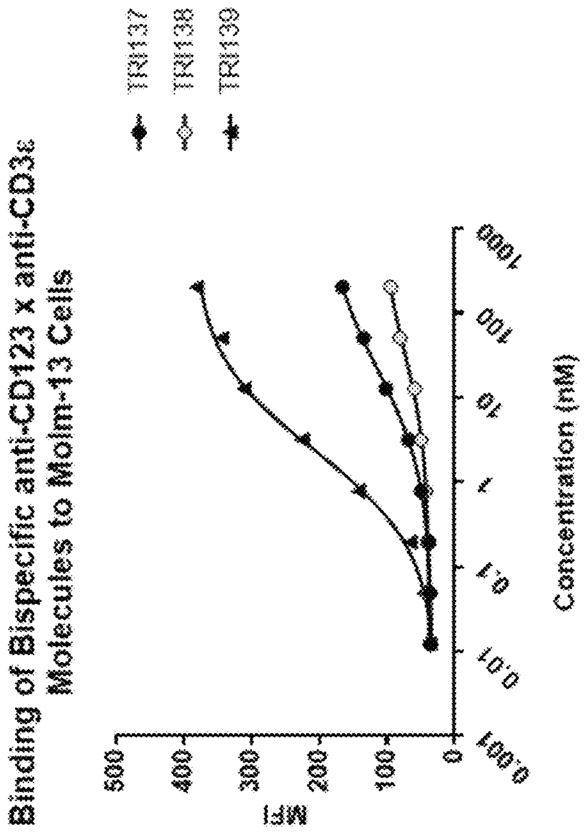
Figure 1D:
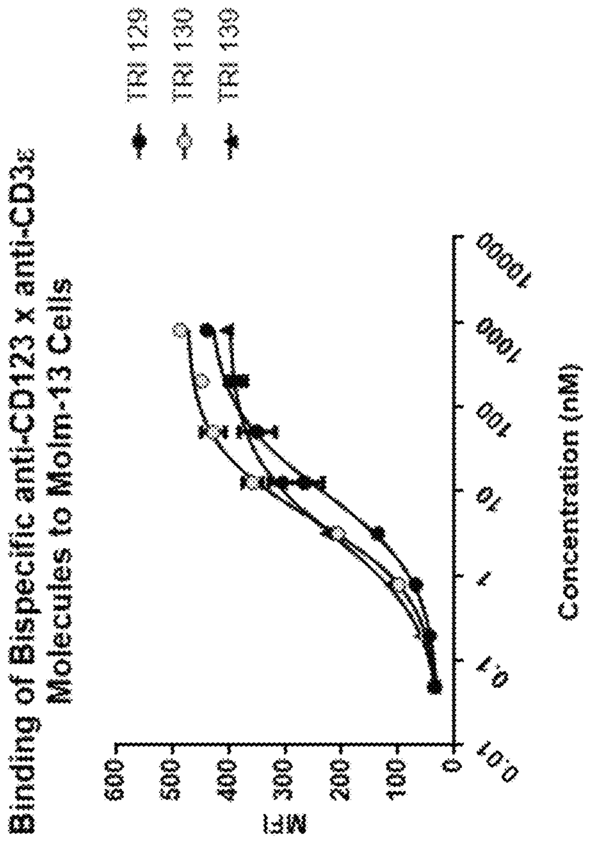

The disclosure provides binding domains that specifically bind to CD123 (also known as interleukin-3 receptor alpha chain) and binding molecules (e.g. polypeptides and proteins) that specifically bind to CD123. These binding molecules may bind specifically to CD123 and to another target. Administration of a therapeutically effective amount of a CD123-binding polypeptide or protein to a patient in need thereof is useful for treatment of certain disorders associated with the over-expression of CD123, including certain cancers. In one embodiment, a CD123-binding polypeptide or protein binds both a target cell over-expressing CD123 and a T-cell, thereby "cross-linking" the target cell over-expressing CD123 and the T-cell. The binding of both domains to their targets elicits potent target-dependent redirected T-cell cytotoxicity (RTCC) (e.g., induces target-dependent T-cell cytotoxicity, T-cell activation and/or T-cell proliferation). The CD123-binding therapeutics of the disclosure offer various advantages in treating patients, for example, effective binding to CD123, efficient induction of RTCC activity, reduced levels of cytokine release and/or a lower risk of adverse events (e.g., toxicity). In certain aspects, the CD123-binding proteins bind to CD123 more effectively in certain formats (e.g., scFv compared to parent antibody) and/or certain orientations (e.g., VL-VH compared to VH-VL), leading to higher potency and improved utility in treating disorders associated with over-expression of CD123.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

As used herein, the term "binding domain" or "binding region" refers to the domain, region, portion, or site of a protein, polypeptide, oligopeptide, or peptide or antibody or binding domain derived from an antibody that possesses the ability to specifically recognize and bind to a target molecule, such as an antigen, ligand, receptor, substrate, or inhibitor (e.g., CD123, CD3). Exemplary binding domains include single-chain antibody variable regions (e.g., domain antibodies, sFv, scFv, scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a CD123-binding polypeptide can have a "first binding domain" and, optionally, a "second binding domain." In certain embodiments, the "first binding domain" is a CD123-binding domain and the format is an antibody or antibody-like protein or domain. In certain embodiments comprising both the first and second binding domains, the second binding domain is a T-cell binding domain such as a scFv derived from a mouse monoclonal antibody (e.g., CRIS-7) or phage display (e.g., I2C) that binds to a T-cell surface antigen (e.g., CD3). In other embodiments, the second binding domain is a second CD123-binding domain. In yet other embodiments, the second binding domain is a binding domain other than a CD123-binding domain or a T-cell binding domain.

"Cytokine release" or "cytokine storm" or "infusion reaction" refers to the release of cytokines from T-cells. When cytokines are released into the circulation, systemic symptoms such as fever, nausea, chills, hypotension, tachycardia, asthenia, headache, rash, scratchy throat, and dyspnea can result. Some patients may experience severe, life-threatening reactions that result from massive release of cytokines. "Reduced" cytokine release refers to the to the reduction in the release of at least one cytokine (e.g., IFNγ, IL-2, TNFα and/or IL-10) following administration of a recombinant polypeptide of the invention as compared to the OKT-3 antibody or other CD3 binding bispecific molecule. Reduced cytokine release can be measured using in vitro assays or in vivo.

A binding domain or protein "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains can be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least 1011 $M^{-1}$, at least $10^{12}$ $M^{-1}$, or at least $10^{13}$ $M^{-1}$. "Low affinity" binding domains refer to those binding domains with a $K_a$ of up to 107 $M^{-1}$, up to 106 $M^{-1}$, up to 105 $M^{-1}$. Alternatively, affinity can be defined as an equilibrium dissociation constant ($K_a$) of a particular binding interaction with units of M (e.g., 10-5 M to 10-13 M). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"CD3" is known in the art as a multi-protein complex of six chains (see, e.g., Abbas and Lichtman, 2003; Janeway et al., p. 172 and 178, 1999), which are subunits of the T-cell receptor complex. In mammals, the CD3 subunits of the T-cell receptor complex are a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T-cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure can be from various animal species, including human, monkey, mouse, rat, or other mammals.

As used herein, a "conservative substitution" is recognized in the art as a substitution of one amino acid for another amino acid that has similar properties. Exemplary conservative substitutions are well-known in the art (see, e.g., WO 97/09433, page 10, published Mar. 13, 1997; Lehninger, Biochemistry, Second Edition; Worth Publishers, Inc. NY: NY (1975), pp. 71-77; Lewin, Genes IV, Oxford University Press, NY and Cell Press, Cambridge, MA (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence. For example, a binding domain can be derived from an antibody, e.g., a Fab, F(ab')2, Fab', scFv, single domain antibody (sdAb), etc.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered according to the IMGT numbering convention (Brochet, X, et al, Nucl. Acids Res. (2008) 36, W503-508) and a position of an amino acid residue in a constant region of an immunoglobulin molecule is numbered according to EU nomenclature (Ward et al., 1995 *Therap. Immunol.* 2:77-94). Other numbering conventions are known in the art (e.g., the Kabat numbering convention (Kabat, Sequences of Proteins of Immunological Interest, 5th ed. Bethesda, MD: Public Health Service, National Institutes of Health (1991)).

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A heterodimer does not include an antibody formed from four polypeptides (i.e., two light chains and two heavy chains). A "homodimer" or "homodimeric protein," as used herein, refers to a dimer formed from two identical polypeptides. The recombinant polypeptides of the invention exist primarily in a dimerized form. All disclosure of the polypeptide, including characteristics and activities (such as binding and RTCC) should be understood to include the polypeptide in its dimer form as well as other multimeric forms.

In some embodiments, a CD123-binding polypeptide comprises, in order from amino-terminus to carboxyl-terminus or in order from carboxyl-terminus to amino-terminus, (i) the CD123-binding domain, (ii) a hinge region, (iii) an immunoglobulin constant region, (iv) a carboxyl-terminus linker (or an amino-terminus linker), and (v) a second binding domain. As used herein and depending on context, a "hinge region" or a "hinge" refers to a polypeptide region between a binding domain (e.g., a CD123-binding domain) and an immunoglobulin constant region. As used herein and depending on context, a "linker" may refer to (1) a polypeptide region between VH and VL regions in a single-chain Fv (scFv) or (2) a polypeptide region between an immunoglobulin constant region and a second binding domain in a CD123-binding polypeptide comprising two binding domains. A polypeptide region between an immunoglobulin constant region and a second binding domain in a CD123-binding polypeptide comprising two binding domains may also be referred to as a "carboxyl-terminus linker" or an "amino-terminus linker." Non-limiting examples of carboxyl-terminus and amino-terminus linkers include flexible linkers comprising glycine-serine (e.g., $(Gly_4Ser)$) repeats (SEQ ID NO: 315), and linkers derived from (a) an interdomain region of a transmembrane protein (e.g., a type I transmembrane protein); (b) a stalk region of a type II C-lectin; or (c) an immunoglobulin hinge. Non-limiting examples of hinges and linkers are provided in Tables 1 and 2. In some embodiments, a "linker" provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids. In some embodiments, a linker is comprised of at least 5 amino acids, at least 7 amino acids or at least 9 amino acids.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region.

An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in US 2013/0129723 and US 2013/0095097.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., *Nature* 321:522 (1986)) and variants thereof, including "reshaping" (Verhoeyen, et al., 1988 *Science* 239:1534-1536; Riechmann, et al., 1988 *Nature* 332:323-337; Tempest, et al., *Bio/Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994:291-312). If derived from a non-human source, other regions of the antibody or immunoglobulin binding proteins and polypeptides, such as the hinge region and constant region domains, can also be humanized.

An "immunoglobulin dimerization domain" or "immunoglobulin heterodimerization domain", as used herein, refers to an immunoglobulin domain of a polypeptide chain that preferentially interacts or associates with a different immunoglobulin domain of a second polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., Cκ or Cλ isotypes), or derivatives thereof, including wild type immunoglobulin CH1 and CL domains and altered (or mutated) immunoglobulin CH1 and CL domains, as provided therein.

An "immunoglobulin constant region" or "constant region" is a term defined herein to refer to a peptide or polypeptide sequence that corresponds to or is derived from part or all of one or more constant region domains. In certain embodiments, the immunoglobulin constant region corresponds to or is derived from part or all of one or more constant region domains, but not all constant region domains of a source antibody. In certain embodiments, the constant region comprises IgG CH2 and CH3 domains, e.g., IgG1 CH2 and CH3 domains. In certain embodiments, the constant region does not comprise a CH1 domain. In certain embodiments, the constant region domains making up the constant region are human. In some embodiments (for example, in certain variations of a CD123-binding polypeptide or protein comprising a second binding domain that specifically binds CD3 or another T-cell surface antigen), the constant region domains of a fusion protein of this disclosure lack or have minimal effector functions of antibody-dependent cell-mediated cytotoxicity (ADCC) and complement activation and complement-dependent cytotoxicity (CDC), while retaining the ability to bind some Fc receptors (such as $F_cRn$, the neonatal Fc receptor) and retaining a relatively long half-life in vivo. In other variations, a fusion protein of this disclosure includes constant domains that retain such effector function of one or both of ADCC and CDC. In certain embodiments, a binding domain of this disclosure is fused to a human IgG1 constant region, wherein the IgG1 constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG1 Fc domain has each of L234, L235, G237, E318, K320, and K322 (according to EU numbering) mutated to an alanine (i.e., L234A, L235A, G237A, E318A, K320A, and K322A, respectively), and optionally an N297A mutation as well (i.e., essentially eliminating glycosylation of the CH2 domain). In another embodiment, the IgG1 Fc domain has each of L234A, L235A, G237A and K322A mutations. For instance, the invention includes a recombinant polypeptide comprising a CD123 binding domain or scFv with an amino acid sequence at least 93%, at least 95%, at least 97%, at least 98%, at least 99% or 100% identical to SEQ ID NO:130; an IgG1 domain comprising the mutations L234A, L235A, G237A and K322A; and a CD3 binding domain. The invention includes a recombinant polypeptide comprising a CD123 binding domain comprising an amino acid sequence at least 93%, at least 95%, at least 97%, at least 98%, at least 99% or 100% identical to SEQ ID NO:130; an IgG1 domain comprising the mutations L234A, L235A, G237A and K322A; and a CD3 binding domain comprising an amino acid sequence at least 93%, at least 95%, at least 97%, at least 98%, at least 99% or 100% identical to SEQ ID NO:192 or SEQ ID NO:193.

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

In some embodiments, a CD123-binding protein comprises a protein scaffold as generally disclosed in, for example, in US Patent Application Publication Nos. 2003/0133939, 2003/0118592, and 2005/0136049. A CD123-binding protein may comprise, in order from amino-terminus to carboxyl-terminus: a first binding domain, a hinge region, and an immunoglobulin constant region. In other embodiments, a CD123-binding protein comprises a protein scaffold as generally disclosed in, for example, in US Patent Application Publication No. 2009/0148447. A CD123-binding protein may comprise, in order from amino-terminus to carboxyl-terminus: an immunoglobulin constant region, a hinge region and a first binding domain.

CD123-binding polypeptides and proteins disclosed herein may incorporate a multi-specific binding protein scaffold. Multi-specific binding proteins and polypeptides using scaffolds are disclosed, for instance, in PCT Application Publication No. WO 2007/146968, U.S. Patent Application Publication No. 2006/0051844, PCT Application Publication No. WO 2010/040105, PCT Application Publication No. WO 2010/003108, U.S. Pat. Nos. 7,166,707 and 8,409,577, which are each incorporated herein by reference in their entirety. A CD123-binding protein may comprise two binding domains (the domains can be designed to specifically bind the same or different targets), a hinge region, a linker (e.g., a carboxyl-terminus or an amino-terminus linker), and an immunoglobulin constant region. A CD123-binding protein may be a homodimeric protein comprising two identical, disulfide-bonded polypeptides.

Figure 11:
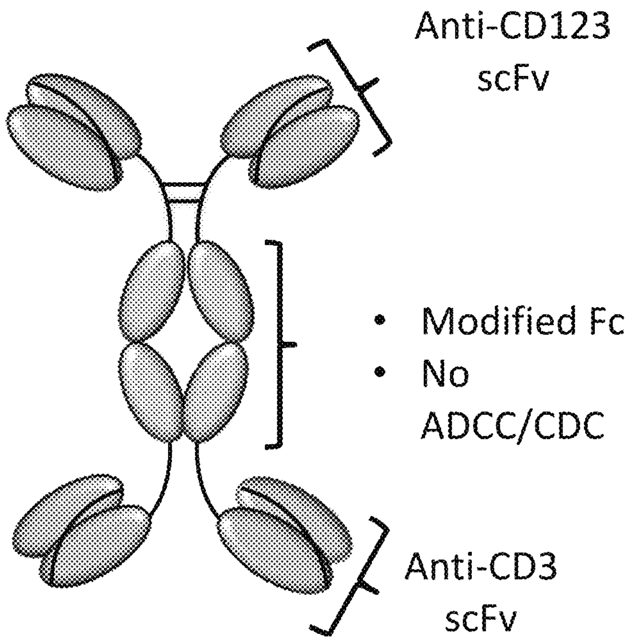
FIG. 11 is an illustration of a recombinant CD123-binding polypeptide capable of RTCC in the CD123-binding domain-hinge domain-immunoglobulin constant domain-CD3 binding domain configuration.

In one embodiment of the invention, the CD123-binding protein comprises, in order from amino-terminus to carboxyl terminus, a first binding domain, a hinge region, an immunoglobulin constant region and a second binding domain. FIG. 11 illustrates a CD123-binding protein in this configuration.

As used herein, the term "junction amino acids" or "junction amino acid residues" refers to one or more (e.g., about 2-10) amino acid residues between two adjacent regions or domains of a polypeptide, such as between a hinge and an adjacent immunoglobulin constant region or between a hinge and an adjacent binding domain or between a peptide linker and an adjacent immunoglobulin variable domain or an adjacent immunoglobulin constant region. Junction amino acids can result from the construct design of a polypeptide (e.g., amino acid residues resulting from the use of a restriction enzyme site during the construction of a nucleic acid molecule encoding a polypeptide).

As used herein, the term "patient in need" or "subject in need" refers to a patient at risk of, or suffering from, a disease, disorder or condition that is amenable to treatment or amelioration with a CD123-binding protein or polypeptide or a composition thereof provided herein. A patient in need may, for instance, be a patient diagnosed with a disease associated with the expression of CD123 such as acute myeloid leukemia (AML), B-lymphoid leukemia, blastic plasmocytoid dendritic neoplasms (BPDCN), hairy cell leukemia (HCL), myelodysplastic syndrome (MDS), acute lymphoblastic leukemia (ALL), refractory anemia with excess blasts (RAEB), chronic myeloid leukemia and Hodgkin's lymphoma.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant.

An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, a "polypeptide" or "polypeptide chain" is a single, linear and contiguous arrangement of covalently linked amino acids. Polypeptides can have or form one or more intrachain disulfide bonds. With regard to polypeptides as described herein, reference to amino acid residues corresponding to those specified by SEQ ID NO includes post-translational modifications of such residues.

As used herein, "CD123-binding protein" may be used interchangeably with "CD123-binding polypeptide," "polypeptide," and "recombinant polypeptide." Such molecules specifically bind to CD123 (e.g., human CD123), also known as Cluster of Differentiation 123, Interleukin-3 receptor alpha chain, and IL3RA. CD123 is a type I transmembrane glycoprotein, with an extracellular domain comprising a predicted Ig-like domain and two FnIII domains. The CD123-binding proteins of the disclosure bind to the extracellular domain of CD123. The term "CD123" may refer to any isoform of CD123. Exemplary human CD123 nucleotide and amino acid sequences are provided in SEQ ID NOs:205 and 206 and SEQ ID NOs:207 and 208, respectively. CD123 associates with the beta chain of the interleukin-3 receptor to form the receptor.

A "protein" is a macromolecule comprising one or more polypeptide chains. A protein can also comprise non-peptidic components, such as carbohydrate groups. Carbohydrates and other non-peptidic substituents can be added to a protein by the cell in which the protein is produced, and will vary with the type of cell. Proteins are defined herein in terms of their amino acid backbone structures; substituents such as carbohydrate groups are generally not specified, but may be present nonetheless. A protein may be an antibody or an antigen-binding fragment of an antibody. In some embodiments, a protein may also be an scFv-Fc-scFv molecule, scFv-scFv dimer, or a diabody.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

"T-cell receptor" (TCR) is a molecule found on the surface of T-cells that, along with CD3, is generally responsible for recognizing antigens bound to major histocompatibility complex (MHC) molecules. It consists of a disulfide-linked heterodimer of the highly variable α and β chains in most T-cells. In other T-cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Abbas and Lichtman, *Cellular and Molecular Immunology* (5th Ed.), Editor: Saunders, Philadelphia, 2003; Janeway et al., *Immunobiology: The Immune System in Health and Disease,* 4$^{th}$ Ed., Current Biology Publications, p 148, 149, and 172, 1999). TCR as used in the present disclosure can be from various animal species, including human, mouse, rat, or other mammals.

"TCR complex," as used herein, refers to a complex formed by the association of CD3 chains with other TCR chains. For example, a TCR complex can be composed of a CD3γ chain, a CD3δ chain, two CD3ε chains, a homodimer of CD3Z chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, Annu. Rev. Immunol., 9:457-92.

The term "having ADCC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)) is capable of mediating complement-dependent cytotoxicity (CDC) through binding of C1q complement protein and activation of the classical complement system. In one embodiment of the invention, the recombinant polypeptide has been modified to abate CDC activity.

"Redirected T-cell cytotoxicity" and "RTCC," as used herein, refer to a T-cell-mediated process in which a cytotoxic T-cell is recruited to a target cell using a multi-specific protein that is capable of specifically binding both the cytotoxic T-cell and the target cell, and whereby a target-dependent cytotoxic T-cell response is elicited against the target cell. Polypeptides and proteins comprising anti-CD123 and anti-CD3 binding domains, as disclosed herein, are capable of RTCC.

As used herein, the term "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a specific binding molecule or compound refers to that amount of the compound sufficient to result in amelioration of one or more symptoms of the disease being treated in a statistically significant manner or a statistically significant improvement in organ function. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

As used herein, the term "variant" or "variants" refers to a nucleic acid or polypeptide differing from a reference nucleic acid or polypeptide, but retaining essential properties thereof. Generally, variants are overall closely similar, and, in many regions, identical to the reference nucleic acid or polypeptide. For instance, a variant may exhibit at least about 70%, at least about 80%, at least about 90%, at least about 95%, at least about 96%, at least about 97%, at least about 98% or at least about 99% sequence identity compared to the active portion or full length reference nucleic acid or polypeptide.

The terms "light chain variable region" (also referred to as "light chain variable domain" or "VL" or $V_L$) and "heavy chain variable region" (also referred to as "heavy chain variable domain" or "$V_H$" or VH) refer to the variable binding region from an antibody light and heavy chain, respectively. The variable binding regions are made up of discrete, well-defined sub-regions known as "complementarity determining regions" (CDRs) and "framework regions" (FRs), generally comprising in order FR1-CDR1-FR2-CDR2-FR3-CDR3-FR4 from amino-terminus to carboxyl-terminus. In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

The present disclosure describes binding domains that specifically bind CD123 (e.g., human CD123), as well as polypeptides and proteins comprising these binding domains. In some embodiments, the CD123-binding proteins and polypeptides comprise a second binding domain, which may bind to CD123 or to a different target. The polypeptides and proteins comprising binding domains of this disclosure can further comprise immunoglobulin constant regions, linker peptides, hinge regions, immunoglobulin dimerization/heterodimerization domains, junctional amino acids, tags, etc. These components of the disclosed polypeptides and proteins are described in further detail below.

Additionally, the CD123-binding polypeptides and proteins disclosed herein can be in the form of an antibody or a fusion protein of any of a variety of different formats (e.g., the fusion protein can be in the form of a CD123-binding bispecific or multi-specific molecule). Non-limiting examples of bispecific molecules include a scFv-Fc-scFv molecule. Some bispecific molecules comprise or consist of an anti-CD123 scFv linked to a second binding domain scFv and do not include other sequences such as an immunoglobulin constant region. In other embodiments, a CD123-binding protein is a diabody.

A CD123-binding protein in accordance with the present disclosure generally includes at least one CD123-binding polypeptide chain comprising (a) a CD123-binding domain as set forth herein. In certain variations, the CD123-binding polypeptide further includes (b) a hinge region carboxyl-terminal to the CD123-binding domain, and (c) an immunoglobulin constant region. In further variations, the CD123-binding polypeptide further includes (d) a carboxyl-terminus linker carboxyl-terminal to the immunoglobulin constant region, and (e) a second binding domain carboxyl-terminal to the carboxyl-terminus linker.

In yet other variations, the CD123-binding polypeptide comprises (b) a hinge region amino-terminal to the CD123-binding domain, and (c) an immunoglobulin sub-region amino-terminal to the hinge region.

In some embodiments, recombinant polypeptides are capable of homodimerization, typically through disulfide bonding, via the immunoglobulin constant region and/or hinge region (e.g., via an immunoglobulin constant region comprising IgG CH2 and CH3 domains and an IgG hinge region). Thus, in certain embodiments of the present disclosure, two identical single chain CD123-binding polypeptides homodimerize to form a dimeric CD123-binding protein. An example of a homodimer of the invention is provided in FIG. 11.

In other embodiments, a CD123-binding polypeptide includes a heterodimerization domain that is capable of heterodimerization with a different heterodimerization domain in a second, non-identical polypeptide chain. In certain variations, the second polypeptide chain for heterodimerization includes a second binding domain. Accordingly, in certain embodiments of the present disclosure, two non-identical polypeptide chains, one comprising the CD123-binding domain and the second optionally comprising a second binding domain, dimerize to form a heterodimeric CD123-binding protein. Examples of types of heterodimers include those described in U.S. Patent Application Publication No. 2013/0095097 and US 2013/0129723.

In some embodiments, a CD123-binding domain, protein or polypeptide is conjugated to a drug or a toxic moiety.

CD123-binding polypeptides, proteins, and their various components used in the therapeutics of the present disclosure are further described below.

As indicated above, the disclosure relates to binding domains that specifically bind CD123. In some variations, the CD123-binding domain is capable of competing for binding to CD123 with an antibody having VL and VH regions having amino acid sequences as shown in SEQ ID NO:194 and SEQ ID NO:196, respectively (e.g., 12F1). The murine anti-CD123 antibody 12F1 is described in, for example, U.S. Patent Application Publication No. 2013/041739 and Kuo et al, (2012) *Protein Eng Design Select*, p 1-9.

The CD123-binding domain may comprise sequences shown in Table 3, and some relevant SEQ ID NOs are summarized in Table 6. In certain embodiments, the CD123-binding domain comprises (i) an immunoglobulin light chain variable region (VL) comprising CDRs LCDR1, LCDR2, and LCDR3, and (ii) an immunoglobulin heavy chain variable region (VH) comprising CDRs HCDR1, HCDR2, and HCDR3 with HCDR1 comprising an amino acid sequence as set forth in SEQ ID NO:12, with HCDR2 comprising an amino acid sequence as set forth in SEQ ID NO:14 and with HCDR3 comprising an amino acid sequence as set forth in SEQ ID NO:16. In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:6 or a sequence that differs from SEQ ID NO:6 by at least one amino acid substitution; (ii) the LCDR2 has an amino acid sequence set forth in WAS or a sequence that differs from WAS by at least one amino acid substitution; (iii) the LCDR3 has an amino acid sequence set forth in SEQ ID NO:10 or a sequence that differs from SEQ ID NO:10 by at least one amino acid substitution; (iv) the HCDR1 has an amino acid sequence set forth in SEQ ID NO:12 or a sequence that differs from SEQ ID NO:12 by at least one amino acid substitution; (v) the HCDR2 has an amino acid sequence set forth in SEQ ID NO:14 or a sequence that differs from SEQ ID NO:14 by at least one amino acid substitution; and (vi) the HCDR3 has an amino acid sequence set forth in SEQ ID NO:16 or a sequence that differs from SEQ ID NO:16 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody. For instance, the invention includes a recombinant polypeptide comprising (i) the LCDR1 has an amino acid sequence set forth in SEQ ID NO:6 or a sequence that differs from SEQ ID NO:6 by one or two amino acid substitutions; (ii) the LCDR2 has an amino acid sequence set forth in WAS or a sequence that differs from WAS by one or two amino acid substitutions; (iii) the LCDR3 has an amino acid sequence set forth in SEQ ID NO:10 or a sequence that differs from SEQ ID NO:10 by one or two amino acid substitutions; (iv) the HCDR1 has an amino acid sequence set forth in SEQ ID NO:12 or a sequence that differs from SEQ ID NO:12 by one or two amino acid substitutions; (v) the HCDR2 has an amino acid sequence set forth in SEQ ID NO:14 or a sequence that differs from SEQ ID NO:14 by one or two amino acid substitutions; and (vi) the HCDR3 has an amino acid sequence set forth in SEQ ID NO:16 or a sequence that differs from SEQ ID NO:16 by one or two amino acid substitutions. The amino acid substitution described above may be a conservative or a non-conservative amino acid substitution.

In related embodiments, a recombinant polypeptide of the invention comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:2) or to a heavy chain variable region ($V_H$) (e.g., SEQ ID NO:4), or both. In one embodiment, the CD123-binding domain of the recombinant polypeptide is an scfv comprising a variable heavy chain comprising SEQ ID NO:4 and a variable light chain comprising SEQ ID NO:2 in the VHVL orientation. In another embodiment, the CD123-binding domain of the recombinant polypeptide is an scFv comprising a variable light chain comprising SEQ ID NO:2 and a variable heavy chain comprising SEQ ID NO:4 in the VLVH orientation. For instance, in certain embodiments, the polypeptide of the invention comprises an amino acid sequence of SEQ ID NO:130 or SEQ ID NO:132. The invention includes a recombinant polypeptide that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of SEQ ID NO:130 or SEQ ID NO:132.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:28 or a sequence that differs from SEQ ID NO:28 by at least one amino acid substitution; (v) the HCDR2 has an amino acid sequence set forth in SEQ ID NO:30 or a sequence that differs from SEQ ID NO:30 by at least one amino acid substitution; and (vi) the HCDR3 has an amino acid sequence set forth in SEQ ID NO:32 or a sequence that differs from SEQ ID NO:32 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:20), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:36 or a sequence that differs from SEQ ID NO:36 by at least one amino acid substitution; (v) the HCDR2 has an amino acid sequence set forth in SEQ ID NO:38 or a sequence that differs from SEQ ID NO:38 by at least one amino acid substitution; and (vi) the HCDR3 has an amino acid sequence set forth in SEQ ID NO:40 or a sequence that differs from SEQ ID NO:40 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:34), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:44 or a sequence that differs from SEQ ID NO:44 by at least one amino acid substitution; (v) the HCDR2 has an amino acid sequence set forth in SEQ ID NO:46 or a sequence that differs from SEQ ID NO:46 by at least one amino acid substitution; and (vi) the HCDR3 has an amino acid sequence set forth in SEQ ID NO:48 or a sequence that differs from SEQ ID NO:48 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:42), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:100 or a sequence that differs from SEQ ID NO:100 by at least one amino acid substitution; (v) the HCDR2 has an amino acid sequence set forth in SEQ ID NO:102 or a sequence that differs from SEQ ID NO:102 by at least one amino acid substitution; and (vi) the HCDR3 has an amino acid sequence set forth in SEQ ID NO:104 or a sequence that differs from SEQ ID NO:104 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:98), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:116 or a sequence that differs from SEQ ID NO:116 by at least one amino acid substitution; (v) the HCDR2 has an amino acid sequence set forth in SEQ ID NO:118 or a sequence that differs from SEQ ID NO:118 by at least one amino acid substitution; and (vi) the HCDR3 has an amino acid sequence set forth in SEQ ID NO:120 or a sequence that differs from SEQ ID NO:120 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:114), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:124 or a sequence that differs from SEQ ID NO:124 by at least one amino acid substitution; (v) the HCDR2 has an amino acid sequence set forth in SEQ ID NO:126 or a sequence that differs from SEQ ID NO:126 by at least one amino acid substitution; and (vi) the HCDR3 has an amino acid sequence set forth in SEQ ID NO:128 or a sequence that differs from SEQ ID NO:128 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:122), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:54 or a sequence that differs from SEQ ID NO:54 by at least one amino acid substitution; (ii) the LCDR2 has an amino acid sequence set forth in SEQ ID NO:56 or a sequence that differs from SEQ ID NO:56 by at least one amino acid substitution; (iii) the LCDR3 has an amino acid sequence set forth in SEQ ID NO:58 or a sequence that differs from SEQ ID NO:58 by at least one amino acid substitution; (iv) the HCDR1 has an amino acid sequence set forth in SEQ ID NO:60 or a sequence that differs from SEQ ID NO:60 by at least one amino acid substitution; (v) the HCDR2 has an amino acid sequence set forth in SEQ ID NO:62 or a sequence that differs from SEQ ID NO:62 by at least one amino acid substitution; and (vi) the HCDR3 has an amino acid sequence set forth in SEQ ID NO:64 or a sequence that differs from SEQ ID NO:64 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:50) or to a heavy chain variable region ($V_H$) (e.g., SEQ ID NO:52), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:70 or a sequence that differs from SEQ ID NO:70 by at least one amino acid substitution; (ii) the LCDR2 has an amino acid sequence set forth in SEQ ID NO:72 or a sequence that differs from SEQ ID NO:72 by at least one amino acid substitution; (iii) the LCDR3 has an amino acid sequence set forth in SEQ ID NO:74 or a sequence that differs from SEQ ID NO:74 by at least one amino acid substitution; (iv) the HCDR1 has an amino acid sequence set forth in SEQ ID NO:76 or a sequence that differs from SEQ ID NO:76 by at least one amino acid substitution; (v) the HCDR2 has an amino acid sequence set forth in SEQ ID NO:78 or a sequence that differs from SEQ ID NO:78 by at least one amino acid substitution; and (vi) the HCDR3 has an amino acid sequence set forth in SEQ ID NO:80 or a sequence that differs from SEQ ID NO:80 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:66) or to a heavy chain variable region ($V_H$) (e.g., SEQ ID NO:68), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:86 or a sequence that differs from SEQ ID NO:86 by at least one amino acid substitution; (ii) the LCDR2 has an amino acid sequence set forth in SEQ ID NO:88 or a sequence that differs from SEQ ID NO:88 by at least one amino acid substitution; (iii) the LCDR3 has an amino acid sequence set forth in SEQ ID NO:90 or a sequence that differs from SEQ ID NO:90 by at least one amino acid substitution; (iv) the HCDR1 has an amino acid sequence set forth in SEQ ID NO:92 or a sequence that differs from SEQ ID NO:92 by at least one amino acid substitution; (v) the HCDR2 has an amino acid sequence set forth in SEQ ID NO:94 or a sequence that differs from SEQ ID NO:94 by at least one amino acid substitution; and (vi) the HCDR3 has an amino acid sequence set forth in SEQ ID NO:96 or a sequence that differs from SEQ ID NO:96 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:82) or to a heavy chain variable region ($V_H$) (e.g., SEQ ID NO:84), or both.

In certain embodiments, a CD123-binding domain comprises humanized immunoglobulin $V_L$ and/or $V_H$ regions. Techniques for humanizing immunoglobulin $V_L$ and $V_H$ regions are known in the art and are discussed, for example, in U.S. Patent Application Publication No. 2006/0153837. In certain embodiments, a CD123-binding domain comprises human immunoglobulin $V_L$ and/or $V_H$ regions.

"Humanization" is expected to result in an antibody that is less immunogenic, with complete retention of the antigen-binding properties of the original molecule. In order to retain all of the antigen-binding properties of the original antibody, the structure of its antigen binding site should be reproduced in the "humanized" version. This can be achieved by grafting only the nonhuman CDRs onto human variable framework domains and constant regions, with or without retention of critical framework residues (Jones et al., *Nature* 321:522 (1986); Verhoeyen et al., *Science* 239:1539 (1988)) or by recombining the entire nonhuman variable domains (to preserve ligand-binding properties), but "cloaking" them with a human-like surface through judicious replacement of exposed residues (to reduce antigenicity) (Padlan, *Molec. Immunol.* 28:489 (1991)).

Essentially, humanization by CDR grafting involves recombining only the CDRs of a non-human antibody onto a human variable region framework and a human constant region. Theoretically, this should substantially reduce or eliminate immunogenicity (except if allotypic or idiotypic differences exist). However, it has been reported that some framework residues of the original antibody also may need to be preserved (Reichmann et al., *Nature,* 332:323 (1988); Queen et al., *Proc. Natl. Acad. Sci. USA,* 86:10,029 (1989)).

The framework residues that need to be preserved are amenable to identification through computer modeling. Alternatively, critical framework residues can potentially be identified by comparing known antigen-binding site structures (Padlan, *Molec. Immunol.,* 31(3):169-217 (1994), incorporated herein by reference).

The residues that potentially affect antigen binding fall into several groups. The first group comprises residues that are contiguous with the antigen site surface, which could therefore make direct contact with antigens. These residues include the amino-terminal residues and those adjacent to the CDRs. The second group includes residues that could alter the structure or relative alignment of the CDRs, either by contacting the CDRs or another peptide chain in the antibody. The third group comprises amino acids with buried side chains that could influence the structural integrity of the variable domains. The residues in these groups are usually found in the same positions (Padlan, 1994, supra) although their positions as identified may differ depending on the numbering system (see Kabat et al., "Sequences of proteins of immunological interest, 5th ed., Pub. No. 91-3242, U.S. Dept. Health & Human Services, NIH, Bethesda, Md., 1991).

Knowledge about humanized antibodies in the art is applicable to the polypeptides according to the disclosure, even if these polypeptides are not antibodies.

In some embodiments, the disclosure relates to CD123-binding domains wherein (i) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:2 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:4; (ii) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:20; (iii) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:34; (iv) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:42; (v) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:50 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:52; (vi) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:66 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:68; (vii) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:82 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:84; (viii) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:122; (ix) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:98; (x) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:106; or (xi) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:114.

In further embodiments, each CDR comprises no more than one, two, or three substitutions, insertions or deletions, as compared to that from a monoclonal antibody or fragment or derivative thereof that specifically binds to a target of interest (e.g., CD123).

In certain embodiments, a CD123-binding protein can comprise one or more additional binding domains (e.g., second binding domain) that bind a target other than CD123. These other binding domains can comprise, for example, a particular cytokine or a molecule that targets the binding domain polypeptide to a particular cell type, a toxin, an additional cell receptor, an antibody, etc.

In certain embodiments, a CD123-binding molecule or protein can comprise a T-cell binding domain for recruitment of T-cells to target cells expressing CD123. In certain embodiments, a CD123-binding protein as described herein can comprise (i) a binding domain that specifically binds a TCR complex or a component thereof (e.g., TCRα, TCRβ, CD3γ, CD3δ, and CD3ε) and (ii) another binding domain that specifically binds to CD123. A CD123-binding protein can utilize essentially any binding domain that binds a T-cell, e.g., an antibody derived binding domain. Exemplary anti-CD3 antibodies from which the CD3 binding domain can be derived include the CRIS-7 monoclonal antibody (Reinherz, E. L. et al. (eds.), *Leukocyte typing II.*, Springer Verlag, New York, (1986); $V_L$ and $V_H$ amino acid sequences respectively shown in SEQ ID NO:209 (QVVLTQSPAIMSAFPGEKVTMTCSASSSVSYMNWYQQKSGTSPKRWIYDSSKLASGVPARFS GSGSGTSYSLTISSMETEDAATYYCQQWSRNPPTFGGGTKLQITR) and SEQ ID NO:210 (QVQLQQSGAELARPGASVKMSCKASGYTFTRSTMHWVKQRPGQGLEWIGYINP SSAYTNYNQKFKDKATLTADKSSSTAYMQLSSLTSEDSAVYYCASPQVHYDYNGFPYWGQGT LVTVSA)); HuM291 (Chau et al. (2001) *Transplantation* 71:941-950; $V_L$ and $V_H$ amino acid sequences respectively shown in SEQ ID NO:211 (DIQMTQSPSSLSASVGDRVTITCSASSSVSYMNWYQQKPGKAPKRLIYDTSKLASGVP SRFSGSGSGTDFTLTISSLQPEDFATYYCQQWSSNPPTFGGGTKVEIK) and SEQ ID NO:212 (QVQLVQSGAEVKKPGASVKVSCKASGYTFISYTMHWVRQAPGQGLEWMGYINPRSGYTHYN QKLKDKATLTADKSASTAYMELSSLRSEDTAVYYCARSAYYDYDGFAYWGQGTLVTVSS)); BC3 monoclonal antibody (Anasetti et al. (1990) *J. Exp. Med.* 172:1691); OKT3 monoclonal antibody (Ortho multicenter Transplant Study Group (1985) *N. Engl. J. Med.* 313:337) and derivatives thereof such as OKT3 ala-ala (also referred to as OKT3 AA-FL or OKT3 FL), a humanized, Fc variant with alanine substitutions at positions 234 and 235 (Herold et al. (2003) *J. Clin. Invest.* 11:409); visilizumab (Carpenter et al. (2002) *Blood* 99:2712), G19-4 monoclonal antibody (Ledbetter et al., 1986, *J. Immunol.* 136:3945), 145-2C11 monoclonal antibody (Hirsch et al. (1988) *J. Immunol.* 140:3766) and I2C monoclonal antibody (see, e.g., US 2011/0293619 and US20120244162). For example, a CD3 binding domain may comprise a CD3 binding domain disclosed in U.S. Patent Application Publication No. 2012/0244162, including a CD3 binding domain comprising a VL region selected from SEQ ID NO: 17, 21, 35, 39, 53, 57, 71, 75, 89, 83, 107, 111, 125, 129, 143, 147, 161, 165, 179 and 183 of US 2012/0244162 and/or a $V_H$ region selected from SEQ ID NO:15, 19, 33, 37, 51, 55, 69, 73, 87, 91. 105, 109, 123, 127, 141, 145, 159, 163, GTK and 181 of US 2012/0244162. In some embodiments, a CD3 binding domain comprises an amino acid sequence selected from SEQ ID NO: 23, 25, 41, 43, 59, 61, 77, 79, 95, 97, 113, 115, 131, 133, 149, 151, 167, DSS, 185, and 187 of US 2012/0244162. In some embodiments, a CD3 binding domain is one described in WO2004/106380, WO2005/040220A1, US 2014/0099318 or derived from a CD3 binding domain thereof. An exemplary anti-TCR antibody is the BMA031 monoclonal antibody (Borst et al. (1990) *Human Immunology* 29:175-188). The CD3 binding domain may be derived from any of the antibodies or sequences described in WO 2013/158856 (incorporated herein by reference in its entirety). In certain variations, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs:162, 163 and 164, respectively, and the HCDR1, HCDR2, and HCDR3 has the amino acid sequences set forth in SEQ ID NOs:165, 166 and 167, respectively; or (b) the LCDR1, LCDR2 and LCDR3 has the amino acid sequences set forth in SEQ ID NO:168, DSS, and SEQ ID NO:170, respectively, and the HCDR1, HCDR2, and HCDR3 has the amino acid sequences set forth in SEQ ID NO: 171, SEQ ID NO:172, and SEQ ID NO:173, respectively. In other aspects, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs: 171, 172 and 173, respectively, and the HCDR1, HCDR2, and HCDR3 has the amino acid sequences set forth in SEQ ID NOs: 174, 175 and 176, respectively; or (b) the LCDR1, LCDR2 and LCDR3 has the amino acid sequences set forth in SEQ ID NOs: 176, GTK and 178, respectively, and the HCDR1, HCDR2, and HCDR3 has the amino acid sequences set forth in SEQ ID NOs: 179, 180 and 181, respectively. In certain embodiments, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs: 182, 183 and 184, respectively, and the HCDR1, HCDR2, and HCDR3 has the amino acid sequences set forth in SEQ ID NOs: 185, 186 and 187, respectively; or (b) the LCDR1, LCDR2 and LCDR3 has the amino acid sequences set forth in SEQ ID NOs: 188, DTS and 190, respectively, and the HCDR1, HCDR2, and HCDR3 has the amino acid sequences set forth in SEQ ID NOs: 191, 192 and 193, respectively. In some aspects, the second binding domains comprising the CDR sequences recited in this paragraph are humanized.

In some embodiments of a CD123-binding protein comprising a second binding domain that specifically binds CD3ε, the second binding domain competes for binding to CD3ε with the CRIS-7, HuM291 or I2C monoclonal antibody. In certain variations, the CD3-binding domain comprises an immunoglobulin light chain variable region ($V_L$) and an immunoglobulin heavy chain variable region ($V_H$) derived from the CRIS-7, HuM291 or I2C monoclonal antibody (e.g., the $V_L$ and $V_H$ of the second binding domain can be humanized variable regions comprising, respectively, the light chain CDRs and the heavy chain CDRs of the monoclonal antibody). A second binding domain may comprise the light chain variable region, the heavy chain variable region, or both, of the DRA222, TSC455, or TSC456 CD3-binding domains. The amino acid sequences of DRA222, TSC455, and TSC456 are provided in Table 3. The DRA222 binding domains are also described in WO 2013/158856. TSC455 may also be referred to as TSC394 F87Y. TSC455 may also be referred to as TSC394 E86D F87Y or TSC394 DY. In some embodiments, the second binding domain specifically binds CD3 and comprises an immunoglobulin light chain variable region and an immunoglobulin heavy chain variable region; wherein the immunoglobulin light chain variable region comprises an amino acid sequence that is at least about 93% identical, at least about 95% identical, at least about 97% identical, at least about 98% identical or at least about 99% identical to the amino acid sequence in SEQ ID NO:157; or at least about 94% identical, at least about 95% identical, at least about 97% identical, at least about 98% identical or at least about 99% identical to the amino acid sequence in SEQ ID NO:158; and wherein the immunoglobulin heavy chain variable region comprises an amino acid sequence that is at least about 82% identical, at least about 85% identical, at least about 87% identical, at least about 90% identical, at least about 92% identical, at least about 95% identical, at least about 97% identical, at least about 98% identical or at least about 99% identical to the amino acid sequence in SEQ ID NO:159. In some embodiments, a CD123-binding polypeptide or protein further comprising a CD3-binding domain may have a low level of high molecular weight aggregates produced during recombinant expression of the polypeptide or protein. A CD123-binding polypeptide or protein further comprising a CD3-binding domain may exhibit a relatively long stability in human serum, depending on the CD3-binding domain present in the polypeptide or protein.

In certain variations, the second binding domain of a CD123-binding polypeptide described herein is a CD3-binding domain and comprises one or more of the CD3-binding sequences (e.g., CDRs or variable regions) disclosed in US 2013/0129730, US 2011/0293619, U.S. Pat. No. 7,635,472, WO 2010/037836, WO 2004/106381, or WO 2011/121110; each incorporated herein by reference in its entirety. In some embodiments, a CD3-binding domain comprises one or more of the following sequences:

| LCDR1 | LCDR2 | LCDR3 |
|---|---|---|
| GSSTGAV TSGYYPN (SEQ ID NO: 289) | GTKFLAP (SEQ ID NO: 292) | ALWYSNR WV (SEQ ID NO: 295) |
| RSSTGAV TSGYYPN (SEQ ID NO: 290) | ATDMRPS (SEQ ID NO: 293) | ALWYSNR WV (SEQ ID NO: 296) |
| GSSTGAV TSGNYPN (SEQ ID NO: 291) | GTKFLAP (SEQ ID NO: 294) | VLWYSNR WV (SEQ ID NO: 297) |

In various embodiments, a CD3-binding domain comprises one or more of the following sequences:

| HCDR1 | HCDR2 | HCDR3 |
|---|---|---|
| IYAMN (SEQ ID NO: 298) | RIRSKYN NYATYYA DSVKS (SEQ ID NO: 301) | HGNFGNS YVSFFAY (SEQ ID NO: 304) |
| KYAMN (SEQ ID NO: 299) | RIRSKYN NYATYYA DSVKD (SEQ ID NO: 302) | HGNFGNS YISYWAY (SEQ ID NO: 305) |
| SYAMN (SEQ ID NO: 300) | RIRSKYN NYATYYA DSVKG (SEQ ID NO: 303) | HGNFGNS YLSFWAY (SEQ ID NO: 306) |

In certain embodiments, the CD123-binding polypeptide used in the methods and compositions described herein is a bispecific single chain molecule comprising a CD123 binding domain and a CD3 binding domain. In some embodiments, a CD123- and/or a CD3- binding domain is derived from an antibody and comprises a variable heavy chain (VH) and a variable light chain (VL). For example, an scFv comprises a VH and VL. These binding domains and variable chains may be arranged in any order that still retains some binding to the target(s). For example, the variable domains may be arranged in the order such as VH CD123-VL CD123-VH CD3-VL CD3; VL CD123-VH CD123-VH CD3-VL CD3; VH CD123-VL CD123-VL CD3-VH CD3; VL CD123-VH CD123-VL CD3-VH CD3; VH CD3-VL CD3-VH CD123-VL CD123; VL CD3-VH CD3-VL CD123-VH CD123; VH CD3-VL CD3-VL CD123-VH CD123; or VL CD3-VH CD3-VH CD123-VL CD123. The pairs of VH regions and VL regions in the binding domain binding to CD3 may be in the format of a single chain antibody (scFv). The VH and VL regions may be arranged in the order VH-VL or VL-VH. In some embodiments, the scFv may bind to CD123 more effectively than the antibody comprising the same VH and VL region sequences in the same orientation. In certain embodiments, the scFv may bind more effectively to CD123 in the VL-VH orientation than in the VH-VL orientation, or vice versa (see, e.g., Example 2). The VH-region may be positioned N-terminally to a linker sequence. The VL region may be positioned C-terminally to the linker sequence. The domain arrangement in the CD3 binding domain of the bispecific single chain molecule may be VH-VL, with said CD3 binding domain located C-terminally to the CD123-binding domain. A bispecific molecule may comprise an scFv binding to CD123 linked to an scFv binding to CD3. These scFvs may be linked with a short peptide. In some embodiments, bispecific single chain molecules do not comprise a hinge region or a constant region (see, for example, US 2013/

0295121, WO 2010/037836, WO 2004/106381 and WO 2011/121110; each incorporated herein by reference in its entirety).

In some embodiments, a binding domain is a single-chain Fv fragment (scFv) that comprises $V_H$ and $V_L$ regions specific for a target of interest. In certain embodiments, the $V_H$ and $V_L$ regions are human or humanized.

In some variations, a binding domain is a single-chain Fv (scFv) comprising immunoglobulin $V_L$ and $V_H$ regions joined by a peptide linker. The use of peptide linkers for joining $V_L$ and $V_H$ regions is well-known in the art, and a large number of publications exist within this particular field. In some embodiments, a peptide linker is a 15 mer consisting of three repeats of a Gly-Gly-Gly-Gly-Ser amino acid sequence ($(Gly_4Ser)_3$) (SEQ ID NO:213). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula $(Gly_4Ser)_n$, wherein n=1-5 (SEQ ID NO:214). Other suitable linkers can be obtained by optimizing a simple linker (e.g., $(Gly_4Ser)_n$) (SEQ ID NO: 315) through random mutagenesis.

In some embodiments, a CD123-binding polypeptide comprises, in order from amino-terminus to carboxyl-terminus (or in order from carboxyl-terminus to amino-terminus), (i) the CD123-binding domain, (ii) a hinge region, (iii) an immunoglobulin constant region, (iv) a carboxyl-terminus linker (or an amino-terminus linker), and (v) the second binding domain. As used herein in the context of a polypeptide construct comprising a first binding domain and a second binding domain, a "hinge region" or a "hinge" refers to a polypeptide region between the first binding domain and the Fc region. A "carboxyl-terminus linker" or "an amino-terminus linker" refers to a polypeptide region between the Fc region and the second binding domain. In some embodiments, a carboxyl-terminus (or an amino-terminus linker) linker comprises or consists of SEQ ID NO:248. In certain embodiments, a hinge is a wild-type human immunoglobulin hinge region. In certain other embodiments, one or more amino acid residues can be added at the amino- or carboxyl-terminus of a wild type immunoglobulin hinge region as part of a fusion protein construct design. For example, additional junction amino acid residues at the hinge amino-terminus can be "RT," "RSS," "TG," or "T," or at the hinge carboxyl-terminus can be "SG", or a hinge deletion can be combined with an addition, such as AP with "SG" added at the carboxyl-terminus.

In certain embodiments, a hinge, a carboxyl-terminus linker, or an amino-terminus linker is an altered immunoglobulin hinge in which one or more cysteine residues in a wild type immunoglobulin hinge region is substituted with one or more other amino acid residues (e.g., serine or alanine).

Exemplary altered immunoglobulin hinges, carboxyl-terminus linkers, and amino-terminus linkers include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, a hinge, a carboxyl-terminus linker, or an amino-terminus linker polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In further embodiments, a hinge, a carboxyl-terminus linker, or an amino-terminus linker present in a CD123-binding polypeptide can be a hinge that is not based on or derived from an immunoglobulin hinge (i.e., not a wild-type immunoglobulin hinge or an altered immunoglobulin hinge). Examples for such hinges and carboxyl-terminus linkers include peptides of about five to about 150 amino acids derived from an interdomain region of a transmembrane protein or stalk region of a type II C-lectin, for instance, peptides of about eight to 25 amino acids and peptides of about seven to 18 amino acids. In another embodiment, a carboxyl-terminus linker or amino-terminus linker comprises a $(Gly_4Ser)$ repeat (SEQ ID NO: 315) such as $(Gly_4Ser)_3PS$ (SEQ ID NO: 316).

In certain embodiments, hinge, carboxyl-terminus linker, and amino-terminal linker sequences have about 5 to 150 amino acids, 5 to 10 amino acids, 10 to 20 amino acids, 20 to amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge or linker can be primarily flexible, but can also provide more rigid characteristics or can contain primarily a-helical structure with minimal β-sheet structure. The lengths or the sequences of the hinges and linkers can affect the binding affinities of the binding domains to which the hinges are directly or indirectly (via another region or domain, such as an heterodimerization domain) connected as well as one or more activities of the Fc region portions to which the hinges or linkers are directly or indirectly connected.

In certain embodiments, hinge, carboxyl-terminus linker, and amino-terminal linker sequences are stable in plasma and serum and are resistant to proteolytic cleavage. The first lysine in the IgG1 upper hinge region can be mutated to minimize proteolytic cleavage, for instance, the lysine can be substituted with methionine, threonine, alanine or glycine, or is deleted.

In some embodiments of the disclosure, a CD123-binding polypeptide is capable of forming a heterodimer with a second polypeptide chain and comprises a hinge region (a) immediately amino-terminal to an immunoglobulin constant region (e.g., amino-terminal to a CH2 domain wherein the immungobloubolin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

Some exemplary hinge, carboxyl-terminus linker, and amino-terminus linker sequences suitable for use in accordance with the present disclosure are shown in the Tables 1 and 2 below. Additional exemplary hinge and linker regions are set forth in SEQ ID NOs: 241-244, 601, 78, 763-791, 228, 379-434, 618-749 of US 2013/0129723 (said sequences incorporated by reference herein).

TABLE 1

Exemplary hinges and linkers

| Name | Amino Acid Sequence | SEQ ID NO |
|---|---|---|
| sss(s)-hIgG1 hinge | EPKSSDKTHTSPPSS | SEQ ID NO: 215 |
| csc(s)-hIgG1 hinge | EPKSCDKTHTSPPCS | SEQ ID NO: 216 |
| ssc(s)-hIgG1 hinge | EPKSSDKTHTSPPCS | SEQ ID NO: 217 |
| scc(s)-hIgG1 hinge | EPKSSDKTHTCPPCS | SEQ ID NO: 218 |
| css(s)-hIgG1 hinge | EPKSCDKTHTSPPSS | SEQ ID NO: 219 |
| scs(s)-hIgG1 hinge | EPKSSDKTHTCPPSS | SEQ ID NO: 220 |
| ccc(s)-hIgG1 hinge | EPKSCDKTHTSPPCS | SEQ ID NO: 221 |
| ccc(p)-hIgG1 hinge | EPKSCDKTHTSPPCP | SEQ ID NO: 222 |
| sss(p)-hIgG1 hinge | EPKSSDKTHTSPPSP | SEQ ID NO: 223 |
| csc(p)-hIgG1 hinge | EPKSCDKTHTSPPCP | SEQ ID NO: 224 |
| ssc(p)-hIgG1 hinge | EPKSSDKTHTSPPCP | SEQ ID NO: 225 |
| scc(p)-hIgG1 hinge | EPKSSDKTHTCPPCP | SEQ ID NO: 226 |
| css(p)-hIgG1 hinge | EPKSCDKTHTSPPSP | SEQ ID NO: 227 |
| scs(p)-hIgG1 hinge | EPKSSDKTHTCPPSP | SEQ ID NO: 228 |
| Scppcp | SCPPCP | SEQ ID NO: 229 |
| STD1 | NYGGGGSGGGGSGGGGSG NS | SEQ ID NO: 230 |
| STD2 | NYGGGGSGGGGSGGGGS GNYGGGGSGGGGSGGGGS GNS | SEQ ID NO: 231 |
| H1 | NS | SEQ ID NO: 232 |
| H2 | GGGGSGNS | SEQ ID NO: 233 |

TABLE 1-continued

Exemplary hinges and linkers

| Name | Amino Acid Sequence | SEQ ID NO |
|---|---|---|
| H3 | NYGGGGSGNS | SEQ ID NO: 234 |
| H4 | GGGGSGGGGSGNS | SEQ ID NO: 235 |
| H5 | NYGGGGSGGGGSGNS | SEQ ID NO: 236 |
| H6 | GGGGSGGGGSGGGGSGNS | SEQ ID NO: 237 |
| H7 | GCPPCPNS | SEQ ID NO: 238 |
| $(G_4S)_3$ | GGGGSGGGGSGGGGS | SEQ ID NO: 239 |
| H105 | SGGGGSGGGGSGGGGS | SEQ ID NO: 240 |
| $(G_4S)_4$ | GGGGSGGGGSGGGGSGGG GS | SEQ ID NO: 241 |
| H75 (NKG2A quadruple mutant) | QRHNNSSLNTGTQMAGHS PNS | SEQ ID NO: 242 |
| H83 (NKG2A derived) | SSLNTGTQMAGHSPNS | SEQ ID NO: 243 |
| H106 (NKG2A derived) | QRHNNSSLNTGTQMAGHS | SEQ ID NO: 244 |
| H81 (NKG2D derived) | EVQIPLTESYSPNS | SEQ ID NO: 245 |
| H91 (NKG2D derived) | NSLANQEVQIPLTESYSP NS | SEQ ID NO: 246 |
| H94 | SGGGGSGGGGSGGGGSPNS | SEQ ID NO: 247 |
| H111 | SGGGGSGGGGSGGGGSPGS | SEQ ID NO: 248 |
| H114 | GGGGSGGGGSGGGGSPS | SEQ ID NO: 288 |

TABLE 2

Exemplary hinges and linkers (derived from H7 hinge, stalk region of a type II C-lectin, or interdomain region of a type I transmembrane protein)

| Name | Amino Acid Sequence | Molecule and/or hinge from which derived | SEQ ID NO |
|---|---|---|---|
| H16 | LSVKADFLTP SIGNS | CD80 | SEQ ID NO: 249 |
| H17 | LSVKADFLTP SISCPPCPNS | CD80 + H7 | SEQ ID NO: 250 |
| H18 | LSVLANFSQP EIGNS | CD86 | SEQ ID NO: 251 |
| H19 | LSVLANFSQP EISCPPCPNS | CD86 + H7 | SEQ ID NO: 252 |

TABLE 2 -continued

Exemplary hinges and linkers (derived from H7 hinge, stalk region of a type II C-lectin, or interdomain region of a type I transmembrane protein)

| Name | Amino Acid Sequence | Molecule and/or hinge from which derived | SEQ ID NO |
|---|---|---|---|
| H20 | LKIQERVSKP KISNS | CD2 | SEQ ID NO: 253 |
| H21 | LKIQERVSKP KISCPPCPNS | CD2 + H7 | SEQ ID NO: 254 |
| H22 | LNVSERPFPP HIQNS | CD22 | SEQ ID NO: 255 |
| H23 | LDVSERPFPP HIQSCPPCPN S | CD22 + H7 | SEQ ID NO: 256 |
| H24 | REQLAEVTLS LKANS | CD80 | SEQ ID NO: 257 |
| H25 | REQLAEVTLS LKACPPCPNS | CD80 + H7 | SEQ ID NO: 258 |
| H26 | RIHQMNSELS VLANS | CD86 | SEQ ID NO: 259 |
| H27 | RIHQMNSELS VLACPPCPNS | CD86 + H7 | SEQ ID NO: 260 |
| H28 | DTKGKNVLEK IFSNS | CD2 | SEQ ID NO: 261 |
| H30 | LPPETQESQE VTLNS | CD22 | SEQ ID NO: 262 |
| H32 | RIHLNVSERP FPPNS | CD22 | SEQ ID NO: 263 |
| H33 | RIHLNVSERP FPPCPPCPNS | CD22 + H7 | SEQ ID NO: 264 |
| H36 | GCPPCPGGGG SNS | H7 | SEQ ID NO: 265 |
| H40 | GCPPCPANS | H7 | SEQ ID NO: 266 |
| H41 | GCPPCPANS | H7 | SEQ ID NO: 267 |
| H42 | GCPPCPNS | H7 | SEQ ID NO: 268 |
| H44 | GGGASCPPCP GNS | H7 | SEQ ID NO: 269 |
| H45 | GGGASCPPCA GNS | H7 | SEQ ID NO: 270 |
| H46 | GGGASCPPCA NS | H7 | SEQ ID NO: 271 |
| H47 | LSVKADFLTP SIGNS | CD80 | SEQ ID NO: 272 |
| H48 | ADFLTPSIGN S | CD80 | SEQ ID NO: 273 |
| H50 | LSVLANFSQP EIGNS | CD86 | SEQ ID NO: 274 |
| H51 | LSVLANFSQP EIGNS | CD86 | SEQ ID NO: 275 |
| H52 | SQPEIVPISN S | CD86 | SEQ ID NO: 276 |
| H53 | SQPEIVPISC PPCPNS | CD86 + H7 | SEQ ID NO: 277 |
| H54 | SVLANFSQPE ISCPPCPNS | CD86 + H7 | SEQ ID NO: 278 |
| H55 | RIHQMNSELS VLANS | CD86 | SEQ ID NO: 279 |
| H56 | QMNSELSVLA NS | CD86 | SEQ ID NO: 280 |
| H57 | VSERPFPPNS | CD22 | SEQ ID NO: 281 |
| H58 | KPFFTCGSAD TCPNS | CD72 | SEQ ID NO: 282 |
| H59 | KPFFTCGSAD TCPNS | CD72 | SEQ ID NO: 283 |
| H60 | QYNCPGQYTF SMPNS | CD69 | SEQ ID NO: 284 |
| H61 | EPAFTPGPNI ELQKDSDCPN S | CD94 | SEQ ID NO: 285 |
| H62 | QRHNNSSLNT RTQKARHCPN S | NKG2A | SEQ ID NO: 286 |
| H63 | NSLFNQEVQI PLTESYCPNS | NKG2D | SEQ ID NO: 287 |

As indicated herein, in certain embodiments, polypeptides of the present disclosure comprise an immunoglobulin constant region (also referred to as a constant region) in a polypeptide chain. The inclusion of an immunoglobulin constant region slows clearance of the homodimeric and heterodimeric proteins formed from two CD123-binding polypeptide chains from circulation after administration to a subject. By mutations or other alterations, an immunoglobulin constant region further enables relatively easy modulation of dimeric polypeptide effector functions (e.g., ADCC, ADCP, CDC, complement fixation, and binding to Fc receptors), which can either be increased or decreased depending on the disease being treated, as known in the art and described herein. In certain embodiments, an immunoglobulin constant region of one or both of the polypeptide chains of the polypeptide homodimers and heterodimers of the present disclosure will be capable of mediating one or more of these effector functions In other embodiments, one or more of these effector functions are reduced or absent in an immunoglobulin constant region of one or both of the polypeptide chains of the polypeptide homodimers and heterodimers of the present disclosure, as compared to a corresponding wild-type immunoglobulin constant region. For example, for dimeric CD123-binding polypeptides designed to elicit RTCC, such as, e.g., via the inclusion of a CD3-binding domain, an immunoglobulin constant region may have reduced or no effector function relative to a corresponding wild-type immunoglobulin constant region.

An immunoglobulin constant region present in polypeptides of the present disclosure can comprise or is derived from part or all of: a CH2 domain, a CH3 domain, a CH4 domain, or any combination thereof. For example, an immunoglobulin constant region can comprise a CH2 domain, a CH3 domain, both CH2 and CH3 domains, both CH3 and CH4 domains, two CH3 domains, a CH4 domain, two CH4 domains, and a CH2 domain and part of a CH3 domain.

A CH2 domain that can form an immunoglobulin constant region of a polypeptide of the present disclosure can be a wild type immunoglobulin CH2 domain or an altered immunoglobulin CH2 domain thereof from certain immunoglobulin classes or subclasses (e.g., IgG1, IgG2, IgG3, IgG4, IgA1, IgA2, or IgD) and from various species (including human, mouse, rat, and other mammals).

In certain embodiments, a CH2 domain is a wild type human immunoglobulin CH2 domain, such as wild type CH2 domains of human IgG1, IgG2, IgG3, IgG4, IgA1, IgA2, or IgD, as set forth in SEQ ID NOS: 115, 199-201 and 195-197, respectively, of US 2013/0129723 (said sequences incorporated by reference herein). In certain embodiments, the CH2 domain is a wild type human IgG1 CH2 domain as set forth in SEQ ID NO:115 of US 2013/0129723 (said sequence incorporated by reference herein).

In certain embodiments, a CH2 domain is an altered immunoglobulin CH2 region (e.g., an altered human IgG1 CH2 domain) that comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO:324 of US 2013/0129723 (said sequence incorporated by reference herein).

In certain embodiments, a CH2 domain is an altered immunoglobulin CH2 region (e.g., an altered human IgG1 CH2 domain) that comprises at least one substitution or deletion at positions 234 to 238. For example, an immunoglobulin CH2 region can comprise a substitution at position 234, 235, 236, 237 or 238, positions 234 and 235, positions 234 and 236, positions 234 and 237, positions 234 and 238, positions 234-236, positions 234, 235 and 237, positions 234, 236 and 238, positions 234, 235, 237, and 238, positions 236-238, or any other combination of two, three, four, or five amino acids at positions 234-238. In addition or alternatively, an altered CH2 region can comprise one or more (e.g., two, three, four or five) amino acid deletions at positions 234-238, for instance, at one of position 236 or position 237 while the other position is substituted. The above-noted mutation(s) decrease or eliminate the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In certain other embodiments, a CH2 domain is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. The above-noted mutation(s) decrease or eliminate the complement-dependent cytotoxicity (CDC) of a polypeptide heterodimer that comprises the altered CH2 domain.

In certain other embodiments, in addition to the amino acid substitution at position 297, an altered CH2 region (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region can comprise one or more (e.g., two, three, four or five) amino acid deletions at positions 234-238, such as at position 236 or position 237. The additional mutation(s) decreases or eliminates the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region (e.g., an altered human IgG1 CH2 domain) in a fusion protein of the present disclosure can contain one or more (e.g., 2, 3, 4, 5, or 6) additional amino acid substitutions (e.g., substituted with alanine) at one or more positions involved in complement fixation (e.g., at positions I253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions I253, H310, E318, K320, K322, and P331, such as one, two, three substitutions at positions E318, K320 and K322. The amino acids at the above-noted positions can be substituted by alanine or serine.

In certain embodiments, an immunoglobulin CH2 region polypeptide comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO:325 of US 2013/0129723, said sequence incorporated by reference herein), human IgG2 CH2 region with alanine substitutions at V234, G236, and N297 (SEQ ID NO:326 of US 2013/0129723, said sequence incorporated by reference herein), human IgG4 CH2 region with alanine substitutions at F234, L235, G237 and N297 and a deletion of G236 (SEQ ID NO:322 of US 2013/0129723, said sequence incorporated by reference herein), human IgG4 CH2 region with alanine substitutions at F234 and N297 (SEQ ID NO:343 of US 2013/0129723, said sequence incorporated by reference herein), human IgG4 CH2 region with alanine substitutions at L235 and N297 (SEQ ID NO:344 of US 2013/0129723, said sequence incorporated by reference herein), human IgG4 CH2 region with alanine substitutions at G236 and N297 (SEQ ID NO:345 of US 2013/0129723, said sequence incorporated by reference herein), and human IgG4 CH2 region with alanine substitutions at G237 and N297 (SEQ ID NO:346 of US 2013/0129723, said sequence incorporated by reference herein).

In certain embodiments, in addition to the amino acid substitutions described above, an altered CH2 region (e.g., an altered human IgG1 CH2 domain) can contain one or more additional amino acid substitutions at one or more positions other than the above-noted positions. Such amino acid substitutions can be conservative or non-conservative amino acid substitutions. For example, in certain embodiments, P233 can be changed to E233 in an altered IgG2 CH2 region (see, e.g., SEQ ID NO:326 of US 2013/0129723, said sequence incorporated by reference herein). In addition or alternatively, in certain embodiments, the altered CH2 region can contain one or more amino acid insertions, deletions, or both. The insertion(s), deletion(s) or substitution(s) can be anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 region in a polypeptide of the present disclosure comprises or is a sequence that is at least 90%, at least 91%, at least 92%, at least 93%, at least 94%, at least 95%, at least 96%, at least 97%, at least 98%, at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a CD123-binding polypeptide of the present disclosure can be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure can be derived from a CH2 region of human IgG1, IgG2 or IgG4, or mouse IgG2a (e.g., IGHG2c), whose sequences are set forth in SEQ ID NOS: 115, 199, 201, and 320 of US 2013/0129723 (said sequences incorporated by reference herein).

In certain embodiments, an altered CH2 domain is a human IgG1 CH2 domain with alanine substitutions at positions 235, 318, 320, and 322 (i.e., a human IgG1 CH2 domain with L235A, E318A, K320A and K322A substitutions) (SEQ ID NO:595 of US 2013/0129723, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions) (SEQ ID NO:596 of US 2013/0129723, said sequence incorporated by reference herein), and optionally an N297 mutation (e.g., to alanine).

In certain embodiments, an altered CH2 domain is an altered human IgG1 CH2 domain with mutations known in the art that enhance immunological activities such as ADCC, ADCP, CDC, complement fixation, Fc receptor binding, or any combination thereof.

The CH3 domain that can form an immunoglobulin constant region of a polypeptide of the present disclosure can be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain is a wild type human immunoglobulin CH3 domain, such as wild type CH3 domains of human IgG1, IgG2, IgG3, IgG4, IgA1, IgA2, IgD, IgE, or IgM as set forth in SEQ ID NOS: 116, 208-210, 204-207, and 212, respectively of US 2013/0129723 (said sequences incorporated by reference herein). In certain embodiments, the CH3 domain is a wild type human IgG1 CH3 domain as set forth in SEQ ID NO:116 of US 2013/0129723 (said sequence incorporated by reference herein). In certain embodiments, a CH3 domain is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain can be a human IgG1 CH3 domain with one or two mutations at positions H433 and N434 (positions are numbered according to EU numbering). The mutations in such positions can be involved in complement fixation. In certain other embodiments, an altered CH3 domain can be a human IgG1 CH3 domain but with one or two amino acid substitutions at position F405 or Y407. The amino acids at such positions are involved in interacting with another CH3 domain. In certain embodiments, an altered CH3 domain can be an altered human IgG1 CH3 domain with its last lysine deleted. The sequence of this altered CH3 domain is set forth in SEQ ID NO:761 of US 2013/0129723 (said sequence incorporated by reference herein).

In certain embodiments, CD123-binding polypeptides forming a polypeptide heterodimer comprise a CH3 pair that comprises so called "knobs-into-holes" mutations (see, Marvin and Zhu, Acta Pharmacologica Sinica 26:649-58, 2005; Ridgway et al., Protein Engineering 9:617-21, 1996). More specifically, mutations can be introduced into each of the two CH3 domains of each polypeptide chain so that the steric complementarity required for CH3/CH3 association obligates these two CH3 domains to pair with each other. For example, a CH3 domain in one single chain polypeptide of a polypeptide heterodimer can contain a T366W mutation (a "knob" mutation, which substitutes a small amino acid with a larger one), and a CH3 domain in the other single chain polypeptide of the polypeptide heterodimer can contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that can form an immunoglobulin constant region of CD123-binding polypeptides of the present disclosure can be a wild type immunoglobulin CH4 domain or an altered immunoglobulin CH4 domain thereof from IgE or IgM molecules. In certain embodiments, the CH4 domain is a wild type human immunoglobulin CH4 domain, such as wild type CH4 domains of human IgE and IgM molecules as set forth in SEQ ID NOS: 213 and 214, respectively, of US 2013/0129723 (said sequences incorporated by reference herein). In certain embodiments, a CH4 domain is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of CD123-binding polypeptides of the present disclosure comprises a combination of CH2, CH3 or CH4 domains (i.e., more than one constant region domain selected from CH2, CH3 and CH4). For example, the immunoglobulin constant region can comprise CH2 and CH3 domains or CH3 and CH4 domains. In certain other embodiments, the immunoglobulin constant region can comprise two CH3 domains and no CH2 or CH4 domains (i.e., only two or more CH3). The multiple constant region domains that form an immunoglobulin constant region can be based on or derived from the same immunoglobulin molecule, or the same class or subclass immunoglobulin molecules. In certain embodiments, the immunoglobulin constant region is an IgG CH2CH3 (e.g., IgG1 CH2CH3, IgG2 CH2CH3, and IgG4 CH2CH3) and can be a human (e.g., human IgG1, IgG2, and IgG4) CH2CH3. For example, in certain embodiments, the immunoglobulin constant region comprises (1) wild type human IgG1 CH2 and CH3 domains, (2) human IgG1 CH2 with N297A substitution (i.e., CH2 (N297A)) and wild type human IgG1 CH3, or (3) human IgG1 CH2 (N297A) and an altered human IgG1 CH3 with the last lysine deleted.

Alternatively, the multiple constant region domains can be based on or derived from different immunoglobulin molecules, or different classes or subclasses immunoglobulin molecules. For example, in certain embodiments, an immunoglobulin constant region comprises both human IgM CH3 domain and human IgG1 CH3 domain. The multiple constant region domains that form an immunoglobulin constant region can be directly linked together or can be linked to each other via one or more (e.g., about 2-10) amino acids.

Exemplary immunoglobulin constant regions are set forth in SEQ ID NOS: 305-309, 321, 323, 341, 342, and 762 of US 2013/0129723 (said sequences incorporated by reference herein).

In certain embodiments, the immunoglobulin constant regions of both CD123-binding polypeptides of a polypeptide dimer are identical to each other. In certain other embodiments, the immunoglobulin constant region of one polypeptide chain of a dimeric protein is different from the immunoglobulin constant region of the other polypeptide chain of the dimer. For example, one immunoglobulin constant region of a heterodimeric protein can contain a CH3 domain with a "knob" mutation, whereas the other immunoglobulin constant region of the heterodimeric protein can contain a CH3 domain with a "hole" mutation.

The disclosure relates to CD123-binding proteins and polypeptides that may comprise any of the sequences shown in Table 3. In some embodiments, CD123-binding proteins and polypeptides may comprise a signal sequence. Sequences for various cloned sequences and components are also presented in Table 3. Amino acid sequences given for polypeptide constructs do not include the human or rabbit immunoglobulin leader sequences. CDR sequences and amino acid substitution positions shown are those defined using the IMGT criteria (Brochet, X, et al, Nucl. Acids Res. (2008) 36, W503-508). Thus, the first residue in FR1 of a heavy or light chain variable domain or region is considered to be position 1.

TABLE 3

Binding Polypeptide Sequences and Components

| Name | Nucleotide Sequence | Amino Acid Sequence | SEQ ID NOs: nucleotide (amino acid) |
|---|---|---|---|
| OMT1 variable light chain domain | gacatcgtgatgacccagtctccagactccctggctgtgtctct gggcgagagggccaccatcaactgcaagtccagccacagtgttt tatacagctccaacaataagaactacttagcttggtaccagcag aaaccaggacagcctcctaagctgctcatttactgggcatctac ccgggaatccggggtccctgaccgattcagtggcagcgggtctg ggacagatttcactctcaccatcagcagcctgcaggctgaagat gtggcagtttattactgtcagcaatattatagtactcctccgac cactttcggcggagggaccaaggtggagatcaaa | divmtqspdslavslger atincksshsvlyssnnk nylawyqqkpgqppklli ywastresgvpdrfsgsg sgtdftltisslqaedva vyycqqyystppttfggg tkveik | SEQ ID NO: 1 (SEQ ID NO: 2) |
| OMT1 variable heavy chain domain | gaggtgcagctgttggagtctgggggaggcttggtacagcctgg ggggtccctgagactctcctgtgcagcctctggattcaccttta gcagctatggcatgagctgggtccgccaggctccagggaagggg ctggagggggtctcagctattagtggtagtggtggtagcacata ctacgcagactccgtgaagggccggttcaccatctccagagaca attccaagaacacgctgtatctgcaaatgaacagcctgagagcc gaggacacggccgtatattactgtgcgaaagaaaagttacgata ttttgactggttatccgatgcttttgatatctggggccaaggga caatggtcaccgtctcttca | evqllesggglvqpggsl rlscaasgftftssygms wvrqapgkglegvsaisg sggstyyadsvkgrftis rdnskntlylqmnslrae dtavyycakeklryfdwl sdafdiwgqgtmvtvss | SEQ ID NO: 3 (SEQ ID NO: 4) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| OMT1 CDR L1 | cacagtgttttatacagctccaacaataagaactac | HSVLYSSNNKNY | SEQ ID NO: 5 (SEQ ID NO: 6) |
| OMT1 CDR L2 | tgggcatct | WAS | SEQ ID NO: 7 (SEQ ID NO: 8) |
| OMT1 CDR L3 | cagcaatattatagtactcctccgaccact | QQYYSTPPTT | SEQ ID NO: 9 (SEQ ID NO: 10) |
| OMT1 CDR H1 | ggattcacctttagcagctatggc | GFTFSSYG | SEQ ID NO: 11 (SEQ ID NO: 12) |
| OMT1 CDR H2 | attagtggtagtggtggtagcaca | ISGSGGST | SEQ ID NO: 13 (SEQ ID NO: 14) |
| OMT1 CDR H3 | gcgaaagaaaagttacgatattttgactggttatccgatgcttt tgatatc | AKEKLRYFDWLSDAFDI | SEQ ID NO: 15 (SEQ ID NO: 16) |
| DB8 variable light chain domain | gacatccagatgacccagtctccatcctccctgtctgcatctgt aggagacagagtcaccatcacttgccgggcaagtcagagcatta gcagctatctgaattggtatcagcagaaaccagggaaagcccc taagctcctgatctatgctgcatccagtttgcaaagtggggtcc catcaaggttcagtggcagtggatctgggacagatttcactctc accatcagcagtctgcaacctgaagattttgcaacttactactg tcaacagagttacagtacccctctcactttcggcggaggtacca aggtggagatcaaa | diqmtqspsslsasvgdr vtitcrasqsissylnwy qqkpgkapklliyaassl qsgvpsrfsgsgsgtdft ltisslqpedfatyycqq systpltfgggtkveik | SEQ ID NO: 17 (SEQ ID NO: 18) |
| DB8 variable heavy chain domain | caggtgcagctggtgcagtctggggctgaggtgaagaagcctgg ggcctcagtgaaggtttcctgcaaggcatctggatacatcttca ccgactactatatgcactgggtgcgtcaggcccctggacaaggg cttgagtggatgggatggatgagccctaacagtggtaacacagg ctatgcacagaagttccagggccgtgtcaccatgacccgcgaca cgtccacgagcacagtctacatggagctgagcagcctgcgttct gaggacacggccgtgtattactgtgcgagagatgcggcggatta cggtgactacgttgcttttgatatctggggccaagggacaatgg tcaccgtctcttca | qvqlvqsgaevkkpgasv kvsckasgyiftdyymhw vrqapgqglewmgwmspn sgntgyaqkfqgrvtmtr dtststvymelsslrsed tavyycardaadygdyva fdiwgqgtmvtvss | SEQ ID NO: 19 (SEQ ID NO: 20) |
| DB8 CDR L1 | cagagcattagcagctat | QSISSY | SEQ ID NO: 21 (SEQ ID NO: 22) |
| DB8 CDR L2 | gctgcatcc | AAS | SEQ ID NO: 23 (SEQ ID NO: 24) |
| DB8 CDR L3 | caacagagttacagtacccctctcact | QQSYSTPLT | SEQ ID NO: 25 (SEQ ID NO: 26) |
| DB8 CDR H1 | ggatacatcttcaccgactactat | GYIFTDYY | SEQ ID NO: 27 (SEQ ID NO: 28) |
| DB8 CDR H2 | atgagccctaacagtggtaacaca | MSPNSGNT | SEQ ID NO: 29 (SEQ ID NO: 30) |
| DB8 CDR H3 | gcgagagatgcggcggattacggtgactacgttgcttttgatat c | ARDAADYGDYVAFDI | SEQ ID NO: 31 (SEQ ID NO: 32) |
| DB60 variable light chain domain | gacatccagatgacccagtctccatcctccctgtctgcatctgt aggagacagagtcaccatcacttgccgggcaagtcagagcatta gcagctatctgaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagagttacagtacccctctcactttcggcggaggtaccaa ggtggagatcaaa | diqmtqspsslsasvgdr vtitcrasqsissylnwy qqkpgkapklliyaassl qsgvpsrfsgsgsgtdft ltisslqpedfatyycqq systpltfgggtkveik | SEQ ID NO: 17 (SEQ ID NO: 18) |
| DB60 variable heavy chain domain | caggtgcagctggtgcagtctggggctgaggtgaagaagcctgg ggcctcagtgaaggtttcctgcaaggcatctggatacaccttca ccagctactatatgcactgggtgcgtcaggcccctggacaaggg cttgagtggatggggtggatcaaccctaacagtggtgacacaag ctatgcacagaagttccagggccgtgtcaccatgacccgcgaca cgtccacgagcacagtctacatggagctgagcagcctgcgttct | qvqlvqsgaevkkpgasv kvsckasgytftsyymhw vrqapgqglewmgwinpn sgdtsyaqkfqgrvtmtr dtststvymelsslrsed tavyycaqdssgsgafdi | SEQ ID NO: 33 (SEQ ID NO: 34) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | gaggacacggccgtgtattactgtgcgcaggatagtagtggttc<br>cggggcttttgatatctggggccaagggacaatggtcaccgtct<br>cttca | wgqgtmvtvss | |
| DB60 CDR L1 | cagagcattagcagctat | QSISSY | SEQ ID NO: 21<br>(SEQ ID NO: 22) |
| DB60 CDR L2 | gctgcatcc | AAS | SEQ ID NO: 23<br>(SEQ ID NO: 24) |
| DB60 CDR L3 | caacagagttacagtacccctctcact | QQSYSTPLT | SEQ ID NO: 25<br>(SEQ ID NO: 26) |
| DB60 CDR H1 | ggatacaccttcaccagctactat | GYTFTSYY | SEQ ID NO: 35<br>(SEQ ID NO: 36) |
| DB60 CDR H2 | atcaaccctaacagtggtgacaca | INPNSGDT | SEQ ID NO: 37<br>(SEQ ID NO: 38) |
| DB60 CDR H3 | gcgcaggatagtagtggttccggggcttttgatatc | AQDSSGSGAFDI | SEQ ID NO: 39<br>(SEQ ID NO: 40) |
| DB65 variable light chain domain | gacatccagatgacccagtctccatcctccctgtctgcatctgt<br>aggagacagagtcaccatcacttgccgggcaagtcagagcatta<br>gcagctatctgaattggtatcagcagaaaccagggaaagcccct<br>aagctcctgatctatgctgcatccagtttgcaaagtggggtccc<br>atcaaggttcagtggcagtggatctgggacagatttcactctca<br>ccatcagcagtctgcaqacctgaagattttgcaacttactactg<br>tcaacagagttacagtacccctctcactttcggcggaggtacca<br>aggtggagatcaaa | diqmtqspsslsasvgdr<br>vtitcrasqsissylnwy<br>qqkpgkapklliyaassl<br>qsgvpsrfsgsgsgtdft<br>ltisslqpedfatyycqq<br>systpltfgggtkveik | SEQ ID NO: 17<br>(SEQ ID NO: 18) |
| DB65 variable heavy chain domain | caggtgcagctggtgcagtctggggctgaggtgaagaagcctgg<br>ggcctcagtgaaggtttcctgcaaggcatctggatacaccttca<br>ccggctactatatgcactgggtgcgtcaggcccctggacaaggg<br>cttgagtggatgggatggatgaaccctaacagtggtaacacagg<br>ctatgcacagaagttccagggccgtgtcaccatgacccgcgaca<br>cgtccacgagcacagtctacatggagctgagcagcctgcgttct<br>gaggacacggccgtgtattactgtgcgaaagaggaaccgatttt<br>tggagtggttatggatgcttttgatatctggggccaagggacaa<br>tggtcaccgtctcctca | qvqlvqsgaevkkpgasv<br>kvsckasgytftgyymhw<br>vrqapgqglewmgwmnpn<br>sgntgyaqkfqgrvtmtr<br>dtststvymelsslrsed<br>tavyycakeepifgvvmd<br>afdiwgqgtmvtvss | SEQ ID NO: 41<br>(SEQ ID NO: 42) |
| DB65 CDR L1 | cagagcattagcagctat | QSISSY | (SEQ ID NO: 21)<br>(SEQ ID NO: 22) |
| DB65 CDR L2 | gctgcatcc | AAS | SEQ ID NO: 23<br>(SEQ ID NO: 24) |
| DB65 CDR L3 | caacagagttacagtacccctctcact | QQSYSTPLT | SEQ ID NO: 25<br>(SEQ ID NO: 26) |
| DB65 CDR H1 | ggatacaccttcaccggctactat | GYTFTGYY | SEQ ID NO: 43<br>(SEQ ID NO: 44) |
| DB65 CDR H2 | atgaaccctaacagtggtaacaca | MNPNSGNT | SEQ ID NO: 45<br>(SEQ ID NO: 46 |
| DB65 CDR H3 | gcgaaagaggaaccgatttttggagtggttatggatgcttttga<br>tatc | AKEEPIFGVVMDAFDI | SEQ ID NO: 47<br>(SEQ ID NO: 48) |
| DB82 variable light chain domain | gacatccagatgacccagtctccatcctccctgtctgcatctgt<br>aggagaccgcgtcaccatcacttgccgggcaagtcagaccataa<br>acaactatttgaactggtatcagcagaaaccagggaaagcccct<br>aagctcctgatctattctgcatctactttgcaaagtggggtccc<br>catcacgtttcagtggcagtggatctgggacagatttcactctc<br>accatcagcagtctgcaacctgaagattttgcaacttactactg<br>tcaccagagttacacttcacctctcactttcggcggaggtacca<br>aggtggagatcaaa | diqmtqspsslsasvgdr<br>vtitcrasqtinnylnwy<br>qqkpgkapklliysastl<br>qsgvpsrfsgsgsgtdft<br>ltisslqpedfatyychq<br>sytspltfgggtkveik | SEQ ID NO: 49<br>(SEQ ID NO: 50) |
| DB82 variable heavy chain domain | gaggtgcagctggtggagtctgggggaggcttggtacagcctgg<br>ggggtccctgcgcctctcctgtgcagcctctggattcaccttta<br>gcagctatgccatgagctgggtccgccaggctccagggaagggg<br>ctggagtgggtctcagttattagtgccaatagtgctggtctagg<br>ccatgcggactctgtgaagggccggttcaccatctcccgcgaca<br>attccaagaacacgctgtatctgcaaatgaacagcctgcgcgcc | evqlvesggglvqpggsl<br>rlscaasgftfssyamsw<br>vrqapgkglewvsvisan<br>saglghadsvkgrftisr<br>dnskntlylqmnslraed<br>tavyycarvgysssadaf | SEQ ID NO: 51<br>(SEQ ID NO: 52) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | gaggacacggccgtatattactgtgcgagagtgggctatagcag<br>ctcggctgatgcttttgatatctggggccaagggacaatggtca<br>ccgtctcctcg | diwgqgtmvtvss | |
| DB82<br>CDR L1 | cagaccataaacaactat | QTINNY | SEQ ID NO: 53<br>(SEQ ID NO: 54) |
| DB82<br>CDR L2 | tctgcatct | SAS | SEQ ID NO: 55<br>(SEQ ID NO: 56) |
| DB82<br>CDR L3 | caccagagttacacttcacctctcact | HQSYTSPLT | SEQ ID NO: 57<br>(SEQ ID NO: 58) |
| DB82<br>CDR H1 | ggattcacctttagcagctatgcc | GFTFSSYA | SEQ ID NO: 59<br>(SEQ ID NO: 60) |
| DB82<br>CDR H2 | attagtgccaatagtgctggtcta | ISANSAGL | SEQ ID NO: 61<br>(SEQ ID NO: 62) |
| DB82<br>CDR H3 | gcgagagtgggctatagcagctcggctgatgcttttgatatc | ARVGYSSSADAFDI | SEQ ID NO: 63<br>(SEQ ID NO: 64) |
| DB83<br>variable<br>light chain<br>domain | gatgttgtgatgactcagtctccactctccctgcccgtcacccc<br>tggagagccggcctccatctcctgcaggtctagtcagagcctcc<br>tgcatagtaatggagacaactatttggattggtacctgcagaag<br>ccagggcagtctccacagctcctgatctatttgggttctaatcg<br>ggcctccggggtccctgaccgtttcagtggcagtggatcaggca<br>cagattttacactgaaaatcagccgtgtggaggctgaggatgtt<br>ggggtttattactgcatgcaagctacacactggccactcacttt<br>cggccctggtaccaaagtggatatcaaa | dvvmtqsplslpvtpgep<br>asiscrssqsllhsngdn<br>yldwylqkpgqspqlliy<br>lgsnrasgvpdrfsgsgs<br>gtdftlkisrveaedvgv<br>yydmqathwpltfgpgtk<br>vdik | SEQ ID NO: 65<br>(SEQ ID NO: 66) |
| DB83<br>variable<br>heavy chain<br>domain | caggtgcagctggtgcagtctggggctgaggtgaagaagcctgg<br>ggcctcagtgaaggtttcctgcaaggcatctggatacaccctt<br>cactagctatgctatgcattgggtgcgtcaggcccctggacaag<br>ggcttgagtggatgggacttgttgatcctgaagatggtgaaaca<br>atatatgcagagaagttccagggccgtgtcaccatgacccgcga<br>cacgtccacgagcacagtctacatggagctgagcagcctgcgtt<br>ctgaggacacggccgtgtattactgtgcgagacgaacgtattac<br>tatgatagtagtggttcccgttatgcttttgatatctggggcca<br>agggaccacggtcaccgtctcttca | qvqlvqsgaevkkpgasv<br>kvsckasgytftsyamhw<br>vrqapgqglewmglvdpe<br>dgetiyaekfqgrvtmtr<br>dtststvymelsslrsed<br>tavyycarrtyyydssgs<br>ryafdiwgqgttvtvss | SEQ ID NO: 67<br>(SEQ ID NO: 68) |
| DB83<br>CDR L1 | cagagcctcctgcatagtaatggagacaactat | QSLLHSNGDNY | SEQ ID NO: 69<br>(SEQ ID NO: 70) |
| DB83<br>CDR L2 | ttggggttct | LGS | SEQ ID NO: 71<br>(SEQ ID NO: 72) |
| DB83<br>CDR L3 | atgcaagctacacactggccactcact | MQATHWPLT | SEQ ID NO: 73<br>(SEQ ID NO: 74) |
| DB83<br>CDR H1 | ggatacaccttcactagctatgct | QYTFTSYA | SEQ ID NO: 75<br>(SEQ ID NO: 76) |
| DB83<br>CDR H2 | gttgatcctgaagatggtgaaaca | VDPEDGET | SEQ ID NO: 77<br>(SEQ ID NO: 78) |
| LB83<br>CDR H3 | gcgagacgaacgtattactatgatagtagtggttcccgttatgc<br>ttttgatatc | ARRTYYYDSSGSRYAFDI | SEQ ID NO: 79<br>(SEQ ID NO: 80) |
| DB86<br>variable<br>light chain<br>domain | gacatccagatgacccagtctccatcctccctgtctgcatctgt<br>aggagaccgcgtcaccatcacttgccgggcaagtcagggcatca<br>gaaatgatttaggttggtatcagcagaaaccagggaaagcccct<br>aagctcctgatctatgctgcatccactttgcaatcaggggtccc<br>atcacgtttcagtggcagtggatctgggacagatttcactctca<br>ccatcagcagtctgcaacctgaagattttgcaacttactactgt<br>caacagagttacggtgcccccctcactttcggcggaggtaccaa<br>ggtggagatcaaa | diqmtqspsslsasvgdr<br>vtitcrasqgirndlgwy<br>qqkpgkapklliyaastl<br>qsgvpsrfsgsgsgtdft<br>ltisslqpedfatyycqq<br>sygapltfgggtkveik | SEQ ID NO: 81<br>(SEQ ID NO: 82) |
| DB86<br>variable<br>heavy chain<br>domain | caggtgcagctggtgcagtctggggctgaggtgaagaagcctgg<br>ggcctcagtgaaggtttcctgcaaggcatctggatatatgttca<br>gtggccattctgcacactgggtgcgtcaggcccctggacaaggg<br>cttgagtggatgggatggatgaaccctaacagtggtaacacagg<br>ctatgcacagaagttccagggccgtgtcaccatgacccgcgaca<br>cgtccacgagcacagtctacatggagctgagcagcctgcgttct | qvqlvqsgaevkkpgasv<br>kvsckasgymfsghsahw<br>vrqapgqglewmgwmnpn<br>sgntgyaqkfqgrvtmtr<br>dtststvymelsslrsed<br>tavyycardssgwydvfd | SEQ ID NO: 83<br>(SEQ ID NO: 84) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | gaggacacggccgtgtattactgtgcgagagatagcagtggctg gtacgatgtctttgactactggggccaggggaccctggtcaccg tctcctca | ywgqgtlvtvss | |
| DB86 CDR L1 | cagggcatcagaaatgat | QGIRND | SEQ ID NO: 85 (SEQ ID NO: 86) |
| DB86 CDR L2 | gctgcatcc caacagagttacggtgcccccctc | AAS | SEQ ID NO: 87 (SEQ ID NO: 88) |
| DB86 CDR L3 | | QQSYGAPLT | SEQ ID NO: 89 (SEQ ID NO: 90) |
| DB86 CDR H1 | ggatatatgttcagtggccattct | GYMFSGHS | SEQ ID NO: 91 (SEQ ID NO: 92) |
| DB86 CDR H2 | atgaaccctaacagtggtaacaca | MNPNSGNT | SEQ ID NO: 93 (SEQ ID NO: 94) |
| LB86 CDR H3 | gcgagagatagcagtggctggtacgatgtctttgactac | ARDSSGWYDVFDY | SEQ ID NO: 95 (SEQ ID NO: 96) |
| DB280 variable light chain domain | gacatccagatgacccagtctccatcctccctgtctgcatctgt aggagacagagtcaccatcacttgccgggcaagtcagagcatta gcagctatctgaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagagttacagtacccctctcactttcggcggaggtaccaa ggtggagatcaaa | diqmtqspsslsasvgdr vtitcrasqsissylnwy qqkpgkapklliyaassl qsgvpsrfsgsgsgtdft ltisslqpedfatyycqq systpltfgggtkveik | SEQ ID NO: 17 (SEQ ID NO: 18) |
| DB280 variable heavy chain domain | caggtgcagctggtgcagtctggggctgaggtgaagaagcctgg ggcctcagtgaaggtttcctgcaaggcatctggatacagcctca acttatactatatgcactgggtgcgtcaggcccctggacaaggg cttgagtggatgggatggatgaaccctaacagtggtaacacagg ctatgcacagaagttccagggccgtgtcaccatgacccgcgaca cgtccacgagcacagtctacatggagctgagcagcctgcgttct gaggacacggccgtgtattactgtgcgagcctcgattgtagtgg tggtagctgctactccgaatatgatgcttttgatatctggggcc aagggaccacggtcaccgtctcctca | qvqlvqsgaevkkpgasv kvsckasgyslnlyymhw vrqapgqglewmgwmnpn sgntgyaqkfqgrvtmtr dtststvymelsslrsed tavyycasldcsggscys eydafdiwgqgttvtvss | SEQ ID NO: 97 (SEQ ID NO: 98) |
| DB280 CDR L1 | cagagcattagcagctat | QSISSY | SEQ ID NO: 21 (SEQ ID NO: 22) |
| DB280 CDR L2 | gctgcatcc | AAS | SEQ ID NO: 23 (SEQ ID NO: 24) |
| DB280 CDR L3 | caacagagttacagtacccctctcact | QQSYSTPLT | SEQ ID NO: 25 (SEQ ID NO: 26) |
| DB280 CDR H1 | ggatacagcctcaacttatactat | GYSLNLYY | SEQ ID NO: 99 (SEQ ID NO: 100) |
| DB280 CDR H2 | atgaaccctaacagtggtaacaca | MNPNSGNT | SEQ ID NO: 101 (SEQ ID NO: 102) |
| LB280 CDR H3 | gcgagcctcgattgtagtggtggtagctgctactccgaatatga tgcttttgatatc | ASLDCSGGSCYEYDAFDI | SEQ ID NO: 103 (SEQ ID NO: 104) |
| DB331 variable light chain domain | gacatccagatgacccagtctccatcctccctgtctgcatctgt aggagacagagtcaccatcacttgccgggcaagtcagagcatta gcagctatctgaattggtatcagcagaaaccagggaaagcccct aagctcctgatctatgctgcatccagtttgcaaagtggggtccc atcaaggttcagtggcagtggatctgggacagatttcactctca ccatcagcagtctgcaacctgaagattttgcaacttactactgt caacagagttacagtacccctctcactttcggcggaggtaccaa ggtggagatcaaa | diqmtqspsslsasvgdr vtitcrasqsissylnwy qqkpgkapklliyaassl qsgvpsrfsgsgsgtdft ltisslqpedfatyycqq systpltfgggtkveik | SEQ ID NO: 17 (SEQ ID NO: 18) |
| DB331 variable heavy chain domain | caggtgcagctggtgcagtctggggctgaggtgaagaagcctgg ggcctcagtgaaggtttcctgcaaggcatctggatacaccttca ccagctactatatgcactgggtgcgtcaggcccctggacaaggg cttgagtggatgggatggatgaaccctaacagtggtaacacagg ctatgcacagaagttccagggccgtgtcaccatgacccgcgaca cgtccacgagcacagtctacatggagctgagcagcctgcgttct | qvqlvqsgaevkkpgasv kvsckasgytftsyymhw vrqapgqglewmgwmnpn sgntgyaqkfqgrvtmtr dtststvymelsslrsed tavyycatdlagealfdp | SEQ ID NO: 105 (SEQ ID NO: 106) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | gaggacacggccgtgtattactgtgcaacagatctcgcgggga<br>agccttgttcgacccctggggccagggcaccctggtcaccgtct<br>cctca | wgqgtlvtvss | |
| DB3331<br>CDR L1 | cagagcattagcagctat | QSISSY | SEQ ID NO: 21<br>(SEQ ID NO: 22) |
| DB3331<br>CDR L2 | gctgcatcc | AAS | SEQ ID NO: 23<br>(SEQ ID NO: 24) |
| DB331<br>CDR L3 | caacagagttacagtacccctctcact | QQSYSTPLT | SEQ ID NO: 25<br>(SEQ ID NO: 26) |
| DB331<br>CDR H1 | ggatacaccttcaccagctactat | GYTFTSYY | SEQ ID NO: 107<br>(SEQ ID NO: 108) |
| DB331<br>CDR H2 | atgaaccctaacagtggtaacaca | MNPNSGNT | SEQ ID NO: 109<br>(SEQ ID NO: 110) |
| DB331<br>CDR H3 | gcaacagatctcgcgggggaagccttgttcgacccc | ATDLAGEALFDP | SEQ ID NO: 111<br>(SEQ ID NO: 112) |
| DB415<br>variable<br>light chain<br>domain | gacatccagatgacccagtctccatcctccctgtctgcatctgt<br>aggagacagagtcaccatcacttgccgggcaagtcagagcatta<br>gcagctatctgaattggtatcagcagaaaccagggaaagcccct<br>aagctcctgatctatgctgcatccagtttgcaaagtggggtccc<br>atcaaggttcagtggcagtggatctgggacagatttcactctca<br>ccatcagcagtctgcaacctgaagattttgcaacttactactgt<br>caacagagttacagtacccctctcactttcggcggaggtaccaa<br>ggtggagatcaaa | diqmtqspsslsasvgdr<br>vtitcrasqsissylnwy<br>qqkpgkapklliyaassl<br>qsgvpsrfsgsgsgtdft<br>ltisslqpedfatyycqq<br>systpltfgggtkveik | SEQ ID NO: 17<br>(SEQ ID NO: 18) |
| DB415<br>variable<br>heavy chain<br>domain | gaggtgcagctggtggagtctgggggaggcttggtacagcctgg<br>ggggtccctgcgcctctcctgtgcagcctctggaatcaccttca<br>gtagttatggcatgcattgggtccgccaggctccagggaagggg<br>ctggagtgggtctcaggtattagttggaatagtggtaacagagt<br>ctatgtggactctgtgaagggccggttcaccatctcccgcgaca<br>attccaagaacacgctgtatctgcaaatgaacagcctgcgcgcc<br>gaggacacggccgtatattactgtgcgagagatactaatgatgc<br>ttttgatatctggggccaagggaccacggtcaccgtctcctca | evqlvesggglvqpggsl<br>rlscaasgitfssygmhw<br>vrqapgkglewvsgiswn<br>sgnrvyvdsvkgrftisr<br>dnskntlylqmnslraed<br>tavyycardtndafdiwg<br>qgttvtvss | SEQ ID NO: 113<br>(SEQ ID NO: 114) |
| DB415<br>CDR L1 | cagagcattagcagctat | QSISSY | SEQ ID NO: 21<br>(SEQ ID NO: 22) |
| DB415<br>CDR L2 | gctgcatcc | AAS | SEQ ID NO: 23<br>(SEQ ID NO: 24) |
| DB415<br>CDR L3 | caacagagttacagtacccctctcact | QQSYSTPLT | SEQ ID NO: 25<br>(SEQ ID NO: 26) |
| DB415<br>CDR H1 | ggaatcaccttcagtagttatggc | GITFSSYG | SEQ ID NO: 115<br>(SEQ ID NO: 116) |
| DB415<br>CDR H2 | attagttggaatagtggtaacaga | ISWNSGNR | SEQ ID NO: 117<br>(SEQ ID NO: 118) |
| DB415<br>CDR H3 | gcgagagatactaatgatgcttttgatatc | ARDTNDAFDI | SEQ ID NO: 119<br>(SEQ ID NO: 120) |
| DB435<br>variable<br>light chain<br>domain | gacatccagatgacccagtctccatcctccctgtctgcatctgt<br>aggagacagagtcaccatcacttgccgggcaagtcagagcatta<br>gcagctatctgaattggtatcagcagaaaccagggaaagcccct<br>aagctcctgatctatgctgcatccagtttgcaaagtggggtccc<br>atcaaggttcagtggcagtggatctgggacagatttcactctca<br>ccatcagcagtctgcaacctgaagattttgcaacttactactgt<br>caacagagttacagtacccctctcactttcggcggaggtaccaa<br>ggtggagatcaaa | diqmtqspsslsasvgdr<br>vtitcrasqsissylnwy<br>qqkpgkapklliyaassl<br>qsgvpsrfsgsgsgtdft<br>ltisslqpedfatyycqq<br>systpltfgggtkveik | SEQ ID NO: 17<br>(SEQ ID NO: 18) |
| DB435<br>variable<br>heavy chain<br>domain | caggtgcagctggtgcagtctggggctgaggtgaagaagcctgg<br>ggcctcagtgaaggtttcctgcaaggcatctggaggcaccttca<br>gcagctatgctatcagctgggtgcgtcaggcccctggacaaggg<br>cttgagtggatgggctggatcacccctcacaatggtaacataaa<br>gtatgcacgggagttccagggccgtgtcaccatgacccgcgaca | qvqlvqsgaevkkpgasv<br>kvsckasggtfssyaisw<br>vrqapgqglewmgwitph<br>ngnikyarefqgrvtmtr<br>dtststvymelsslrsed | SEQ ID NO: 121<br>(SEQ ID NO: 122) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | cgtccacgagcacagtctacatggagctgagcagcctgcgttct gaggacacggccgtgtattactgtgcgaaagatctgaactggaa cgcagcctttgactactggggccaggggaccctggtcaccgtct cctca | tavyycakdlnwnaafdy wgqgtlvtvss | |
| DB435 CDR L1 | cagagcattagcagctat | QSISSY | SEQ ID NO: 21 (SEQ ID NO: 22) |
| DB435 CDR L2 | gctgcatcc | AAS | SEQ ID NO: 233 (SEQ ID NO: 24) |
| DB435 CDR L3 | caacagagttacagtacccctctcact | QQSYSTPLT | SEQ ID NO: 25 (SEQ ID NO: 26) |
| DB435 CDR H1 | ggaggcaccttcagcagctatgct | GGTFSSYA | SEQ ID NO: 123 (SEQ ID NO: 124) |
| DB435 CDR H2 | atcacccctcacaatggtaacata | ITPHNGNI | SEQ ID NO: 125 (SEQ ID NO: 126) |
| DB435 CDR H3 | gcgaaagatctgaactggaacgcagcctttgactac | AKDLNWNAAFDY | SEQ ID NO: 127 (SEQ ID NO: 128) |
| OMT1 VHVL x TSC456 scFv-Fc-scFv TRI129 | atggaagcaccagcgcagcttctcttcctcctgctactctggct cccagataccaccggtgaggtgcagctgttggagtctgggggag gcttggtacagcctggggggtccctgagactctcctgtgcagcc tctggattcacctttagcagctatggcatgagctgggtccgcca ggctccagggaaggggctggagggggtctcagctattagtggta gtggtggtagcacatactacgcagactccgtgaagggccggttc accatctccagagacaattccaagaacacgctgtatctgcaaat gaacagcctgagagccgaggacacggccgtatattactgtgcga aagaaaagttacgatattttgactggttatccgatgcttttgat atctggggccaagggacaatggtcaccgtctcttcaggtggagg cggttcaggcggaggtggatccggcggtggcggctccggtggcg gcggatctgacatcgtgatgacccagtctccagactccctggct gtgtctctgggcgagagggccaccatcaactgcaagtccagcca cagtgttttatacagctccaacaataagaactacttagcttggt accagcagaaaccaggacagcctcctaagctgctcatttactgg gcatctacccgggaatccggggtccctgaccgattcagtggcag cgggtctgggacagatttcactctcaccatcagcagcctgcagg ctgaagatgtggcagtttattactgtcagcaatattatagtact cctccgaccactttcggcggagggaccaaggtggagatcaaatc ctcgagtgagcccaaatcttctgacaaaactcacacatgcccac cgtgcccagcacctgaagccgcgggtgcaccgtcagtcttcctc ttccccccaaaacccaaggacaccctcatgatctcccggacccc tgaggtcacatgcgtggtggtggacgtgagccacgaagaccctg aggtcaagttcaactggtacgtggacggcgtggaggtgcataat gccaagacaaagccgcgggaggagcagtacaacagcacgtaccg tgtggtcagcgtcctcaccgtcctgcaccaggactggctgaatg gcaaggaatacaagtgcgcggtctccaacaaagccctcccagcc cccatcgagaaaaccatctccaaagccaaagggcagccccgaga accacaggtgtacaccctgcccccatcccgggatgagctgacca agaaccaggtcagcctgacctgcctggtcaaaggcttctatcca agcgacatcgccgtggagtgggagagcaatgggcagccggagaa caactacaagaccacgcctcccgtgctggactccgacggctcct tcttcctctacagcaagctcaccgtggacaagagcaggtggcag caggggaacgtcttctcatgctccgtgatgcatgaggctctgca caaccactacacgcagaagagcctctccctgtctccgggttccg gaggagggggttcaggtgggggaggttctggcggcgggggaagc ccttcacaggtgcaactggtgcagagtggacccgaggttaaaaa accagggtcctccgttaaggttagctgcaaagcctctggctaca cattttccaggagtacaatgcactgggtgaggcaggctcctgga cagggactcgagtggatcgggtatatcaacccatctagcgccta taccaattacaaccaaaagtttaaggaccgagttaccattaccg ctgacaaatccaccagtacagcttatatggagctgtcatctctt aggtccgaggacactgctgtttattactgcgctcgtcctcaggt tcactatgactataatggttttccctactggggtcagggaaccc tggtgactgtctcttctggcggtggaggcagcggtgggggtggg tctggaggcggtggcagtggcggcggaggctctgatattcagat gactcagtctcctagcactctcagcgccagcgtgggggatcgtg tgacaatgacttgctccgctagcagtagtgtgtcttacatgaat tggtatcagcagaagcccgggaaagcacctaagcgctggatcta tgactcttccaagctggcaagtggtgtcccctcacggttctctg gctcaggttctggtactgactatactttgactatctcctccctc | evqllesggglvqpggsl rlscaasgftfssygmsw vrqapgkglegvsiasgs ggstyyadsvkgrftisr dnskntlylqmnslraed tavyycakeklryfdwls dafdiwgqgtmvtvssgg ggsggggsggggsggggs divmtqspdslavslger atincksshsvlyssnnk nylawyqqkpgqppklli ywastresgvpdrfsgsg sgtdftltisslqaedva vyycqqyystppttfggg tkveiksssepkssdkth tcppcpapeaagapsvfl fppkpkdtlmisrtpevt cvvvdvshedpevkfnwy vdgvevhnaktkpreeqy nstyrvvsvltvlhqdwl ngkeykcavsnkalpapi ektiskakgqprepqvyt lppsrdeltknqvsltcl vkgfypsdiavewesngq pennykttppvldsdgsf flyskltvdksrwqqgnv fscsvmhealhnhytqks lslspgsggggsggggsg gggspsqvqlvqsgpevk kpgssvkvsckasgytfs rstmhwvrqapgqglewi gyinpssaytnynqkfkd rvtitadkststaymels slrsedtavyycarpqvh ydyngfpywgqgtlvtvs sggggsggggsggggsgg ggsdiqmtqspstlsasv gdrvtmtcsasssvysmn wyqqkpgkapkrwiydss klasgvpsrfsgsgsgtd ytltisslqpddfatyyc qqwsrnpptfgggtkvei krs | SEQ ID NO: 129 (SEQ ID NO: 130) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | cagcccgatgatttcgctacctattattgtcagcagtggagccg<br>taacccacccactttcggaggcggtaccaaagtggagatcaaga<br>ggtcataa | | |
| OMT1<br>VLVH x<br>TSC456<br>scFv-Fc-<br>scFv<br>TRI130 | atggaagcaccagcgcagcttctcttcctcctgctactctggct<br>cccagataccaccggtgacatcgtgatgacccagtctccagact<br>ccctggctgtgtctctgggcgagagggccaccatcaactgcaag<br>tccagccacagtgttttatacagctccaacaataagaactactt<br>agcttggtaccagcagaaaccaggacagcctcctaagctgctca<br>tttactgggcatctacccgggaatccggggtccctgaccgattc<br>agtggcagcgggtctgggacagatttcactctcaccatcagcag<br>cctgcaggctgaagatgtggcagtttattactgtcagcaatatt<br>atagtactcctccgaccactttcggcggagggaccaaggtggag<br>atcaaaggtggaggcggttcaggcggaggtggatccggcggtgg<br>cggctccggtggcggcggatctgaggtgcagctgttggagtctg<br>gggggaggcttggtacagcctggggggtccctgagactctcctgt<br>gcagcctctggattcacctttagcagctatggcatgagctgggt<br>ccgccaggctccagggaaggggctggaggggtctcagctatta<br>gtggtagtggtggtagcacatactacgcagactccgtgaagggc<br>cggttcaccatctccagagacaattccaagaacacgctgtatct<br>gcaaatgaacagcctgagagccgaggacacggccgtatattact<br>gtgcgaaagaaaagttacgatattttgactggttatccgatgct<br>tttgatatctggggccaagggacaatggtcaccgtctcctcgag<br>tgagcccaaatcttctgacaaaactcacacatgcccaccgtgcc<br>cagcacctgaagccgcgggtgcaccgtcagtcttcctcttcccc<br>ccaaaacccaaggacaccctcatgatctcccggacccctgaggt<br>cacatgcgtggtggtggacgtgagccacgaagaccctgaggtca<br>agttcaactggtacgtggacggcgtggaggtgcataatgccaag<br>acaaagccgcgggaggagcagtacaacagcacgtaccgtgtggt<br>cagcgtcctcaccgtcctgcaccaggactggctgaatggcaagg<br>aatacaagtgcgcggtctccaacaaagccctcccagcccccatc<br>gagaaaaccatctccaaagccaaagggcagccccgagaaccaca<br>ggtgtacaccctgcccccatcccgggatgagctgaccaagaacc<br>aggtcagcctgacctgcctggtcaaaggcttctatccaagcgac<br>atcgccgtggagtgggagagcaatgggcagccggagaacaacta<br>caagaccacgcctcccgtgctggactccgacggctccttcttcc<br>tctacagcaagctcaccgtggacaagagcaggtggcagcagggg<br>aacgtcttctcatgctccgtgatgcatgaggctctgcacaacca<br>ctacacgcagaagagcctctccctgtctccgggttccggaggag<br>gggttcaggtgggggaggttctggcggcgggggaagcccttca<br>caggtgcaactggtgcagagtggacccgaggttaaaaaaccagg<br>gtcctccgttaaggttagctgcaaagcctctggctacacatttt<br>ccaggagtacaatgcactgggtgaggcaggctcctggacaggga<br>ctcgagtggatcgggtatatcaacccatctagcgcctataccaa<br>ttacaaccaaaagtttaaggaccgagttaccattaccgctgaca<br>aatccaccagtacagcttatatggagctgtcatctcttaggtcc<br>gaggacactgctgtttattactgcgctcgtcctcaggttcacta<br>tgactataatggttttccctactggggtcagggaaccctggtga<br>ctgtctcttctggcggtggaggcagcggtgggggtgggtctgga<br>ggcggtggcagtggcggcggaggctctgatattcagatgactca<br>gtctcctagcactctcagcgccagcgtgggggatcgtgtgacaa<br>tgacttgctccgctagcagtagtgtgtcttacatgaattgtatc<br>agcagaagcccgggaaagcacctaagcgctggatctatgactct<br>tccaagctggcaagtggtgtcccctcacggttctctggctcagg<br>ttctggtactgactatactttgactatctcctccctccagcccg<br>atgatttcgctacctattattgtcagcagtggagccgtaaccca<br>cccactttcggaggcggtaccaaagtggagatcaagaggtcata<br>a | divmtqspdslavslger<br>atincksshsvlyssnnk<br>nylawyqqkpgqppklli<br>ywastresgvpdrfsgsg<br>sgtdftltisslqaedva<br>vyycqqyystpptfggg<br>tkveikggggsggggsgg<br>ggsggggsevqllesggg<br>lvqpggslrlscaasgft<br>fssygmswvrqapgkgle<br>gvsaisgsggstyyadsv<br>kgrftisrdnskntlylq<br>mnslraedtavyycakek<br>lryfdwlsdafdiwgqgt<br>mvtvsssepkssdkthtc<br>ppcpapeaagagsvflfp<br>pkpkdtlmisrtpevtcv<br>vvdvshedpevkfnwyvd<br>gvevhnaktkpreeqyns<br>tyrvvsvltvlhqdwlng<br>keykavsnkalpapiekt<br>iskakgqprepqvytlpp<br>srdeltknqvsltclvkg<br>fypsdiavewesngqpen<br>nykttppvldsdgsffly<br>skltvdksrwqqgnvfsc<br>svmhealhnhytqkslsl<br>spgsggggsggggsgggg<br>spsqvqlvqsgpevkkpg<br>ssvkvsckasgytfsrst<br>mhwvrqapgqglewigyi<br>npssaytnynqkfkdrvt<br>itadkststaymelsslr<br>sedtavyycarpqvhydy<br>ngfpywgqgtlvtvssgg<br>ggsggggsggggsggggs<br>diqmtqspstlsasvgdr<br>vtmtcsasssvsymnwyq<br>qkpgkapkrwiydsskla<br>sgvpsrfsgsgsgtdytl<br>tisslqpddfatyycqqw<br>srnpptfgggtkveikrs | SEQ ID NO: 131<br>(SEQ ID NO: 132) |
| DB8 VHVL x<br>TSC456<br>scFv-Fc-<br>scFv<br>TRI123 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatacatcttcaccgactactatatgcactgggtgcgtca<br>ggcccctggacaagggcttgagtggatgggatggatgagcccta<br>acagtggtaacacaggctatgcacagaagttccagggccgtgtc<br>accatgacccgcgacacgtccacgagcacagtctacatggagct<br>gagcagcctgcgttctgaggacacggccgtgtattactgtgcga<br>gagatgcggcggattacggtgactacgttgcttttgatatctgg<br>ggccaagggacaatggtcaccgtctcttcaggcggcggcggcag<br>cggcggcggcggcagcggcggcggaggctccggcggcggcggca<br>gcgacatccagatgacccagtctccatcctccctgtctgcatct<br>gtaggagacagagtcaccatcacttgccgggcaagtcagagcat<br>tagcagctatctgaattggtatcagcagaaaccagggaaagccc<br>ctaagctcctgatctatgctgcatccagtttgcaaagtggggtc | qvqlvqsgaevkkpgasv<br>kvsckasgyiftdyymhw<br>vrqapgqglewmgwmspn<br>sgntgyaqkfqgrvtmtr<br>dtststvymelsslrsed<br>tavyycardaadygdyva<br>fdiwgqgtmvtvssgggg<br>sggggsggggsggggsdi<br>qmtqspsslsasvgdrvt<br>itcrasqsissylnwyqq<br>kpgkapklliyaasslqs<br>gvpsrfsgsgsgtdftlt<br>isslqpedfatyycqqsy<br>stpltfgggtkveiksss<br>epkssdkthtcppcpape | SEQ ID NO: 133<br>(SEQ ID NO: 134) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| | ccatcaaggttcagtggcagtggatctgggacagatttcactct | aagapsvflfppkpkdtl | |
| | caccatcagcagtctgcaacctgaagattttgcaacttactact | misrptevtcvvvdvshe | |
| | gtcaacagagttacagtacccctctcactttcggcggaggtacc | dpevkfnwyvdgvevhna | |
| | aaggtggagatcaaatcctcgagtgagcccaaatcttctgacaa | ktkpreeqynstyrvvsv | |
| | aactcacacatgcccaccgtgcccagcacctgaagccgcgggtg | ltvlhqdwlngkeykcav | |
| | caccgtcagtcttcctcttccccccaaaacccaaggacaccctc | snkalpapiektiskakg | |
| | atgatctcccggacccctgaggtcacatgcgtggtggtggacgt | qprepqvytlppsrdelt | |
| | gagccacgaagaccctgaggtcaagttcaactggtacgtggacg | knqvsltclvkgfypsdi | |
| | gcgtggaggtgcataatgccaagacaaagccgcgggaggagcag | avewesngqpennykttp | |
| | tacaacagcacgtaccgtgtggtcagcgtcctcaccgtcctgca | pvldsdgsfflyskltvd | |
| | ccaggactggctgaatggcaaggaatacaagtgcgcggtctcca | ksrwqqgnvfscscmhea | |
| | acaaagccctcccagcccccatcgagaaaaccatctccaaagcc | lhnhytqkslslspgsgg | |
| | aaagggcagccccgagaaccacaggtgtacaccctgcccccatc | ggsggggsggggsgsqvq | |
| | ccgggatgagctgaccaagaaccaggtcagcctgacctgcctgg | lvqsgpevkkpgssvkvs | |
| | tcaaaggcttctatccaagcgacatcgccgtggagtgggagagc | ckasgytfsrstmhwvrq | |
| | aatgggcagccggagaacaactacaagaccacgcctcccgtgct | apgqglewigyinpssay | |
| | ggactccgacggctccttcttcctctacagcaagctcaccgtgg | tnynqkfkdrvtitadks | |
| | acaagagcaggtggcagcaggggaacgtcttctcatgctccgtg | tstaymelsslrsedtav | |
| | atgcatgaggctctgcacaaccactacacgcagaagagcctctc | yycarpqvhydyngfpyw | |
| | cctgtctccgggttccggaggagggggttcaggtgggggaggtt | gqgtlvtvssggggsggg | |
| | ctggcggcgggggaagcccttcacaggtgcaactggtgcagagt | gsggggsggggsggggsd | |
| | ggacccgaggttaaaaaaccagggtcctccgttaaggttagctg | iqmtqspstlsasvgdrv | |
| | caaagcctctggctacacatttccaggagtacaatgcactggg | tmtcsasssvysmnwyqq | |
| | tgaggcaggctcctggacagggactcgagtgatcgggtatatca | kpgkapkrwiydssklas | |
| | acccatctagcgcctataccaattacaaccaaaagtttaaggac | qvpsrfsgsgsgtdytlt | |
| | cgagttaccattaccgctgacaaatccaccagtacagcttatat | isslqpddfatyycqqws | |
| | ggagctgtcatctcttaggtccgaggacactgctgtttattact | rnpptfgggtkveikrs | |
| | gcgctcgtcctcaggttcactatgactataatggttttccctac | | |
| | tggggtcagggaaccctggtgactgtctcttctggcggtggagg | | |
| | cagcggtgggggtgggtctggaggcggtggcagtggcggcggag | | |
| | gctctgatattcagatgactcagtctcctagcactctcagcgcc | | |
| | agcgtgggggatcgtgtgacaatgacttgctccgctagcagtag | | |
| | tgtgtcttacatgaattggtatcagcagaagcccgggaaagcac | | |
| | ctaagcgctggatctatgactcttccaagctggcaagtggtgtc | | |
| | ccctcacggttctctggctcaggttctggtactgactatacttt | | |
| | gactatctcctccctccagcccgatgatttcgctacctattatt | | |
| | gtcagcagtggagccgtaacccacccactttcggaggcggtacc | | |
| | aaagtggagatcaagaggtcataa | | |
| DB8 VLVH x | atggaagcaccagcgcagcttctcttcctcctgctactctggct | diqmtqspsslsasvgdr | SEQ ID NO: 135 |
| TSC456 | cccagataccaccggtgacatccagatgacccagtctccatcct | vtitcrasqsissylnwy | (SEQ ID NO: 136) |
| scFv-Fc- | ccctgtctgcatctgtaggagacagagtcaccatcacttgccgg | qqkpgkapklliyaassl | |
| scFv | gcaagtcagagcattagcagctatctgaattggtatcagcagaa | qsgvpsrfsgsgsgtdft | |
| TRI124 | accagggaaagcccctaagctcctgatctatgctgcatccagtt | ltisslqpedfatyycqq | |
| | tgcaaagtggggtcccatcaaggttcagtggcagtggatctggg | systpltfgggtkveikg | |
| | acagatttcactctcaccatcagcagtctgcaacctgaagattt | gggsggggsggggsgggg | |
| | tgcaacttactactgtcaacagagttacagtacccctctcactt | sqvqlvqsgaevkkpgas | |
| | tcggcggaggtaccaaggtggagatcaaaggcggcggcggcagc | vkvsckasgyiftdyymh | |
| | ggcggcggcggcagcggcggcggaggctccggcggcggcggcag | wvrqapgqglewmgwmsp | |
| | ccaggtgcagctggtgcagtctggggctgaggtgaagaagcctg | nsgntgyaqkfqgrvtmt | |
| | gggcctcagtgaaggtttcctgcaaggcatctggatacatcttc | rdtststvymelsslrse | |
| | accgactactatatgcactgggtgcgtcaggcccctggacaagg | dtavyycardaadygdyv | |
| | gcttgagtggatgggatggatgagccctaacagtggtaacacag | afdiwgqgtmvtvsssep | |
| | gctatgcacagaagttccagggccgtgtcaccatgacccgcgac | kssdkthtcppcpapeaa | |
| | acgtccacgagcacagtctacatggagctgagcagcctgcgttc | gapsvflfppkpkdtlmi | |
| | tgaggacaggccgtgtattactgtgcgagagatgcggcggatta | srtpevtcvvvdvshedp | |
| | cggtgactacgttgcttttgatatctggggccaagggacaatgg | evkfnwyvdgvevhnakt | |
| | tcaccgtctcctcgagtgagcccaaatcttctgacaaaactcac | kpreeqynstyrvvsvlt | |
| | acatgcccaccgtgcccagcacctgaagccgcgggtgcaccgtc | vlhqdwlngkeykcavsn | |
| | agtcttcctcttccccccaaaacccaaggacaccctcatgatct | kalpapiektiskakgqp | |
| | cccggacccctgaggtcacatgcgtggtggtggacgtgagccac | repqvytlppsrdeltkn | |
| | gaagaccctgaggtcaagttcaactggtacgtggacggcgtgga | qvsltclvkgfypsdiav | |
| | ggtgcataatgccaagacaaagccgcgggaggagcagtacaaca | ewesngqpennykttppv | |
| | gcacgtaccgtgtggtcagcgtcctcaccgtcctgcaccaggac | ldsdgsfflyskltvdks | |
| | tggctgaatggcaaggaatacaagtgcgcggtctccaacaaagc | rwqqgnvfscsvmhealh | |
| | cctcccagcccccatcgagaaaaccatctccaaagccaaagggc | nhytqkslslspgsgggg | |
| | agccccgagaaccacaggtgtacaccctgcccccatcccgggat | sggggsggggspsqvqlv | |
| | gagctgaccaagaaccaggtcagcctgacctgcctggtcaaagg | qsgpevkkpgssvkvsck | |
| | cttctatccaagcgacatcgccgtggagtgggagagcaatgggc | asgytfsrstmhwvrqap | |
| | agccggagaacaactacaagaccacgcctcccgtgctggactcc | gqglewigyinpssaytn | |
| | gacggctccttcttcctctacagcaagctcaccgtggacaagag | ynqkfkdrvtitadksts | |
| | caggtggcagcaggggaacgtcttctcatgctccgtgatgcatg | taymelsslrsedtavyy | |
| | aggctctgcacaaccactacacgcagaagagcctctccctgtct | carpqvhydyngfpywgq | |
| | ccgggttccggaggagggggttcaggtgggggaggttctggcgg | gtlvtvssggggsggggs | |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | cgggggaagcccttcacaggtgcaactggtgcagagtggacccg | ggggsggggsdiqmtqsp | |
| | aggttaaaaaaccagggtcctccgttaaggttagctgcaaagcc | stlsasvgdrvtmtcsas | |
| | tctggctacacattttccaggagtacaatgcactgggtgaggca | ssvsymnwyqqkpgkapk | |
| | ggctcctggacagggactcgagtggatcgggtatatcaacccat | rwiydssklasgvpsrfs | |
| | ctagcgcctataccaattacaaccaaaagtttaaggaccgagtt | gsgsgtdytltisslqpd | |
| | accattaccgctgacaaatccaccagtacagcttatatggagct | dfatyycqqwsrnpptfg | |
| | gtcatctcttaggtccagaggacactgctgtttattactgcgct | ggtkveikrs | |
| | cgtcctcaggttcactatgactataatggttttccctactgggg | | |
| | tcagggaaccctggtgactgtctcttctggcggtggaggcagcg | | |
| | gtgggggtgggtctggaggcggtggcagtggcggcggaggctct | | |
| | gatattcagatgactcagtctcctagcactctcagcgccagcgt | | |
| | gggggatcgtgtgacaatgacttgctccgctagcagtagtgtgt | | |
| | cttacatgaattggtatcagcagaagcccgggaaagcacctaag | | |
| | cgctggatctatgactcttccaagctggcaagtggtgtcccctc | | |
| | acggttctctggctcaggttctggtactgactatactttgacta | | |
| | tctcctccctccagcccgatgatttcgctacctattattgtcag | | |
| | cagtggagccgtaacccacccactttcggaggcggtaccaaagt | | |
| | ggagatcaagaggtcataa | | |
| DB8 VHVL x | atggaagcaccagcgcagcttctcttcctcctgctactctggct | qvqlvqsgaevkkpgasv | SEQ ID NO: 137 |
| TSC456 | cccagataccaccggtcaggtgcagctggtgcagtctggggctg | kvsckasgyiftdyymhw | (SEQ ID NO: 138) |
| scFv-Fc- | aggtgaagaagcctggggcctcagtgaaggtttcctgcaaggca | vrqapgqglewmgwmspn | |
| scFv | tctggatacatcttcaccgactactatatgcactgggtgcgtca | sgntgyaqkfqgrvtmtr | |
| TRI137 | ggcccctggacaagggcttgagtggatgggatggatgagcccta | dtststvymelsslrsed | |
| | acagtggtaacacaggctatgcacagaagttccagggccgtgtc | tavyycardaadygdyva | |
| | accatgacccgcgacacgtccacgagcacagtctacatggagct | fdiwgqgtmvtvssgggg | |
| | gagcagcctgcgttctgaggacacggccgtgtattactgtgcga | sggggsggggsggggsdi | |
| | gagatgcggcggattacggtgactacgttgcttttgatatctgg | qmtqspsslsasvgdrvt | |
| | ggccaagggacaatggtcaccgtctcttcaggtggaggcggttc | itcrasqsissylnwyqq | |
| | aggcggaggtggatccggcggtggcggctccggtggcggcggat | kpgkapklliyaasslqs | |
| | ctgacatccagatgacccagtctccatcctccctgtctgcatct | gvpsrfsgsgsgtdftlt | |
| | gtaggagacagagtcaccatcacttgccgggcaagtcagagcat | isslqpedfatyycqqsy | |
| | tagcagctatctgaattggtatcagcagaaaccagggaaagccc | stpltfgggtkveiksss | |
| | ctaagctcctgatctatgctgcatccagtttgcaaagtggggtc | epkssdkthtcppcpape | |
| | ccatcaaggttcagtggcagtggatctgggacagatttcactct | aagapsvflfppkpkdtl | |
| | caccatcagcagtctgcaacctgaagattttgcaacttactact | misrtpevtcvvvdvshe | |
| | gtcaacagagttacagtacccctctcactttcggcggaggtacc | dpevkfnwyvdgvevhna | |
| | aaggtggagatcaaatcctcgagtgagcccaaatcttctgacaa | ktkpreeqynstyrvvsv | |
| | aactcaccatgcccaccgtgcccagcacctgaagccgcgggtgc | ltvlhqdwlngkeykcav | |
| | accgtcagtcttcctcttccccccaaaacccaaggacaccctca | snkalpapiektiskakg | |
| | tgatctcccggacccctgaggtcacatgcgtggtggtggacgtg | qprepqvytlppsrdelt | |
| | agccacgaagaccctgaggtcaagttcaactggtacgtggacgg | knqvsltclvkgfypsdi | |
| | cgtggaggtgcataatgccaagacaaagccgcgggaggagcagt | avewesngqpennykttp | |
| | acaacagcacgtaccgtgtggtcagcgtcctcaccgtcctgcac | pvldsdgsfflyskltvd | |
| | caggactggctgaatggcaaggaatacaagtgcgcggtctccaa | ksrwqqgnvfscsvmhea | |
| | caaagccctcccagcccccatcgagaaaaccatctccaaagcca | lhnhytqkslslspgsgg | |
| | aagggcagccccgagaaccacaggtgtacaccctgcccccatcc | ggsggggsggggspsqvq | |
| | cgggatgagctgaccaagaaccaggtcagcctgacctgcctggt | lvqsgpevkkpgssvkvs | |
| | caaaggcttctatccaagcgacatcgccgtggagtgggagagca | ckasgytfsrstmhwvrq | |
| | atgggcagccggagaacaactacaagaccacgcctcccgtgctg | apgqglewigyinpssay | |
| | gactccgacggctccttcttcctctacagcaagctcaccgtgga | tnynqkfkdrvtitadks | |
| | caagagcaggtggcagcaggggaacgtcttctcatgctccgtga | tstaymelsslrsedtav | |
| | tgcatgaggctctgcacaaccactacacgcagaagagcctctcc | yycarpqvhydyngfpyw | |
| | ctgtctccgggttccggaggagggggttcaggtggggggaggttc | gqgtlvtvssggggsggg | |
| | tggcggcgggggaagcccttcacaggtgcaactggtgcagagtg | gsggggsggggsdiqmtq | |
| | gacccgaggttaaaaaaccagggtcctccgttaaggttagctgc | spstlsasvgdrvtmtcs | |
| | aaagcctctggctacacattttccaggagtacaatgcactgggt | asssvsymnwyqqkpgka | |
| | gaggcaggctcctggacagggactcgagtggatcgggtatatca | pkrwiydssklasgvpsr | |
| | acccatctagcgcctataccaattacaaccaaaagtttaaggac | fsgsgsgtdytltisslq | |
| | cgagttaccattaccgctgacaaatccaccagtacagcttatat | pddfatyycqqwsrnppt | |
| | ggagctgtcatctcttaggtccgaggacactgctgtttattact | fgggtkveikrs | |
| | gcgctcgtcctcaggttcactatgactataatggttttccctac | | |
| | tggggtcagggaaccctggtgactgtctcttctggcggtggagg | | |
| | cagcggtgggggtgggtctggaggcggtggcagtggcggcggag | | |
| | gctctgatattcagatgactcagtctcctagcactctcagcgcc | | |
| | agcgtgggggatcgtgtgacaatgacttgctccgctagcagtag | | |
| | tgtgtcttacatgaattggtatcagcagaagcccgggaaagcac | | |
| | ctaagcgctggatctatgactcttccaagctggcaagtggtgtc | | |
| | ccctcacggttctctggctcaggttctggtactgactatacttt | | |
| | gactatctcctccctccagcccgatgatttcgctacctattatt | | |
| | gtcagcagtggagccgtaacccacccactttcggaggcggtacc | | |
| | aaagtggagatcaagaggtcatga | | |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| DB60<br>VHVL x<br>TSC456<br>scFv-Fc-<br>scFv<br>TRI125 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatacaccttcaccagctactatatgcactgggtgcgtca<br>ggcccctggacaagggcttgagtggatggggtggatcaacccta<br>acagtggtgacacaagctatgcacagaagttccagggccgtgtc<br>accatgacccgcgacacgtccacgagcacagtctacatggagct<br>gagcagcctgcgttctgaggacacggccgtgtattactgtgcgc<br>aggatagtagtggttccggggcttttgatatctggggccaaggg<br>acaatggtcaccgtctcttcaggcggcggcggcagcggcggcgg<br>cggcagcggcggcggaggctccggcggcggcggcagcgacatcc<br>agatgacccagtctccatcctccctgtctgcatctgtaggagac<br>agagtcaccatcacttgccgggcaagtcagagcattagcagcta<br>tctgaattggtatcagcagaaaccagggaaagcccctaagctcc<br>tgatctatgctgcatccagtttgcaaagtggggtcccatcaagg<br>ttcagtggcagtggatctgggacagatttcactctcaccatcag<br>cagtctgcaacctgaagattttgcaacttactactgtcaacaga<br>gttacagtacccctctcactttcggcggaggtaccaaggtggag<br>atcaaatcctcgagtgagcccaaatcttctgacaaaactcacac<br>atgcccaccgtgcccagcacctgaagccgcgggtgcaccgtcag<br>tcttcctcttccccccaaaacccaaggacaccctcatgatctcc<br>cggacccctgaggtcacatgcgtggtggtggacgtgagccacga<br>agaccctgaggtcaagttcaactggtacgtggacggcgtggagg<br>tgcataatgccaagacaaagccgcgggaggagcagtacaacagc<br>acgtaccgtgtggtcagcgtcctcaccgtcctgcaccaggactg<br>gctgaatggcaaggaatacaagtgcgcggtctccaacaaagccc<br>tcccagcccccatcgagaaaaccatctccaaagccaaagggcag<br>ccccgagaaccacaggtgtacaccctgcccccatcccgggatga<br>gctgaccaagaaccaggtcagcctgacctgcctggtcaaaggct<br>tctatccaagcgacatcgccgtggagtgggagagcaatgggcag<br>ccggagaacaactacaagaccacgcctcccgtgctggactccga<br>cggctccttcttcctctacagcaagctcaccgtggacaagagca<br>ggtggcagcaggggaacgtcttctcatgctccgtgatgcatgag<br>gctctgcacaaccactacacgcagaagagcctctccctgtctcc<br>gggttccggaggagggggttcaggtgggggaggttctggcggcg<br>ggggaagcccttcacaggtgcaactggtgcagagtggacccgag<br>gttaaaaaaccagggtcctccgttaaggttagctgcaaagcctc<br>tggctacacattttccaggagtacaatgcactgggtgaggcagg<br>ctcctggacagggactcgagtggatcgggtatatcaacccatct<br>agcgcctataccaattacaaccaaaagtttaaggaccgagttac<br>cattaccgctgacaaatccaccagtacagcttatatggagctgt<br>catctcttaggtccgaggacactgctgtttattactgcgctcgt<br>cctcaggttcactatgactataatggttttccctactggggtca<br>gggaaccctggtgactgtctcttctggcggtggaggcagcggtg<br>gggggtgggtctggaggcggtggcagtggcggcggaggctctgat<br>attcagatgactcagtctcctagcactctcagcgccagcgtggg<br>ggatcgtgtgacaatgacttgctccgctagcagtagtgtgtctt<br>acatgaattggtatcagcagaagcccgggaaagcacctaagcgc<br>tggatctatgactcttccaagctggcaagtggtgtcccctcacg<br>gttctctggctcaggttctggtactgactatactttgactatct<br>cctccctccagcccgatgatttcgctacctattattgtcagcag<br>tggagccgtaacccacccactttcggaggcggtaccaaagtgga<br>gatcaagaggtcataa | qvqlvqsgaevkkpgasv<br>kvsckasgytftsyymhw<br>vrqapgqglewmgwinpn<br>sgdtsyaqkfqgrvtmtr<br>dtststvymelsslrsed<br>tavyycaqdssgsgafdi<br>wgqgtmvtvssggggsgg<br>ggsggggsggggsdiqmt<br>qspsslsasvgdrvtitc<br>rasqsissylnwyqqkpg<br>kapklliyaasslqsgvp<br>srfsgsgsgtdftltiss<br>lqpedfatyycqqsystp<br>ltfgggtkveiksssepk<br>ssdkthtcppcpapeaag<br>apsvflfppkpkdtlmis<br>rtpevtcvvvdvshedpe<br>vkfnwyvdgvevhnaktk<br>preeqynstyrvvsvltv<br>lhqdwlngkeykcavsnk<br>alpapiektiskakgqpr<br>epqvytlppsrdeltknq<br>vsltclvkgfypsdiave<br>wesngqpennykttppvl<br>dsdgsfflyskltvdksr<br>wqqgnvfscsvmhealhn<br>hytqkslslspgsggggs<br>ggggsggggspsqvqlvq<br>sgpevkkpgssvkvscka<br>sgytfsrstmhwvrqapg<br>qglewigyinpssaytny<br>nqkfkdrvtitadkstst<br>aymelsslrsedtavyyc<br>arpqvhydyngfpywgqg<br>tlvtvssggggsggggsg<br>gggsggggsdiqmtqsps<br>tlsasvgdrvtmtcsass<br>svsymnwyqqkpgkapkr<br>wiydssklasgvpsrfsg<br>sgsgtdytltisslqpdd<br>fatyycqqwsrnpptfgg<br>gtkveikrs | SEQ ID NO: 139<br>(SEQ ID NO: 140) |
| DB65<br>VHVL x<br>TSC456<br>scFv-Fc-<br>scFv<br>TRI126 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatacaccttcaccggctactatatgcactgggtgcgtca<br>ggcccctggacaagggcttgagtggatgggatggatgaacccta<br>acagtggtaacacaggctatgcacagaagttccagggccgtgtc<br>accatgacccgcgacacgtccacgagcacagtctacatggagct<br>gagcagcctgcgttctgaggacacggccgtgtattactgtgcga<br>aagaggaaccgatttttggagtggttatggatgcttttgatatc<br>tggggccaagggacaatggtcaccgtctcctcaggcggcggcgg<br>cagcggcggcggcggcagcggcggcggaggctccggcggcggcg<br>gcagcgacatccagatgacccagtctccatcctccctgtctgca<br>tctgtaggagacagagtcaccatcacttgccgggcaagtcagag<br>cattagcagctatctgaattggtatcagcagaaaccagggaaag<br>cccctaagctcctgatctatgctgcatccagtttgcaaagtggg<br>gtcccatcaaggttcagtggcagtggatctgggacagatttcac<br>tctcaccatcagcagtctgcaacctgaagattttgcaacttact<br>actgtcaacagagttacagtacccctctcactttcggcggaggt<br>accaaggtggagatcaaatcctcgagtgagcccaaatcttctga | qvqlvqsgaevkkpgasv<br>kvsckasgytftgyymhw<br>vrqapgqglewmgwmnpn<br>sgntgyaqkfqgrvtmtr<br>dtststvymelsslrsed<br>tavyycakeepifgvvmd<br>afdiwgqgtmvtvssggg<br>gsggggsggggsggggsd<br>iqmtqspsslsasvgdrv<br>titcrasqsissylnwyq<br>qkpgkapklliyaasslq<br>sgvpsrfsgsgsgtdftl<br>tisslqpedfatyycqqs<br>ystpltfgggtkveikss<br>sepkssdkthtcppcpap<br>eaagapsvflfppkpkdt<br>lmisrtpevtcvvvdvsh<br>edpevkfnwyvdgvevhn<br>aktkpreeqynstyrvvs | SEQ ID NO: 141<br>(SEQ ID NO: 142) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | caaaactcacacatgcccaccgtgcccagcacctgaagccgcgg<br>gtgcaccgtcagtcttcctcttccccccaaaacccaaggacacc<br>ctcatgatctcccggacccctgaggtcacatgcgtggtggtgga<br>cgtgagccacgaagaccctgaggtcaagttcaactggtacgtgg<br>acggcgtggaggtgcataatgccaagacaaagccgcgggaggag<br>cagtacaacagcacgtaccgtgtggtcagcgtcctcaccgtcct<br>gcaccaggactggctgaatggcaaggaatacaagtgcgcggtct<br>ccaacaaagccctcccagcccccatcgagaaaaccatctccaaa<br>gccaaagggcagccccgagaaccacaggtgtacaccctgccccc<br>atcccgggatgagctgaccaagaaccaggtcagcctgacctgcc<br>tggtcaaaggcttctatccaagcgacatcgccgtggagtgggag<br>agcaatgggcagccggagaacaactacaagaccacgcctcccgt<br>gctggactccgacggctccttcttcctctacagcaagctcaccg<br>tggacaagagcaggtggcagcaggggaacgtcttctcatgctcc<br>gtgatgcatgaggctctgcacaaccactacacgcagaagagcct<br>ctccctgtctccgggttccggaggagggggttcaggtgggggag<br>gttctggcggcgggggaagcccttcacaggtgcaactggtgcag<br>agtggacccgaggttaaaaaaccagggtcctccgttaaggttag<br>ctgcaaagcctctggctacacattttccaggagtacaatgcact<br>gggtgaggcaggctcctggacagggactcgagtggatcgggtat<br>atcaacccatctagcgcctataccaattacaaccaaaagtttaa<br>ggaccgagttaccattaccgctgacaaatccaccagtacagctt<br>atatggagctgtcatctcttaggtccgaggacactgctgtttat<br>tactgcgctcgtcctcaggttcactatgactataatggttttcc<br>ctactggggtcagggaaccctggtgactgtctcttctggcggtg<br>gaggcagcggtgggggtgggtctggaggcggtggcagtggcggc<br>ggaggctctgatattcagatgactcagtctcctagcactctcag<br>cgccagcgtgggggatcgtgtgacaatgacttgctccgctagca<br>gtagtgtgtcttacatgaattggtatcagcagaagcccgggaaa<br>gcacctaagcgctggatctatgactcttccaagctggcaagtgg<br>tgtccccatcacggttctctggctcaggttctgtactgactata<br>ctttgactatctcctccctccagcccgatgatttcgctacctat<br>tattgtcagcagtggagccgtaacccacccactttcggaggcgg<br>taccaaagtggagatcaagaggtcataa | vltvlhqdwlngkeykca<br>vsnkalpapiektiskak<br>qprepqvytlppsrdelt<br>knqvsltclvkgfypsdi<br>avewesngqpennykttp<br>pvldsdgsfflyskltvd<br>ksrwqqgnvfscscmhea<br>lhnhytqkslslspgsgg<br>ggsggggsggggspsqvq<br>lvqsgpevkkpgssvkvs<br>ckasgytfsrstmhwvrq<br>apgqglewigyinpssay<br>tnynqkfkdrvtitadks<br>tstaymelsslrsedtav<br>yycarpqvhydyngfpyw<br>gqgtlvtvssggggsggg<br>gsggggsggggsdiqmtq<br>spstlsasvgdrvtmtcs<br>asssvsymnwyqqkpgka<br>pkrwiydssklasgvpsr<br>fsgsgsgtdytlisslqp<br>ddfatyycqqwsrnpptf<br>gggtkveikrs | |
| DB82<br>VLVH x<br>TSC456<br>scFv-Fc-<br>scFv<br>TRI127 | atggaagcaccagcgcagcttctcttcctcctgctactctggct<br>cccagataccaccggtgacatccagatgacccagtctccatcct<br>ccctgtctgcatctgtaggagaccgcgtcaccatcacttgccgg<br>gcaagtcagaccataaacaactatttgaactggtatcagcagaa<br>accagggaaagcccctaagctcctgatctattctgcatctactt<br>tgcaaagtggggtcccatcacgtttcagtggcagtggatctggg<br>acagatttcactctcaccatcagcagtctgcaacctgaagattt<br>tgcaacttactactgtcaccagagttacacttcacctctcactt<br>tcggcggaggtaccaaggtggagatcaaaggcggcggcggcagc<br>ggcggcggcggcagcggcggcggaggctccggcggcggcggcag<br>cgaggtgcagctggtggagtctgggggaggcttggtacagcctg<br>gggggtccctgcgcctctcctgtgcagcctctggattcaccttt<br>agcagctatgccatgagctgggtccgccaggctccagggaaggg<br>gctggagtgggtctcagttattagtgccaatagtgctggtctag<br>gccatgcggactctgtgaagggccggttcaccatctcccgcgac<br>aattccaagaacacgctgtatctgcaaatgaacagcctgcgcgc<br>cgaggacacggccgtatattactgtgcgagagtgggctatagca<br>gctcggctgatgcttttgatatctggggccaagggacaatggtc<br>accgtctcctcgagtgagcccaaatcttctgacaaaactcacac<br>atgcccaccgtgcccagcacctgaagccgcgggtgcaccgtcag<br>tcttcctcttccccccaaaacccaaggacaccctcatgatctcc<br>cggacccctgaggtcacatgcgtggtggtggacgtgagccacga<br>agaccctgaggtcaagttcaactggtacgtggacggcgtggagg<br>tgcataatgccaagacaaagccgcgggaggagcagtacaacagc<br>acgtaccgtgtggtcagcgtcctcaccgtcctgcaccaggactg<br>gctgaatggcaaggaatacaagtgcgcggtctccaacaaagccc<br>tcccagcccccatcgagaaaaccatctccaaagccaaagggcagc<br>cccgagaaccacaggtgtacaccctgcccccatcccgggatgag<br>ctgaccaagaaccaggtcagcctgacctgcctggtcaaaggctt<br>ctatccaagcgacatcgccgtggagtgggagagcaatgggcagc<br>cggagaacaactacaagaccacgcctcccgtgctggactccgac<br>ggctccttcttcctctacagcaagctcaccgtggacaagagcag<br>gtggcagcaggggaacgtcttctcatgctccgtgatgcatgagg<br>ctctgcacaaccactacacgcagaagagcctctccctgtctccg<br>ggttccggaggagggggttcaggtgggggaggttctggcggcgg<br>gggaagcccttcacaggtgcaactggtgcagagtggacccgagg<br>ttaaaaaaccagggtcctccgttaaggttagctgcaaagcctct<br>ggctacacattttccaggagtacaatgcactgggtgaggcaggc<br>tcctggacagggactcgagtggatcgggtatatcaacccatcta | diqmtqspsslsasvgdr<br>vtitcrasqtinnylnwy<br>qqkpgkapklliysastl<br>qsgvpsrfsgsgsgtdft<br>ltisslqpedfatyychq<br>sytspltfgggtkveikg<br>gggsggggsggggsgggg<br>sevqlvesggglvqpggs<br>lrlscaasgftfssyams<br>wvrqapgkglewvsvisa<br>nsaglghadsvkgrftis<br>rdnskntlylqmnslrae<br>dtavyycarvgysssada<br>fdiwgqgtmvtvsssepk<br>ssdkthtcppcpapeaag<br>apsvflfppkpkdtlmis<br>rtpevtcvvvdvshedpe<br>vkfnwyvdgvevhnaktk<br>preeqynstyrvvsvltv<br>lhqdwlngkeykcavsnk<br>alpapiektiskakgqpr<br>epqvytlppsrdeltknq<br>vsltclvkgfypsdiave<br>wesngqpennykttppvl<br>dsdgsfflyskltvdksr<br>wqqgnvfscsvmhealhn<br>hytqkslslspgsggggs<br>ggggsggggspsqvqlvq<br>sgpevkkpgssvkvscka<br>sgytfsrstmhwvrqapg<br>qglewigyinpssaytny<br>nqkfkdrvtitadkstst<br>aymelsslrsedtavyyc<br>arpqvhydyngfpywgqg<br>tlvtvssggggsggggsg<br>gggsggggsdiqmtqsps<br>tlsasvgdrvtmtcsass<br>svsymnwyqqkpgkapkr<br>wiydssklasgvpsrfsg | SEQ ID NO: 143<br>(SEQ ID NO: 144) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | gcgcctataccaattacaaccaaaagtttaaggaccgagttacc<br>attaccgctgacaaatccaccagtacagcttatatggagctgtc<br>atctcttaggtccgaggacactgctgtttattactgcgctcgtc<br>ctcaggttcactatgactataatggttttccctactggggtcag<br>ggaaccctggtgactgtctcttctggcggtggaggcagcggtgg<br>gggtgggtctggaggcggtggcagtggcggcggaggctctgata<br>ttcagatgactcagtctcctagcactctcagcgccagcgtgggg<br>gatcgtgtgacaatgacttgctccgctagcagtagtgtgtctta<br>catgaattggtatcagcagaagcccgggaaagcacctaagcgct<br>ggatctatgactcttccaagctggcaagtggtgtcccctcacgg<br>ttctctggctcaggttctggtactgactatactttgactatctc<br>ctccctccagcccgatgatttcgctacctattattgtcagcagt<br>ggagccgtaacccacccactttcggaggcggtaccaaagtggag<br>atcaagaggtcataa | sgsgtdytltisslqpdd<br>fatyycqqwsrnpptfgg<br>gtkveikrs | |
| DB83<br>VHVL x<br>TSC456<br>scFv-Fc-<br>scFv<br>TRI134 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatacaccttcactagctatgctatgcattgggtgcgtca<br>ggcccctggacaagggcttgagtggatgggacttgttgatcctg<br>aagatggtgaaacaatatatgcagagaagttccagggccgtgtc<br>accatgacccgcgacacgtccacgagcacagtctacatggagct<br>gagcagcctgcgttctgaggacacggccgtgtattactgtgcga<br>gacgaacgtattactatgatagtagtggttcccgttatgctttt<br>gatatctggggccaagggaccacggtcaccgtctcttcaggcgg<br>cggcggcagcggcggcggcggcagcggcggcggaggctccggcg<br>gcggcggcagcgatgttgtgatgactcagtctccactctccctg<br>cccgtcacccctggagagccggcctccatctcctgcaggtctag<br>tcagagcctcctgcatagtaatggagacaactatttggattggt<br>acctgcagaagccagggcagtctccacagctcctgatctatttg<br>ggttctaatcgggcctccggggtccctgaccgtttcagtggcag<br>tggatcaggcacagattttacactgaaaatcagccgtgtggagg<br>ctgaggatgttggggtttattactgcatgcaagctacacactgg<br>ccactcactttcggccctggtaccaaagtggatatcaaatcctc<br>gagtgagcccaaatcttctgacaaaactcacacatgcccaccgt<br>gcccagcacctgaagccgcgggtgcaccgtcagtcttcctcttc<br>cccccaaaacccaaggacaccctcatgatctcccggacccctga<br>ggtcacatgcgtggtggtggacgtgagccacgaagaccctgagg<br>tcaagttcaactggtacgtggacggcgtggaggtgcataatgcc<br>aagacaaagccgcgggaggagcagtacaacagcacgtaccgtgt<br>ggtcagcgtcctcaccgtcctgcaccaggactggctgaatggca<br>aggaatacaagtgcgcggtctccaacaaagccctcccagccccc<br>atcgagaaaaccatctccaaagccaaagggcagccccgagaacc<br>acaggtgtacaccctgcccccatcccgggatgagctgaccaaga<br>accaggtcagcctgacctgcctggtcaaaggcttctatccaagc<br>gacatcgccgtggagtgggagagcaatgggcagccggagaacaa<br>ctacaagaccacgcctcccgtgctggactccgacggctccttct<br>tcctctacagcaagctcaccgtggacaagagcaggtggcagcag<br>gggaacgtcttctcatgctccgtgatgcatgaggctctgcacaa<br>ccactacacgcagaagagcctctccctgtctccgggttccggag<br>gaggggggttcaggtgggggaggttctggcggcgggggaagccct<br>tcacaggtgcaactggtgcagagtggacccgaggttaaaaaacc<br>agggtcctccgttaaggttagctgcaaagcctctggctacacat<br>tttccaggagtacaatgcactgggtgaggcaggctcctggacag<br>ggactcgagtggatcgggtatatcaacccatctagcgcctatac<br>caattacaaccaaaagtttaaggaccgagttaccattaccgctg<br>acaaatccaccagtacagcttatatggagctgtcatctcttagg<br>tccgaggacactgctgtttattactgcgctcgtcctcaggttca<br>ctatgactataatggttttccctactggggtcagggaaccctgg<br>tgactgtctcttctggcggtggaggcagcggtgggggtgggtct<br>ggaggcggtggcagtggcggcggaggctctgatattcagatgac<br>tcagtctcctagcactctcagcgccagcgtgggggatcgtgtga<br>caatgacttgctccgctagcagtagtgtgtcttacatgaattgg<br>tatcagcagaagcccgggaaagcacctaagcgctggatctatga<br>ctcttccaagctggcaagtggtgtcccctcacggttctctggct<br>caggttctggtactgactatactttgactatctcctccctccag<br>cccgatgatttcgctacctattattgtcagcagtggagccgtaa<br>cccacccactttcggaggcggtaccaaagtggagatcaagaggt<br>cataa | qvqlvqsgaevkkpgasv<br>kvsckasgytftsyamhw<br>vrqapgqglewmglvdpe<br>dgetiyaekfqgrvtmtr<br>dtststvymelsslrsed<br>tavyycarrtyyydssgs<br>ryafdiwgqgttvtvssg<br>gggsggggsggggsgggg<br>sdvvmtqsplslpvtpge<br>pasiscrssqsllhsngd<br>nyldwylqkpgqspqlli<br>ylgsnrasgvpdrfsgsg<br>sgtdftlkisrveaedvg<br>vyycmqathwpltfgpgt<br>kvdikssepkssdktht<br>cppcpapeaagapsvflf<br>ppkpkdtlmisrtpevtc<br>vvvdvshedpevkfnwyv<br>dgvevhnaktkpreeqyn<br>styrvvsvltvlhqdwln<br>gkeykcavsnkalpapie<br>ktiskakgqprepqvytl<br>ppsrdeltknqvsltclv<br>kgfypsdiavewesngqp<br>ennykttppvldsdgsff<br>lyskltvdksrwqqgnvf<br>scsvmhealhnhytqksl<br>slspgsggggsggggsgg<br>ggspsqvqlvqsgpevkk<br>pgssvkvsckasgytfsr<br>stmhwvrqapgqglewig<br>yinpssaytnynqkfkdr<br>vtitadkststaymelss<br>lrsedtavyycarpqvhy<br>dyngfpysgqgtlvtvss<br>ggggsggggsggggsggg<br>gsdiqmtqspstlsasvg<br>drvtmtcsasssvsymnw<br>yqqkpgkapkrwiydssk<br>lasgvpsrfsgsgsgtdy<br>tltisslqpddfatyycq<br>qwsrnpptfgggtkveik<br>rs | SEQ ID NO: 145<br>(SEQ ID NO: 146) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| DB86<br>VHVL x<br>TSC456<br>scFv-Fc-<br>scFv<br>TRI128 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatatatgttcagtggccattctgcacactgggtgcgtca<br>ggcccctggacaagggcttgagtggatgggatggatgaacccta<br>acagtggtaacacaggctatgcacagaagttccagggccgtgtc<br>accatgacccgcgacacgtccacgagcacagtctacatggagct<br>gagcagcctgcgttctgaggacacggccgtgtattactgtgcga<br>gagatagcagtggctggtacgatgtctttgactactggggccag<br>gggaccctggtcaccgtctcctcaggtggaggcggttcaggcgg<br>aggtggatccggcggtggcggctccggtggcggcggatctgaca<br>tccagatgacccagtctccatcctccctgtctgcatctgtagga<br>gaccgcgtcaccatcacttgccgggcaagtcagggcatcagaaa<br>tgatttaggttggtatcagcagaaaccagggaaagcccctaagc<br>tcctgatctatgctgcatccactttgcaatcaggggtcccatca<br>cgtttcagtggcagtggatctgggacagatttcactctcaccat<br>cagcagtctgcaacctgaagattttgcaacttactactgtcaac<br>agagttacggtgccccctcactttcggcggaggtaccaaggtg<br>gagatcaaatcctcgagtgagcccaaatcttctgacaaaactca<br>cacatgcccaccgtgcccagcacctgaagccgcgggtgcaccgt<br>cagtcttcctcttccccccaaaacccaaggacaccctcatgatc<br>tcccggacccctgaggtcacatgcgtggtggtggacgtgagcca<br>cgaagaccctgaggtcaagttcaactggtacgtggacggcgtgg<br>aggtgcataatgccaagacaaagccgcgggaggagcagtacaac<br>agcacgtaccgtgtggtcagcgtcctcaccgtcctgcaccagga<br>ctggctgaatggcaaggaatacaagtgcgcggtctccaacaaag<br>ccctcccagcccccatcgagaaaaccatctccaaagccaaaggg<br>cagccccgagaaccacaggtgtacaccctgcccccatcccggga<br>tgagctgaccaagaaccaggtcagcctgacctgcctggtcaaag<br>gcttctatccaagcgacatcgccgtggagtgggagagcaatggg<br>cagccggagaacaactacaagaccacgcctcccgtgctggactc<br>cgacggctccttcttcctctacagcaagctcaccgtggacaaga<br>gcaggtggcagcaggggaacgtcttctcatgctccgtgatgcat<br>gaggctctgcacaaccactacacgcagaagagcctctccctgtc<br>tccgggttccggaggaggggggttcaggtgggggaggttctggcg<br>gcgggggaagcccttcacaggtgcaactggtgcagagtggaccc<br>gaggttaaaaaaccagggtcctccgttaaggttagctgcaaagc<br>ctctggctacacattttccaggagtacaatgcactgggtgaggc<br>aggctcctggacagggactcgagtggatcgggtatatcaaccca<br>tctagcgcctataccaattacaaccaaaagtttaaggaccgagt<br>taccattaccgctgacaaatccaccagtacagcttatatggagc<br>tgtcatctcttaggtccgaggacactgctgtttattactgcgct<br>cgtcctcaggttcactatgactataatggttttccctactgggg<br>tcagggaaccctggtgactgtctcttctggcggtggaggcagcg<br>gtgggggtgggtctggaggcggtggcagtggcggcggaggctct<br>gatattcagatgactcagtctcctagcactctcagcgccagcgt<br>gggggatcgtgtgacaatgacttgctccgctagcagtagtgtgt<br>cttacatgaattggtatcagcagaagcccgggaaagcacctaag<br>cgctggatctatgactcttccaagctggcaagtggtgtcccctc<br>acggttctctggctcaggttctggtactgactatactttgacta<br>tctcctccctccagcccgatgatttcgctacctattattgtcag<br>cagtggagccgtaacccacccactttcggaggcggtaccaaagt<br>ggagatcaagaggtcataa | qvqlvqsgaevkkpgasv<br>kvsckasgymfsghsahw<br>vrqapgqglewmgwmnpn<br>sgntgyaqkfqgrvtmtr<br>dtststvymelsslrsed<br>tavyycardssgwydvfd<br>ywgqgtlvtvssggggsg<br>gggsggggsggggsdiqm<br>tqspsslsasvgdrvtit<br>crasqgirndlgwyqqkp<br>gkapklliyaastlqsgv<br>psrfsgsgsgtdftltis<br>slqpedfatyycqqsyga<br>pltfgggtkveiksssep<br>kssdkthtcppcpapeaa<br>gagsvflfppkpkdtlmi<br>srtpevtcvvvdvshedp<br>evkfnwyvdgvevhnakt<br>kpreeqynstyrvvsvlt<br>vlhqdwlngkeykcavsn<br>kalpapiektiskakgqp<br>repqvytlppsrdeltkn<br>qvsltclvkgfypsdiav<br>ewesngqpennykttppv<br>ldsdgsfflyskltvdks<br>rwqqgnvfscsvmhealh<br>nhytqkslslspgsgggg<br>sggggsggggspsqvqlv<br>qsgpevkkpgssvkvsck<br>asgytfsrstmhwvrqap<br>gqglewigyinpssaytn<br>ynqkfkdrvtitadksts<br>taymelsslrsedtavyy<br>carpqvhydyngfpywgq<br>gtlvtvssggggsggggs<br>ggggsggggsdiqmtqsp<br>stlsasvgdrvtmtcsas<br>ssvsymnwyqqkpgkapk<br>rwiydssklasgvpsrfs<br>gsgsgtdytltisslqpd<br>dfatyycqqwsrnpptfg<br>ggtkveikrs | SEQ ID NO: 147<br>(SEQ ID NO: 148) |
| DB280<br>VHVL x<br>TSC456<br>scFv-Fc-<br>scFv<br>TRI131 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggatacagcctcaacttatactatatgcactgggtgcgtca<br>ggcccctggacaagggcttgagtggatgggatggatgaacccta<br>acagtggtaacacaggctatgcacagaagttccagggccgtgtc<br>accatgacccgcgacacgtccacgagcacagtctacatggagct<br>gagcagcctgcgttctgaggacacggccgtgtattactgtgcga<br>gcctcgattgtagtggtggtagctgctactccgaatatgatgct<br>tttgatatctggggccaagggaccacggtcaccgtctcctcagg<br>cggcggcggcagcggcggcggcggcagcggcggcggaggctccg<br>gcggcggcggcagcgacatccagatgacccagtctccatcctcc<br>ctgtctgcatctgtaggagacagagtcaccatcacttgccgggc<br>aagtcagagcattagcagctatctgaattggtatcagcagaaac<br>cagggaaagcccctaagctcctgatctatgctgcatccagtttg<br>caaagtggggtcccatcaaggttcagtggcagtggatctgggac<br>agatttcactctcaccatcagcagtctgcaacctgaagattttg<br>caacttactactgtcaacagagttacagtacccctctcactttc<br>ggcggaggtaccaaggtggagatcaaatcctcgagtgagcccaa | qvqlvqsgaevkkpgasv<br>kvsckasgyslnlyymhw<br>vrqapgqglewmgwmnpn<br>sgntgyaqkfqgrvtmtr<br>dtststvymelsslrsed<br>tavyycasldcsggscys<br>eydafdiwgqgttvtvss<br>ggggsggggsggggsggg<br>gsdiqmtqspsslsasvg<br>drvtitcrasqsissyln<br>wyqqkpgkapklliyaas<br>slqsgvpsrfsgsgsgtd<br>ftltisslqpedfatyyc<br>qqsystpltfgggtkvei<br>ksssepkssdkthtcppc<br>papeaagapsvflfppkp<br>kdtlmisrtpevtcvvvd<br>vshedpevkfnwyvdgve<br>vhnaktkpreeqynstyr | SEQ ID NO: 149<br>(SEQ ID NO: 150) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | atcttctgacaaaactcacacatgcccaccgtgcccagcacctg | vvsvltvlhqdwlngkey | |
| | aagccgcgggtgcaccgtcagtcttcctcttccccccaaaaccc | kcavsnkalpapiektis | |
| | aaggacaccctcatgatctcccggacccctgaggtcacatgcgt | kakgqprepqvytlppsr | |
| | ggtggtggacgtgagccacgaagaccctgaggtcaagttcaact | deltknqvsltclvkgfy | |
| | ggtacgtggacggcgtggaggtgcataatgccaagacaaagccg | psdiavewesngqpenny | |
| | cgggaggagcagtacaacagcacgtaccgtgtggtcagcgtcct | kttppvldsdgsfflysk | |
| | caccgtcctgcaccaggactggctgaatggcaaggaatacaagt | ltvdksrwqqgnvfscsv | |
| | gcgcggtctccaacaaagccctcccagcccccatcgagaaaacc | mhealhnhytqkslslsp | |
| | atctccaaagccaaagggcagccccgagaaccacaggtgtacac | gsggggsggggsggggsp | |
| | cctgcccccatcccgggatgagctgaccaagaaccaggtcagcc | sqvqlvqsgpevkkpgss | |
| | tgacctgcctggtcaaaggcttctatccaagcgacatcgccgtg | vkvscksgytfsrstmhw | |
| | gagtgggagagcaatgggcagccggagaacaactacaagaccac | vrqapgqglewigyinps | |
| | gcctcccgtgctggactccgacggctccttcttcctctacagca | saytnynqkfkdrvtita | |
| | agctcaccgtggacaagagcaggtggcagcaggggaacgtcttc | dkststaymelsslrsed | |
| | tcatgctccgtgatgcatgaggctctgcacaaccactacacgca | tavyycarpqvhydyngf | |
| | gaagagcctctccctgtctccgggttccggaggagggggttcag | pywgqgtlvtvssggggs | |
| | gtgggggaggttctggcggcgggggaagcccttcacaggtgcaa | ggggsggggsggggsdiq | |
| | ctggtgcagagtggacccgaggttaaaaaaccagggtcctccgt | mtqspstlsasvgdrvtm | |
| | taaggttagctgcaaagcctctggctacacattttccaggagta | tcsasssvsymnwyqqkp | |
| | caatgcactgggtgaggcaggctcctggacagggactcgagtgg | gkapkrwiydssklasgv | |
| | atcgggtatatcaacccatctagcgcctataccaattacaacca | psrfsgsgsgtdtyltis | |
| | aaagtttaaggaccgagttaccattaccgctgacaaatccacca | slqpddfatyycqqwsrn | |
| | gtacagcttatatggagctgtcatctcttaggtccgaggacact | pptfggtkveikrs | |
| | gctgtttattactgcgctcgtcctcaggttcactatgactataa | | |
| | tggttttccctactggggtcagggaaccctggtgactgtctctt | | |
| | ctggcggtggaggcagcggtgggggtgggtctggaggcggtggc | | |
| | agtggcggcggaggctctgatattcagatgactcagtctcctag | | |
| | cactctcagcgccagcgtgggggatcgtgtgacaatgacttgct | | |
| | ccgctagcagtagtgtgtcttacatgaattggtatcagcagaag | | |
| | cccgggaaagcacctaagcgctggatctatgactcttccaagct | | |
| | ggcaagtggtgtcccctcacggttctctggctcaggttctggta | | |
| | ctgactatactttgactatctcctccctccagcccgatgatttc | | |
| | gctacctattattgtcagcagtggagccgtaacccacccacttt | | |
| | cggaggcggtaccaaagtggagatcaagaggtcataa | | |
| DB331 | atggaagcaccagcgcagcttctcttcctcctgctactctggct | qvqlvqsgaevkkpgasv | SEQ ID NO: 151 |
| VHVL x | cccagataccaccggtcaggtgcagctggtgcagtctggggctg | kvsckasgytftsyymhw | (SEQ ID NO: 152) |
| TSC456 | aggtgaagaagcctggggcctcagtgaaggtttcctgcaaggca | vrqapgqglewmgwmnpn | |
| scFv-Fc- | tctggatacaccttcaccagctactatatgcactgggtgcgtca | sgntgyaqkfqgrvtmtr | |
| scFv | ggcccctggacaagggcttgagtggatgggatggatgaacccta | dtststvymelsslrsed | |
| TRI132 | acagtggtaacacaggctatgcacagaagttccagggccgtgtc | tavyycatdlagealfdp | |
| | accatgacccgcgacacgtccacgagcacagtctacatggagct | wgqgtlvtvssggggsgg | |
| | gagcagcctgcgttctgaggacacggccgtgtattactgtgcaa | ggsggggsggggsdiqmt | |
| | cagatctcgcgggggaagccttgttcgaccccctggggccagggc | qspsslsasvgdrvtitc | |
| | accctggtcaccgtctcctcaggcggcggcggcagcggcggcgg | rasqsissylnwyqqkpg | |
| | cggcagcggcggcggaggctccggcggcggcggcagcgacatcc | kapklliyaasslqsgvp | |
| | agatgacccagtctccatcctccctgtctgcatctgtaggagac | srfsgsgsgtdftltiss | |
| | agagtcaccatcacttgccgggcaagtcagagcattagcagcta | lqpedfatyycqqsystp | |
| | tctgaattggtatcagcagaaaccagggaaagcccctaagctcc | ltfgggtkveiksssepk | |
| | tgatctatgctgcatccagtttgcaaagtggggtcccatcaagg | ssdkthtcppcpapeaag | |
| | ttcagtggcagtggatctgggacagatttcactctcaccatcag | apsvflfppkpkdtlmis | |
| | cagtctgcaacctgaagattttgcaacttactactgtcaacaga | rtpevtcvvvdvshedpe | |
| | gttacagtacccctctcactttcggcggaggtaccaaggtggag | vkfnwyvdgvevhnaktk | |
| | atcaaatcctcgagtgagcccaaatcttctgacaaaactcacac | preeqynstyrvvsvltv | |
| | atgcccaccgtgcccagcacctgaagccgcgggtgcaccgtcag | lhqdwlngkeykcavsnk | |
| | tcttcctcttccccccaaaacccaaggacaccctcatgatctcc | alpapiektiskakgqpr | |
| | cggacccctgaggtcacatgcgtggtggtggacgtgagccacga | epqvytlppsrdeltknq | |
| | agaccctgaggtcaagttcaactggtacgtggacggcgtggagg | vsltclvkgfypsdiave | |
| | tgcataatgccaagacaaagccgcgggaggagcagtacaacagc | wesngqpennykttppvl | |
| | acgtaccgtgtggtcagcgtcctcaccgtcctgcaccaggactg | dsdgsfflyskltvdksr | |
| | gctgaatggcaaggaatacaagtgcgcggtctccaacaaagccc | wqqgnvfscsvmhealhn | |
| | tcccagcccccatcgagaaaaccatctccaaagccaaagggcag | hytqkslslspgsggggs | |
| | ccccgagaaccacaggtgtacaccctgcccccatcccgggatga | ggggsggggspsqvqlvq | |
| | gctgaccaagaaccaggtcagcctgacctgcctggtcaaaggct | sgpevkkpgssvkvscka | |
| | tctatccaagcgacatcgccgtggagtgggagagcaatgggcag | sgytfsrstmhwvrqapg | |
| | ccggagaacaactacaagaccacgcctcccgtgctggactccga | qglewigyinpssaytny | |
| | cggctccttcttcctctacagcaagctcaccgtggacaagagca | nqkfkdrvtitadkstst | |
| | ggtggcagcaggggaacgtcttctcatgctccgtgatgcatgag | aymelsslrsedtavyyc | |
| | gctctgcacaaccactacacgcagaagagcctctccctgtctcc | arpqvhydyngfpywgqg | |
| | gggttccggaggagggggttcaggtgggggaggttctggcggcg | tlvtvssggggsggggsg | |
| | ggggaagcccttcacaggtgcaactggtgcagagtggacccgag | gggsggggsdiqmtqsps | |
| | gttaaaaaaccagggtcctccgttaaggttagctgcaaagcctc | tlsasvgdrvtmtcsass | |
| | tggctacacattttccaggagtacaatgcactgggtgaggcagg | svsymnwyqqkpgkapkr | |
| | ctcctggacagggactcgagtggatcgggtatatcaacccatct | wiydssklasgvpsrfsg | |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | agcgcctataccaattacaaccaaaagtttaaggaccgagttac | sgsgtdytltisslqpdd | |
| | cattaccgctgacaaatccaccagtacagcttatatggagctgt | fatyycqqwsrnpptfgg | |
| | catctcttaggtccgaggacactgctgtttattactgcgctcgt | gtkveikrs | |
| | cctcaggttcactatgactataatggttttccctactggggtca | | |
| | gggaaccctggtgactgtctcttctggcggtggaggcagcggtg | | |
| | gggtgggtctggaggcggtggcagtggcggcggaggctctgat | | |
| | attcagatgactcagtctcctagcactctcagcgccagcgtggg | | |
| | ggatcgtgtgacaatgacttgctccgctagcagtagtgtgtctt | | |
| | acatgaattggtatcagcagaagcccgggaaagcacctaagcgc | | |
| | tggatctatgactcttccaagctggcaagtggtgtcccctcacg | | |
| | gttctctggctcaggttctggtactgactatactttgactatct | | |
| | cctccctccagcccgatgatttcgctacctattattgtcagcag | | |
| | tggagccgtaacccacccactttcggaggcggtaccaaagtgga | | |
| | gatcaagaggtcataa | | |
| DB415 | atggaagcaccagcgcagcttctcttcctcctgctactctggct | evqlvesggglvqpggsl | SEQ ID NO: 153 |
| VHVL x | cccagataccaccggtgaggtgcagctggtggagtctgggggag | rlscaasgitfssygmhw | (SEQ ID NO: 154) |
| TSC456 | gcttggtacagcctggggggtccctgcgcctctcctgtgcagcc | vrqapgkglewvsgiswn | |
| scFv-Fc- | tctggaatcaccttcagtagttatggcatgcattgggtccgcca | sgnrvyvdsvkgrftisr | |
| scFv | ggctccagggaaggggctggagtgggtctcaggtattagttgga | dnskntlylqmnslraed | |
| TRI138 | atagtggtaacagagtctatgtggactctgtgaagggccggttc | tavyycardtndafdiwg | |
| | accatctcccgcgacaattccaagaacacgctgtatctgcaaat | qgttvtvssggggsgggg | |
| | gaacagcctgcgcgccgaggacacggccgtatattactgtgcga | sggggsggggsdiqmtqs | |
| | gagatactaatgatgcttttgatatctggggccaagggaccacg | psslsasvgdrvtitcra | |
| | gtcaccgtctcctcaggtggaggcggttcaggcggaggtggatc | sqsissylnwyqqkpgka | |
| | cggcggtggcggctccggtggcggcggatctgacatccagatga | pklliyaasslqsgvpsr | |
| | cccagtctccatcctccctgtctgcatctgtaggagacagagtc | fsgsgsgtdftltisslq | |
| | accatcacttgccgggcaagtcagagcattagcagctatctgaa | pedfatyycqqsystplt | |
| | ttggtatcagcagaaaccagggaaagcccctaagctcctgatct | fgggtkveiksssepkss | |
| | atgctgcatccagtttgcaaagtggggtcccatcaaggttcagt | dkthtcppcpapeaagap | |
| | ggcagtggatctgggacagatttcactctcaccatcagcagtct | svflfppkpkdtlmisrt | |
| | gcaacctgaagattttgcaacttactactgtcaacagagttaca | pevtcvvvdvshedpevk | |
| | gtacccctctcactttcggcggaggtaccaaggtggagatcaaa | fnwyvdgvevhnaktkpr | |
| | tcctcgagtgagcccaaatcttctgacaaaactcacacatgccc | eeqynstyrvvsvltvlh | |
| | accgtgcccagcacctgaagccgcgggtgcaccgtcagtcttcc | qdwlngkeykcavsnkal | |
| | tcttccccccaaaacccaaggacaccctcatgatctcccggacc | papiektiskakgqprep | |
| | cctgaggtcacatgcgtggtggtggacgtgagccacgaagaccc | qvytlppsrdeltknqvs | |
| | tgaggtcaagttcaactggtacgtggacggcgtggaggtgcata | ltclvkgfypsdiavewe | |
| | atgccaagacaaagccgcgggaggagcagtacaacagcacgtac | sngqpennykttppvlds | |
| | cgtgtggtcagcgtcctcaccgtcctgcaccaggactggctgaa | dgsfflyskltvdksrwq | |
| | tggcaaggaatacaagtgcgcggtctccaacaaagccctcccag | qgnvfscsvmhealhnhy | |
| | cccccatcgagaaaaccatctccaaagccaaagggcagccccga | tqkslslspgsggggsgg | |
| | gaaccacaggtgtacaccctgcccccatcccgggatgagctgac | ggsggggspsqvqlvqsg | |
| | caagaaccaggtcagcctgacctgcctggtcaaaggcttctatc | pevkkpgssvkvsckasg | |
| | caagcgacatcgccgtggagtgggagagcaatgggcagccggag | ytfsrstmhwvrqapgqg | |
| | aacaactacaagaccacgcctcccgtgctggactccgacggctc | lewigyinpssaytnynq | |
| | cttcttcctctacagcaagctcaccgtggacaagagcaggtggc | kfkdrvtitadkststay | |
| | agcaggggaacgtcttctcatgctccgtgatgcatgaggctctg | melsslrsedtavyycar | |
| | cacaaccactacacgcagaagagcctctccctgtctccgggttc | pqvhydyngfpywgqgtl | |
| | cggaggagggggttcaggtgggggaggttctggcggcgggggaa | vtvssggggsggggsggg | |
| | gcccttcacaggtgcaactggtgcagagtggacccgaggttaaa | gsggggsdiqmtqspstl | |
| | aaaccagggtcctccgttaaggttagctgcaaagcctctggcta | sasvgdrvtmtcsasssv | |
| | cacattttccaggagtacaatgcactgggtgaggcaggctcctg | symnwyqqkpgkapkrwi | |
| | gacagggactggagtggatcgggtatatcaacccatctagcgcc | ydssklasgvpsrfsgsg | |
| | tataccaattacaaccaaaagtttaaggaccgagttaccattac | sgtdytltisslqpddfa | |
| | cgctgacaaatccaccagtacagcttatatggagctgtcatctc | tyycqqwsrnpptfgggt | |
| | ttaggtccgaggacactgctgtttattactgcgctcgtcctcag | kveikrs | |
| | gttcactatgactataatggttttccctactggggtcagggaac | | |
| | cctggtgactgtctcttctggcggtggaggcagcggtgggggtg | | |
| | ggtctggaggcggtggcagtggcggcggaggctctgatattcag | | |
| | atgactcagtctcctagcactctcagcgccagcgtgggggatcg | | |
| | tgtgacaatgacttgctccgctagcagtagtgtgtcttacatga | | |
| | attggtatcagcagaagcccgggaaagcacctaagcgctggatc | | |
| | tatgactcttccaagctggcaagtggtgtcccctcacggttctc | | |
| | tggctcaggttctggtactgactatactttgactatctcctccc | | |
| | tccagcccgatgatttcgctacctattattgtcagcagtggagc | | |
| | cgtaacccacccactttcggaggcggtaccaaagtggagatcaa | | |
| | gaggtcatga | | |

TABLE 3-continued

Binding Polypeptide Sequences and Components

| Name | Nucleotide Sequence | Amino Acid Sequence | SEQ ID NOs: nucleotide (amino acid) |
|---|---|---|---|
| DB435<br>VHVL x<br>TSC456<br>scFv-Fc-<br>scFv<br>TRI139 | atggaagcaccagcgcagcttctcttcctcctgctactctggct<br>cccagataccaccggtcaggtgcagctggtgcagtctggggctg<br>aggtgaagaagcctggggcctcagtgaaggtttcctgcaaggca<br>tctggaggcaccttcagcagctatgctatcagctgggtgcgtca<br>ggcccctggacaagggcttgagtggatgggctggatcacccctc<br>acaatggtaacataaagtatgcacgggagttccagggccgtgtc<br>accatgacccgcgacacgtccacgagcacagtctacatggagct<br>gagcagcctgcgttctgaggacacggccgtgtattactgtgcga<br>aagatctgaactggaacgcagcctttgactactggggccagggg<br>accctggtcaccgtctcctcaggtggaggcggttcaggcggagg<br>tggatccggcggtggcggctccggtggcggcggatctgacatcc<br>agatgacccagtctcatcctccctgtctgcatctgtaggagaca<br>gagtcaccatcacttgccgggcaagtcagagcattagcagctat<br>ctgaattggtatcagcagaaaccagggaaagcccctaagctcct<br>gatctatgctgcatccagtttgcaaagtggggtcccatcaaggt<br>tcagtggcagtggatctgggacagatttcactctcaccatcagc<br>agtctgcaacctgaagattttgcaacttactactgtcaacagag<br>ttacagtacccctctcactttcggcggaggtaccaaggtggaga<br>tcaaatcctcgagtgagcccaaatcttctgacaaaactcacaca<br>tgcccaccgtgcccagcacctgaagccgcgggtgcaccgtcagt<br>cttcctcttccccccaaaacccaaggacaccctcatgatcccgg<br>acccctgaggtcacatgcgtggtggtggacgtgagccacgaaga<br>ccctgaggtcaagttcaactggtacgtggacggcgtggaggtgc<br>ataatgccaagacaaagccgcgggaggagcagtacaacagcacg<br>taccgtgtggtcagcgtcctcaccgtcctgcaccaggactggct<br>gaatggcaaggaatacaagtgcgcggtctccaacaaagccctcc<br>cagcccccatcgagaaaaccatctccaaagccaaagggcagccc<br>cgagaaccacaggtgtacaccctgcccccatcccgggatgagct<br>gaccaagaaccaggtcagcctgacctgcctggtcaaaggcttct<br>atccaagcgacatcgccgtggagtgggagagcaatgggcagccg<br>gagaacaactacaagaccacgcctcccgtgctggactccgacgg<br>ctccttcttcctctacagcaagctcaccgtggacaagagcaggt<br>ggcagcaggggaacgtcttctcatgctccgtgatgcatgaggct<br>ctgcacaaccactacacgcagaagagcctctccctgtctccggg<br>ttccggaggagggggttcaggtgggggaggttctggcggcgggg<br>gaagcccttcacaggtgcaactggtgcagagtggacccgaggtt<br>aaaaaaccagggtcctccgttaaggttagctgcaaagcctctgg<br>ctacacattttccaggagtacaatgcactgggtgaggcaggctc<br>ctggacagggactggagtggatcgggtatatcaacccatctagc<br>gcctataccaattacaaccaaaagtttaaggaccgagttaccat<br>taccgctgacaaatccaccagtacagcttatatggagctgtcat<br>ctcttaggtccgaggacactgctgtttattactgcgctcgtcct<br>caggttcactatgactataatggttttccctactggggtcaggg<br>aaccctggtgactgtctcttctggcggtggaggcagcggtgggg<br>gtgggtctggaggcggtggcagtggcggcggaggctctgatatt<br>cagatgactcagtctcctagcactctcagcgccagcgtgggga<br>tcgtgtgacaatgacttgctccgctagcagtagtgtgtcttaca<br>tgaattggtatcagcagaagcccgggaaagcacctaagcgctgg<br>atctatgactcttccaagctggcaagtggtgtcccctcacggtt<br>ctctggctcaggttctggtactgactatactttgactatctcct<br>ccctccagcccgatgatttcgctacctattattgtcagcagtgg<br>agccgtaacccacccactttcggaggcggtaccaaagtggagat<br>caagaggtcatga | qvqlvqsgaevkkpgasv<br>kvsckasggtfssyaisw<br>vrqapgqglewmgwitph<br>ngnikyarefgqrvtmtr<br>dtststvymelslrsedt<br>avyycakdlnwnaafdyw<br>gqgtlvtvssggggsggg<br>gsggggsggggsdiqmtq<br>spsslsasvgdrvtitcr<br>asqsissylnwyqqkpgk<br>apklliyaasslqsgvps<br>rfsgsgsgtdftltissl<br>qpedfatyycqqsystpl<br>tfgggtkveiksssepks<br>sdkthtcppcpapeaaga<br>psvflfppkpkdtlmisr<br>tpevtcvvvdvshedpev<br>kfnwyvdgvevhnaktkp<br>reeqynstyrvvsvltvl<br>hqdwlngkeykcavsnka<br>lpapiektiskakgqpre<br>pqvytlppsrdeltknqv<br>sltclvkgfypsdiavew<br>esngqpennykttppvld<br>sdgsfflyskltvdksrw<br>qqgnvfscsvmhealhnh<br>ytqkslslspgsggggsg<br>gggsggggspsqvqlvqs<br>gpevkkpgssvkvsckas<br>gytfsrstmhwvrqapgq<br>glewigyinpssaytnyn<br>qkfkdrvtitadkststa<br>ymelsslrsedtavyyca<br>rpqvhydyngfpywgqgt<br>lvtvssggggsggggsgg<br>ggsggggsdiqmtqspst<br>lsasvgdrvtmtcsasss<br>vsymnwyqqkpgkapkrw<br>iydssklasgvpsrfsgs<br>gsgtdytltisslqpddf<br>atyycqqwsrnpptfggg<br>tkveikrs | SEQ ID NO: 155<br>(SEQ ID NO: 156) |
| Cris7 and<br>DRA222 VH<br>CDR1<br>(Kabat) | | RSTMH | (SEQ ID NO: 165) |
| Cris7 and<br>DRA222 VH<br>CDR2<br>(Kabat) | | YINPSSAYTNYNQKFK | (SEQ ID NO: 166) |
| Cris7 and<br>DRA222 VH<br>CDR3<br>(Kabat) | | QVHYDYNGFPY | (SEQ ID NO: 167) |
| Cris7 and<br>DRA222 VL<br>CDR1<br>(Kabat) | | SASSSVSYMN | (SEQ ID NO: 162) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| Cris7 and DRA222 VL CDR2 (Kabat) | | DSSKLAS | (SEQ ID NO: 163) |
| Cris7 and DRA222 VL CDR3 (Kabat) | | QQWSRNPPT | (SEQ ID NO: 164) |
| Cris7 and DRA222 VH CDR1 (IMGT) | | GYTFTRST | (SEQ ID NO: 171) |
| Cris7 and DRA222 VH CDR2 (IMGT) | | INPSSAYT | (SEQ ID NO: 172) |
| Cris7 and DRA222 VH CDR3 (IMGT) | | QQWSRNPPT | (SEQ ID NO: 173) |
| Cris7 and DRA222 VL CDR1 (IMGT) | | ASSSVSY | (SEQ ID NO: 168) |
| Cris7 and DRA222 VL CDR2 (IMGT) | | DSS | (SEQ ID NO: 169) |
| Cris7 and DRA222 VL CDR3 (IMGT) | | QQWSRNPPT | (SEQ ID NO: 170) |
| I2C VH CDR1 (Kabat) | | KYAMN | (SEQ ID NO: 174) |
| I2C VH CDR2 (Kabat) | | RIRSKYNNYATYYADSVK D | (SEQ ID NO: 175) |
| I2C VH CDR3 (Kabat) | | HGNFGNSYISYWAY | (SEQ ID NO: 176) |
| I2C VL CDR1 (Kabat) | | GSSTGAVTSGNYPN | (SEQ ID NO: 307) |
| I2C VL CDR2 (Kabat) | | GTKFLAP | (SEQ ID NO: 308) |
| I2C VL CDR3 (Kabat) | | VLWYSNRWV | (SEQ ID NO: 309) |
| I2C VH CDR1 (IMGT) | | GFTFNKYA | (SEQ ID NO: 179) |
| I2C VH CDR2 (IMGT) | | IRSKYNNYAT | (SEQ ID NO: 180) |

TABLE 3-continued

| Name | Nucleotide Sequence | Amino Acid Sequence | SEQ ID NOs: nucleotide (amino acid) |
|---|---|---|---|
| Binding Polypeptide Sequences and Components | | | |
| I2C VH CDR3 (IMGT) | | VRHGNFGNSYISYWAY | (SEQ ID NO: 181) |
| I2C VL CDR1 (IMGT) | | TGAVTSGNY | (SEQ ID NO: 310) |
| I2C VL CDR2 (IMGT) | | GTK | (SEQ ID NO: 177) |
| I2C VL CDR3 (IMGT) | | VLWYSNRWV | (SEQ ID NO: 178) |
| HuM291 VH CDR1 (Kabat) | | SYTMH | (SEQ ID NO: 185) |
| HuM291 VH CDR2 (Kabat) | | YINPRSGYTHYNQKLKD | (SEQ ID NO: 186) |
| HuM291 VH CDR3 (Kabat) | | SAYYDYDGFAY | (SEQ ID NO: 187) |
| HuM291 VL CDR1 (Kabat) | | SASSSVSYMN | (SEQ ID NO: 182) |
| HuM291 VL CDR2 (Kabat) | | DTSKLAS | (SEQ ID NO: 183) |
| HuM291 VL CDR3 (Kabat) | | QQWSSNPPT | (SEQ ID NO: 184) |
| HuM291 VH CDR1 (IMGT) | | GYTFISYT | (SEQ ID NO: 191) |
| HuM291 VH CDR2 (IMGT) | | INPRSGYT | (SEQ ID NO: 192) |
| HuM291 VH CDR3 (IMGT) | | ARSAYYDYDGFAY | (SEQ ID NO: 193) |
| HuM291 VL CDR1 (IMGT) | | ASSSVSY | (SEQ ID NO: 188) |
| HuM291 VL CDR2 (IMGT) | | DTS | (SEQ ID NO: 189) |
| HuM291 VL CDR3 (IMGT) | | QQWSSNPPT | (SEQ ID NO: 190) |
| TSC455 (anti-CD3) TSC394 F87Y scFv | | QVQLVQSGPEVKKPGSSV KVSCKASGYTFSRSTMHW VRQAPGQGLEWIGYINPS SAYTNYNQKFKDRVTITA DKSTSTAYMELSSLRSED TAVYYCARPQVHYDYNGF PYWGQGTLVTVSSGGGGS GGGGSGGGGSGGGGSDIQ MTQSPSTLSASVGDRVTM | (SEQ ID NO: 311) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| | | TCSASSSVSYMNWYQQKPGKAPKRWIYDSSKLASGVPSRFSGSGSGTEYTLTISSLQPDDFATYYCQQWSRNPPTFGGGTKVEIKRSSS | |
| TSC456 (anti-CD3) TSC394 E86D F87Y scFv | | QVQLVQSGPEVKKPGSSVKVSCKASGYTFSRSTMHWVRQAPGQGLEWIGYINPSSAYTNYNQKFKDRVTITADKSTSTAYMELSSLRSEDTAVYYCARPQVHYDYNGFPYWGQGTLVTVSSGGGGSGGGGSGGGGSGGGGSDIQMTQSPSTLSASVGDRVTMTCSASSSVSYMNWYQQKPGKAPKRWIYDSSKLASGVPSRFSGSGSGTDYTLTISSLQPDDFATYYCQQWSRNPPTFGGGTKVEIKRSSS | (SEQ ID NO: 312) |
| TSC455 and TSC456 variable heavy domain | | QVQLVQSGPEVKKPGSSVKVSCKASGYTFSRSTMHWVRQAPGQGLEWIGYINPSSAYTNYNQKFKDRVTITADKSTSTAYMELSSLRSEDTAVYYCARPQVHYDYNGFPYWGQGTLVTVSS | (SEQ ID NO: 159) |
| TSC455 variable light domain | | DIQMTQSPSTLSASVGDRVTMTCSASSSVSYMNWYQQKPGKAPKRWIYDSSKLASGVPSRFSGSGSGTEYTLTISSLQPDDFATYYCQQWSRNPPTFGGGTKVEIKRS | (SEQ ID NO: 157) |
| TSC456 variable light domain | | DIQMTQSPSTLSASVGDRVTMTCSASSSVSYMNWYQQKPGKAPKRWIYDSSKLASGVPSRFSGSGSGTDYTLISSLQPDDFATYYCQQSWRNPPTFGGGTKVEIKRS | (SEQ ID NO: 158) |
| DRA222 (anti-CD3) scFv | | QVQLVESGGGVVQPGRSLRLSCKASGYTFTRSTMHWVRQAPGQGLEWIGYINPSSAYTNYNQKFKDRFTISADKSKSTAFLQMDSLRPEDTGVFYCARPQVHYDYNGFPYWGQGTPVTVSSGGGGSGGGGSGGGGSAQDIQMTQSPSSLSASVGDRVTMTCSASSSVSYMNWYQQKPGKAPKRWIYDSSKLASGVPARFSGSGSGTDYTLTISSLQPEDFATYYCQQWSRNPPTFGGGTKLQITSSS | (SEQ ID NO: 313) |
| DRA222 variable heavy domain | | QVQLVESGGGVVQPGRSLRLSCKASGYTFTRSTMHWVRQAPGQGLEWIGYINPSSAYTNYNQKFKDRFTISADKSKSTAFLQMDSLRPEDTGVFYCARPQVHYDYNGFPYWGQGTPVTVSS | (SEQ ID NO: 161) |
| DRA222 variable light domain | | DIQMTQSPSSLSASVGDRVTMTCSASSSVSYMNWYQQPGKAPKRWIYDSSKLASGVPARFSGSGSGTDYTLTISSLQPEDFATYYCQQWSRNPPTFGGGTKLQITS | (SEQ ID NO: 160) |

CD123-binding proteins may comprise any of the CD123-binding domains described above. In some aspects, CD123-binding proteins comprise humanized $V_H$ or $V_L$ amino acid sequences, or both.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:2 or SEQ ID NO:4. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:2 and SEQ ID NO:4. The polypeptides may comprise an amino acid sequence that is at least about 95%, at least about 97% identical, at least about 99% or 100% identical to the amino acid sequence set forth in SEQ ID NO:2 or SEQ ID NO:4. In some embodiments, the polypeptide comprises an amino acid sequence that is that is at least about 95%, at least about 97% identical, or at least about 99% identical to the amino acid sequence set forth in SEQ ID NO:130 or SEQ ID NO:132. In some embodiments, the polypeptide comprises an amino acid sequence that is that is at least about 95%, at least about 97% identical, or at least about 99% identical to the scFv portion of the amino acid sequence set forth in SEQ ID NO:130 or SEQ ID NO:132. In certain embodiments, the polypeptide comprises or consists of an amino acid sequence set forth in SEQ ID NO:2, SEQ ID NO:4, SEQ ID NO:130, or SEQ ID NO:132.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:20. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:20. The polypeptides may comprise an amino acid sequence that is at least about 95%, at least about 97% identical, at least about 99% or 100% identical to the amino acid sequence set forth in SEQ ID NO:18 or SEQ ID NO:20. In some embodiments, the polypeptide comprises an amino acid sequence that is that is at least about 95%, at least about 97% identical, or at least about 99% identical to the amino acid sequence set forth in SEQ ID NO:134, SEQ ID NO:136, or SEQ ID NO:138. In some embodiments, the polypeptide comprises an amino acid sequence that is that is at least about 95%, at least about 97% identical, or at least about 99% identical to the scFv portion of the amino acid sequence set forth in SEQ ID NO:134, SEQ ID NO:136, or SEQ ID NO:138. In certain embodiments, the polypeptide comprises or consists of an amino acid sequence set forth in SEQ ID NO:18, SEQ ID NO:20, SEQ ID NO:134, SEQ ID NO:136, or SEQ ID NO:138.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:34. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:34. The polypeptides may comprise an amino acid sequence that is at least about 95%, at least about 97% identical, at least about 99% or 100% identical to the amino acid sequence set forth in SEQ ID NO:18 or SEQ ID NO:34. In some embodiments, the polypeptide comprises an amino acid sequence that is that is at least about 95%, at least about 97% identical, or at least about 99% identical to the amino acid sequence set forth in SEQ ID NO:140. In some embodiments, the polypeptide comprises an amino acid sequence that is that is at least about 95%, at least about 97% identical, or at least about 99% identical to the scFv portion of the amino acid sequence set forth in SEQ ID NO:140. In certain embodiments, the polypeptide comprises or consists of an amino acid sequence set forth in SEQ ID NO:18, SEQ ID NO:34, or SEQ ID NO:140.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:42. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:42. The polypeptides may comprise an amino acid sequence that is at least about 95%, at least about 97% identical, at least about 99% or 100% identical to the amino acid sequence set forth in SEQ ID NO:18 or SEQ ID NO:42. In some embodiments, the polypeptide comprises an amino acid sequence that is that is at least about 95%, at least about 97% identical, or at least about 99% identical to the amino acid sequence set forth in SEQ ID NO:142. In some embodiments, the polypeptide comprises an amino acid sequence that is that is at least about 95%, at least about 97% identical, or at least about 99% identical to the scFv portion of the amino acid sequence set forth in SEQ ID NO:142. In certain embodiments, the polypeptide comprises or consists of an amino acid sequence set forth in SEQ ID NO:18, SEQ ID NO:42, or SEQ ID NO:142.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:50 or SEQ ID NO:52. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:50 and SEQ ID NO:52. The polypeptides may comprise an amino acid sequence that is at least about 95%, at least about 97% identical, at least about 99% or 100% identical to the amino acid sequence set forth in SEQ ID NO:50 or SEQ ID NO:52. In some embodiments, the polypeptide comprises an amino acid sequence that is that is at least about 95%, at least about 97% identical, or at least about 99% identical to the amino acid sequence set forth in SEQ ID NO:144. In some embodiments, the polypeptide comprises an amino acid sequence that is that is at least about 95%, at least about 97% identical, or at least about 99% identical to the scFv portion of the amino acid sequence set forth in SEQ ID NO:144. In certain embodiments, the polypeptide comprises or consists of an amino acid sequence set forth in SEQ ID NO:50, SEQ ID NO:52, or SEQ ID NO:144.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:66 or SEQ ID NO:68. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:66 and SEQ ID NO:68. The polypeptides may comprise an amino acid sequence that is at least about 95%, at least about 97% identical, at least about 99% or 100% identical to the amino acid sequence set forth in SEQ ID NO:66 or SEQ ID NO:68. In some embodiments, the polypeptide comprises an amino acid sequence that is that is at least about 95%, at least about 97% identical, or at least about 99% identical to the amino acid sequence set forth in SEQ ID NO:146. In some embodiments, the polypeptide comprises an amino acid sequence that is that is at least about 95%, at least about 97% identical, or at least about 99% identical to the scFv portion of the amino acid sequence set forth in SEQ ID NO:146. In certain embodiments, the polypeptide comprises or consists of an amino acid sequence set forth in SEQ ID NO:66, SEQ ID NO:68, or SEQ ID NO:146.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:82 or SEQ ID NO:84. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:82 and SEQ ID NO:84. The polypeptides may comprise an amino acid sequence that is at least about 95%, at least about 97% identical, at least about 99% or 100% identical to the amino acid sequence set forth in SEQ ID NO:82 or SEQ ID NO:84. In some embodiments, the polypeptide comprises an amino acid sequence that is that is at least about 95%, at least about 97% identical, or at least about 99% identical to the amino acid sequence set forth in SEQ ID NO:148. In some embodiments, the polypeptide comprises an amino acid sequence that is that is at least about 95%, at least about 97% identical, or at least about 99% identical to the scFv portion of the amino acid sequence set forth in SEQ ID NO:148. In certain embodiments, the polypeptide comprises or consists of an amino acid sequence set forth in SEQ ID NO:82, SEQ ID NO:84, or SEQ ID NO:148.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:98. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:98. The polypeptides may comprise an amino acid sequence that is at least about 95%, at least about 97% identical, at least about 99% or 100% identical to the amino acid sequence set forth in SEQ ID NO:18 or SEQ ID NO:150. In some embodiments, the polypeptide comprises an amino acid sequence that is that is at least about 95%, at least about 97% identical, or at least about 99% identical to the amino acid sequence set forth in SEQ ID NO:150. In some embodiments, the polypeptide comprises an amino acid sequence that is that is at least about 95%, at least about 97% identical, or at least about 99% identical to the scFv portion of the amino acid sequence set forth in SEQ ID NO:140. In certain embodiments, the polypeptide comprises or consists of an amino acid sequence set forth in SEQ ID NO:18, SEQ ID NO:98, or SEQ ID NO:150.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:106. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:106. The polypeptides may comprise an amino acid sequence that is at least about 95%, at least about 97% identical, at least about 99% or 100% identical to the amino acid sequence set forth in SEQ ID NO:18 or SEQ ID NO:106. In some embodiments, the polypeptide comprises an amino acid sequence that is that is at least about 95%, at least about 97% identical, or at least about 99% identical to the amino acid sequence set forth in SEQ ID NO:152. In some embodiments, the polypeptide comprises an amino acid sequence that is that is at least about 95%, at least about 97% identical, or at least about 99% identical to the scFv portion of the amino acid sequence set forth in SEQ ID NO:152. In certain embodiments, the polypeptide comprises or consists of an amino acid sequence set forth in SEQ ID NO:18, SEQ ID NO:106, or SEQ ID NO:152.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:114. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:114. The polypeptides may comprise an amino acid sequence that is at least about 95%, at least about 97% identical, at least about 99% or 100% identical to the amino acid sequence set forth in SEQ ID NO:18 or SEQ ID NO:114. In some embodiments, the polypeptide comprises an amino acid sequence that is that is at least about 95%, at least about 97% identical, or at least about 99% identical to the amino acid sequence set forth in SEQ ID NO:154. In some embodiments, the polypeptide comprises an amino acid sequence that is that is at least about 95%, at least about 97% identical, or at least about 99% identical to the scFv portion of the amino acid sequence set forth in SEQ ID NO:154. In certain embodiments, the polypeptide comprises or consists of an amino acid sequence set forth in SEQ ID NO:18, SEQ ID NO:114, or SEQ ID NO:154.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:122. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:122. The polypeptides may comprise an amino acid sequence that is at least about 95%, at least about 97% identical, at least about 99% or 100% identical to the amino acid sequence set forth in SEQ ID NO:18 or SEQ ID NO:122. In some embodiments, the polypeptide comprises an amino acid sequence that is that is at least about 95%, at least about 97% identical, or at least about 99% identical to the amino acid sequence set forth in SEQ ID NO:156. In some embodiments, the polypeptide comprises an amino acid sequence that is that is at least about 95%, at least about 97% identical, or at least about 99% identical to the scFv portion of the amino acid sequence set forth in SEQ ID NO:156. In certain embodiments, the polypeptide comprises or consists of an amino acid sequence set forth in SEQ ID NO:18, SEQ ID NO:122, or SEQ ID NO:156.

The polypeptides disclosed herein may have improved characteristics compared to other CD123-binding domains or polypeptides. For example, a CD123-binding domain or polypeptide may exhibit a reduced isoelectric point compared to the isoelectric point of a different CD123-binding domain or polypeptide. "Isoelectric point" or "pI" is the pH at which net charge is zero. The isoelectric point of a protein may be measured by any suitable method, e.g., analytical capillary isoelectric focusing chromatography.

A CD123-binding domain or protein disclosed herein may bind to CD123 (e.g., human CD123) with a higher affinity than the parent antibody.

In one embodiment of the invention, the recombinant polypeptide comprises, in order from amino to carboxyl terminus, (i) a human or humanized CD123-binding domain, (ii) a hinge region, (iii) an immunoglobulin constant region, (iv) a carboxyl-terminus linker, and (v) a human or humanized second binding domain that specifically binds a T-cell, CD3, CD3ε or a T-cell receptor (TCR) complex or a component of a T-cell receptor complex, wherein the human or humanized CD123-binding domain comprises an amino acid sequence at least about 80%, at least about 90%, at least about 95%, at least about 96%, at least about 97%, at least about 98%, at least about 99% or at least about 99.5% identical to SEQ ID NO:2 and SEQ ID NO:4 and wherein the human or humanized second binding domain that specifically binds a T-cell, CD3, CD3ε or a T-cell receptor (TCR) complex or a component of a T-cell receptor complex comprises an amino acid sequence at least about 80%, at least about 90%, at least about 95%, at least about 96%, at least about 97%, at least about 98%, at least about 99% or at least about 99.5% identical to SEQ ID NO:311 or SEQ ID NO:312.

In one embodiment of the invention, the recombinant polypeptide does not contain a CD123-binding domain derived from murine antibody 12F1 (SEQ ID Nos: 195 and 197). For instance, in one embodiment, the CD123-binding domain does not comprise a heavy chain or light chain variable domain that is significantly identical to a heavy chain or light chain variable domain of 12F1 (e.g., is not 95% identical or greater to 12F1 heavy and light chain variable domains) or does not contain all six CDRs as contained in murine 12F1. In one embodiment of the invention, the CD123-binding domain does not compete for binding to CD123 with murine antibody 12F1 (SEQ ID NOs:195 and 197). In one embodiment of the invention, the recombinant polypeptide is cross-reactive to cynomolgous CD123 whereas antibody 12F1 (and humanized derivatives thereof) is not cross-reactive to cynomolgous CD123.

TABLE 4

12F1 Murine Antibody Sequences

| Name | Nucleotide Sequence | Amino Acid Sequence | SEQ ID Nos: nucleotide (amino acid) |
|---|---|---|---|
| 12F1 murine variable light chain domain | gacatcatgatgtcccagtcccccctcctccctg gccgtgtccgtgggcgagaagttcaccatgac ctgcaagtcctcccagtccctgttcttcggctcc acccagaagaactacctggcctggtaccagca gaagcccggccagtcccccaagctgctgatct actgggcctccacccgggagtccggcgtgccc | dimmsqspsslavsvgekftmtckssqs lffgstqknylawyqqkpgqspklliywa stresgvpdrftgsgsgtdftlaissvmpe dlavyycqqyynypwtfgggtkleik | SEQ ID NO: 194 (SEQ ID NO: 195) |

TABLE 4-continued

| 12F1 Murine Antibody Sequences | | | |
|---|---|---|---|
| Name | Nucleotide Sequence | Amino Acid Sequence | SEQ ID Nos: nucleotide (amino acid) |
| | gaccggttcaccggctccggctccggcaccga cttcaccctggccatctcctccgtgatgcccga ggacctggccgtgtactactgccagcagtacta caactacccctggaccttcggcggcggcacca agctggagatcaag | | |
| 12F1 murine variable heavy chain domain | cagctgcaggagtccggccccggcct ggtgaagccctcccagtccctgtccctg acctgctccgtgaccgactactccatca cctccggctactactggaactggattcg gcagttccccggcaacaagctggagtg gatgggctacatctcctacgacggctcc aacaactacaacccctccctgaagaac cggatctccatcacccgggacacctcc aagaaccagttcttcctgaagctgtcctc cgtgaccaccgaggacaccgccacct actactgctcccggggcgagggcttct acttcgactcctggggccagggcacca ccctgaccgtgtcctcg | vqlqesgpglvkpsqslsltcsvtd ysitsgyywnwirqfpgnklew mgyisydgsnnynpslknrisitr dtsknqfflklssvttedtatyycsr gegfyfdswgqgttltvss | SEQ ID NO: 196 (SEQ ID NO: 197) |

In one embodiment, the polypeptide of the invention (including in dimer form) binds to human CD123 and non-human primate (NHP) CD123 with specificity. In another embodiment of the invention, the polypeptide binds to cynomolgus monkey CD123.

The disclosure also includes nucleic acids (e.g., DNA or RNA) encoding CD123-binding domains and polypeptides described herein. Nucleic acids of the disclosure include nucleic acids having a region that is substantially identical to a polynucleotide as listed in Table 3, infra. In certain embodiments, a nucleic acid in accordance with the present disclosure has at least 80%, typically at least about 90%, and more typically at least about 95% or at least about 98% identity to a polypeptide-encoding polynucleotide as listed in Table 3. Nucleic acids of the disclosure also include complementary nucleic acids. In some instances, the sequences will be fully complementary (no mismatches) when aligned. In other instances, there can be up to about a 20% mismatch in the sequences. In some embodiments of the disclosure are provided nucleic acids encoding both first and second polypeptide chains of a heterodimeric CD123-binding protein of the disclosure. The nucleic acid sequences provided herein can be exploited using codon optimization, degenerate sequence, silent mutations, and other DNA techniques to optimize expression in a particular host, and the present disclosure encompasses such sequence modifications.

The invention includes a recombinant polypeptide encoded by a nucleic acid comprising at nucleic acid sequence at least about 80%, at least about 85%, at least about 90%, at least about 95%, at least about 96%, at least about 97%, at least about 98%, at least about 99% and at least $10^{0}$% identical to the nucleic acid sequence of SEQ ID NO:1 and/or SEQ ID NO:3. The invention includes a recombinant polypeptide encoded by a nucleic acid comprising at nucleic acid sequence at least about 80%, at least about 85%, at least about 90%, at least about 95%, at least about 96%, at least about 97%, at least about 98%, at least about 99% and at least $10^{0}$% identical to the nucleic acid sequence of SEQ ID NO:131.

The disclosure relates to an isolated nucleic acid molecule encoding CD123-binding domains, proteins and polypeptides (or portions thereof) described herein, wherein said nucleic acid molecule comprises a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

Polynucleotide molecules comprising a desired polynucleotide sequence are propagated by placing the molecule in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like. The disclosure relates to an expression vector comprising a nucleic acid segment, wherein said nucleic acid segment may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, NY, 2001), and Ausubel et al., *Short Protocols in Molecular Biology* (4th ed., John Wiley & Sons, 1999). For instance, the recombinant polypeptides of the invention can be expressed from CHO and HEK293 cells.

For example, for recombinant expression of a homodimeric CD123-binding protein comprising two identical CD123-binding polypeptides as described herein, an expression vector will generally include a nucleic acid segment encoding the CD123-binding polypeptide, operably linked to a promoter. For recombinant expression of a heterodimeric CD123-binding protein, comprising different first and second polypeptide chains, the first and second polypeptide chains can be co-expressed from separate vectors in the host cell for expression of the entire heterodimeric protein. Alternatively, for the expression of heterodimeric CD123-binding proteins, the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding CD123-binding protein.

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830). In certain variations, a secretory signal sequence for use in accordance with the present disclosure has the amino acid sequence MEAPAQLLFLLLLWLPDTTG (SEQ ID NO:198).

Cultured mammalian cells are suitable hosts for production of recombinant proteins for use within the present disclosure. Methods for introducing exogenous DNA into mammalian host cells include calcium phosphate-mediated transfection (Wigler et al., *Cell* 14:725, 1978; Corsaro and Pearson, Somatic Cell Genetics 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, UT); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Virginia. Strong transcription promoters can be used, such as promoters from SV- or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, NJ, 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, MD). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, a recombinant virus can be used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, CA). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells can be utilized according to the methods of Mcknight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

CD123-binding proteins may be purified by conventional protein purification methods, typically by a combination of chromatographic techniques. See generally *Affinity Chromatography: Principles* & Methods (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

The present disclosure provides methods for treating a subject with a disorder characterized by over-expression of CD123. Generally, such methods include administering to a subject in need of such treatment the polypeptide or CD123-binding protein as described herein. In some embodiments, the CD123-binding protein comprises at least one effector function selected from antibody-dependent cell-mediated cytotoxicity (ADCC) and complement-dependent cytotoxicity (CDC), such that the CD123-binding protein induces ADCC and/or CDC against CD123-expressing cells in the subject.

In other embodiments, where the polypeptide comprises a second binding domain that specifically binds a T-cell (e.g., to a TCR complex or component thereof, such as CD3E), the polypeptide or CD123-binding protein induces redirected T-cell cytotoxicity (RTCC) against CD123-expressing cells in the subject. In some embodiments, RTCC polypeptides (e.g., polypeptides that induce RTCC) comprise a modified constant domain to reduce or remove ADCC and/or CDC activity.

In certain variations of the method, the disorder is a cancer. Exemplary cancers amenable to treatment in accordance with the present disclosure include, for example, acute myeloid leukemia (AML), B-lymphoid leukemia, blastic plasmocytoid dendritic neoplasm (BPDCN), hairy cell leukemia, myelodysplastic syndrome, acute lymphoblastic leukemia, refractory anemia with excess blasts, chronic myeloid leukemia and Hodgkin's lymphoma.

The disclosure also encompasses a use of a CD123-binding polypeptide for the manufacture of a medicament for treatment of a disorder (e.g., cancer) characterized by over-expression of CD123. In one embodiment, the CD123-binding polypeptide has RTCC activity, e.g., it comprises an anti-CD123 and anti-CD3 binding domain. In one embodiment, the disclosure includes a CD123-binding polypeptide for use in treating a disorder (e.g., cancer) characterized by over-expression of CD123.

In one embodiment, the disclosure provides a method of treating a patient diagnosed with acute myeloid leukemia, B-lymphoid leukemia, blastic plasmocytoid dendritic neoplasms, hairy cell leukemia, myelodysplastic syndrome, acute lymphoblastic leukemia, refractory anemia with excess blasts, chronic myeloid leukemia, Hodgkin's lymphoma or other cancer associated with the expression of CD123 by administering a therapeutically effective amount of a pharmaceutical composition comprising a recombinant polypeptide at least about 80%, at least about 85%, at least about 90%, at least about 95%, at least about 96%, at least about 97%, at least about 98%, at least about 99% or at least about 100% identical to the amino acid sequence of SEQ ID NO:130 or 132.

In some embodiments, the disclosure provides a method of treating a patient with a cancer, comprising administering to the patient a CD123-binding polypeptide comprising the amino acid sequence set forth in SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, or SEQ ID NO:156.

In some embodiments, for treatment methods and uses described herein, a polypeptide of the invention is delivered in a manner consistent with conventional methodologies associated with management of the disease or disorder for which treatment is sought. In accordance with the disclosure herein, a therapeutically effective amount of the polypeptide or CD123-binding protein in dimer form is administered to a subject in need of such treatment for a time and under conditions sufficient to prevent or treat the disease or disorder.

Subjects for administration of polypeptides as described herein include patients at high risk for developing a particular disorder characterized by CD123 over-expression as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting CD123-expressing cells.

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the disclosure, accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T-cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, CD123-expressing cells can be implemented as an independent treatment program or as a follow-up, adjunct, or coordinate treatment regimen to other treatments.

For administration, the polypeptide of the invention (e.g., in dimer form) may be formulated as a pharmaceutical composition. A pharmaceutical composition may comprise: (i) a CD123-binding polypeptide; and (ii) a pharmaceutically acceptable carrier, diluent or excipient. A pharmaceutical composition comprising a CD123-binding protein can be formulated according to known methods to prepare pharmaceutically useful compositions, whereby the therapeutic molecule is combined in a mixture with a pharmaceutically acceptable carrier, diluent or excipient. A carrier is said to be a "pharmaceutically acceptable carrier" if its administration can be tolerated by a recipient patient. Sterile phosphate-buffered saline is one example of a pharmaceutically acceptable carrier. Other suitable carriers, diluents or excipients are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc.

A pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising a polypeptide of the invention may be administered to a subject in a therapeutically effective amount. According to the methods of the present disclosure, a CD123-binding protein can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration.

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering a CD123-binding protein as described herein. For administration of the CD123-binding protein, a dosage may range from, for instance, about 0.1 μg to 100 mg/kg or 1 μg/kg to about 50 mg/kg, or 10 μg to 5 mg/kg of the subject's body weight.

Dosage of the pharmaceutical composition can be varied by the attending clinician to maintain a desired concentration at a target site.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measureable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, MD.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

The disclosure will be further clarified by the following examples, which are intended to be purely exemplary of the disclosure and in no way limiting.

EXAMPLES

Example 1: Generation of Humanized Variants of Anti-CD123 Antibodies and Construction of Monospecific and Bispecific CD123-Binding Molecules Isolation of Monospecific CD123-Binding Molecules by Phage Display anti-CD123-specific scFv binding molecules were isolated from SuperHuman library, Distributed Bio Inc. (South San Francisco, CA), using soluble phage display panning technique against biotinylated recombinant CD123 protein (SEQ ID NO:200) following Distributed Bio protocols and as described previously by Ayriss, J et al, (2007) *J Proteome Res*., p 1072-82. Binding specificity of clones was characterized by ELISA using CD123 and unrelated recombinant protein with identical purification tag. Flow cytometry using HEK293 cells transfected with human and cynomolgus monkey variants of CD123, SEQ ID NO: 201 and SEQ ID NO:203, respectively, was used to identify clones binding to CD123 in the context of cell surface. Nucleotide and amino acid sequences of binding molecules referred to in these Examples can be found in Table 5.

Isolation of Monospecific CD123-Binding Molecules by Hybridoma Generation

Anti-CD123-specific antibodies were isolated from a hybridoma library generated after immunizing OmniMice (Ligand Inc, San Diego, CA) with recombinant human CD123 ectodomain (SEQ ID NO:200). Binding specificity of individual clones was confirmed by testing binding using flow cytometry on HEK293 cells transfected with human and cynomolgus monkey variants of CD123, SEQ ID NO:201 and 203, respectively, and further confirmed by lack of binding to parental HEK293 cells. Sequences were obtained by RT-PCR using the OneStep RT-PCR Kit (QIAGEN Inc., Valencia, CA), following a modified version of the manufacturer's protocol. Briefly, cells from each clone were scraped from frozen cell bank vials and resuspended in RNase-free water. This cell suspension was then used as template in a RT-PCR reaction using sets of gene-specific primers that flank the heavy, kappa or lambda variable domains. Sequencing was performed using a reverse primer in the constant domains for each of these fragments. Sequences were then converted to scFv format by amplifying the variable domains using primers that contain overlapping sequences and were assembled into a mammalian expression vector using NEBuilder® HiF DNA Assembly Cloning Kit (New England Biolabs, Beverly, MA).

TABLE 5

CD123 sequences used for immunization and screening

| Name | Nucleotide Sequence | Amino Acid Sequence | SEQ ID NOs: nucleotide (amino acid) |
|---|---|---|---|
| human CD123 ectodomain, with Avi-3xFLAG-His affinity tag TRI032 | atggaagcaccagcgcagcttctcttcctcctgctactctggctcccagat<br>accaccggtaaggaggaccccaacccccccatcaccaacctgaggatga<br>aggccaaggcccagcagctgacctgggacctgaacaggaacgtgacag<br>acatcgaatgcgtgaaggatgccgactacagcatgcccgccgtgaacaa<br>ctcctactgccagttcggcgccatcagcctgtgcgaggtgacaaactaca<br>ccgtgagagtggccaaccccccttcagcacctggatcctgtttcccgaga<br>acagcggcaaaccctgggctggcgctgagaacctgacctgctggatccac<br>gacgtggactttctgtcctgcagctgggctgtgggacccggagctcctgcc<br>gatgtgcagtacgacctgtacctgaatgtggccaacagaagacagcagt<br>acgagtgcctgcattacaagaccgacgcccagggaaccaggatcggctg<br>caggtttgatgacatcagcaggctgtcctccggcagccagtccagccaca<br>tcctggtgagaggcagatccgccgccttcggcattccctgcacagacaag | kedpnppitnlrmkaka<br>qqltwdlnrnvtdiecvk<br>dadysmpavnnsycqf<br>gaislcevtnytvrvanp<br>pfstwilfpensgkpwa<br>gaenltcwihdvdflscs<br>wavgpgapadvqydly<br>lnvanrrqqyeclhyktd<br>aqgtrigcrfddisrlssgs<br>qsshilvrgrsaafgipct<br>dkfvvfsqieiltppnmt<br>akcnkthsfmhwkmr | SEQ ID NO: 199 (SEQ ID NO: 200) |

TABLE 5-continued

CD123 sequences used for immunization and screening

| Name | Nucleotide Sequence | Amino Acid Sequence | SEQ ID NOs: nucleotide (amino acid) |
|---|---|---|---|
| | ttcgtcgtcttcagccagatcgagattctgacccccccaacatgaccgcc aagtgtaacaagacccacagcttcatgcactggaagatgaggagccact tcaacaggaagttcaggtacgagctccagatccagaagaggatgcagcc cgtgatcaccgagcaggtgagggacaggacatccttccagctgctgaatc ccggcacatacaccgtgcagatcagggccagggaaagggtgtacgagtt cctgtccgcctggagcacccccagaggttcgagtgtgaccaggaggag ggagccaataccagggcctggagatcctcgagtctcaacgatatttttga agcccaaaaaattgagtggcatgaagattacaaggacgatgacgacaa agactataaggacgacgacgataaggattacaaggatgacgatgataag caccatcatcatcaccatcaccaccaccactga | shfnrkfryelqiqkrmq pviteqvrdrtsfqllnpg tytvqirarervyeflsaw stpqrfecdqeegantr awrssslndifeaqkie whedykddddkdykd dddkdykddddkhhh hhhhhhh | |
| Full-length human CD123 sequence, isoform 2 TRI074 | atggtcctcctttggctcacgctgctcctgatcgccctgccctgtctcctgca aacgaaggaaggtgggaagccttgggcaggtgcggagaatctgacctgc tggattcatgacgtggatttcttgagctgcagctgggcggtaggcccgggg gcccccgcggacgtccagtacgacctgtacttgaacgttgccaacaggcg tcaacagtacgagtgtcttcactacaaaacggatgctcagggaacacgta tcgggtgtcgtttcgatgacatctctcgactctccagcggttctcaaagttc ccacatcctggtgcggggcaggagcgcagccttcggtatcccctgcacag ataagtttgtcgtcttttcacagattgagatattaactccacccaacatgac tgcaaagtgtaataagacacattcctttatgcactggaaaatgagaagtc atttcaatcgcaaatttcgctatgagcttcagatacaaaagagaatgcag cctgtaatcacagaacaggtcagagacagaacctccttccagctactcaa tcctggaacgtacacagtacaaataagagcccgggaaagagtgtatgaa ttcttgagcgcctggagcacccccagcgcttcgagtgcgaccaggagga gggcgcaaacacacgtgcctggcggacgtcgctgctgatcgcgctgggg acgctgctggccctggtctgtgtcttcgtgatctgcagaaggtatctggtga tgcagagactctttccccgcatccctcacatgaaagaccccatcggtgaca gcttccaaaacgacaagctggtggtctgggaggcgggcaaagccggcct ggaggagtgtctggtgactgaagtacaggtcgtgcagaaaactacgcgt acgcggccgctcgagcagaaactcatctcagaagaggatctggcagcaa atgatatcctggattacaaggatgacgacgataaggtttaa | ggkpwagaenltcwih dvdflscswavgpgapa dvqydlylnvanrrqqy eclhyktdaqgtrigcrfd disrlssgsqsshilvrgrs aafgipctdkfvvfsqieil tppnmtakcnkthsfm hwkmrshfnrkfryelq iqkrmqpviteqvrdrts fqllnpgtytvqirarerv yeflsawstpqrfecdq eegantrawrtsllialgtl lalvcvfvicrrylvmqrlf priphmkdpigdsfqn dklwweagkagleecl vtevqvvqkttrtrpleq kliseedlaandildykd dddkv | SEQ ID NO: 201 (SEQ ID NO: 202) |
| Full-length cynomolgus CD123 sequence, isoform 1 TRI114 | atggaagccccccgcccagctgctcttcctgctgctcctgtggctgcctgac accaccggcaaggaagaccccaatgccccccatcaggaacctgagaatga aggagaaggcccagcagctcatgtgggatctgaacaggaacgtgaccga cgtggagtgtatcaagggcaccgactactccatgcccgccatgaataaca gctattgccagttcggcgccatcagcctgtgcgaggtcaccaactacacc gtgagagtggccagcccccccttctccacctggattctgttccctgagaac agcggcacccctagggctggcgctgagaatctgacatgctgggtccatga cgtggacttcctgagctgcagctgggtggtgggacctgctgctcccgctga cgtgcagtacgatctgtatctgaacaaccccaactcccacgagcagtaca ggtgcctgcactacaagacagacgctagaggcacccagatcggctgcag gttcgatgatatcgcccctctgagcaggggatcccagagctcccatatcct ggtgaggggcaggtccgccgctgtgagcattccttgcaccgacaagttcg tcttcttcagccagatcgagaggctgacccccctaacatgacaggcgag tgcaacgagacccacagcttcatgcactggaagatgaagagccatttcaa caggaaattcaggtacgaactgaggattcagaagagaatgcagcccgtg aggacagagcaggtgagggatacaaccagcttccagctgcccaatcctg gcacctataccgtgcagatcagggctagagagaccgtgtacgagtttctg tccgcctggagcacccccagaggtttgaatgtgaccaggaggagggag cctccagcagggcttggagaaccagcctcctcatcgccctgggcacactg ctggctctgctgtgtgtgttcctgatctgcagaaggtacctggtgatgcaga ggctcttccctaggattccccacatgaaggaccccatcggcgacaccttcc agcaggacaaactggtggtgtgggaagccggaaaggccggcctggagg aatgcctcgtgtccgaggtgcaggtggtggagaagacctaa | kedpnapirnlrmkeka qqlmwdlnrnvtdveci kgtdysmpamnnsyc qfgaislcevtnytvrvas ppfstwilfpensgtpra gaenltcwvhdvdflscs wvvgpaapadvqydly Innpnsheqyrclhykt dargtqigcrfddiaplsr gsqsshilvrgrsaavsip ctdkfvffsqierltppn mtgecnethsfmhwk mkshfnrkfryelriqkr mqpvrteqvrdttsfql pnpgtytvqiraretvye flsawstpqrfecdqee gassrawrtsllialgtllal Icvflicrrylvmqrlfpri phmkdpigdtfqqdkl vvweagkagleeclvse vqvvekt | SEQ ID NO: 203 (SEQ ID NO: 204) |

Preparation of Bispecific CD123-Binding Molecules

Bispecific CD123-binding molecules targeting CD123 and CD3 epsilon, TRI129 (SEQ ID NO:129 (nucleic acid), SEQ ID NO:130 (amino acid)); TRI130 (SEQ ID NO:131 (nucleic acid), SEQ ID NO:132 (amino acid)); TRI1123 (SEQ ID NO:133 (nucleic acid), SEQ ID NO:134 (amino acid)); TRI124 (SEQ ID NO:135 (nucleic acid), SEQ ID NO:136 (amino acid)); TRI137 (SEQ ID NO:137 (nucleic acid), SEQ ID NO:138 (amino acid)); TRI125 (SEQ ID NO:139 (nucleic acid), SEQ ID NO:140 (amino acid)); TRI126 (SEQ ID NO:141 (nucleic acid), SEQ ID NO:142 (amino acid)); TRI127 (SEQ ID NO:143 (nucleic acid), SEQ ID NO:144 (amino acid)); TRI134 (SEQ ID NO:145 (nucleic acid), SEQ ID NO:146 (amino acid)); TRI128 (SEQ ID NO:147 (nucleic acid), SEQ ID NO:148 (amino acid)); TRI131 (SEQ ID NO:149 (nucleic acid), SEQ ID NO:150 (amino acid)); TRI132 (SEQ ID NO:151 (nucleic acid), SEQ ID NO:152 (amino acid)); TRI138 (SEQ ID NO:153 (nucleic acid), SEQ ID NO:154 (amino acid)); and TRI139 (SEQ ID NO:155 (nucleic acid), SEQ ID NO:156 (amino acid)), were made using standard molecular biology techniques, starting with existing bispecific binding molecules as templates and using the methods generally disclosed in, e.g., PCT Application Publication No. WO 2007/146968, U.S. Patent Application Publication No. 2006/0051844, PCT Application Publication No. WO 2010/040105, PCT Application Publication No. WO 2010/

003108, and U.S. Pat. No. 7,166,707 (see also Table 3). Insertion of the N-terminal anti-CD123 scFv binding domain was accomplished through digestion of the parental template and scFv insert with the restriction enzymes HindIII and XhoI, desired fragments were identified and isolated by agarose gel purification, and ligated. Insertion of the C-terminal anti-CD3 epsilon scFv binding domain was accomplished through digestion of the parental template and scFv insert with the restriction enzymes EcoRI and NotI, desired fragments were identified and isolated by agarose gel purification, and ligated.

Assembly of constructs with human scFv domains was accomplished by a three piece ligation using a HindIII/BamHI fragment, a BamHI/XhoI fragment, and a destination vector cut with HindIII/XhoI. This was used to produce the gene sequences corresponding to the humanized bispecific molecules shown in Table 4.

TABLE 6

Composition of Initial Humanized Constructs

| Construct ID | scFv Orientation | Nucleotide SEQ ID NO | Amino acid SEQ ID NO |
|---|---|---|---|
| TRI129 | VHVL | 129 | 130 |
| TRI130 | VLVH | 131 | 132 |
| TRI123 | VHVL | 133 | 134 |
| TRI124 | VLVH | 135 | 136 |
| TRI139 | VHVL | 155 | 156 |
| TRI137 | VHVL | 137 | 138 |
| TRI125 | VHVL | 139 | 140 |
| TRI126 | VHVL | 141 | 142 |
| TRI127 | VLVH | 143 | 144 |
| TRI131 | VHVL | 149 | 150 |
| TRI132 | VHVL | 151 | 152 |
| TRI134 | VHVL | 145 | 146 |
| TRI128 | VHVL | 147 | 148 |
| TRI138 | VHVL | 153 | 154 |

Expression and Purification of CD123-Binding Molecules and Antibodies

Bispecific CD123-binding molecules disclosed herein were produced by both transient transfection of human HEK293 cells and, in some instances, also stable transfection of CHO cells. Transfected cells were purified from cell culture supernatants by Protein A affinity chromatography. If aggregates were detected after affinity chromatography, secondary size exclusion chromatography was also performed to ensure homogeneity of the protein.

Example 2: Binding of CD123-Binding Molecules to CD123(+) Cell Lines

To confirm that binding activity to CD123 on the surface of cancer cells was retained anti-CD123×anti-CD3ε molecules and cross-reactivity to cynomolgus CD123, flow cytometry was used to quantitate binding of constructed CD123-binding molecules to cell lines expressing CD123.

Binding of Monospecific and Bispecific Proteins to CD123 (+) Cell Lines

Binding studies on the CD123(+) Molm-13 (Matsuo, Y et al, 1997, Leukemia 11, 1469-1477.) cancer cell line and cynomolgus CD123 expressing CHO cells were performed by standard flow cytometry-based staining procedures. The Molm-13 cell line was obtained from DSMZ (Braunschweig, Germany). The Molm-13 cell line was cultured according to the provided protocols. Chinese hamster ovary (CHO) cells stably expressing the full length cynomolgus CD123 protein were developed in-house. A typical experiment would label 100,000 cells per well, in 96-well plates, with a range of 1,000 nM to 0.012 nM binding molecule in 100 μl of PBS buffer with 0.2% BSA and 2 mM EDTA, for 30 min on ice, followed by washes and incubation with PE-labeled minimum cross species reactive secondary antibody, goat anti-human IgG Fcγ, F(ab')2 (Jackson Laboratory) for 30 minutes on ice. Signal from bound molecules was detected using a LSR-II™ flow cytometer (BD Biosciences) and analyzed by FlowJo flow cytometry analysis software. Mean fluorescence intensity (MFI) of bound molecules on cells was determined after exclusion of doublets. Nonlinear regression analysis to determine EC50 values was performed in GraphPad Prism 7® graphing and statistics software.

FIGS. 1A, 1B, 1C and 1D show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in three independent experiments to the CD123 (+) Molm-13 human tumor cell line. These experiments utilized bispecific constructs prepared from transiently transfected HEK293 cells. Four of the molecules demonstrated comparable maximum levels of binding at saturating concentrations. Observed EC50 values for TRI125, TRI129, TRI130 and TRI139 were between 2-10 nM. Experiments were repeated for TRI129 and TRI130 from stably transfected CHO cells with similar results (data not shown).

Figure 2A:
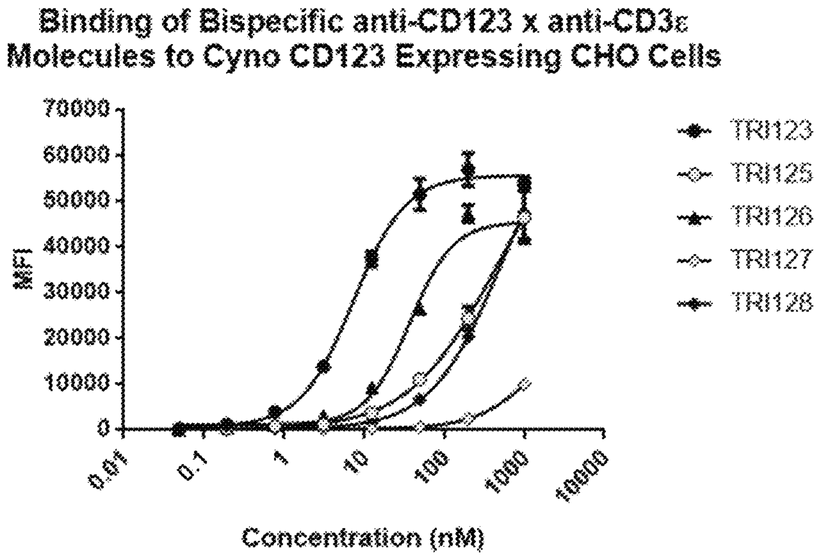
FIG. 2A-FIG. 2C show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments to CHO cells stably expressing cynomolgus CD123 protein.
Figure 2B:
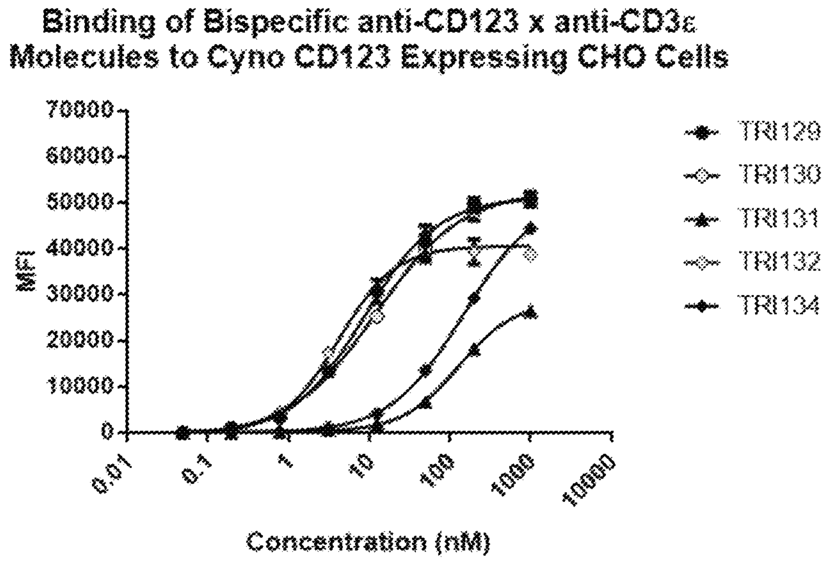
Figure 2C:
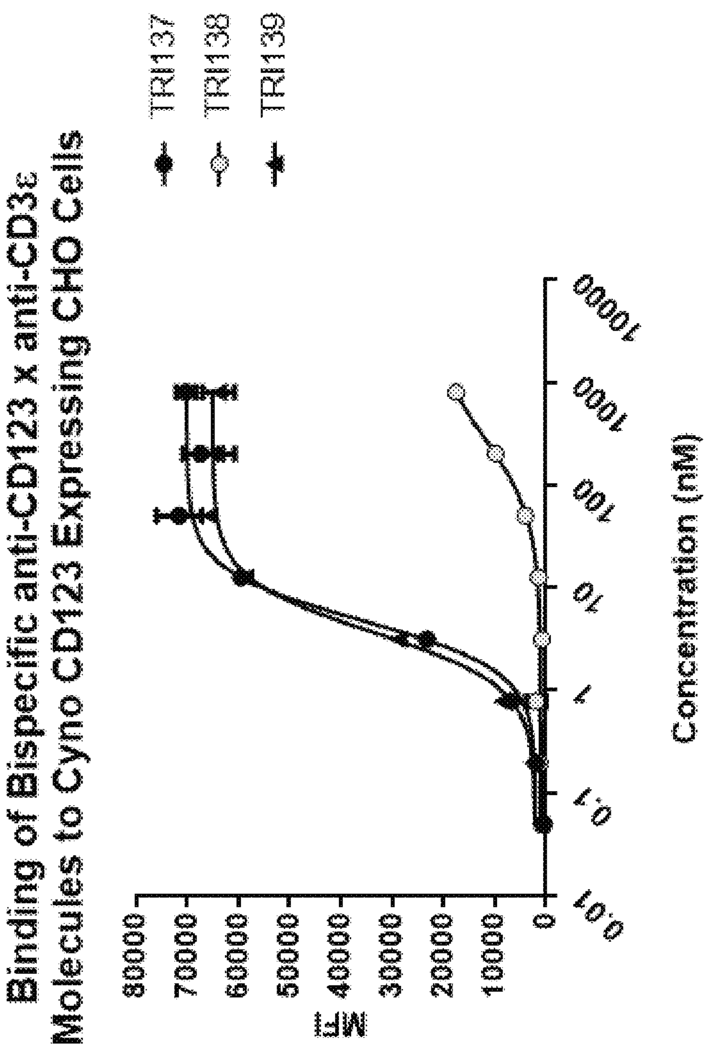

FIGS. 2A, 2B and 2C show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments to CHO cells stably expressing cynomolgus CD123 protein. Seven of the molecules demonstrated comparable maximum levels of binding at saturating concentrations. Observed EC50 values for TRI123, TRI126, TRI129, TRI130, TRI132, TRI137 and TRI139 were between 3-38 nM.

These results confirm the constructed anti-CD123×anti-CD3ε molecules retain binding activity to human CD123 on the surface of cancer cells and are cross-reactive with cynomolgus CD123.

Example 3: Redirected T Cell Cytotoxicity Assays with CD123(+) Cell Lines

To confirm that bispecific molecules binding to both CD123 and CD3ε could redirect T-cell cytotoxicity against a CD123(+) cell line, chromium-51 release assays were used to quantify target cell lysis induced by T-cells.

Chromium-51 Release Assays with CD123(+) Cell Lines

The Molm-13 human tumor cell line was cultured according to the provided protocols. Peripheral blood mononuclear cells (PBMC) were isolated from human blood using standard ficoll gradients. The isolated cells were washed in saline buffer. PBMC were cultured for 24 hours with Human T-Activator CD3/CD28 Dynabeads® (catalogue #11131D, Gibco Life Technologies, Carlsbad, California, USA) to activate T-cells using the manufacturers protocols. After 24 hours of culture PBMC were harvested and placed in a magnetic field to remove the Dynabeads. The isolated cells were washed in RPMI media+10% human serum. During the assay, concentrations of bispecific molecules with final concentration ranging from 1000 pM to 0.061 pM were added to the activated PBMC (approximately 100,000 per well).

Approximately $2.5\times10^6$ Molm-13 target cells were treated with 0.125 mCi of 51Cr and incubated for 90 minutes in a 37° C., 5% CO2 humidified incubator. After incubation, cells were washed 3 times with assay media (RPMI with 10% human serum) and re-suspended in 12.5 mL of assay media. From this suspension, 50 μL was dispensed per well into 96 well U-bottom plates (approximately 10,000 cells per well) to bring the total volume to 200 μL per well, and the PBMC to target cell ratio to 10:1. A zero lysis control was generated by target cells only, omitting the PBMC. A total lysis control was generated by including 0.20% NP-40 as the treatment with target cells only. A background lysis control was generated by target cells with PBMC in the absence of bispecific molecules.

Plates were incubated for 4 hours at 37° C., 5% CO2 in a humidified incubator, after which they were centrifuged at 1000 rpm for 3 minutes, and 25 μL of supernatant was transferred from each well to the corresponding well of a 96-well Luma sample plate. Sample plates were allowed to air dry in a chemical safety hood for 18 hours, and then radioactivity was read on a TopCount microplate scintillation counter (PerkinElmer) using a standard protocol.

Percent specific lysis was calculated using the formula: ((signal in drug treated sample−background signal from samples with Target Cell only)/(signal in total lysis wells−background signal from samples with Target Cell only))×100.

Figure 3A:
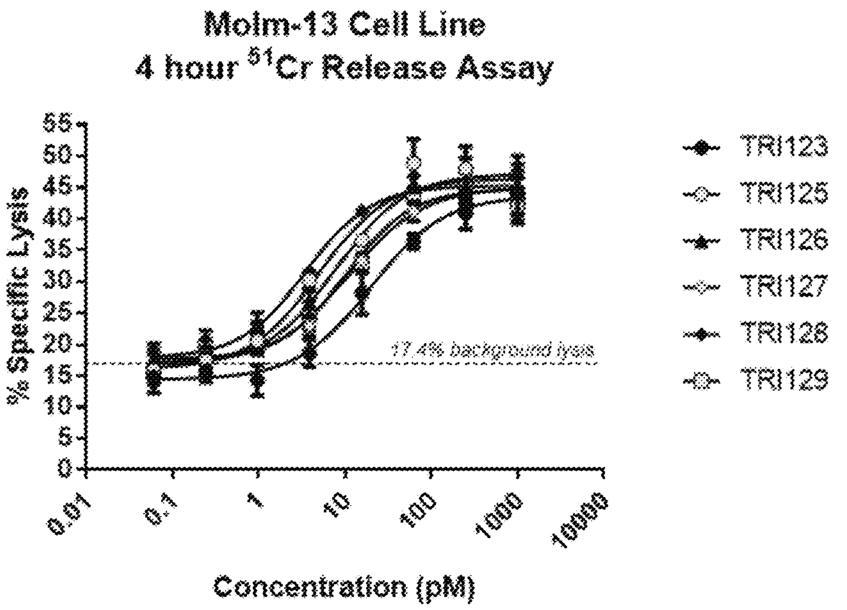
FIG. 3A-FIG. 3C show the results from chromium-51 release assays with the Molm-13 cell line measured at 4 hours using 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments. All of the bispecific anti-CD123×anti-CD3ε molecules showed efficient target cell lysis at 4 hours ranging between 24-48% maximum specific lysis.
Figure 3B:
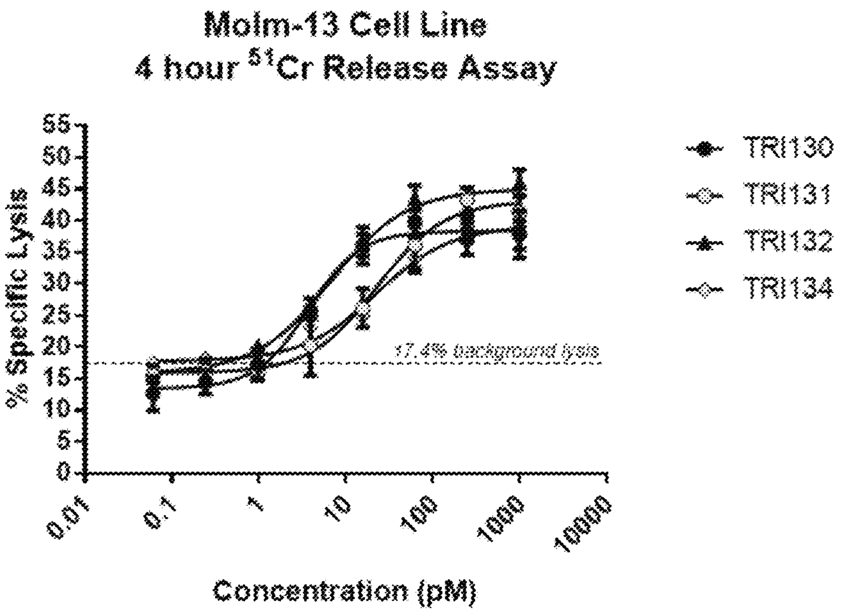
Figure 3C:
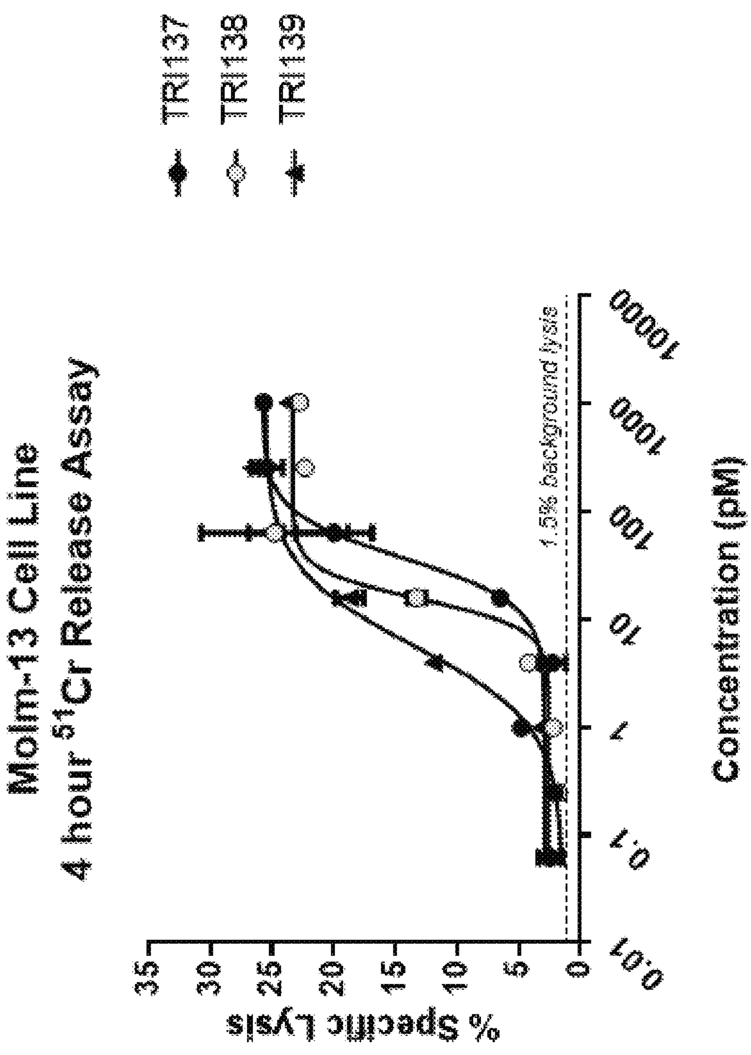

FIGS. 3A, 3B and 3C show chromium-51 release assays with the Molm-13 cell line measured at 4 hours using 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments. All of the bispecific anti-CD123×anti-CD3ε molecules showed efficient target cell lysis at 4 hours ranging between 24-48% maximum specific lysis. Measured EC50 values ranged between 3-37 PM at 4 hours.

Redirected T cell cytotoxicity assays were also performed with CHO cells stably expressing cynomolgus CD123 protein (TRI129 and TRI130) with (i) Molm-13 (human CD123+ cells) and human T-cells, (ii) Molm-13 (human CD123+ cells) and cynomolgous T-cells and (iii) CHO cells stably expressing cynomolgous CD123 and human T-cells. The data show that TRI129 and TRI130 are cross-reactive to human and cynomolgous CD123+ cells and T-cells.

These results confirm that the bispecific molecules binding to both CD123 and CD3ε could redirect T-cell cytotoxicity against a CD123(+) cell line.

Example 4: Target-Dependent T-Cell Proliferation Induced Against CD123(+) Cell Line by Anti-CD123 Bispecific Molecules To compare the effectiveness of different bispecific CD123-binding molecules at inducing target-dependent T-cell proliferation, six different anti-CD123×anti-CD3ε bispecific molecules including TRI123, TRI126, TRI129, TRI130, TRI132 and TRI139 were tested in two independent experiments.

T-cell proliferation was assessed by flow cytometry using a CD123(+) cell line, Molm-13. Peripheral blood mononuclear cells (PBMC) were isolated from human blood using standard density-gradient separation methods. The isolated cells were washed in saline buffer. T-cells were further isolated using a Pan T-cell Isolation Kit II from Miltenyi Biotec (Bergisch Gladbach, Germany) using the manufacturer's protocol. Molm-13 cells were irradiated to prevent cell division using a Faxitron-CellRad X-Ray Irradiation System from Faxitron Bioptics LLC (Tucson, Arizona, USA).

Proliferation was assessed by labeling isolated T-cell populations with CFSE. CFSE-labeled T-cells were plated in U-bottom 96-well plates at 120,000 cells/well, respectively, with 30,000 Molm-13 tumor cells/well, to achieve approximate T-cell to tumor cell ratios of 4:1. Concentrations of test molecules ranging from 2,000 pM to 0.002 pM were added to the cell mixtures to a final volume of 200 μl/well in RPMI 1640 media supplemented with 10% human AB serum, sodium pyruvate, antibiotics and non-essential amino acids. Plates were incubated at 37° C., 5% CO2 in humidified incubators. After 4 days, cells were labeled with antibodies for flow cytometric analysis in original plates to minimize cell losses, using saline buffer with 0.1% bovine serum albumin and 2 mM EDTA. After centrifugation and removal of supernatant, the cell pellets were resuspended with a mixture of the following dye-labeled antibodies in 50 μl volumes: CD5-PE, CD8-Pacific Blue, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of $CD4^+$ ($CD8^-$) or $CD8^+$ T-cells that had undergone at least one cell division, according to their CFSE profile, by gating sequentially on forward vs side scatter, $7AAD^-$, $CD5^+$, $CD4^+$ or $CD8^+$ T-cells ($7AAD^-$, $CD5^+$ $CD8^-$ or $7AAD^-$ $CD5^+$ $CD8^+$, respectively). Graphs were plotted using GraphPad Prism 7.0.

Figure 4B:
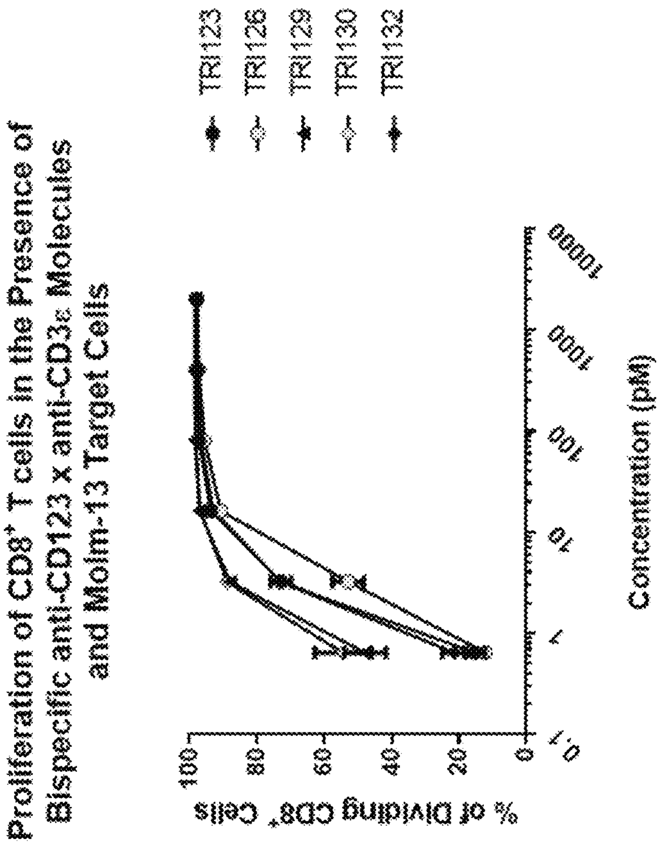
FIG. 4A-FIG. 4D show an induction of T-cell proliferation at low concentrations (10 pM).
Figure 4A:
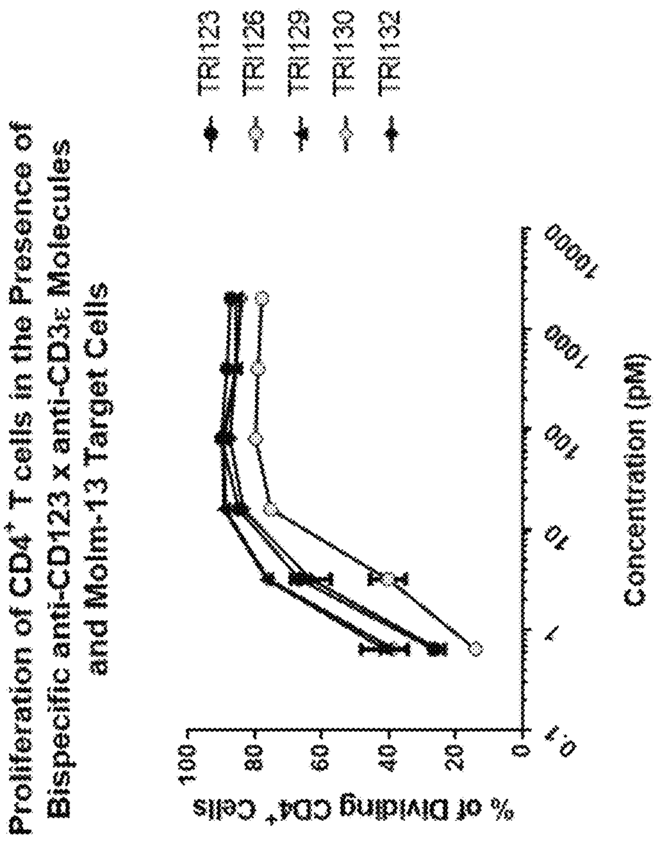
Figure 4C:
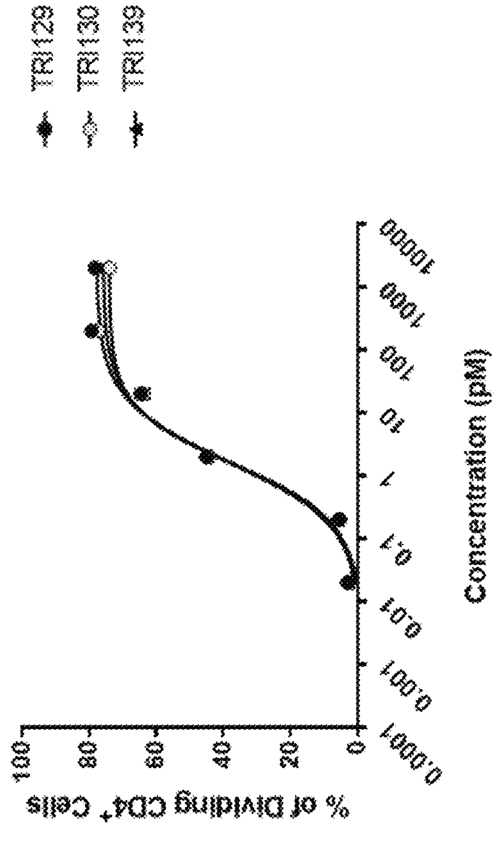
Figure 4D:
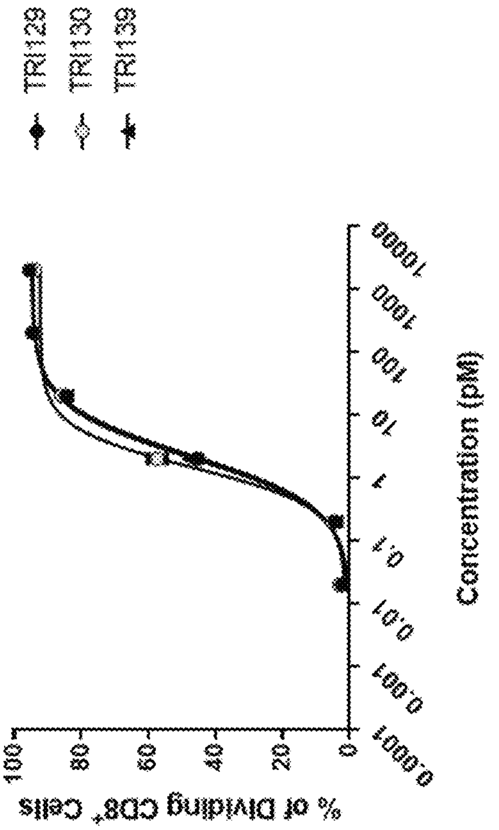
Figure 5B:
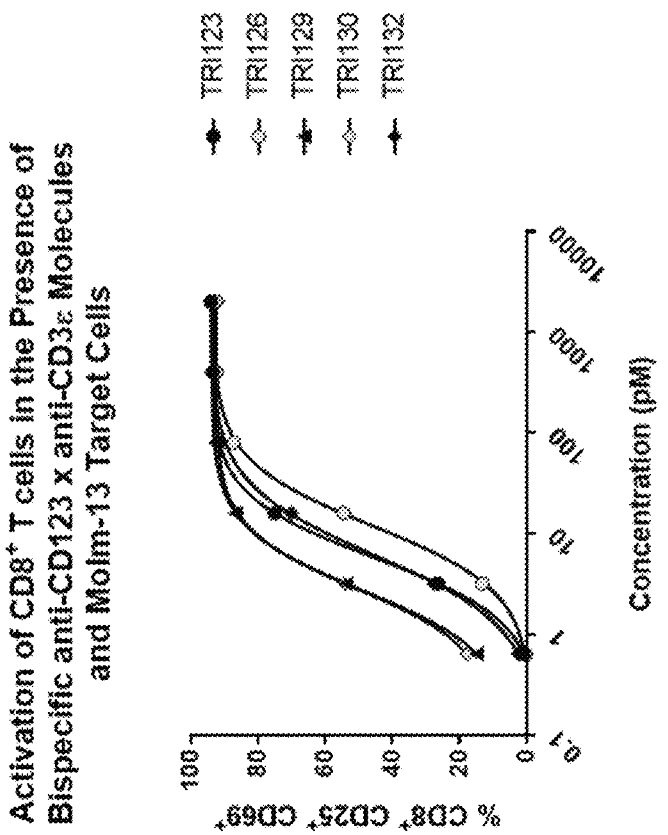
FIG. 5A-FIG. 5D show target dependent activation of CD4+ and CD8+ T-cells in the presence of Molm-13 cells.
Figure 5A:
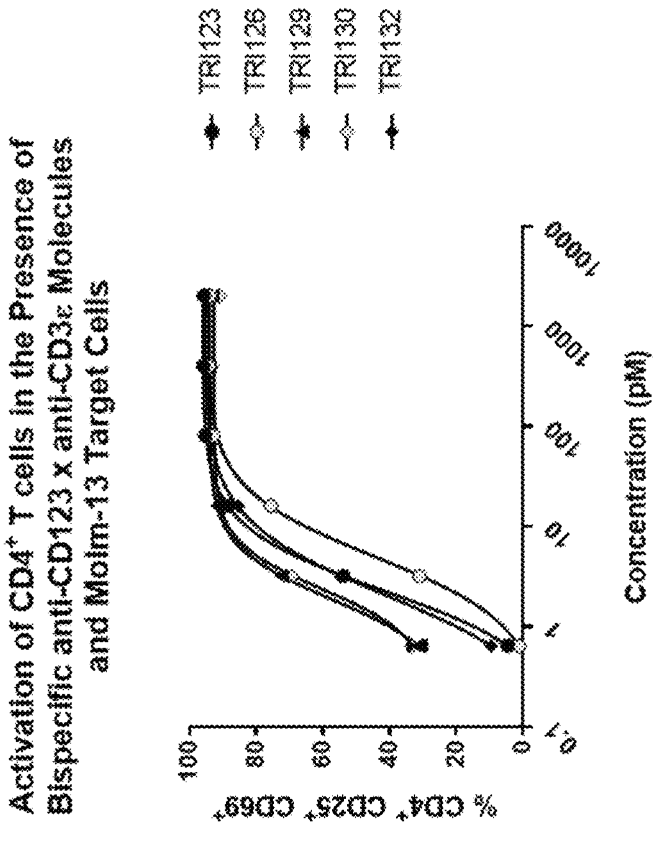
Figure 5C:
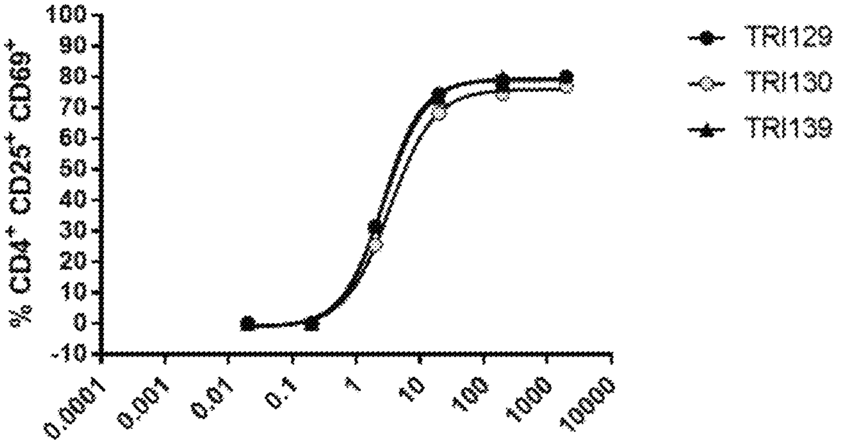
Figure 5D:
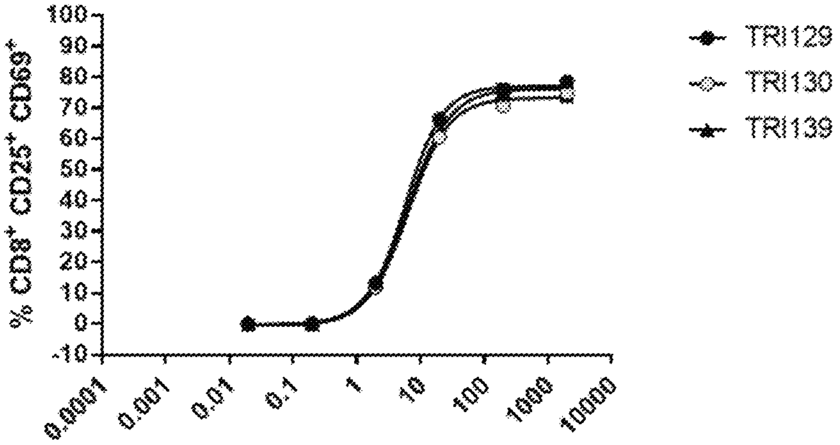

Analysis of dividing T-cell populations (FIGS. 4A and 4B) revealed a significant increase in the percent of proliferating cells in the presence of Molm-13 cells. All molecules showed robust induction of T-cell proliferation at low concentrations (10 pM), and proliferation was slightly higher in the $CD8^+$ (FIG. 4B) than the $CD4^+$ ($CD8^-$) (FIG. 4A) T-cell population. $EC_{50}$ values were determined with TRI129, TRI130 and TRI139 for both CD4 (FIG. 4C) and CD8 (FIG. 4D) populations demonstrating similar potency for all three anti-CD123×anti-CD3ε bispecific molecules.

These results confirm that bispecific molecules binding to both CD123 and CD3ε could induce target-dependent T-cell proliferation against a CD123(+) cell line.

Example 5: Determination of Pharmacokinetics in a Representative Non-Clinical Species To determine the pharmacokinetics in a relevant non-clinical species, a bispecific anti-CD123×anti-CD3 molecule is tested in a Non-Human Primate (NHP) species (e.g., cynomolgus monkeys) for pharmacokinetic (PK) and toxicology assessment of the anti-CD123×anti-CD3 molecule. Cross-reactivity of the anti-CD123 binding domain to NHP CD123 is tested by ELISA or surface plasmon resonance assays (similar to Example 2). Since there is 85.7% sequence identity between NHP and human CD123, equivalent binding is expected. PK and immunogenicity assays can be developed and used to detect and quantify the anti-CD123×anti-CD3 molecule in the presence of cyno serum, as well as to evaluate the immunogenicity response in NHP. Upon successful completion of these tasks to justify cynomolgus monkeys as a relevant tox species for CD123-targeting molecules, a single dose PK/tolerability experiment is performed. The study can be performed at a qualified clinical research organization (CRO). The study results are examined for PK parameters and any adverse events including unexplainable adverse events that cannot be attributed to the mechanism of action of the drug or to anti-drug antibodies (ADA). A toxicologist verifies and interprets the study results and supports continued development of the lead. PK parameters derived from this study are used to design future toxicology studies in non-human primates and/or clinical studies in human patients.

Example 6: Testing of Safety and Tolerability Upon Human Clinical Administration To determine the safety and tolerability in humans of a lead bispecific molecule targeting CD123 and CD3, the following phase 1 clinical trial could be conducted. The first-in-human study of an anti-CD123×anti-CD3 bispecific molecule can be a dose-escalation study to identify the maximum tolerated dose (MTD) in human administration.

As bispecific anti-CD123×anti-CD3 molecules are agonistic, the starting dose is set at a dose producing the Minimum Anticipated Biological Effect Level (MABEL) based on in vitro activity of anti-CD123×anti-CD3. Human pharmacokinetics (PK) are estimated using PK values determined in non-clinical models (mice or non-human primates) and allometric scaling to predict a dose yielding the MABEL. Bispecific molecule is dosed using either intravenous infusion or subcutaneous injection. Dose escalation follows a standard 3+3 design, with an anticipated 12 dose cohorts (N=24-72 patients). Dose frequency is dependent on observed PK in non-clinical studies, but could be weekly (QW), every other week (Q2W), every third week (Q3W), or monthly (Q4W). Dosing continues until disease progression (as defined by either the immune-related response criteria (irRC) or the response criteria in solid tumors (RECIST)).

Primary endpoint of the study is safety, defining an MTD and any dose limiting toxicities. Secondary endpoints of the study is PK, immunogenicity, and objective responses in tumor volume assessed either by irRC or RECIST criteria. For patients with hematologic malignancies, additional criteria may be assessed, such as the presence of minimal residual disease (MRD status). As appropriate or feasible, biomarker samples are taken from whole blood as well as from lymph node or bone marrow biopsies to monitor the effects on the immune system as well as effects on the cancer or malignancy.

Inclusion criteria for a phase 1 study may be broad and allow for inclusion of patients with refractory or relapsed disease from multiple indications where CD123 expression has been previously shown to be high, such as acute myeloid leukemia (AML), B-lymphoid leukemia, blastic plasmocytoid dendritic neoplasm (BPDCN), and hairy cell leukemia. Patients entering the study require evidence of CD123 expression from immunohistochemical (IHC) analysis from either archival biopsy samples of the primary tumor or from a pre-treatment biopsy of a recurrent tumor from a metastatic site.

A bispecific anti-CD123×anti-CD3 molecule is determined to be sufficiently safe if patients dosed at the MTD or dose levels below the MTD show evidence of clinical benefit, either from objective responses from the irRC or RECIST criteria or changes in potentially prognostic serum biomarkers, such as CTC, PSA, or TAG72.

TABLE 7

Human CD123 isoform sequences (National Center for Biotechnology Information)

| Name | Nucleotide Sequence (mRNA) | Amino Acid Sequence (complete) | SEQ ID NO (Amino Acid SEQ ID NO) |
|---|---|---|---|
| CD123 isoform 1 NM_002183.3 NP_002174.1 | GTCAGGTTCATGGTTACGAAGCTG CTGACCCCAGGATCCCAGCCCGTG GGAGAGAAGGGGGTCTCTGACA GCCCCCACCCCTCCCCACTGCCAG ATCCTTATTGGGTCTGAGTTTCAG GGGTGGGGCCCCAGCTGGAGGT TATAAAACAGCTCAATCGGGGAGT ACAACCTTCGGTTTCTCTTCGGGG AAAGCTGCTTTCAGCGCACACG GGAAGATATCAGAAACATCCTAGG ATCAGGACACCCCAGATCTTCTCA ACTGGAACCACGAAGGCTGTTT CTTCCACACAGTACTTTGATCTCC ATTTAAGCAGGCACCTCTGTCCTG CGTTCCGGAGCTGCGTTCCCGA TGGTCCTCCTTTGGCTCACGCTGC TCCTGATCGCCCTGCCCTGTCTCC TGCAAACGAAGGAAGATCCAAA CCCACCAATCACGAACCTAAGGAT GAAAGCAAAGGCTCAGCAGTTGAC CTGGGACCTTAACAGAAATGTG ACCGATATCGAGTGTGTTAAAGAC GCCGACTATTCTATGCCGGCAGTG AACAATAGCTATTGCCAGTTTG GAGCAATTTCCTTATGTGAAGTGA CCAACTACACCGTCCGAGTGGCCA ACCCACCATTCTCCACGTGGAT CCTCTTCCCTGAGAACAGTGGGAA GCCTTGGGCAGGTGCGGAGAATCT GACCTGCTGGATTCATGACGTG GATTTCTTGAGCTGCAGCTGGGCG GTAGGCCCGGGGGCCCCCGCGGAC GTCCAGTACGACCTGTACTTGA | MVLLWLTLLLIALPCLLQ TKEDPNPPITNLRMKAKA QQLTWDLNRNVTDIECVK DADYSMPAVNNSYCQF GAISLCEVTNYTVRVANP PFSTWILFPENSGKPWAG AENLTCWIHDVDFLSCSW AVGPGAPADVQYDLYL NVANRRQQYECLHYKTDA QGTRIGCRFDDISRLSSG SQSSHILVRGRSAAFGIP CTDKFVVFSQIEILTP PNMTAKCNKTHSFMHWKM RSHFNRKFRYELQIQKRM QPVITEQVRDRTSFQLLN PGTYTVQIRARERVYE FLSAWSTPQRFECDQEEG ANTRAWRTSLLIALGTLL ALVCVFVICRRYLVMQRL FPRIPHMKDPIGDSFQ NDKLVVWEAGKAGLEECL VTEVQVVQKT | SEQ ID NO: 205 (SEQ ID NO: 206) |

TABLE 7-continued

Human CD123 isoform sequences (National Center for Biotechnology Information)

| Name | Nucleotide Sequence (mRNA) | Amino Acid Sequence (complete) | SEQ ID NO (Amino Acid SEQ ID NO) |
| --- | --- | --- | --- |
| | ACGTTGCCAACAGGCGTCAACAGT<br>ACGAGTGTCTTCACTACAAAACGG<br>ATGCTCAGGGAACACGTATCGG<br>GTGTCGTTTCGATGACATCTCTCG<br>ACTCTCCAGCGGTTCTCAAAGTTC<br>CCACATCCTGGTGCGGGGCAGG<br>AGCGCAGCCTTCGGTATCCCCTGC<br>ACAGATAAGTTTGTCGTCTTTTCA<br>CAGATTGAGATATTAACTCCAC<br>CCAACATGACTGCAAAGTGTAATA<br>AGACACATTCCTTTATGCACTGGA<br>AAATGAGAAGTCATTTCAATCG<br>CAAATTTCGCTATGAGCTTCAGAT<br>ACAAAAGAGAATGCAGCCTGTAAT<br>CACAGAACAGGTCAGAGACAGA<br>ACCTCCTTCCAGCTACTCAATCCT<br>GGAACGTACACAGTACAAATAAGA<br>GCCCGGGAAAGAGTGTATGAAT<br>TCTTGAGCGCCTGGAGCACCCCCC<br>AGCGCTTCGAGTGCGACCAGGAGG<br>AGGGCGCAAACACACGTGCCTG<br>GCGGACGTCGCTGCTGATCGCGCT<br>GGGGACGCTGCTGGCCCTGGTCTG<br>TGTCTTCGTGATCTGCAGAAGG<br>TATCTGGTGATGCAGAGACTCTTT<br>CCCCGCATCCCTCACATGAAAGAC<br>CCCATCGGTGACAGCTTCCAAA<br>ACGACAAGCTGGTGGTCTGGGAGG<br>CGGGCAAAGCCGGCCTGGAGGAGT<br>GTCTGGTGACTGAAGTACAGGT<br>CGTGCAGAAAACTTGAGACTGGGG<br>TTCAGGGCTTGTGGGGGTCTGCCT<br>CAATCTCCCTGGCCGGGCCAGG<br>CGCCTGCACAGACTGGCTGCTGGA<br>CCTGCGCACGCAGCCCAGGAATGG<br>ACATTCCTAACGGGTGGTGGGC<br>ATGGGAGATGCCTGTGTAATTTCG<br>TCCGAAGCTGCCAGGAAGAAGAAC<br>AGAACTTTGTGTGTTTATTTCA<br>TGATAAAGTGATTTTTTTTTTTTT<br>AACCCAAAA | | |
| CD123<br>isoform 2<br>NM_001267713.1<br>NP_001251642.1 | GTCAGGTTCATGGTTACGAAGCTG<br>CTGACCCCAGGATCCCAGCCCGTG<br>GGAGAGAAGGGGGTCTCTGACA<br>GCCCCCACCCCTCCCCACTGCCAG<br>ATCCTTATTGGGTCTGAGTTTCAG<br>GGGTGGGGCCCCAGCTGGAGGT<br>TATAAAACAGCTCAATCGGGGAGT<br>ACAACCTTCGGTTTCTCTTCGGGG<br>AAAGCTGCTTTCAGCGCACACG<br>GGAAGATATCAGAAACATCCTAGG<br>ATCAGGACACCCCAGATCTTCTCA<br>ACTGGAACCACGAAGGCTGTTT<br>CTTCCACACAGTACTTTGATCTCC<br>ATTTAAGCAGGCACCTCTGTCCTG<br>CGTTCCGGAGCTGCGTTCCCGA<br>TGGTCCTCCTTTGGCTCACGCTGC<br>TCCTGATCGCCCTGCCCTGTCTCC<br>TGCAAACGAAGGAAGGTGGGAA<br>GCCTTGGGCAGGTGCGGAGAATCT<br>GACCTGCTGGATTCATGACGTGGA<br>TTTCTTGAGCTGCAGCTGGGCG<br>GTAGGCCCGGGGGCCCCCGCGGAC<br>GTCCAGTACGACCTGTACTTGAAC<br>GTTGCCAACAGGCGTCAACAGT<br>ACGAGTGTCTTCACTACAAAACGG<br>ATGCTCAGGGAACACGTATCGGGT<br>GTCGTTTCGATGACATCTCTCG<br>ACTCTCCAGCGGTTCTCAAAGTTC<br>CCACATCCTGGTGCGGGGCAGGAG<br>CGCAGCCTTCGGTATCCCCTGC<br>ACAGATAAGTTTGTCGTCTTTTCA | MVLLWLTLLLIALPCLLQ<br>TKEGGKPWAGAENLTCWI<br>HDVDFLSCSWAVGPGAPA<br>DVQYDLYLNVANRRQQ<br>YECLHYKTDAQGTRIGCR<br>FDDISRLSSGSQSSHILV<br>RGRSAAFGIPCTDKFWF<br>SQIEILTPPNMTAKCN<br>KTHSFMHWKMRSHFNRKF<br>RYELQIQKRMQPVITEQV<br>RDRTSFQLLNPGTYTVQI<br>RARERVYEFLSAWSTP<br>QRFECDQEEGANTRAWRT<br>SLLIALGTLLALVCVFVI<br>CRRYLVMQRLFPRIPHMK<br>DPIGDSFQNDKLVVWE<br>AGKAGLEECLVTEVQVVQ<br>KT | SEQ ID NO: 207<br>(SEQ ID NO: 208) |

TABLE 7-continued

Human CD123 isoform sequences (National Center for Biotechnology Information)

| Name | Nucleotide Sequence (mRNA) | Amino Acid Sequence (complete) | SEQ ID NO (Amino Acid SEQ ID NO) |
|---|---|---|---|
| | CAGATTGAGATATTAACTCCACCC AACATGACTGCAAAGTGTAATA AGACACATTCCTTTATGCACTGGA AAATGAGAAGTCATTTCAATCGCA AATTTCGCTATGAGCTTCAGAT ACAAAAGAGAATGCAGCCTGTAAT CACAGAACAGGTCAGAGACAGAAC CTCCTTCCAGCTACTCAATCCT GGAACGTACACAGTACAAATAAGA GCCCGGGAAAGAGTGTATGAATTC TTGAGCGCCTGGAGCACCCCCC AGCGCTTCGAGTGCGACCAGGAGG AGGGCGCAAACACACGTGCCTGGC GGACGTCGCTGCTGATCGCGCT GGGGACGCTGCTGGCCCTGGTCTG TGTCTTCGTGATCTGCAGAAGGTA TCTGGTGATGCAGAGACTCTTT CCCCGCATCCCTCACATGAAAGAC CCCATCGGTGACAGCTTCCAAAAC GACAAGCTGGTGGTCTGGGAGG CGGGCAAAGCCGGCCTGGAGGAGT GTGTGGTGACTGAAGTACAGGTCG TGCAGAAAACTTGAGACTGGGG TTCAGGGCTTGTGGGGGTCTGCCT CAATCTCCCTGGCCGGGCCAGGCG CCTGCACAGACTGGCTGCTGGA CCTGCGCACGCAGCCCAGGAATGG ACATTCCTAACGGGTGGTGGGCAT GGGAGATGCCTGTGTAATTTCG TCCGAAGCTGCCAGGAAGAAGAAC AGAACTTTGTGTGTTTATTTCATG ATAAAGTGATTTTTTTTTTTTT AACCCAAAA | | |

Example 7: Target-Dependent T-Cell Activation Induced Against CD123(+) Cell Line by Anti-CD123 Bispecific Molecules To compare the effectiveness of different bispecific CD123-binding molecules at inducing target-dependent T-cell activation of $CD4^+$ and $CD8^+$ T-cells, six different anti-CD123×anti-CD3ε bispecific molecules including TRI123, TRI126, TRI129, TRI130, TRI132 and TRI139 were tested in two independent experiments.

T-cell activation was assessed by flow cytometry using a CD123(+) cell line, Molm-13. Peripheral blood mononuclear cells (PBMC) were isolated from human blood using standard density-gradient separation methods. The isolated cells were washed in saline buffer. T-cells were further isolated using a Pan T-cell Isolation Kit II from Miltenyi Biotec (Bergisch Gladbach, Germany) using the manufacturer's protocol.

T-cells were plated in U-bottom 96-well plates at 120,000 cells/well, respectively, with 30,000 Molm-13 tumor cells/well, to achieve approximate T-cell to tumor cell ratios of 4:1. Concentrations of test molecules ranging from 2,000 pM to 0.002 pM were added to the cell mixtures to a final volume of 200 μl/well in RPMI 1640 media supplemented with 10% human AB serum, sodium pyruvate, antibiotics and non-essential amino acids. Plates were incubated at 37° C., 5% CO2 in humidified incubators. After 20 hours, cells were labeled with antibodies for flow cytometric analysis in original plates to minimize cell losses, using saline buffer with 0.1% bovine serum albumin and 2 mM EDTA. After centrifugation and removal of supernatant, the cell pellets were resuspended with a mixture of the following dye-labeled antibodies in 50 μl volumes: CD69-FITC, CD5-PE, CD8-Pacific Blue, CD4-APC, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of $CD4^+$ ($CD8^-$) or $CD8^+$ T-cells that had upregulated CD69 and CD25, by gating sequentially on forward vs side scatter, $7AAD^-$, $CD5^+$, $CD4^+$ or $CD8^+$ T-cells ($7AAD^-$, $CD5^+$ $CD4^+$ or $7AAD^-$ $CD5^+$ $CD8^+$, respectively). Graphs were plotted using GraphPad Prism 7.0.

Analysis of activated T-cells after 20 hours (FIG. 5) revealed a significant increase in the percent of activated $CD4^+$ and $CD8^+$ T-cells in the presence of Molm-13 cells. All molecules tested induced maximal activation of T-cells in the presence of Molm-13 target cells at low concentrations ranging from 1-100 pM (FIG. 5). $EC_{50}$ values were determined with TRI129, TRI130 and TRI139 for both $CD4^+$ (FIG. 5C) and $CD8^+$ (FIG. 5D) $CD25^+$ $CD69^+$ populations demonstrating similar potency for all three anti-CD123×anti-CD3ε bispecific molecules.

These results demonstrate that bispecific molecules binding to both CD123 and CD3ε could induce target-dependent T-cell activation against a CD123(+) cell line.

Example 8: Binding of Bispecific Proteins to CD123

To determine the kinetics and affinity of the bispecific to CD123, the TRI-129 and TRI-130 bispecific proteins were expressed via transient transfection in HEK293 cells and purified using a combination of affinity purification and size exclusion purification. The extracellular domain of CD123 was transiently expressed with an affinity tag on the C-terminus and purified using a combination of affinity purification and size exclusion purification. The analyses were performed using a BIACORE™ T200 instrument (Biacore Inc., Piscataway, NJ). The BIACORE™ T200 is a surface plasmon resonance (SPR)-based biosensor system that is designed to provide real-time kinetic binding data.

SPR binding studies of bispecific molecules to recombinant monomeric CD123 ectodomain (ECD) were conducted at 25° C. in HBS-EP+ buffer. AffiniPure F(ab')2 fragment Goat anti-human IgG Fcγ fragment-specific (Jackson Immuno Research) at 20 μg/mL in 10 mM sodium acetate (pH 4.5) was immobilized at a density of 3600 response units (RU) on the surface of a CM5 research-grade sensor chip (R-1005-30, GE Healthcare) by standard amine coupling chemistry. The bispecific molecules at 200 nM in HBS-EP+buffer were captured by the immobilized anti-Fc F(ab')2 fragment at a flow rate of 30 μL/min for 120 sec to reach a stable 2000 RU response. Different concentrations of CD123 ECD (3-48 nM by 2-fold dilutions, including buffer as blank) were flowed over the captured bispecific molecules at 30 μL/min for 120 sec followed by a 300 sec dissociation period. Optimal regeneration was achieved by one injection of 10 mM glycine (pH 1.7) at a flow rate of 30 μL/min for 15 sec followed by one injection of 50 mM NaOH at 30 μL/min for 15 sec. A two minute stabilization with HBS-EP+ buffer was completed before the subsequent run.

Sensorgrams obtained from kinetic SPR measurements were analyzed by the double subtraction method. The signal from the reference flow cell was subtracted from the analyte binding response obtained from flow cells with immobilized or captured ligands. Buffer reference responses were then averaged from multiple injections. The averaged buffer reference responses were then subtracted from analyte binding responses, and the final double-referenced data were analyzed with BIACORE™ T200 Evaluation software (2.0, GE Healthcare), globally fitting data to derive kinetic parameters (Table 8). All sensorgrams were fitted using a simple one-to-one binding model.

TABLE 8

Derived kinetic parameters for αCD123 bispecific molecules to CD123 ECD.

| Molecule | $k_a$ (1/Ms) | $k_d$ (1/s) | KD (nM) |
|---|---|---|---|
| TRI-129 | $1.79 \times 10^5$ | $2.05 \times 10^{-3}$ | 11.4 |
| TRI-130 | $1.72 \times 10^5$ | $4.72 \times 10^{-4}$ | 2.7 |

Figure 6:
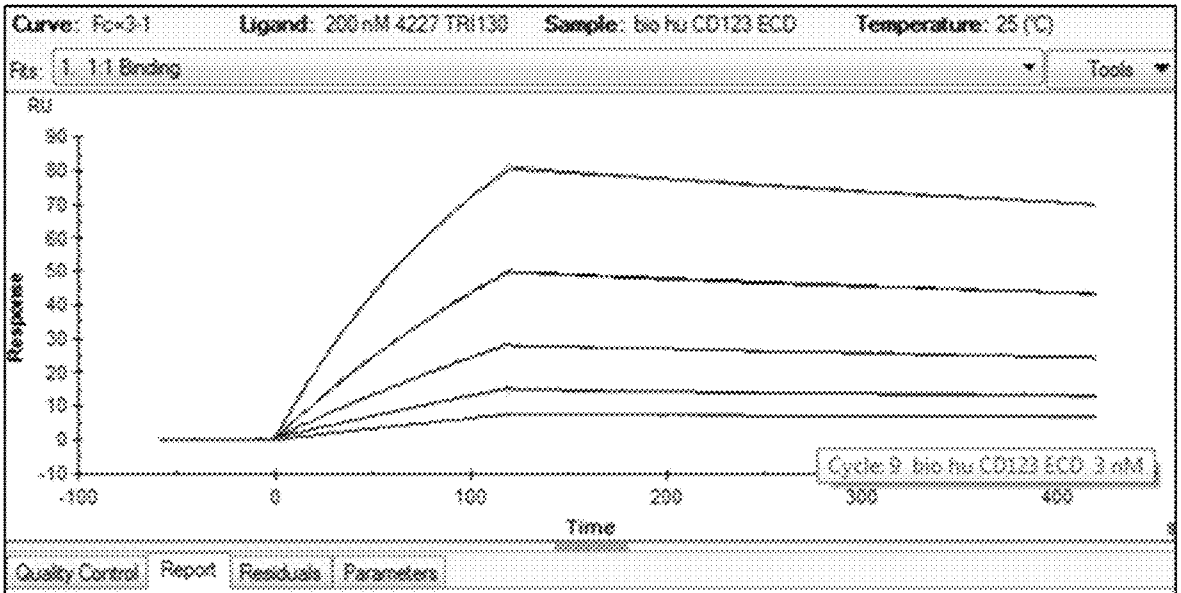
FIG. 6 shows an example of SPR analysis of TRI-130 at different ECD concentrations.

An example of the SPR analysis of TRI-130 at different ECD concentrations ranging from 3 nM to 48 nM is shown in FIG. 6. Thermodynamic and kinetic rate constants of binding were calculated using the BIACORE™ Evaluation software. For example, the affinity (KD) of TRI-130 for CD123 extracellular domain (ECD) was determined to be $2.74\times10^{-9}$ M with a ka of $1.72\times10^5$ $M^{-1}s^{-1}$ and a kd of $4.72\times10^{-4}$ $s^{-1}$. The affinity of TRI-129 for the CD123 was determined to be $1.14\times10^{-8}$ M with a ka of 1.79×105 $M^{-1}s^{-1}$ and a kd of $2.05\times10^{-3}$ $s^{-1}$.

Example 9: Differential Scanning Calorimetry

Thermal stability of the CD123 binding domain was assessed using Differential Scanning calorimetry (DSC). DSC measures heat capacity changes associated with the molecule's thermal denaturation when heated at a constant rate. Tm (thermal transition midpoint) value of CD123 binding domain scfv, which is a measure of its stability, can be extracted from the melting curve.

DSC thermal stability study was conducted using a MicroCal VP-Capillary DSC system (Malvern Instrument). An exact match of buffer, PBS pH7.4, was used as the reference. 500 μL of a 0.5 mg/mL solution of each protein sample with reference was loaded on the instrument and heated from 25° C. to 100° C. at a rate of one degree celsius per minute. Melting curve was analyzed using Origin 7 platform software "MicroCal VP-Capillary DSC Automated Analysis Software." Tm of each melting transition was calculated using "non-2 state curser integration" method.

TABLE 9

Assessment of thermal stability of domains

| Sample | TmOnset | Tm1 (αCD3 scFv) | Tm2 (αCD123 scFv and Fc CH2) | Tm3 (Fc CH3) |
|---|---|---|---|---|
| TRI129 | 51.19 | 59.59 | 64.48 | 83.87 |
| TRI130 | 53.19 | 59.59 | 65.71 | 84.64 |

Example 10: Pharmacokinetic Activity

To determine the pharmacokinetic activity of bispecific molecules, female Balb/c mice were injected intravenously (IV) with 200 mg (~10 mg/kg) of either TRI129 or TRI130 (n=30 for each molecule, TRI129 or TRI130). At each time point, blood was collected by cardiac puncture from 3 mice. Time points were: 15 minutes, 2, 6, 24, 48, 72, 96, 168, 336 and 504 hours. Blood was processed to serum, aliquoted and frozen. TRI129 and TRI130 concentrations in serum samples were determined by enzyme linked immunosorbent assay (ELISA). Serum concentrations over time were used to determine PK parameter estimates by non-compartmental analysis (NCA) and compartmental analysis. Serum concentration over time profiles were analyzed with Phoenix 64 software. Graphs were plotted using GraphPad Prism 7.0. NCA parameter analysis of the resulting data is provided in Table 10.

TABLE 10

| NCA parameter analysis of data | | | | |
|---|---|---|---|---|
| Bispecific | T ½ | Clearance | Volume | AUC |
| TRI-129 | 229 hours (9.5 days) | 0.204 ml/hr/kg | 67.54 ml/kg | 38750 hr * μg/ml |
| TRI-130 | 301 hours (12.5 days) | 0.186 ml/hr/kg | 80.84 ml/kg | 37309 hr * μg/ml |

Figure 7:
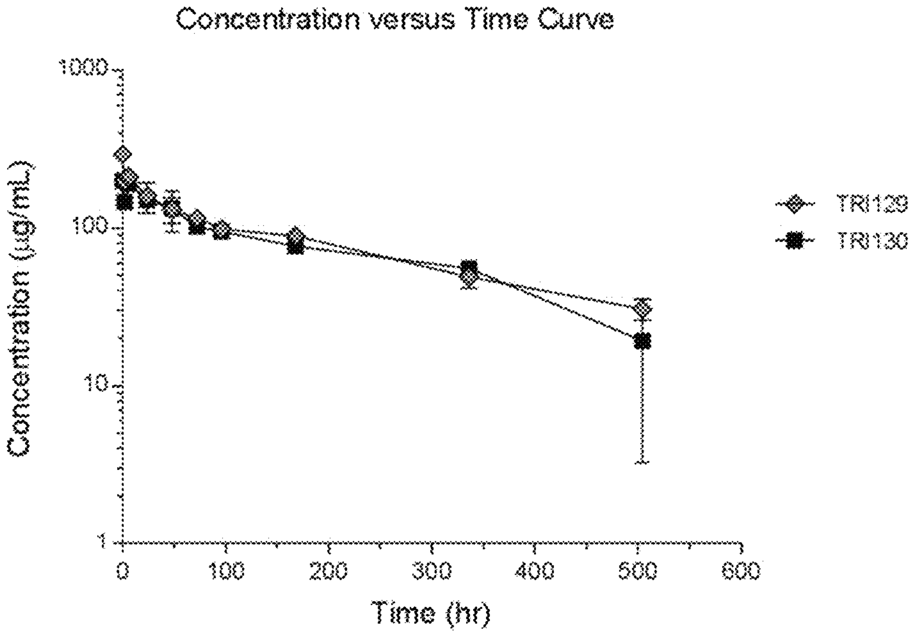
FIG. 7 shows concentration versus time curves for TRI129 and TRI130 bispecific molecules.

FIG. 7 shows concentration versus time curves for TRI129 and TRI130 bispecific molecules.

Example 11: In Vivo Efficacy of Anti-CD123×Anti-CD3 Binding Molecules

Figure 8:
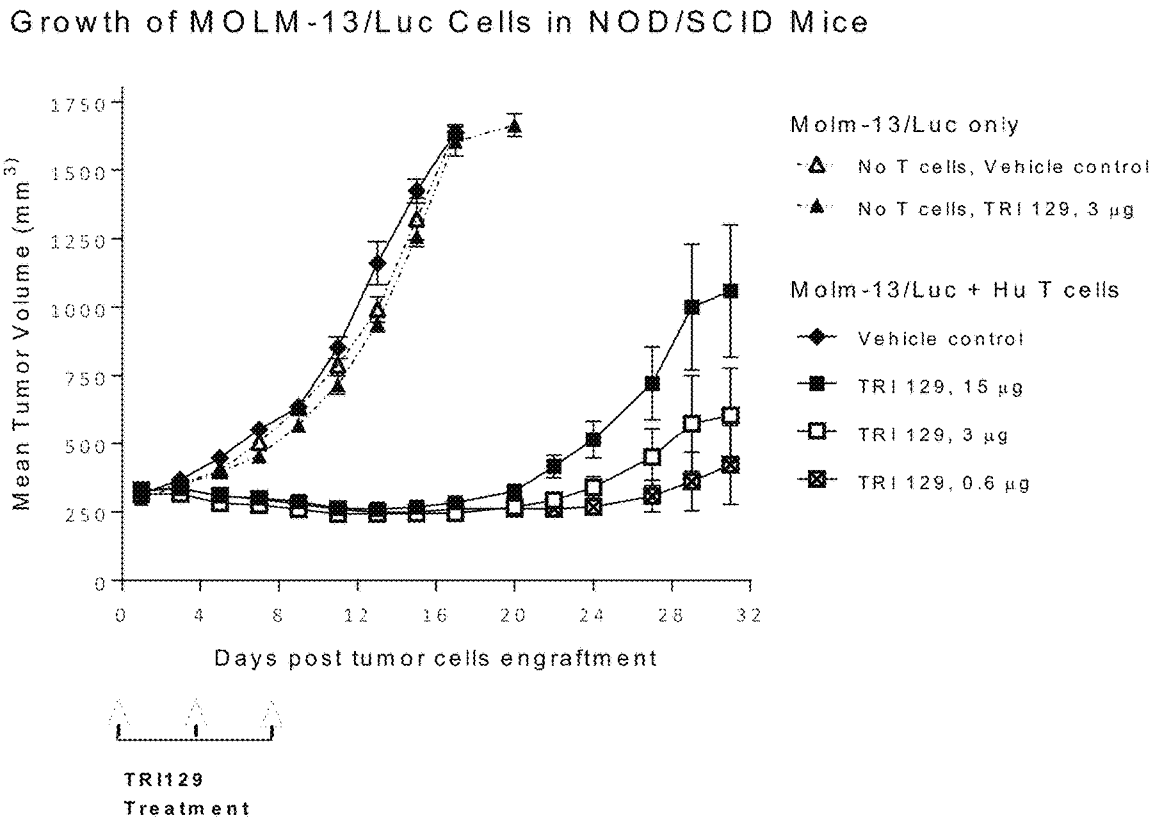
FIG. 8 shows reduction in tumor volume in a mouse tumor model treated with TRI129.
Figure 9:
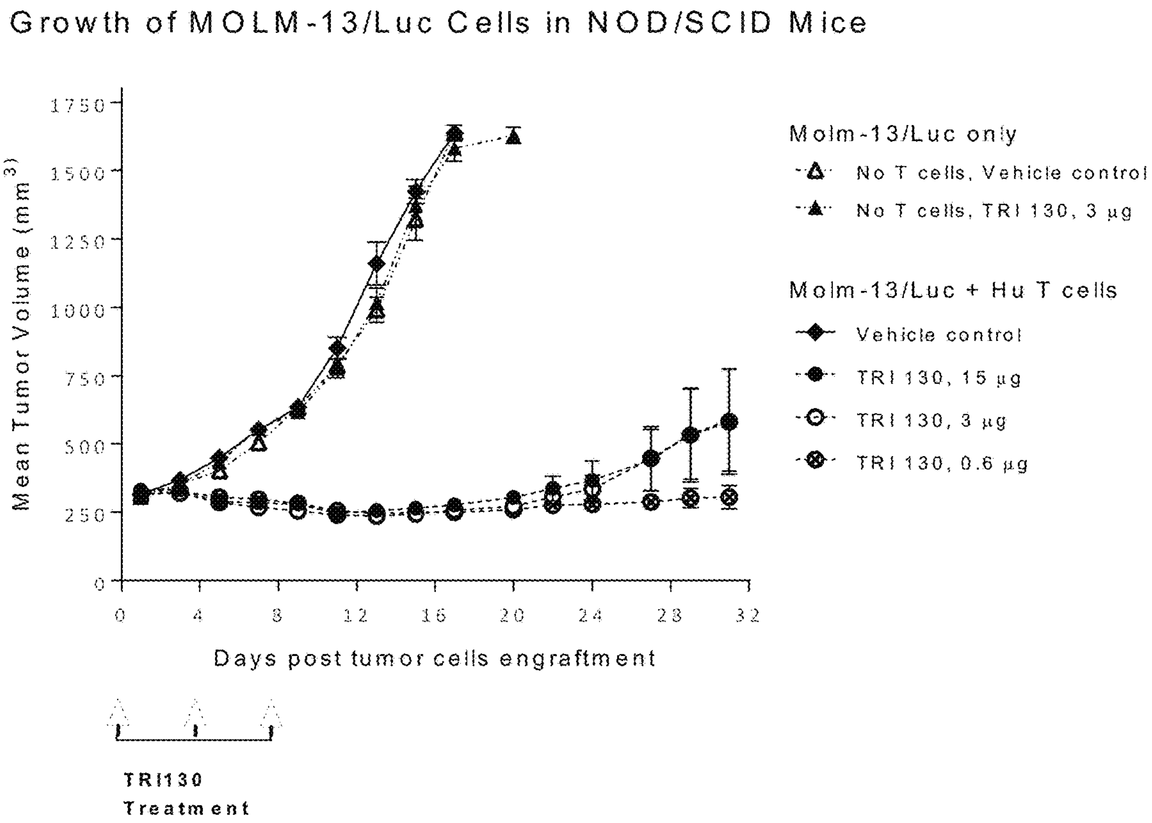
FIG. 9 shows reduction in tumor volume in a mouse tumor model treated with TRI130.
Figure 10:
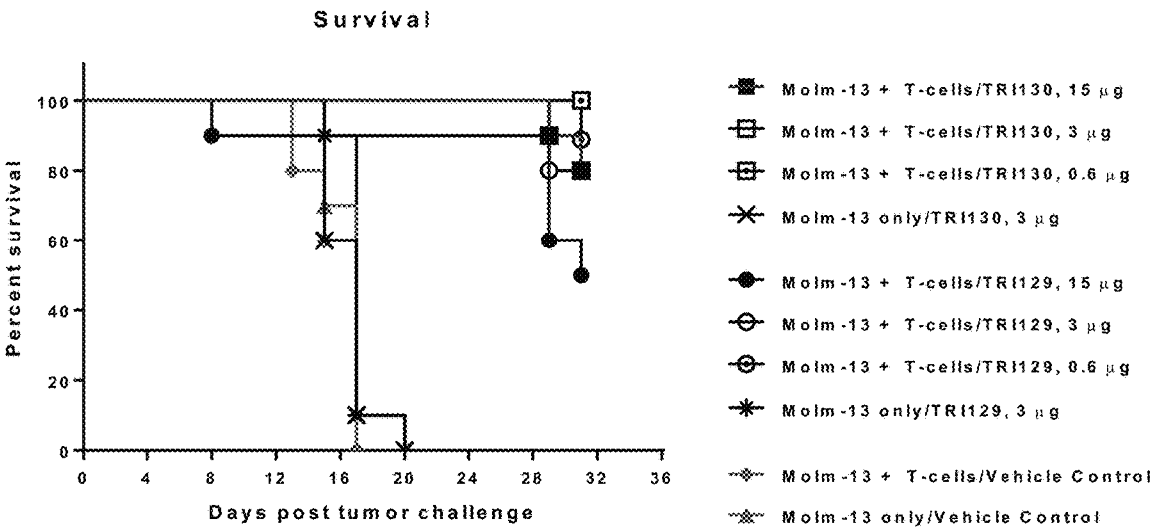
FIG. 10 shows that treatment of a mouse tumor model with TRI129 or TRI130 results in increase in survival.

To determine if TRI129 and TRI130 are capable of inhibiting tumor growth and prolonging survival in vivo, a rodent model of human acute myeloid leukemia was utilized. MOLM-13/LUC cells were co-mixed with donor T-cells and matrigel and implanted into the flank of NOD/SCID mice on day 0 of the study. Animals were treated in groups of 10 mice per group with T-cells from one donor with vehicle, TRI129 or TRI130 on study Day 0, 4 and 8 at doses of 15, 3 and 0.6 μg of protein in a total volume of 200 μl. Tumor growth was measured with calipers over time during the study and survival events were recorded each time a mouse reached the endpoint (tumor volume ≥1500 $mm^3$) and was euthanized. As shown FIGS. 8 and 9 there was minimal impact of TRI129 and TRI130 in the absence of donor T-cells and minimal impact of T-cells on tumor growth by the donor T-cells alone. Significant inhibition of tumor growth was seen after treatment with both TRI129 and TRI130 at all doses tested in the presence of donor T-cells. Significant differences in median survival of mice were determined using Kaplan-Meier survival analysis with a log-rank test for comparing survival curves. As shown FIG. 10, the survival of mice treated with all tested doses of TRI129 and TRI130 in the presence of co-implanted human T-cells was significantly prolonged relative to all control groups. Neither the co-implantation of T-cells with vehicle treatment nor the treatment of tumors with TRI129 or TRI130 in the absence of human T-cells extended survival compared to mice implanted with tumor cells alone and treated with vehicle. This result demonstrates both TRI129 and TRI130 are capable of driving inhibition of tumor growth and prolonging survival in a Xenograft model of acute myeloid leukemia.

Example 12: TRI-130 Cytotoxicity is Specific to CD123 Expressing Cell Lines

Figure 12:
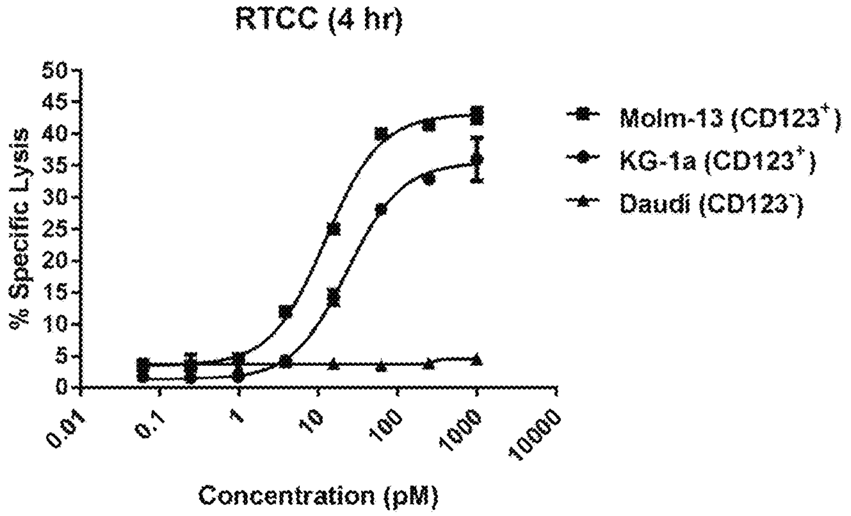
FIG. 12 shows the results from a chromium-51 release assay with the Molm-13, KG-1a and Daudi cell lines measured at 4 hours using the TRI130 bispecific anti-CD123×anti-CD3ε molecule. This assay measured the cytotoxicity of TRI130 incubated with CD123-positive or C123-negative tumor cell lines and purified human T-cells.
Figure 12:
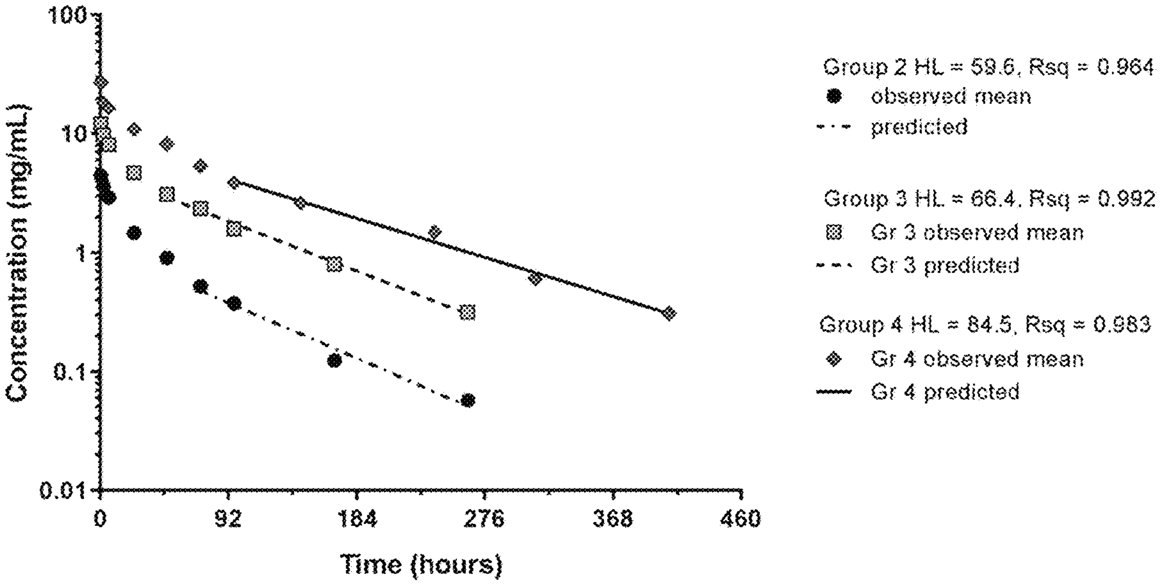

To confirm the specificity of TRI130 and compare its cytotoxic activity on tumor cell lines expressing different levels of CD123, chromium-51 release assays were used to quantify target cell lysis induced by T cells. CD123 expression levels on the CD123 positive MOLM-13 and KG-1a AML tumor cells lines were compared to the CD123 negative Daudi Burkitt's lymphoma tumor cell line by flow cytometry. CD123 expression was detected using a commercially available human CD123 phycoerythrin (PE) conjugated antibody. Positive CD123 expression was detected on MOLM-13 and KG-1a but not on Daudi cells. MOLM-13 and KG-1a cells expressed 10,000 and 2,000 receptors on average per cell respectively (data not shown). Different concentrations of TRI130 were incubated with MOLM-13, KG-1a or Daudi cell lines and purified human T-cells freshly isolated from human peripheral blood then pre-activated with anti-CD3×anti-CD28 coupled beads for 24 hours. TRI130 induced cytotoxicity only in the cell lines which were positive for CD123 expression and demonstrated comparable potency between the MOLM-13 and KG-1a AML tumor cell lines (FIG. 12). Cytotoxicity was measured as percent of specific tumor cell lysis, estimated using a chromium-51 release assay with 4 hr and 24 hr time points (data not shown). These results confirm that TRI130 induced redirected T-cell cytotoxicity is specific to CD123 expressing target cells and demonstrate potent TRI130 cytotoxicity on AML tumor cell lines expressing different levels of the CD123 protein.

Example 13: TRI130 Induced Cytotoxicity with Naïve T-Cells at Different Effector to Target Cell Ratios To examine TRI130 induced cytotoxicity activity at different effector to target cell ratios, KG-1a cells which express moderate levels of CD123 were incubated with different concentrations of TRI130 and purified T-cells from five different human donors that were not pre-activated. KG-1a target cells were cultured with T-cells at effector to target cell ratios of 10:1, 5:1 and 1:1. TRI130 induced cytotoxic activity at all effector to target cell ratios tested was comparable across all five donors (data not shown). Cytotoxicity was measured as percent of specific tumor cell lysis, which was estimated using a 24-hour chromium-51 release assay. These results demonstrate potent TRI130 induced cytotoxicity at different effector to target cell ratios with naïve T-cells and minimal variability in activity between normal donors.

Example 14: Single-Dose Pharmacokinetic and Tolerability Study in Cynomolgus Monkeys A single-dose pharmacokinetic and tolerability study was conducted to determine the tolerability, immunogenicity and pharmacokinetic characteristics following intravenous administration of TRI130. The study design is shown in Table 11. The intravenous route of administration was selected for the study as this is the intended route for human dosing.

Binding to NHP CD3ε was determined using the anti-CD3 binding domain in a mono-specific scFv-Fc fusion format. The anti-CD3 scFv-Fc was tested on Chinese cynomolgus macaque T-cells by flow cytometry. Binding levels were variable, with individual monkeys showing high, intermediate or low levels of binding compared to human cells (data not shown).

TABLE 11

Experimental Design of Pharmacokinetic Study in Cynomolgus Monkeys

| Group No. | No. of Males[a] | Test Material | Dosing Day and Time[b] | Dose Level (mg/kg) | Dose Con-centration (mg/mL) | Dose Volume (mL/kg) |
|---|---|---|---|---|---|---|
| 1 | 3 | Control | Day 1 | 0 | 0 | 5 |
| 2 | 3 | TRI130 | Day 1 | 0.25 | 0.05 | 5 |
| 3 | 3 | TRI130 | Day 1: 2 hr | 0.5 | 0.1 | 5 |
| 4 | 3 | TRI130 | Day 1: 24 hr | 1.0 | 0.2 | 5 |

[a]Animals were released from study on Day 36.
[b]Dosing for Groups 1 and 2 was started consecutively, without a delay between groups. Dosing was delayed by 2 hour from the end of the third animal in Group 2 and the start of the first animal in Group 3; Dosing for Group 4 was delayed by 24 hours from the start of dosing for Group 1.

body temperatures, and blood samples for cytokine analysis. The dose was well tolerated, and 24 hours later, a second sentinel animal was dosed at 0.25 mg/kg (initially anticipated as the Phase II high dose level) which was also well tolerated.

Dose levels for Phase II were selected in an attempt to produce graded responses to TRI130, and incorporated results of the Phase I sentinels. Because dose levels in Phase I were well tolerated by sentinel animals, with no abnormal clinical observations, elevated cytokine release levels, or increased body temperature, the Phase II dose levels selected were 0.25, 0.5 and 1 mg/kg, which are 2500 times the expected human PAD equivalent (Table 12). Adjusting this margin by up to 100-fold difference in activity, this study achieved up to 25-fold higher doses than the human PAD.

TABLE 12

Dose Equivalents of TRI130 Compared to Expected Pharmacologically Active Dose (PAD)

| Group No. | Test Material | Dose Level (mg/kg) | Mass Equivalent to Expected PAD (~0.4 mcg/kg) | Adjusted Dose Equivalence Based on Cyno Response |
|---|---|---|---|---|
| 1 | Control | 0 | 0 | 0 |
| 2 | TRI130 | 0.25 | 625X | 6.25X |
| 3 | TRI130 | 0.5 | 1250X | 12.5X |
| 4 | TRI130 | 1 | 2500X | 25X |

The following parameters and end points were evaluated in the single dose NHP study: clinical signs, body weights, food consumption, clinical pathology parameters (hematology, coagulation, and clinical chemistry), pharmacokinetics (PK), immunogenicity, cytokine profiles, and flow cytometry.

Dose levels tested ranged from the expected maximum human dose to high multiples of the expected human dose (Table 12). The anticipated pharmacologically active dose (PAD) in humans is in the range of 0.4 mcg/kg based on the in vivo xenograft model (Example 11), which is 625× below the dose of Group 2. However, based on in vitro activity assays (T-cell activation, proliferation and cytokine release), there is a 10 to 100-fold reduction in the response of cynomolgus T-cells to TRI130 compared to that of human T-cells. Therefore, the dose in Group 2 is expected to be ~6.25 to 62.5× the biologic equivalent to the human PAD. Groups 3 and 4 evaluate a 2 and 4-fold excess of the latter dose.

TRI130 interacts with CD3 on T-cells, and with the target molecule CD123 on immune cell populations including plasmacytoid dendritic cells (pDC) and basophils, which express high levels of CD123, but make up less than 1% of circulating leukocytes. Published data describing other bispecifics targeting CD123 noted significant cytokine release (Chichili et al. Sci Transl Med. 2015 May 27; 7(289): 289ra82).

Due to the expectation for cytokine release, this study was conducted in 2 phases. In Phase I, two sentinel animals received TRI130 to determine appropriate dose levels for Phase II, which would include treatment Groups 2-4. A dose level of 0.05 mg/kg (initially anticipated as the Phase II mid-dose level) was chosen for the first sentinel, and this animal was closely monitored for signs of cytokine release syndrome, including collection of post-dose observations, Pharmacokinetics of Single Dose TRI130 in Cynomolgus Monkeys Serum concentrations were determined using a standard ELISA method using the extracellular domain of CD123 to capture TRI130, and a biotinylated anti-ID antibody (5H5) recognizing the anti-CD3 binding domain to detect bound TRI130. For most animals a rapid drop in serum concentration at late time points corresponded to the presence of anti-drug antibodies (ADA). A standard bridging ELISA using TRI130+/−biotin was used to measure ADA titers in serum samples collected at late time points. ADA titers were relatively low for 7 of the 9 animals treated with TRI130, and titer values tended to increase over time (data not shown). However, titer also appeared to decrease with increasing doses of TRI130, and the onset of ADA was later for higher doses, meaning that higher doses were not correlated to increased levels of immunogenicity, as would normally be expected. Because TRI130 is a human protein, detecting ADA at late time points in NHP serum samples is considered a normal response, and immunogenicity in NHP is not predictive of human responses.

Non-compartmental analysis (NCA) of serum concentrations detected in the ELISA assay calculated a mean terminal half-life for TRI130 of up to 84 hours in animals dosed with 1 mg/kg (Table 13). Individually, one animal in group 4 had apparent subcutaneous accumulation of TRI130, while another in the group had significant early induction of ADA resulting in a much shorter half-life. Sparse sampling and uniform weighting were used for NCA, and serum concentrations clearly influenced by ADA were excluded from the analysis.

TABLE 13

| NCA PK Parameter Estimates for Individual Animals Dosed with TRI130 | | | | |
|---|---|---|---|---|
| NCA with Sparse sampling | | Uniform Weighting | | |
| Parameter | Units | Group 2 | Group 3 | Group 4 |
| Rsq adjusted | | 0.964 | 0.992 | 0.983 |
| HL Lambda z | hr | 59.55 | 66.44 | 84.46 |
| Tmax | hr | 0.25 | 0.25 | 0.25 |
| Cmax | ug/ml | 4.386 | 12.124 | 27.075 |
| Cmax/D | kg * ug/ml/ug | 0.018 | 0.024 | 0.027 |
| Tlast | hr | 264 | 264 | 408 |
| Clast | ug/ml | 0.0573 | 0.317 | 0.309 |
| AUCall | hr * ug/ml | 143.7 | 515.8 | 1329.7 |
| AUCINF | hr * ug/ml | 148.6 | 546.2 | 1367.4 |
| AUCINF/D | hr * kg * ug/ml/ug | 0.594 | 1.092 | 1.367 |
| Vz | ml/kg | 144.57 | 87.75 | 89.11 |
| Cl | ml/hr/kg | 1.683 | 0.915 | 0.731 |
| MRTlast | hr | 49.45 | 64.30 | 88.42 |
| MRTINF | hr | 59.41 | 80.75 | 100.58 |
| Vss | ml/kg | 99.96 | 73.92 | 73.56 |

In addition to NCA, compartmental analysis was run for individual animals and the treatment groups, using precompiled WinNonlin® 2 compartment models, with the appropriate dosing and weighting schemes. Results are shown in FIG. 13 and were similar to NCA parameter estimates, with PK parameter estimates determined using NCA or compartmental analysis, were not similar across treatment groups in that half-life increased and clearance decreased with increasing doses, likely due to target mediated binding of TRI130.

TABLE 14

| Treatment (Dose/Route) | NHP ID | V1 (mL/hr) | CL (mL/hr/kg) | V2 (mL/hr) | CLD2 (mL/hr/kg) | AUC (hr*μg/mL) | Alpha HL (hr) | Beta HL (hr) | Cmax (μg/mL) | Tmax (hr) |
|---|---|---|---|---|---|---|---|---|---|---|
| 0.25 mg/kg IV | 2001 | 59.32 | 2.463 | 24.36 | 4.427 | 101.5 | 2.568 | 24.79 | 4.22 | .25 |
| 0.25 mg/kg IV | 2002 | 50.87 | 1.864 | 32.19 | 1.820 | 134.1 | 6.293 | 36.85 | 4.91 | .25 |
| 0.25 mg/kg IV | 2003 | 61.16 | 1.470 | 43.41 | 3.341 | 170.1 | 4.859 | 53.46 | 4.09 | .25 |
| Group 2 mean | | 56.54 | 1.917 | 32.7 | 3.028 | 130.4 | 4.32 | 35.45 | 4.42 | .25 |
| 0.5 mg/kg IV | 3001 | 41.664 | 0.874 | 25.193 | 1.293 | 572 | 7.569 | 58.99 | 12.0 | .25 |
| 0.5 mg/kg IV | 3002 | 45.703 | 1.072 | 41.354 | 3.339 | 467 | 4.180 | 60.72 | 10.94 | .25 |
| 0.5 mg/kg IV | 3003 | 38.939 | 1.058 | 28.973 | 2.692 | 473 | 3.966 | 47.98 | 12.84 | .25 |
| Group 3 mean | | 41.87 | 1.002 | 32.43 | 2.540 | 499 | 4.608 | 55.65 | 11.94 | .25 |
| 1 mg/kg IV | 4101 | 27.93 | 0.926 | 22.08 | 16.533 | 1080 | 0.511 | 37.85 | 35.81 | .25 |
| 1 mg/kg IV | *4002 | 76.83 | 0.854 | 16.024 | 0.133 | 1172 | 46.2 | 112.6 | 11.27 | 6 |
| 1 mg/kg IV | 4003 | 48.22 | 0.706 | 25.34 | 0.492 | 1417 | 18.996 | 88.92 | 20.74 | .25 |
| Group 4 mean | | 39.31 | 0.826 | 45.2 | 5.22 | 74.22 | 4.15 | 5.6 | 74.22 | 2.17 |

Compartmental Analysis for NHP Given a Single IV Dose of TRI130

*Received at least part of the TRI130 dose SC, and parameter estimates were analyzed using a SC model Group means were analyzed using the WinNonlin® precompiled model #7 with sparse sampling and appropriate weighting V1: Volume for the 1st (central) compartment CL: Clearance from the central or 1st compartment V2: Volume for the 2nd compartment CLD2: Clearance from the 2nd compartment AUC: Area under the concentration time curve Alpha HL: Half-life associated with the macro constant Alpha Beta HL: Half-life associated with the macro constant Beta Cmax: Maximum observed concentration half-life for the one animal in group 4 (4003) without significant ADA or partial subcutaneous dosing, determined to be almost 89 hours. Animal 4002 in group 4 had a gradual increase in serum drug levels over time, and a Tmax at 6 hours (Table 14); therefore, its data was best fit using a 2-compartment model for extravascular dosing, instead of IV bolus dosing.

Tolerability of Single Dose TRI130 in Cynomolgus Monkeys

A single dose administration of TRI130 to cynomolgus monkeys was clinically well-tolerated at dose levels up to and including 1 mg/kg. At these doses, there were no test-article related clinical observations or changes to body weights, food consumption, clinical chemistry or coagulation parameters.

Administration of TRI130 was associated with decreased lymphocytes in peripheral blood (FIG. 14). TRI130-related, transient decreases in lymphocytes were observed at the 2-hour post-dose time point at all doses. In addition, there appeared to be a reduction in basophil counts in Groups 2 and 3 by hematology measurements (FIG. 15), with a slightly longer time to return to baseline levels, compared to the vehicle control (Group 1). The mean reduction in lymphocytes and basophils was less in Group 4, in part due to one animal that had a limited response and one animal that had apparent subcutaneous rather than intravenous injection, therefore Group 4 was excluded from the mean lymphocyte and basophil data shown in FIGS. 14 and 15. All groups dosed with TRI130 had an increase in neutrophils compared to the vehicle control group (data not shown). The changes noted with the hematology panel were mostly back to baseline levels by about 1 week after dosing.

Administration of TRI130 was not associated with changes in clinical chemistry, including CRP, or with changes in coagulation parameters.

The serum cytokine measurements indicated a minimal spike in some cytokines, including the T cell cytokines IL-10 and IL-2 and secondary cytokines such as MCP-1. The peak levels of cytokine detected were at 2 or 6 hours post-dose. In total, a bead based multi-plex cytokine kit was used to determine the levels of 23 individual cytokines, including T-specific cytokines (such as IL-2, IL-4, IL-5, IL-6, IL-10, IL-17, IFNγ, TNFα), and cytokines that are made by other cell types (such as MCP-1). Examples of cytokines detected in the study are presented in Table 15. Notably, the levels detected in the 1 mg/kg dose were lower than the mid and low dose group, however animal 4003, with more normal IV bolus pharmacokinetic parameters had responses more similar to the other groups. The other animal in Group 4 with an apparent subcutaneous dose (4002) had delayed peak response for some cytokines, consistent with a later Tmax. In general, cytokine levels returned to baseline levels by 96 hours post dose. The minimal cytokine secretion did not translate into any observable clinical post-dose event or changes in body weight or food intake (as noted above). The cytokine secretion is consistent with the mechanism of action of TRI130, which, when the target protein (CD123) is present, would result in some activation of T-cells in the system.

Administration of TRI130 by single intravenous (slow bolus) injection was well-tolerated in cynomolgus monkeys at levels of 0.25, 0.5 and 1 mg/kg. Based on these results, the no-observed-adverse-effect level (NOAEL) was considered to be 1 mg/kg. The serum half-life estimate for TRI130 was 84 hours, with normal clearance and volume of distribution in the high dose group. Lower doses had faster clearance and shorter half-life estimates, suggesting target mediated binding of TRI130 to target cells in cynomolgus monkeys. These observations will be confirmed and extended to higher dose levels in the 28-day repeat-dose GLP toxicology study in cynomolgus monkeys.

TABLE 15

Serum Cytokine Measurements of Dose Groups in Pilot Tolerability and PK

IL-2 (pg/mL)
Animal Number

| Time (hr) | 1001 | 1002 | 1003 | 2001 | 2002 | 2003 | 3001 | 3002 | 3003 | 4002** | 4003 | 4101 |
|---|---|---|---|---|---|---|---|---|---|---|---|---|
| −2 | 42.99 | 52.08 | 70.02 | 76.99 | 60.12 | 81.64 | 76.9 | 41.08 | 97.16 | 78.73 | 106.78 | 107.28 |
| 2* | 55.76 | 51.55 | 53.32 | 246.18 | 159.64 | 221.29 | 166.71 | 86.29 | 192.19 | 109.13 | 223.75 | 137.68 |
| 6 | 82.8 | 60.68 | 58.67 | 190.48 | 117.8 | 178.14 | 115.89 | 74.43 | 136.17 | 107.15 | 157.95 | 164.69 |
| 24 | 69.55 | 55.59 | 69.55 | 143.35 | 78.45 | 119.31 | 88.21 | 56.5 | 139.8 | 137.23 | 103.91 | 120.8 |
| 48 | 50.47 | 58.67 | 62.33 | 91.49 | 54.72 | 99.24 | 74.84 | 41.08 | 102.32 | 89.56 | 88.89 | 120.57 |
| 96 | 40.83 | 60.84 | 63.64 | 69.51 | 62.99 | 75.07 | 74.84 | 36.36 | 101.84 | 83.33 | 79.99 | 136.56 |

IL-10 (pg/mL)

| Time (hr) | 1001 | 1002 | 1003 | 2001 | 2002 | 2003 | 3001 | 3002 | 3003 | 4002 | 4003 | 4101 |
|---|---|---|---|---|---|---|---|---|---|---|---|---|
| −2 | 40.27 | 35.8 | 78.98 | 39.22 | 16.6 | 71.08 | 15.15 | | 28.55 | 24.47 | 62.01 | 78.63 |
| 2 | 46.96 | 31.32 | 44.73 | 630.12 | 174.18 | 576.67 | 115.32 | 26.19 | 216.4 | 55.71 | 410.84 | 90.55 |
| 6 | 74.59 | 43.62 | 43.62 | 372.62 | 84.78 | 179.93 | 74.77 | 14.35 | 97.4 | 66.75 | 100.11 | 157.86 |
| 24 | 71.28 | 43.62 | 59.15 | 150.06 | 31.29 | 100.78 | 48.18 | | 123.88 | 69.12 | 63.59 | 60.43 |
| 48 | 38.04 | 34.68 | 56.94 | 49.44 | 29.02 | 71.08 | 21.47 | | 41.12 | 27.57 | 83.39 | 64.38 |
| 96 | 35.8 | 48.07 | 55.83 | 44.9 | 26.76 | 60.82 | 30.13 | | 48.96 | 41.58 | 37.67 | 85.77 |

IL-1ra (pg/mL)

| Time (hr) | 1001 | 1002 | 1003 | 2001 | 2002 | 2003 | 3001 | 3002 | 3003 | 4002 | 4003 | 4101 |
|---|---|---|---|---|---|---|---|---|---|---|---|---|
| −2 | 29.81 | 10.23 | 21.72 | 14.83 | 7.73 | 27.36 | 17.29 | 7.12 | 21.98 | 10.52 | 24.41 | 26.4 |
| 2 | 39.08 | 14.46 | 20.93 | 91.35 | 31.08 | 73.18 | 38.46 | 21.7 | 69.77 | 22.41 | 51.87 | 36.56 |
| 6 | 48.42 | 22.51 | 16.11 | 253.47 | 21.34 | 102.43 | 36.06 | 23.07 | 135.59 | 18.67 | 48.27 | 59.32 |
| 24 | 33.55 | 10.66 | 18.14 | 101.05 | 13.27 | 26.61 | 59.08 | 7.7 | 96.11 | 20.97 | 21.69 | 18.1 |
| 48 | 15.29 | 10.66 | 20.14 | 15.99 | 21.72 | 21.34 | 8.56 | 2.69 | 21.7 | 11.99 | 21.83 | 20.11 |
| 96 | 11.09 | 15.29 | 13.21 | 13.27 | 6.1 | 15.21 | 11.13 | 5.08 | 14.51 | 9.63 | 12.14 | 26.11 |

TABLE 15-continued

Serum Cytokine Measurements of Dose Groups in Pilot Tolerability and PK

| IL-6 (pg/mL) | | | | | | | | | | | | |
|---|---|---|---|---|---|---|---|---|---|---|---|---|
| Time (hr) | 1001 | 1002 | 1003 | 2001 | 2002 | 2003 | 3001 | 3002 | 3003 | 4002 | 4003 | 4101 |
| −2 | | | | | | | | | | | 1.61 | |
| 2 | 4.46 | 8.2 | 28.17 | 40.23 | 11.18 | 46.47 | 7.41 | | 59.97 | 4.71 | 29.12 | 9.24 |
| IL-2 (pg/mL) Animal Number | | | | | | | | | | | | |
| 6 | 7.29 | 11.3 | | 9.75 | | 34.34 | 15.76 | | 6.65 | 3.31 | 13.75 | 58.68 |
| 24 | 26.34 | | | 0.03 | | 5.95 | 135.1 | | | 0.42 | | 0.88 |
| 48 | | | | | | | | | | | | |
| 96 | | | | | | | | | | | | 0.3 |

| MCP-1 (pg/mL) | | | | | | | | | | | | |
|---|---|---|---|---|---|---|---|---|---|---|---|---|
| Time (hr) | 1001 | 1002 | 1003 | 2001 | 2002 | 2003 | 3001 | 3002 | 3003 | 4002 | 4003 | 4101 |
| −2 | 255.62 | 294.77 | 362.89 | 390.54 | 391.05 | 445.7 | 342.49 | 158.31 | 547.6 | 618.1 | 769.48 | 807.72 |
| 2 | 386.37 | 322.52 | 281.46 | 5860.97 | 1690.25 | 3737.21 | 1429.67 | 520.19 | 3744.09 | 918.3 | 5948.11 | 1144.13 |
| 6 | 563.16 | 393.99 | 316.14 | 2747.2 | 936.33 | 1720.26 | 669.27 | 491.71 | 1119.4 | 1063.89 | 1565.33 | 1972.29 |
| 24 | 484.46 | 346.71 | 378.37 | 1188.25 | 571.67 | 874.9 | 508.46 | 288.4 | 1126.98 | 1287.69 | 781.38 | 1043.59 |
| 48 | 285.74 | 398.27 | 379.72 | 518.2 | 435.71 | 634.29 | 358.73 | 211.71 | 672.02 | 789.58 | 706.93 | 1084.58 |
| 96 | 254.56 | 400.97 | 366.57 | 404.11 | 416.68 | 433.94 | 380.1 | 193.43 | 599.64 | 666.4 | 526.84 | 1167.58 |

**animal 4002 had a serum concentration of TRIBO Tmax at 6 hrs that suggested a subcutaneous route of administration, and indicated a slower accumulation of TRI130 in the animal. This animal's peak cytokine levels were somewhat delayed compared to the other animals.

Example 15: Therapeutic Efficacy of TRI130 in a Disseminated Xenograft Mouse Model of Acute Myeloid Leukemia (AML)

To examine the therapeutic efficacy of TRI130 in mice with established disseminated tumors, a rodent model of human acute myeloid leukemia was utilized. MOLM-13 cells modified to express firefly luciferase were used to allow tumor quantification by bioluminescent imaging. For the study, 100,000 MOLM-13 Luc cells were injected intravenously into the lateral tail vein of 24 NSG male mice. MOLM-13 Luc cells were allowed to establish in the mice for 4 days prior to initiation of treatments. Mice were assigned into 3 groups of 8 mice each. One group received no additional treatments as a control. The remaining two groups received 7 million human T-cells with the first treatments. Treatments consisted of PBS vehicle control or TRI130 at 3 μg on days 4, 8 and 12. Treatments were administered intravenously via the tail vein. Treatments were delivered in 0.2 mL of Dulbecco's Phosphate Buffered Saline (PBS) containing no molecule (vehicle control) or 3 μg of TRI130. The injection included 7 million purified human T-cells for the day 4 treatment only. TRI130 treatment resulted in a rapid significant reduction in skeletal tumor burden (FIG. 16, FIG. 17 and Table 16). Residual non-skeletal tumor burden expanded following TRI130 treatments. Upon necropsy and the end of the study, it was determined this residual tumor burden was associated with the male reproductive tract and was observed in both the vehicle and the TRI130 group with the main difference between the being the absence of skeletal tumor burden. Treatment of established disseminated MOLM-13 Luc tumors in male mice with TRI130 resulted in a significant reduction in tumor burden, $p<0.0001$, relative to T-cell only controls (Table 16). There was no significant difference between the MOLM-13 Luc only and vehicle control groups. Tumor burden distribution was altered by TRI130 treatment with skeletal sites cleared of bioluminescent signal.

TABLE 16

Statistical Comparison of Mean Tumor Volume through Day 14
JMP Repeated-Measures ANOVA Analysis with Tukey's HSD Method

| Treatment | p-Value |
|---|---|
| Vehicle vs. 3 μg TRI130 | <.0001* |
| Vehicle vs. MOLM-13 only | 0.5385 |
| MOLM-13 only vs. 3 μg TRI130 | <.0001* |

*indicates p-value <0.05 significant difference

Example 16: Construction of an Anti-CD123×Anti-CD3 MGD006-Like Molecule

In order to compare TRI130 activity to another bispecific format an anti-CD123×anti-CD3 bispecific was generated containing the CD123 and CD3 binding domain sequences of MGD006 obtained from WO 2015/026892 (nucleic acid sequences corresponded to SEQ ID NOs: 2 and 4; amino acid sequences corresponded to SEQ ID Nos: 1 and 3) engineered in the format reported in Chichili et al. Sci Transl Med. 2015 May 27; 7(289):289ra82 with an added Avidin-Flag-HIS sequence to enable purification. The resulting MGD006-like construct is referred to as TRI168.

Example 17: Human T-Cell Activation, Cytotoxicity and Cytokine Release in Response to TRI130 and TRI168

To compare the activity of TRI130 and the TRI168 proteins in vitro, T-cells were isolated from normal donor peripheral blood mononuclear cells (PBMC) and incubated with various concentrations of TRI130 and TRI168 in the presence of CD123+ tumor cells (MOLM-13).

T-cell activation was assessed after 24 hours of culture by flow cytometry. After centrifugation and removal of supernatant, the cell pellets were resuspended with a mixture of the following dye-labeled antibodies in 50 μl volumes: CD69-FITC, CD5-PE, CD8-Pacific Blue, CD4-APC, CD25-

PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of CD4+ (CD8-) or CD8+ T-cells that had upregulated CD69 and CD25, by gating sequentially on forward vs side scatter, 7AAD−, CD5+, CD4+ or CD8+ T-cells (7AAD−, CD5+ CD4+ or 7AAD− CD5+ CD8+, respectively). Graphs were plotted using GraphPad Prism 7.0. TRI130 and TRI168 induced similar, dose-dependent T-cell activation in the presence of CD123+ target cells with both donors tested (FIG. 18). The figure shows the percentage of CD4+ and CD8+ T-cells that were CD69 and CD25 positive. $EC_{50}$ values were determined with TRI130 and TRI168 for both CD4+ and CD8+ CD25+ CD69+ populations demonstrating similar potency for both molecules. No T-cell activation was observed in the absence of CD123+ target cells (Not Shown).

Molm-13 cytotoxicity was assessed after 24 hours of culture by flow cytometry as described above. The sample files were analyzed using FlowJo software to quantitate cytotoxicity by gating sequentially on forward vs side scatter, 7AAD−, CD5− cells. Graphs were plotted using GraphPad Prism 7.0. TRI130 and TRI168 induced similar, dose-dependent Molm-13 cytoxicity with both donors tested (FIG. 19). The figure shows the total number of viable Molm-13 cells after 24 hours of culture with purified T-cells, TRI130 and TRI168.

Levels of a selected subset of cytokines commonly produced by activated T-cells including IFNγ, IL-2, TNFα and IL-10 were measured in the 24-hour culture supernatants using multiplexed analyte assays. TRI168 induced higher levels of cytokine secretion compared to TRI130 with both donors tested in the presence of CD123+ Molm-13 target cells (FIG. 20).

Rare normal immune cell populations including plasmacytoid dendritic cells and basophils expressing high levels of CD123 are present in PBMC samples and represent targets for anti-CD123×anti-CD3 bispecific molecules. To examine the levels of cytokine secretion induced by TRI130 and TRI168 in the absence of exogenously added target cells, normal donor PBMC were cultured for 24 hours with various concentrations of both proteins and cytokines measured in the resulting supernatants using multiplexed analyte assays. Similar to cultures with purified T-cells and MOLM-13 cells, TRI168 induced higher levels of IFNγ, IL-2, TNFα and IL-10 compared to TRI130 (FIG. 21).

Taken together these results demonstrate comparable in vitro T-cell activation and cytotoxicity of exogenously added CD123+ tumor cells with TRI130 and the MGD006-like anti-CD123×anti-CD3 bispecific TRI168. Notably, TRI168 induces much higher levels of secreted T-cell cytokines in cultures of both purified T-cells with Molm-13 tumor cells and normal donor PBMC samples compared to TRI130. In the clinic, drugs that induce strong T-cell activation can cause a series of adverse events, termed "cytokine release syndrome" (CRS), due to excessive cytokine release. Released cytokines cause a systemic inflammatory response that can lead to life-threatening complications which can limit drug administration.

Example 18: TRI130 Induced Cytotoxicity of AML Cell Samples

To determine if TRI130 is capable of inducing cytotoxicity in primary AML cells, PBMC samples from AML subjects were cultured for several days with various concentrations of TRI130. Cytotoxicity of AML cells was assessed by flow cytometry after four days of culture. After centrifugation and removal of supernatant, the cell pellets were resuspended with a mixture including the following dye-labeled antibodies in 50 μl volumes: CD69-FITC, CD5-APC, CD19-Pacific Blue, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to quantitate cytotoxicity in the non-B, non-T cell compartment by gating sequentially on forward vs side scatter, 7AAD−, CD5−, CD19−, CD25− cells. Graphs were plotted using GraphPad Prism 7.0. TRI130 induced a dose dependent loss of non-B, non-T AML cell samples in both donors tested (FIG. 22). The figure shows the total number of viable non-B, non-T-cells after 96 hours of culture. Similar results were obtained at 24 and 48 hours (data not shown). These results demonstrate that TRI130 is capable of inducing cytotoxicity in cultures of primary human AML PBMC samples.

The invention claimed is:

1. A method for treating a hematological cancer in a subject, wherein said hematological cancer is characterized by overexpression of CD123, the method comprising administering to the subject a therapeutically effective amount of a pharmaceutical composition comprising a recombinant polypeptide comprising a CD123 binding domain and a CD3 binding domain;

wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises the amino acid sequence set forth in SEQ ID NO:6; the LCDR2 comprises the amino acid sequence set forth in WAS; the LCDR3 comprises the amino acid sequence set forth in SEQ ID NO:10, the HCDR1 comprises the amino acid sequence set forth in SEQ ID NO:12; the HCDR2 comprises the amino acid sequence set forth in SEQ ID NO:14; and the HCDR3 comprises the amino acid sequence set forth in SEQ ID NO:16; and wherein the CD3-binding domain comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 of the CD3-binding domain comprise the amino acid sequences set forth in SEQ ID NO:162, SEQ ID NO:163, and SEQ ID NO:164, respectively, and the HCDR1, HCDR2, and HCDR3 of the CD3-binding domain comprise the amino acid sequences set forth in SEQ ID NO: 165, SEQ ID NO:166, and SEQ ID NO:167, respectively;

(b) the LCDR1, LCDR2 and LCDR3 of the CD3-binding domain comprise the amino acid sequences set forth in SEQ ID NO:168, DSS, and SEQ ID NO:170, respectively, and the HCDR1, HCDR2, and HCDR3 of the CD3-binding domain comprise the amino acid sequences set forth in SEQ ID NO: 171, SEQ ID NO:172, and SEQ ID NO:173, respectively;

(c) the LCDR1, LCDR2 and LCDR3 of the CD3-binding domain comprise the amino acid sequences set forth in SEQ ID NO: 307, SEQ ID NO: 308 and SEQ ID NO:309, respectively, and the HCDR1, HCDR2, and HCDR3 of the CD3-binding domain comprise the amino acid sequences set forth in SEQ ID NO: 174, SEQ ID NO: 175 and SEQ ID NO:176, respectively;

(d) the LCDR1, LCDR2 and LCDR3 of the CD3-binding domain comprise the amino acid sequences set forth in SEQ ID NO: 310, GTK and SEQ ID NO: 178, respectively, and the HCDR1, HCDR2, and HCDR3 of the CD3-binding domain comprise the amino acid sequences set forth in SEQ ID NO: 179, SEQ ID NO: 180 and SEQ ID NO: 181, respectively;

(e) the LCDR1, LCDR2 and LCDR3 of the CD3-binding domain comprise the amino acid sequences set forth in SEQ ID NO: 182, SEQ ID NO: 183 and SEQ ID NO: 184, respectively, and the HCDR1, HCDR2, and HCDR3 of the CD3-binding domain comprise the amino acid sequences set forth in SEQ ID NO: 185, SEQ ID NO: 186 and SEQ ID NO: 187, respectively; or (f) the LCDR1, LCDR2 and LCDR3 of the CD3-binding domain comprise the amino acid sequences set forth in SEQ ID NO: 188, DTS and SEQ ID NO: 190, respectively, and the HCDR1, HCDR2, and HCDR3 of the CD3-binding domain comprise the amino acid sequences set forth in SEQ ID NO: 191, SEQ ID NO: 192 and SEQ ID NO: 193, respectively.

2. The method of claim 1, wherein the CD3-binding domain comprises an immunoglobulin light chain variable region and an immunoglobulin heavy chain variable region;

wherein the immunoglobulin light chain variable region of the CD3-binding domain comprises the amino acid sequence of SEQ ID NO: 160; and wherein the immunoglobulin heavy chain variable region of the CD3-binding domain comprises the amino acid sequence of SEQ ID NO: 161.

3. The method of claim 1, wherein the CD123-binding domain comprises:

(i) an immunoglobulin light chain variable region comprising the amino acid sequence of SEQ ID NO:2; and (ii) an immunoglobulin heavy chain variable region comprising the amino acid sequence of SEQ ID NO:4.

4. The method of claim 1, wherein the CD123-binding domain is a single chain variable fragment (scFv), and the CD3-binding domain is an scFv.

5. The method of claim 1, wherein the recombinant polypeptide comprises in order from amino terminus to carboxyl terminus, (i) the CD123-binding domain, (ii) a hinge region, (iii) an immunoglobulin constant region, (iv) a carboxyl-terminus linker, and (v) the CD3-binding domain.

6. The method of claim 5, wherein the carboxyl-terminus linker comprises an amino acid sequence comprising $(Gly_4Ser)_n$, wherein n=1-7 (SEQ ID NO:314).

7. The method of claim 6, wherein n=3-5.

8. The method of claim 5, wherein the carboxyl-terminus linker comprises SEQ ID NO:288.

9. The method of claim 5, wherein the immunoglobulin constant region comprises immunoglobulin CH2 and CH3 domains of IgG1, IgG2, IgG3, IgG4, IgA1, IgA2 or IgD.

10. The method of claim 5, wherein the immunoglobulin constant region comprises a human IgG1 CH2 domain comprising the substitutions L234A, L235A, G237A, and K322A, according to the EU numbering system.

11. The method of claim 1, wherein the pharmaceutical composition comprises a dimeric protein comprising two identical copies of the recombinant polypeptide.

12. The method of claim 1, wherein the hematological cancer is acute myeloid leukemia (AML), B-lymphoid leukemia, blastic plasmocytoid dendritic neoplasm (BPDCN), hairy cell leukemia, acute lymphoblastic leukemia, refractory anemia with excess blasts, myelodysplastic syndrome, chronic myeloid leukemia or Hodgkin's lymphoma.

13. The method of claim 1, wherein the administration of the pharmaceutical composition does not cause excessive cytokine release.

14. The method of claim 13, wherein the cytokine is IFN-γ, TNF-α, IL-6, IL-2, IL-10, IL-17, IL-4, MCP-1, or any combination thereof.

15. The method of claim 1, wherein the pharmaceutical composition is administered by a single intravenous injection.

* * * * *

SEQUENCE LISTING

```
Sequence total quantity: 316
SEQ ID NO: 1            moltype = DNA  length = 342
FEATURE                 Location/Qualifiers
misc_feature            1..342
                        note = OMT1 variable light chain domain
source                  1..342
                        mol_type = other DNA
                        organism = synthetic construct
SEQUENCE: 1
gacatcgtga tgacccagtc tccagactcc ctggctgtgt ctctgggcga gagggccacc  60
atcaactgca agtccagcca cagtgtttta tacagctcca acaataagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttatagtact  300
cctccgacca ctttcggcgg agggaccaag gtggagatca aa                     342

SEQ ID NO: 2            moltype = AA  length = 114
FEATURE                 Location/Qualifiers
REGION                  1..114
                        note = OMT1 variable light chain domain
source                  1..114
```

```
                         mol_type = protein
                         organism = synthetic construct
SEQUENCE: 2
DIVMTQSPDS LAVSLGERAT INCKSSHSVL YSSNNKNYLA WYQQKPGQPP KLLIYWASTR  60
ESGVPDRFSG SGSGTDFTLT ISSLQAEDVA VYYCQQYYST PPTTFGGGTK VEIK        114

SEQ ID NO: 3             moltype = DNA  length = 372
FEATURE                  Location/Qualifiers
misc_feature             1..372
                         note = OMT1 variable heavy chain domain
source                   1..372
                         mol_type = other DNA
                         organism = synthetic construct
SEQUENCE: 3
gaggtgcagc tgttggagtc tgggggaggc ttggtacagc ctggggggtc cctgagactc  60
tcctgtgcag cctctggatt cacctttagc agctatggca tgagctgggt ccgccaggct  120
ccagggaagg ggctggaggg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtat attactgtgc gaaagaaaag  300
ttacgatatt ttgactggtt atccgatgct tttgatatct ggggccaagg gacaatggtc  360
accgtctctt ca                                                       372

SEQ ID NO: 4             moltype = AA  length = 124
FEATURE                  Location/Qualifiers
REGION                   1..124
                         note = OMT1 variable heavy chain domain
source                   1..124
                         mol_type = protein
                         organism = synthetic construct
SEQUENCE: 4
EVQLLESGGG LVQPGGSLRL SCAASGFTFS SYGMSWVRQA PGKGLEGVSA ISGSGGSTYY  60
ADSVKGRFTI SRDNSKNTLY LQMNSLRAED TAVYYCAKEK LRYFDWLSDA FDIWGQGTMV  120
TVSS                                                                124

SEQ ID NO: 5             moltype = DNA  length = 36
FEATURE                  Location/Qualifiers
misc_feature             1..36
                         note = OMT1 CDR L1
source                   1..36
                         mol_type = other DNA
                         organism = synthetic construct
SEQUENCE: 5
cacagtgttt tatacagctc caacaataag aactac                             36

SEQ ID NO: 6             moltype = AA  length = 12
FEATURE                  Location/Qualifiers
REGION                   1..12
                         note = OMT1 CDR L1
source                   1..12
                         mol_type = protein
                         organism = synthetic construct
SEQUENCE: 6
HSVLYSSNNK NY                                                       12

SEQ ID NO: 7             moltype =   length =
SEQUENCE: 7
000

SEQ ID NO: 8             moltype =   length =
SEQUENCE: 8
000

SEQ ID NO: 9             moltype = DNA  length = 30
FEATURE                  Location/Qualifiers
misc_feature             1..30
                         note = OMT1 CDR L3
source                   1..30
                         mol_type = other DNA
                         organism = synthetic construct
SEQUENCE: 9
cagcaatatt atagtactcc tccgaccact                                    30

SEQ ID NO: 10            moltype = AA  length = 10
FEATURE                  Location/Qualifiers
REGION                   1..10
                         note = OMT1 CDR L3
source                   1..10
                         mol_type = protein
                         organism = synthetic construct
```

```
SEQUENCE: 10
QQYYSTPPTT                                                  10

SEQ ID NO: 11          moltype = DNA  length = 24
FEATURE                Location/Qualifiers
misc_feature           1..24
                       note = OMT1 CDR H1
source                 1..24
                       mol_type = other DNA
                       organism = synthetic construct
SEQUENCE: 11
ggattcacct ttagcagcta tggc                                  24

SEQ ID NO: 12          moltype = AA  length = 8
FEATURE                Location/Qualifiers
REGION                 1..8
                       note = OMT1 CDR H1
source                 1..8
                       mol_type = protein
                       organism = synthetic construct
SEQUENCE: 12
GFTFSSYG                                                    8

SEQ ID NO: 13          moltype = DNA  length = 24
FEATURE                Location/Qualifiers
misc_feature           1..24
                       note = OMT1 CDR H2
source                 1..24
                       mol_type = other DNA
                       organism = synthetic construct
SEQUENCE: 13
attagtggta gtggtggtag caca                                  24

SEQ ID NO: 14          moltype = AA  length = 8
FEATURE                Location/Qualifiers
REGION                 1..8
                       note = OMT1 CDR H2
source                 1..8
                       mol_type = protein
                       organism = synthetic construct
SEQUENCE: 14
ISGSGGST                                                    8

SEQ ID NO: 15          moltype = DNA  length = 51
FEATURE                Location/Qualifiers
misc_feature           1..51
                       note = OMT1 CDR H3
source                 1..51
                       mol_type = other DNA
                       organism = synthetic construct
SEQUENCE: 15
gcgaaagaaa agttacgata ttttgactgg ttatccgatg cttttgatat c    51

SEQ ID NO: 16          moltype = AA  length = 17
FEATURE                Location/Qualifiers
REGION                 1..17
                       note = OMT1 CDR H3
source                 1..17
                       mol_type = protein
                       organism = synthetic construct
SEQUENCE: 16
AKEKLRYFDW LSDAFDI                                          17

SEQ ID NO: 17          moltype = DNA  length = 321
FEATURE                Location/Qualifiers
misc_feature           1..321
                       note = DB8, DB60, DB65, DB280, DB331, DB415, DB435 variable
                        light chain domain
source                 1..321
                       mol_type = other DNA
                       organism = synthetic construct
SEQUENCE: 17
gacatccaga tgacccagtc tccatcctcc ctgtctgcat ctgtaggaga cagagtcacc  60
atcacttgcc gggcaagtca gagcattagc agctatctga attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctctcac tttcggcgga  300
ggtaccaagg tggagatcaa a                                     321
```

```
SEQ ID NO: 18          moltype = AA  length = 107
FEATURE                Location/Qualifiers
REGION                 1..107
                       note = DB8, DB60, DB65, DB280, DB331, DB415, DB435 variable
                        light chain domain
source                 1..107
                       mol_type = protein
                       organism = synthetic construct
SEQUENCE: 18
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIK                107

SEQ ID NO: 19          moltype = DNA  length = 366
FEATURE                Location/Qualifiers
misc_feature           1..366
                       note = DB8 variable heavy chain domain
source                 1..366
                       mol_type = other DNA
                       organism = synthetic construct
SEQUENCE: 19
caggtgcagc tggtgcagtc tggggctgag gtgaagaagc ctggggcctc agtgaaggtt  60
tcctgcaagg catctggata catcttcacc gactactata tgcactgggt gcgtcaggcc  120
cctggacaag ggcttgagtg gatgggatgg atgagcccta acagtggtaa cacaggctat  180
gcacagaagt tccagggccg tgtcaccatg acccgcgaca cgtccacgag cacagtctac  240
atggagctga gcagcctgcg ttctgaggac acggccgtgt attactgtgc gagagatgcg  300
gcggattacg gtgactacgt tgcttttgat atctggggcc aagggacaat ggtcaccgtc  360
tcttca                                                             366

SEQ ID NO: 20          moltype = AA  length = 122
FEATURE                Location/Qualifiers
REGION                 1..122
                       note = DB8 variable heavy chain domain
source                 1..122
                       mol_type = protein
                       organism = synthetic construct
SEQUENCE: 20
QVQLVQSGAE VKKPGASVKV SCKASGYIFT DYYMHWVRQA PGQGLEWMGW MSPNSGNTGY  60
AQKFQGRVTM TRDTSTSTVY MELSSLRSED TAVYYCARDA ADYGDYVAFD IWGQGTMVTV  120
SS                                                                 122

SEQ ID NO: 21          moltype = DNA  length = 18
FEATURE                Location/Qualifiers
misc_feature           1..18
                       note = DB8, DB60, DB65, DB280, DB331, DB415, DB435 CDR L1
source                 1..18
                       mol_type = other DNA
                       organism = synthetic construct
SEQUENCE: 21
cagagcatta gcagctat                                                18

SEQ ID NO: 22          moltype = AA  length = 6
FEATURE                Location/Qualifiers
REGION                 1..6
                       note = DB8, DB60, DB65, DB280, DB331, DB415, DB435 CDR L1
source                 1..6
                       mol_type = protein
                       organism = synthetic construct
SEQUENCE: 22
QSISSY                                                             6

SEQ ID NO: 23          moltype =   length =
SEQUENCE: 23
000

SEQ ID NO: 24          moltype =   length =
SEQUENCE: 24
000

SEQ ID NO: 25          moltype = DNA  length = 27
FEATURE                Location/Qualifiers
misc_feature           1..27
                       note = DB8, DB60, DB65, DB280, DB331, DB415, DB435 CDR L3
source                 1..27
                       mol_type = other DNA
                       organism = synthetic construct
SEQUENCE: 25
caacagagtt acagtacccc tctcact                                      27

SEQ ID NO: 26          moltype = AA  length = 9
```

```
FEATURE                 Location/Qualifiers
REGION                  1..9
                        note = DB8, DB60, DB65, DB280, DB331, DB415, DB435 CDR L3
source                  1..9
                        mol_type = protein
                        organism = synthetic construct
SEQUENCE: 26
QQSYSTPLT                                                               9

SEQ ID NO: 27           moltype = DNA  length = 24
FEATURE                 Location/Qualifiers
misc_feature            1..24
                        note = DB8 and DB60 CDR H1
source                  1..24
                        mol_type = other DNA
                        organism = synthetic construct
SEQUENCE: 27
ggatacatct tcaccgacta ctat                                              24

SEQ ID NO: 28           moltype = AA  length = 8
FEATURE                 Location/Qualifiers
REGION                  1..8
                        note = DB8 CDR H1
source                  1..8
                        mol_type = protein
                        organism = synthetic construct
SEQUENCE: 28
GYIFTDYY                                                                8

SEQ ID NO: 29           moltype = DNA  length = 24
FEATURE                 Location/Qualifiers
misc_feature            1..24
                        note = DB8 CDR H2
source                  1..24
                        mol_type = other DNA
                        organism = synthetic construct
SEQUENCE: 29
atgagcccta acagtggtaa caca                                              24

SEQ ID NO: 30           moltype = AA  length = 8
FEATURE                 Location/Qualifiers
REGION                  1..8
                        note = DB8 CDR H2
source                  1..8
                        mol_type = protein
                        organism = synthetic construct
SEQUENCE: 30
MSPNSGNT                                                                8

SEQ ID NO: 31           moltype = DNA  length = 45
FEATURE                 Location/Qualifiers
misc_feature            1..45
                        note = DB8 CDR H3
source                  1..45
                        mol_type = other DNA
                        organism = synthetic construct
SEQUENCE: 31
gcgagagatg cggcggatta cggtgactac gttgcttttg atatc                       45

SEQ ID NO: 32           moltype = AA  length = 15
FEATURE                 Location/Qualifiers
REGION                  1..15
                        note = DB8 CDR H3
source                  1..15
                        mol_type = protein
                        organism = synthetic construct
SEQUENCE: 32
ARDAADYGDY VAFDI                                                        15

SEQ ID NO: 33           moltype = DNA  length = 357
FEATURE                 Location/Qualifiers
misc_feature            1..357
                        note = DB60 variable heavy chain domain
source                  1..357
                        mol_type = other DNA
                        organism = synthetic construct
SEQUENCE: 33
caggtgcagc tggtgcagtc tggggctgag gtgaagaagc ctggggcctc agtgaaggtt  60
tcctgcaagg catctggata caccttcacc agctactata tgcactgggt gcgtcaggcc  120
```

```
cctggacaag ggcttgagtg gatggggtgg atcaacccta acagtggtga cacaagctat  180
gcacagaagt tccagggccg tgtcaccatg acccgcgaca cgtccacgag cacagtctac  240
atggagctga gcagcctgcg ttctgaggac acggccgtgt attactgtgc gcaggatagt  300
agtggttccg ggcttttga tatctggggc caagggacaa tggtcaccgt ctcttca     357

SEQ ID NO: 34          moltype = AA  length = 119
FEATURE                Location/Qualifiers
REGION                 1..119
                       note = DB60 variable heavy chain domain
source                 1..119
                       mol_type = protein
                       organism = synthetic construct
SEQUENCE: 34
QVQLVQSGAE VKKPGASVKV SCKASGYTFT SYYMHWVRQA PGQGLEWMGW INPNSGDTSY  60
AQKFQGRVTM TRDTSTSTVY MELSSLRSED TAVYYCAQDS SGSGAFDIWG QGTMVTVSS   119

SEQ ID NO: 35          moltype = DNA  length = 24
FEATURE                Location/Qualifiers
misc_feature           1..24
                       note = DB60 CDR H1
source                 1..24
                       mol_type = other DNA
                       organism = synthetic construct
SEQUENCE: 35
ggatacacct tcaccagcta ctat                                         24

SEQ ID NO: 36          moltype = AA  length = 8
FEATURE                Location/Qualifiers
REGION                 1..8
                       note = DB60 CDR H1
source                 1..8
                       mol_type = protein
                       organism = synthetic construct
SEQUENCE: 36
GYTFTSYY                                                           8

SEQ ID NO: 37          moltype = DNA  length = 24
FEATURE                Location/Qualifiers
misc_feature           1..24
                       note = DB60 CDR H2
source                 1..24
                       mol_type = other DNA
                       organism = synthetic construct
SEQUENCE: 37
atcaacccta acagtggtga caca                                         24

SEQ ID NO: 38          moltype = AA  length = 8
FEATURE                Location/Qualifiers
REGION                 1..8
                       note = DB60 CDR H2
source                 1..8
                       mol_type = protein
                       organism = synthetic construct
SEQUENCE: 38
INPNSGDT                                                           8

SEQ ID NO: 39          moltype = DNA  length = 36
FEATURE                Location/Qualifiers
misc_feature           1..36
                       note = DB60 CDR H3
source                 1..36
                       mol_type = other DNA
                       organism = synthetic construct
SEQUENCE: 39
gcgcaggata gtagtggttc cggggctttt gatatc                            36

SEQ ID NO: 40          moltype = AA  length = 12
FEATURE                Location/Qualifiers
REGION                 1..12
                       note = DB60 CDR H3
source                 1..12
                       mol_type = protein
                       organism = synthetic construct
SEQUENCE: 40
AQDSSGSGAF DI                                                      12

SEQ ID NO: 41          moltype = DNA  length = 369
FEATURE                Location/Qualifiers
misc_feature           1..369
```

```
                        note = DB65 variable heavy chain domain
source                  1..369
                        mol_type = other DNA
                        organism = synthetic construct
SEQUENCE: 41
caggtgcagc tggtgcagtc tggggctgag gtgaagaagc ctggggcctc agtgaaggtt  60
tcctgcaagg catctggata caccttcacc ggctactata tgcactgggt gcgtcaggcc  120
cctggacaag ggcttgagtg gatgggatgg atgaacccta acagtggtaa cacaggctat  180
gcacagaagt tccagggccg tgtcaccatg acccgcgaca cgtccacgag cacagtctac  240
atggagctga gcagcctgcg ttctgaggac acggccgtgt attactgtgc gaaagaggaa  300
ccgatttttg gagtggttat ggatgctttt gatatctggg gccaagggac aatggtcacc  360
gtctcctca                                                          369

SEQ ID NO: 42           moltype = AA  length = 123
FEATURE                 Location/Qualifiers
REGION                  1..123
                        note = DB65 variable heavy chain domain
source                  1..123
                        mol_type = protein
                        organism = synthetic construct
SEQUENCE: 42
QVQLVQSGAE VKKPGASVKV SCKASGYTFT GYYMHWVRQA PGQGLEWMGW MNPNSGNTGY  60
AQKFQGRVTM TRDTSTSTVY MELSSLRSED TAVYYCAKEE PIFGVVMDAF DIWGQGTMVT  120
VSS                                                                123

SEQ ID NO: 43           moltype = DNA  length = 24
FEATURE                 Location/Qualifiers
misc_feature            1..24
                        note = DB65 CDR H1
source                  1..24
                        mol_type = other DNA
                        organism = synthetic construct
SEQUENCE: 43
ggatacacct tcaccggcta ctat                                         24

SEQ ID NO: 44           moltype = AA  length = 8
FEATURE                 Location/Qualifiers
REGION                  1..8
                        note = DB65 CDR H1
source                  1..8
                        mol_type = protein
                        organism = synthetic construct
SEQUENCE: 44
GYTFTGYY                                                           8

SEQ ID NO: 45           moltype = DNA  length = 24
FEATURE                 Location/Qualifiers
misc_feature            1..24
                        note = DB65 CDR H2
source                  1..24
                        mol_type = other DNA
                        organism = synthetic construct
SEQUENCE: 45
atgaacccta acagtggtaa caca                                         24

SEQ ID NO: 46           moltype = AA  length = 8
FEATURE                 Location/Qualifiers
REGION                  1..8
                        note = DB65 CDR H2
source                  1..8
                        mol_type = protein
                        organism = synthetic construct
SEQUENCE: 46
MNPNSGNT                                                           8

SEQ ID NO: 47           moltype = DNA  length = 48
FEATURE                 Location/Qualifiers
misc_feature            1..48
                        note = DB65 CDR H3
source                  1..48
                        mol_type = other DNA
                        organism = synthetic construct
SEQUENCE: 47
gcgaaagagg aaccgatttt tggagtggtt atggatgctt ttgatatc               48

SEQ ID NO: 48           moltype = AA  length = 16
FEATURE                 Location/Qualifiers
REGION                  1..16
                        note = DB65 CDR H3
```

```
source                  1..16
                        mol_type = protein
                        organism = synthetic construct
SEQUENCE: 48
AKEEPIFGVV MDAFDI                                                  16

SEQ ID NO: 49           moltype = DNA  length = 321
FEATURE                 Location/Qualifiers
misc_feature            1..321
                        note = DB82 variable light chain domain
source                  1..321
                        mol_type = other DNA
                        organism = synthetic construct
SEQUENCE: 49
gacatccaga tgacccagtc tccatcctcc ctgtctgcat ctgtaggaga ccgcgtcacc  60
atcacttgcc gggcaagtca gaccataaac aactatttga actggtatca gcagaaacca  120
gggaaagccc ctaagctcct gatctattct gcatctactt tgcaaagtgg ggtcccatca  180
cgtttcagtg gcagtggatc tgggacagat ttcactctca ccatcagcag tctgcaacct  240
gaagattttg caacttacta ctgtcaccag agttacactt cacctctcac tttcggcgga  300
ggtaccaagg tggagatcaa a                                            321

SEQ ID NO: 50           moltype = AA  length = 107
FEATURE                 Location/Qualifiers
REGION                  1..107
                        note = DB82 variable light chain domain
source                  1..107
                        mol_type = protein
                        organism = synthetic construct
SEQUENCE: 50
DIQMTQSPSS LSASVGDRVT ITCRASQTIN NYLNWYQQKP GKAPKLLIYS ASTLQSGVPS  60
RFSGSGSGTD FTLTISSLQP EDFATYYCHQ SYTSPLTFGG GTKVEIK                107

SEQ ID NO: 51           moltype = DNA  length = 363
FEATURE                 Location/Qualifiers
misc_feature            1..363
                        note = DB82 variable heavy chain domain
source                  1..363
                        mol_type = other DNA
                        organism = synthetic construct
SEQUENCE: 51
gaggtgcagc tggtggagtc tgggggaggc ttggtacagc ctgggggtc cctgcgcctc   60
tcctgtgcag cctctggatt cacctttagc agctatgcca tgagctgggt ccgccaggct  120
ccagggaagg ggctggagtg ggtctcagtt attagtgcca atagtgctgg tctaggccat  180
gcggactctg tgaagggccg gttcaccatc tcccgcgaca attccaagaa cacgctgtat  240
ctgcaaatga acagcctgcg cgccgaggac acggccgtat attactgtgc gagagtgggc  300
tatagcagct cggctgatgc ttttgatatc tggggccaag ggacaatggt caccgtctcc  360
tcg                                                                363

SEQ ID NO: 52           moltype = AA  length = 121
FEATURE                 Location/Qualifiers
REGION                  1..121
                        note = DB82 variable heavy chain domain
source                  1..121
                        mol_type = protein
                        organism = synthetic construct
SEQUENCE: 52
EVQLVESGGG LVQPGGSLRL SCAASGFTFS SYAMSWVRQA PGKGLEWVSV ISANSAGLGH  60
ADSVKGRFTI SRDNSKNTLY LQMNSLRAED TAVYYCARVG YSSSADAFDI WGQGTMVTVS  120
S                                                                  121

SEQ ID NO: 53           moltype = DNA  length = 18
FEATURE                 Location/Qualifiers
misc_feature            1..18
                        note = DB82 CDR L1
source                  1..18
                        mol_type = other DNA
                        organism = synthetic construct
SEQUENCE: 53
cagaccataa acaactat                                                18

SEQ ID NO: 54           moltype = AA  length = 6
FEATURE                 Location/Qualifiers
REGION                  1..6
                        note = DB82 CDR L1
source                  1..6
                        mol_type = protein
                        organism = synthetic construct
SEQUENCE: 54
QTINNY                                                             6
```

```
SEQ ID NO: 55          moltype =   length =
SEQUENCE: 55
000

SEQ ID NO: 56          moltype =   length =
SEQUENCE: 56
000

SEQ ID NO: 57          moltype = DNA  length = 27
FEATURE                Location/Qualifiers
misc_feature           1..27
                       note = DB82 CDR L3
source                 1..27
                       mol_type = other DNA
                       organism = synthetic construct
SEQUENCE: 57
caccagagtt acacttcacc tctcact                                  27

SEQ ID NO: 58          moltype = AA  length = 9
FEATURE                Location/Qualifiers
REGION                 1..9
                       note = DB82 CDR L3
source                 1..9
                       mol_type = protein
                       organism = synthetic construct
SEQUENCE: 58
HQSYTSPLT                                                      9

SEQ ID NO: 59          moltype = DNA  length = 24
FEATURE                Location/Qualifiers
misc_feature           1..24
                       note = DB82 CDR H1
source                 1..24
                       mol_type = other DNA
                       organism = synthetic construct
SEQUENCE: 59
ggattcacct ttagcagcta tgcc                                     24

SEQ ID NO: 60          moltype = AA  length = 8
FEATURE                Location/Qualifiers
REGION                 1..8
                       note = DB82 CDR H1
source                 1..8
                       mol_type = protein
                       organism = synthetic construct
SEQUENCE: 60
GFTFSSYA                                                       8

SEQ ID NO: 61          moltype = DNA  length = 24
FEATURE                Location/Qualifiers
misc_feature           1..24
                       note = DB82 CDR H2
source                 1..24
                       mol_type = other DNA
                       organism = synthetic construct
SEQUENCE: 61
attagtgcca atagtgctgg tcta                                     24

SEQ ID NO: 62          moltype = AA  length = 8
FEATURE                Location/Qualifiers
REGION                 1..8
                       note = DB82 CDR H2
source                 1..8
                       mol_type = protein
                       organism = synthetic construct
SEQUENCE: 62
ISANSAGL                                                       8

SEQ ID NO: 63          moltype = DNA  length = 42
FEATURE                Location/Qualifiers
misc_feature           1..42
                       note = DB82 CDR H3
source                 1..42
                       mol_type = other DNA
                       organism = synthetic construct
SEQUENCE: 63
gcgagagtgg gctatagcag ctcggctgat gcttttgata tc                 42
```

```
SEQ ID NO: 64          moltype = AA  length = 14
FEATURE                Location/Qualifiers
REGION                 1..14
                       note = DB82 CDR H3
source                 1..14
                       mol_type = protein
                       organism = synthetic construct
SEQUENCE: 64
ARVGYSSSAD AFDI                                                   14

SEQ ID NO: 65          moltype = DNA  length = 336
FEATURE                Location/Qualifiers
misc_feature           1..336
                       note = DB83 variable light chain domain
source                 1..336
                       mol_type = other DNA
                       organism = synthetic construct
SEQUENCE: 65
gatgttgtga tgactcagtc tccactctcc ctgcccgtca cccctggaga gccggcctcc  60
atctcctgca ggtctagtca gagcctcctg catagtaatg gagacaacta tttggattgg  120
tacctgcaga agccagggca gtctccacag ctcctgatct atttgggttc taatcgggcc  180
tccggggtcc ctgaccgttt cagtggcagt ggatcaggca cagattttac actgaaaatc  240
agccgtgtgg aggctgagga tgttggggtt tattactgca tgcaagctac acactggcca  300
ctcactttcg gccctggtac caaagtggat atcaaa                           336

SEQ ID NO: 66          moltype = AA  length = 112
FEATURE                Location/Qualifiers
REGION                 1..112
                       note = DB83 variable light chain domain
source                 1..112
                       mol_type = protein
                       organism = synthetic construct
SEQUENCE: 66
DVVMTQSPLS LPVTPGEPAS ISCRSSQSLL HSNGDNYLDW YLQKPGQSPQ LLIYLGSNRA  60
SGVPDRFSGS GSGTDFTLKI SRVEAEDVGV YYCMQATHWP LTFGPGTKVD IK          112

SEQ ID NO: 67          moltype = DNA  length = 375
FEATURE                Location/Qualifiers
misc_feature           1..375
                       note = DB83 variable heavy chain domain
source                 1..375
                       mol_type = other DNA
                       organism = synthetic construct
SEQUENCE: 67
caggtgcagc tggtgcagtc tggggctgag gtgaagaagc ctggggcctc agtgaaggtt  60
tcctgcaagg catctggata caccttcact agctatgcta tgcattgggt gcgtcaggcc  120
cctggacaag ggcttgagtg gatgggactt gttgatcctg aagatggtga aacaatatat  180
gcagagaagt tccagggccg tgtcaccatg acccgcgaca cgtccacgag cacagtctac  240
atggagctga gcagcctgcg ttctgaggac acggccgtgt attactgtgc gagacgaacg  300
tattactatg atagtagtgg ttcccgttat gcttttgata tctggggcca agggaccacg  360
gtcaccgtct cttca                                                  375

SEQ ID NO: 68          moltype = AA  length = 125
FEATURE                Location/Qualifiers
REGION                 1..125
                       note = DB83 variable heavy chain domain
source                 1..125
                       mol_type = protein
                       organism = synthetic construct
SEQUENCE: 68
QVQLVQSGAE VKKPGASVKV SCKASGYTFT SYAMHWVRQA PGQGLEWMGL VDPEDGETIY  60
AEKFQGRVTM TRDTSTSTVY MELSSLRSED TAVYYCARRT YYYDSSGSRY AFDIWGQGTT  120
VTVSS                                                             125

SEQ ID NO: 69          moltype = DNA  length = 33
FEATURE                Location/Qualifiers
misc_feature           1..33
                       note = DB83 CDR L1
source                 1..33
                       mol_type = other DNA
                       organism = synthetic construct
SEQUENCE: 69
cagagcctcc tgcatagtaa tggagacaac tat                              33

SEQ ID NO: 70          moltype = AA  length = 11
FEATURE                Location/Qualifiers
REGION                 1..11
                       note = DB83 CDR L1
source                 1..11
```

```
                        mol_type = protein
                        organism = synthetic construct
SEQUENCE: 70
QSLLHSNGDN Y                                                                 11

SEQ ID NO: 71           moltype =   length =
SEQUENCE: 71
000

SEQ ID NO: 72           moltype =   length =
SEQUENCE: 72
000

SEQ ID NO: 73           moltype = DNA  length = 27
FEATURE                 Location/Qualifiers
misc_feature            1..27
                        note = DB83 CDR L3
source                  1..27
                        mol_type = other DNA
                        organism = synthetic construct
SEQUENCE: 73
atgcaagcta cacactggcc actcact                                                27

SEQ ID NO: 74           moltype = AA  length = 9
FEATURE                 Location/Qualifiers
REGION                  1..9
                        note = DB83 CDR L3
source                  1..9
                        mol_type = protein
                        organism = synthetic construct
SEQUENCE: 74
MQATHWPLT                                                                    9

SEQ ID NO: 75           moltype = DNA  length = 24
FEATURE                 Location/Qualifiers
misc_feature            1..24
                        note = DB83 CDR H1
source                  1..24
                        mol_type = other DNA
                        organism = synthetic construct
SEQUENCE: 75
ggatacacct tcactagcta tgct                                                   24

SEQ ID NO: 76           moltype = AA  length = 8
FEATURE                 Location/Qualifiers
REGION                  1..8
                        note = DB83 CDR H1
source                  1..8
                        mol_type = protein
                        organism = synthetic construct
SEQUENCE: 76
GYTFTSYA                                                                     8

SEQ ID NO: 77           moltype = DNA  length = 24
FEATURE                 Location/Qualifiers
misc_feature            1..24
                        note = DB83 CDR H2
source                  1..24
                        mol_type = other DNA
                        organism = synthetic construct
SEQUENCE: 77
gttgatcctg aagatggtga aaca                                                   24

SEQ ID NO: 78           moltype = AA  length = 8
FEATURE                 Location/Qualifiers
REGION                  1..8
                        note = DB83 CDR H2
source                  1..8
                        mol_type = protein
                        organism = synthetic construct
SEQUENCE: 78
VDPEDGET                                                                     8

SEQ ID NO: 79           moltype = DNA  length = 54
FEATURE                 Location/Qualifiers
misc_feature            1..54
                        note = DB83 CDR H3
source                  1..54
                        mol_type = other DNA
```

```
                        organism = synthetic construct
SEQUENCE: 79
gcgagacgaa cgtattacta tgatagtagt ggttcccgtt atgcttttga tatc       54

SEQ ID NO: 80           moltype = AA  length = 18
FEATURE                 Location/Qualifiers
REGION                  1..18
                        note = DB83 CDR H3
source                  1..18
                        mol_type = protein
                        organism = synthetic construct
SEQUENCE: 80
ARRTYYYDSS GSRYAFDI                                               18

SEQ ID NO: 81           moltype = DNA  length = 321
FEATURE                 Location/Qualifiers
misc_feature            1..321
                        note = DB86 variable light chain domain
source                  1..321
                        mol_type = other DNA
                        organism = synthetic construct
SEQUENCE: 81
gacatccaga tgacccagtc tccatcctcc ctgtctgcat ctgtaggaga ccgcgtcacc  60
atcacttgcc gggcaagtca gggcatcaga aatgatttag gttggtatca gcagaaacca  120
gggaaagccc ctaagctcct gatctatgct gcatccactt tgcaatcagg ggtcccatca  180
cgtttcagtg gcagtggatc tgggacagat ttcactctca ccatcagcag tctgcaacct  240
gaagattttg caacttacta ctgtcaacag agttacggtg cccccctcac tttcggcgga  300
ggtaccaagg tggagatcaa a                                            321

SEQ ID NO: 82           moltype = AA  length = 107
FEATURE                 Location/Qualifiers
REGION                  1..107
                        note = DB86 variable light chain domain
source                  1..107
                        mol_type = protein
                        organism = synthetic construct
SEQUENCE: 82
DIQMTQSPSS LSASVGDRVT ITCRASQGIR NDLGWYQQKP GKAPKLLIYA ASTLQSGVPS  60
RFSGSGSGTD FTLTISSLQP EDFATYYCQQ SYGAPLTFGG GTKVEIK                107

SEQ ID NO: 83           moltype = DNA  length = 360
FEATURE                 Location/Qualifiers
misc_feature            1..360
                        note = DB86 variable heavy chain domain
source                  1..360
                        mol_type = other DNA
                        organism = synthetic construct
SEQUENCE: 83
caggtgcagc tggtgcagtc tggggctgag gtgaagaagc ctggggcctc agtgaaggtt  60
tcctgcaagg catctggata tatgttcagt ggccattctg cacactgggt gcgtcaggcc  120
cctggacaag ggcttgagtg gatgggatgg atgaacccta acagtggtaa cacaggctat  180
gcacagaagt tccagggccg tgtcaccatg acccgcgaca cgtccacgag cacagtctac  240
atggagctga gcagcctgcg ttctgaggac acggccgtgt attactgtgc gagagatagc  300
agtggctggt acgatgtctt tgactactgg ggccagggga ccctggtcac cgtctcctca  360

SEQ ID NO: 84           moltype = AA  length = 120
FEATURE                 Location/Qualifiers
REGION                  1..120
                        note = DB86 variable heavy chain domain
source                  1..120
                        mol_type = protein
                        organism = synthetic construct
SEQUENCE: 84
QVQLVQSGAE VKKPGASVKV SCKASGYMFS GHSAHWVRQA PGQGLEWMGW MNPNSGNTGY  60
AQKFQGRVTM TRDTSTSTVY MELSSLRSED TAVYYCARDS SGWYDVFDYW GQGTLVTVSS  120

SEQ ID NO: 85           moltype = DNA  length = 18
FEATURE                 Location/Qualifiers
misc_feature            1..18
                        note = DB86 CDR L1
source                  1..18
                        mol_type = other DNA
                        organism = synthetic construct
SEQUENCE: 85
cagggcatca gaaatgat                                               18

SEQ ID NO: 86           moltype = AA  length = 6
FEATURE                 Location/Qualifiers
REGION                  1..6
```

```
                       note = DB86 CDR L1
source                 1..6
                       mol_type = protein
                       organism = synthetic construct
SEQUENCE: 86
QGIRND                                                          6

SEQ ID NO: 87          moltype =   length =
SEQUENCE: 87
000

SEQ ID NO: 88          moltype =   length =
SEQUENCE: 88
000

SEQ ID NO: 89          moltype = DNA  length = 24
FEATURE                Location/Qualifiers
misc_feature           1..24
                       note = DB86 CDR L3
source                 1..24
                       mol_type = other DNA
                       organism = synthetic construct
SEQUENCE: 89
caacagagtt acggtgcccc cctc                                      24

SEQ ID NO: 90          moltype = AA  length = 9
FEATURE                Location/Qualifiers
REGION                 1..9
                       note = DB86 CDR L3
source                 1..9
                       mol_type = protein
                       organism = synthetic construct
SEQUENCE: 90
QQSYGAPLT                                                       9

SEQ ID NO: 91          moltype = DNA  length = 24
FEATURE                Location/Qualifiers
misc_feature           1..24
                       note = DB86 CDR H1
source                 1..24
                       mol_type = other DNA
                       organism = synthetic construct
SEQUENCE: 91
ggatatatgt tcagtggcca ttct                                      24

SEQ ID NO: 92          moltype = AA  length = 8
FEATURE                Location/Qualifiers
REGION                 1..8
                       note = DB86 CDR H1
source                 1..8
                       mol_type = protein
                       organism = synthetic construct
SEQUENCE: 92
GYMFSGHS                                                        8

SEQ ID NO: 93          moltype = DNA  length = 24
FEATURE                Location/Qualifiers
misc_feature           1..24
                       note = DB86 CDR H2
source                 1..24
                       mol_type = other DNA
                       organism = synthetic construct
SEQUENCE: 93
atgaacccta acagtggtaa caca                                      24

SEQ ID NO: 94          moltype = AA  length = 8
FEATURE                Location/Qualifiers
REGION                 1..8
                       note = DB86 CDR H2
source                 1..8
                       mol_type = protein
                       organism = synthetic construct
SEQUENCE: 94
MNPNSGNT                                                        8

SEQ ID NO: 95          moltype = DNA  length = 39
FEATURE                Location/Qualifiers
misc_feature           1..39
                       note = DB86 CDR H3
```

```
source                1..39
                      mol_type = other DNA
                      organism = synthetic construct
SEQUENCE: 95
gcgagagata gcagtggctg gtacgatgtc tttgactac                           39

SEQ ID NO: 96         moltype = AA  length = 13
FEATURE               Location/Qualifiers
REGION                1..13
                      note = DB86 CDR H3
source                1..13
                      mol_type = protein
                      organism = synthetic construct
SEQUENCE: 96
ARDSSGWYDV FDY                                                       13

SEQ ID NO: 97         moltype = DNA  length = 378
FEATURE               Location/Qualifiers
misc_feature          1..378
                      note = DB280 variable heavy chain domain
source                1..378
                      mol_type = other DNA
                      organism = synthetic construct
SEQUENCE: 97
caggtgcagc tggtgcagtc tggggctgag gtgaagaagc ctggggcctc agtgaaggtt  60
tcctgcaagg catctggata cagcctcaac ttatactata tgcactgggt gcgtcaggcc  120
cctggacaag ggcttgagtg gatgggatgg atgaacccta acagtggtaa cacaggctat  180
gcacagaagt tccagggccg tgtcaccatg acccgcgaca cgtccacgag cacagtctac  240
atggagctga gcagcctgcg ttctgaggac acggccgtgt attactgtgc gagcctcgat  300
tgtagtggtg gtagctgcta ctccgaatat gatgcttttg atatctgggg ccaagggacc  360
acggtcaccg tctcctca                                                  378

SEQ ID NO: 98         moltype = AA  length = 126
FEATURE               Location/Qualifiers
REGION                1..126
                      note = DB280 variable heavy chain domain
source                1..126
                      mol_type = protein
                      organism = synthetic construct
SEQUENCE: 98
QVQLVQSGAE VKKPGASVKV SCKASGYSLN LYYMHWVRQA PGQGLEWMGW MNPNSGNTGY  60
AQKFQGRVTM TRDTSTSTVY MELSSLRSED TAVYYCASLD CSGGSCYSEY DAFDIWGQGT  120
TVTVSS                                                               126

SEQ ID NO: 99         moltype = DNA  length = 24
FEATURE               Location/Qualifiers
misc_feature          1..24
                      note = DB280 CDR H1
source                1..24
                      mol_type = other DNA
                      organism = synthetic construct
SEQUENCE: 99
ggatacagcc tcaacttata ctat                                           24

SEQ ID NO: 100        moltype = AA  length = 8
FEATURE               Location/Qualifiers
REGION                1..8
                      note = DB280 CDR H1
source                1..8
                      mol_type = protein
                      organism = synthetic construct
SEQUENCE: 100
GYSLNLYY                                                             8

SEQ ID NO: 101        moltype = DNA  length = 24
FEATURE               Location/Qualifiers
misc_feature          1..24
                      note = DB280 CDR H2
source                1..24
                      mol_type = other DNA
                      organism = synthetic construct
SEQUENCE: 101
atgaacccta acagtggtaa caca                                           24

SEQ ID NO: 102        moltype = AA  length = 8
FEATURE               Location/Qualifiers
REGION                1..8
                      note = DB280 CDR H2
source                1..8
```

```
                         mol_type = protein
                         organism = synthetic construct
SEQUENCE: 102
MNPNSGNT                                                      8

SEQ ID NO: 103           moltype = DNA  length = 57
FEATURE                  Location/Qualifiers
misc_feature             1..57
                         note = DB280 CDR H3
source                   1..57
                         mol_type = other DNA
                         organism = synthetic construct
SEQUENCE: 103
gcgagcctcg attgtagtgg tggtagctgc tactccgaat atgatgcttt tgatatc     57

SEQ ID NO: 104           moltype = AA  length = 19
FEATURE                  Location/Qualifiers
REGION                   1..19
                         note = DB280 CDR H3
source                   1..19
                         mol_type = protein
                         organism = synthetic construct
SEQUENCE: 104
ASLDCSGGSC YSEYDAFDI                                          19

SEQ ID NO: 105           moltype = DNA  length = 357
FEATURE                  Location/Qualifiers
misc_feature             1..357
                         note = DB331 variable heavy chain domain
source                   1..357
                         mol_type = other DNA
                         organism = synthetic construct
SEQUENCE: 105
caggtgcagc tggtgcagtc tggggctgag gtgaagaagc ctggggcctc agtgaaggtt  60
tcctgcaagg catctggata caccttcacc agctactata tgcactgggt gcgtcaggcc  120
cctggacaag ggcttgagtg gatgggatgg atgaacccta acagtggtaa cacaggctat  180
gcacagaagt tccagggccg tgtcaccatg acccgcgaca cgtccacgag cacagtctac  240
atggagctga gcagcctgcg ttctgaggac acggccgtgt attactgtgc aacagatctc  300
gcgggggaag ccttgttcga cccctggggc cagggcaccc tggtcaccgt ctcctca     357

SEQ ID NO: 106           moltype = AA  length = 119
FEATURE                  Location/Qualifiers
REGION                   1..119
                         note = DB331 variable heavy chain domain
source                   1..119
                         mol_type = protein
                         organism = synthetic construct
SEQUENCE: 106
QVQLVQSGAE VKKPGASVKV SCKASGYTFT SYYMHWVRQA PGQGLEWMGW MNPNSGNTGY  60
AQKFQGRVTM TRDTSTSTVY MELSSLRSED TAVYYCATDL AGEALFDPWG QGTLVTVSS   119

SEQ ID NO: 107           moltype = DNA  length = 24
FEATURE                  Location/Qualifiers
misc_feature             1..24
                         note = DB331 CDR H1
source                   1..24
                         mol_type = other DNA
                         organism = synthetic construct
SEQUENCE: 107
ggatacacct tcaccagcta ctat                                    24

SEQ ID NO: 108           moltype = AA  length = 8
FEATURE                  Location/Qualifiers
REGION                   1..8
                         note = DB331 CDR H1
source                   1..8
                         mol_type = protein
                         organism = synthetic construct
SEQUENCE: 108
GYTFTSYY                                                      8

SEQ ID NO: 109           moltype = DNA  length = 24
FEATURE                  Location/Qualifiers
misc_feature             1..24
                         note = DB331 CDR H2
source                   1..24
                         mol_type = other DNA
                         organism = synthetic construct
SEQUENCE: 109
```

```
atgaaccta acagtggtaa caca                                   24

SEQ ID NO: 110         moltype = AA  length = 8
FEATURE                Location/Qualifiers
REGION                 1..8
                       note = DB331 CDR H2
source                 1..8
                       mol_type = protein
                       organism = synthetic construct
SEQUENCE: 110
MNPNSGNT                                                    8

SEQ ID NO: 111         moltype = DNA  length = 36
FEATURE                Location/Qualifiers
misc_feature           1..36
                       note = DB331 CDR H3
source                 1..36
                       mol_type = other DNA
                       organism = synthetic construct
SEQUENCE: 111
gcaacagatc tcgcgggga agccttgttc gacccc                     36

SEQ ID NO: 112         moltype = AA  length = 12
FEATURE                Location/Qualifiers
REGION                 1..12
                       note = DB331 CDR H3
source                 1..12
                       mol_type = protein
                       organism = synthetic construct
SEQUENCE: 112
ATDLAGEALF DP                                               12

SEQ ID NO: 113         moltype = DNA  length = 351
FEATURE                Location/Qualifiers
misc_feature           1..351
                       note = DB415 variable heavy chain domain
source                 1..351
                       mol_type = other DNA
                       organism = synthetic construct
SEQUENCE: 113
gaggtgcagc tggtggagtc tgggggaggc ttggtacagc ctgggggtc cctgcgcctc  60
tcctgtgcag cctctggaat caccttcagt agttatggca tgcattgggt ccgccaggct  120
ccagggaagg ggctggagtg ggtctcaggt attagttgga atagtggtaa cagagtctat  180
gtggactctg tgaagggccg gttcaccatc tcccgcgaca attccaagaa cacgctgtat  240
ctgcaaatga acagcctgcg cgccgaggac acggccgtat attactgtgc gagagatact  300
aatgatgctt ttgatatctg gggccaaggg accacggtca ccgtctcctc a          351

SEQ ID NO: 114         moltype = AA  length = 117
FEATURE                Location/Qualifiers
REGION                 1..117
                       note = DB415 variable heavy chain domain
source                 1..117
                       mol_type = protein
                       organism = synthetic construct
SEQUENCE: 114
EVQLVESGGG LVQPGGSLRL SCAASGITFS SYGMHWVRQA PGKGLEWVSG ISWNSGNRVY  60
VDSVKGRFTI SRDNSKNTLY LQMNSLRAED TAVYYCARDT NDAFDIWGQG TTVTVSS     117

SEQ ID NO: 115         moltype = DNA  length = 24
FEATURE                Location/Qualifiers
misc_feature           1..24
                       note = DB415 CDR H1
source                 1..24
                       mol_type = other DNA
                       organism = synthetic construct
SEQUENCE: 115
ggaatcacct tcagtagtta tggc                                  24

SEQ ID NO: 116         moltype = AA  length = 8
FEATURE                Location/Qualifiers
REGION                 1..8
                       note = DB415 CDR H1
source                 1..8
                       mol_type = protein
                       organism = synthetic construct
SEQUENCE: 116
GITFSSYG                                                    8

SEQ ID NO: 117         moltype = DNA  length = 24
```

```
FEATURE                 Location/Qualifiers
misc_feature            1..24
                        note = DB415 CDR H2
source                  1..24
                        mol_type = other DNA
                        organism = synthetic construct
SEQUENCE: 117
attagttgga atagtggtaa caga                                        24

SEQ ID NO: 118          moltype = AA  length = 8
FEATURE                 Location/Qualifiers
REGION                  1..8
                        note = DB415 CDR H2
source                  1..8
                        mol_type = protein
                        organism = synthetic construct
SEQUENCE: 118
ISWNSGNR                                                          8

SEQ ID NO: 119          moltype = DNA  length = 30
FEATURE                 Location/Qualifiers
misc_feature            1..30
                        note = DB415 CDR H3
source                  1..30
                        mol_type = other DNA
                        organism = synthetic construct
SEQUENCE: 119
gcgagagata ctaatgatgc ttttgatatc                                  30

SEQ ID NO: 120          moltype = AA  length = 10
FEATURE                 Location/Qualifiers
REGION                  1..10
                        note = DB415 CDR H3
source                  1..10
                        mol_type = protein
                        organism = synthetic construct
SEQUENCE: 120
ARDTNDAFDI                                                        10

SEQ ID NO: 121          moltype = DNA  length = 357
FEATURE                 Location/Qualifiers
misc_feature            1..357
                        note = DB435 variable heavy chain domain
source                  1..357
                        mol_type = other DNA
                        organism = synthetic construct
SEQUENCE: 121
caggtgcagc tggtgcagtc tggggctgag gtgaagaagc ctggggcctc agtgaaggtt  60
tcctgcaagg catctggagg caccttcagc agctatgcta tcagctgggt gcgtcaggcc  120
cctggacaag ggcttgagtg gatgggctgg atcacccctc acaatggtaa cataaagtat  180
gcacgggagt tccagggccg tgtcaccatg acccgcgaca cgtccacgag cacagtctac  240
atggagctga gcagcctgcg ttctgaggac acggccgtgt attactgtgc gaaagatctg  300
aactggaacg cagcctttga ctactggggc caggggaccc tggtcaccgt ctcctca    357

SEQ ID NO: 122          moltype = AA  length = 119
FEATURE                 Location/Qualifiers
REGION                  1..119
                        note = DB435 variable heavy chain domain
source                  1..119
                        mol_type = protein
                        organism = synthetic construct
SEQUENCE: 122
QVQLVQSGAE VKKPGASVKV SCKASGGTFS SYAISWVRQA PGQGLEWMGW ITPHNGNIKY  60
AREFQGRVTM TRDTSTSTVY MELSSLRSED TAVYYCAKDL NWNAAFDYWG QGTLVTVSS   119

SEQ ID NO: 123          moltype = DNA  length = 24
FEATURE                 Location/Qualifiers
misc_feature            1..24
                        note = DB435 CDR H1
source                  1..24
                        mol_type = other DNA
                        organism = synthetic construct
SEQUENCE: 123
ggaggcacct tcagcagcta tgct                                        24

SEQ ID NO: 124          moltype = AA  length = 8
FEATURE                 Location/Qualifiers
REGION                  1..8
                        note = DB435 CDR H1
```

```
source                  1..8
                        mol_type = protein
                        organism = synthetic construct
SEQUENCE: 124
GGTFSSYA                                                          8

SEQ ID NO: 125          moltype = DNA  length = 24
FEATURE                 Location/Qualifiers
misc_feature            1..24
                        note = DB435 CDR H2
source                  1..24
                        mol_type = other DNA
                        organism = synthetic construct
SEQUENCE: 125
atcacccctc acaatggtaa cata                                        24

SEQ ID NO: 126          moltype = AA  length = 8
FEATURE                 Location/Qualifiers
REGION                  1..8
                        note = DB435 CDR H2
source                  1..8
                        mol_type = protein
                        organism = synthetic construct
SEQUENCE: 126
ITPHNGNI                                                          8

SEQ ID NO: 127          moltype = DNA  length = 36
FEATURE                 Location/Qualifiers
misc_feature            1..36
                        note = DB435 CDR H3
source                  1..36
                        mol_type = other DNA
                        organism = synthetic construct
SEQUENCE: 127
gcgaaagatc tgaactggaa cgcagccttt gactac                           36

SEQ ID NO: 128          moltype = AA  length = 12
FEATURE                 Location/Qualifiers
REGION                  1..12
                        note = DB435 CDR H3
source                  1..12
                        mol_type = protein
                        organism = synthetic construct
SEQUENCE: 128
AKDLNWNAAF DY                                                     12

SEQ ID NO: 129          moltype = DNA  length = 2340
FEATURE                 Location/Qualifiers
misc_feature            1..2340
                        note = OMT1 VHVL x TSC456 scFv-Fc-scFv TRI129
source                  1..2340
                        mol_type = other DNA
                        organism = synthetic construct
SEQUENCE: 129
atggaagcac cagcgcagct tctcttcctc ctgctactct ggctcccaga taccaccggt  60
gaggtgcagc tgttggagtc tgggggaggc ttggtacagc ctggggggtc cctgagactc  120
tcctgtgcag cctctggatt cacctttagc agctatggca tgagctgggt ccgccaggct  180
ccagggaagg ggctggaggg ggtctcagct attagtggta gtggtggtag cacatactac  240
gcagactccg tgaagggccg gttcaccatc tccagagaca attccaagaa cacgctgtat  300
ctgcaaatga acagcctgag agccgaggac acggccgtat attactgtgc gaaagaaaag  360
ttacgatatt ttgactggtt atccgatgct tttgatatct ggggccaagg gacaatggtc  420
accgtctctt caggtggagg cggttcaggc ggaggtggat ccggcggtgg cggctccggt  480
ggcggcggat ctgacatcgt gatgacccag tctccagact ccctggctgt gtctctgggc  540
gagagggcca ccatcaactg caagtccagc cacagtgttt tatacagctc caacaataag  600
aactacttag cttggtacca gcagaaacca ggacagcctc ctaagctgct catttactgg  660
gcatctaccc gggaatccgg ggtccctgac cgattcagtg gcagcgggtc tgggacagat  720
ttcactctca ccatcagcag cctgcaggct gaagatgtgg cagtttatta ctgtcagcaa  780
tattatagta ctcctccgac cactttcggc ggagggacca aggtggagat caaatcctcg  840
agtgagccca aatcttctga caaaactcac acatgcccac cgtgcccagc acctgaagcc  900
gcgggtgcac cgtcagtctt cctcttcccc ccaaaaccca aggacaccct catgatctcc  960
cggacccctg aggtcacatg cgtggtggtg gacgtgagcc acgaagaccc tgaggtcaag  1020
ttcaactggt acgtggacgg cgtggaggtg cataatgcca agacaaagcc gcgggaggag  1080
cagtacaaca gcacgtaccg tgtggtcagc gtcctcaccg tcctgcacca ggactggctg  1140
aatggcaagg aatacaagtg cgcggtctcc aacaaagccc tcccagcccc catcgagaaa  1200
accatctcca aagccaaagg gcagccccga gaaccacagg tgtacaccct gcccccatcc  1260
cgggatgagc tgaccaagaa ccaggtcagc ctgacctgcc tggtcaaagg cttctatcca  1320
agcgacatcg ccgtggagtg ggagagcaat gggcagccgg agaacaacta caagaccacg  1380
cctcccgtgc tggactccga cggctccttc ttcctctaca gcaagctcac cgtggacaag  1440
agcaggtggc agcaggggaa cgtcttctca tgctccgtga tgcatgaggc tctgcacaac  1500
```

```
cactacacgc agaagagcct ctccctgtct ccgggttccg gaggaggggg ttcaggtggg  1560
ggaggttctg gcggcggggg aagcccttca caggtgcaac tggtgcagag tggacccgag  1620
gttaaaaaac cagggtcctc cgttaaggtt agctgcaaag cctctggcta cacattttcc  1680
aggagtacaa tgcactgggt gaggcaggct cctggacagg gactcgagtg gatcgggtat  1740
atcaacccat ctagcgccta taccaattac aaccaaaagt ttaaggaccg agttaccatt  1800
accgctgaca aatccaccag tacagcttat atggagctgt catctcttag gtccgaggac  1860
actgctgttt attactgcgc tcgtcctcag gttcactatg actataatgg ttttccctac  1920
tggggtcagg gaaccctggt gactgtctct tctggcggtg gaggcagcgg tgggggtggg  1980
tctggaggcg gtggcagtgg cggcggaggc tctgatattc agatgactca gtctcctagc  2040
actctcagcg ccagcgtggg ggatcgtgtg acaatgactt gctccgctag cagtagtgtg  2100
tcttacatga attggtatca gcagaagccc gggaaagcac ctaagcgctg gatctatgac  2160
tcttccaagc tggcaagtgg tgtcccctca cggttctctg gctcaggttc tggtactgac  2220
tatactttga ctatctcctc cctccagccc gatgatttcg ctacctatta ttgtcagcag  2280
tggagccgta acccacccac tttcggaggc ggtaccaaag tggagatcaa gaggtcataa  2340

SEQ ID NO: 130          moltype = AA  length = 759
FEATURE                 Location/Qualifiers
REGION                  1..759
                        note = OMT1 VHVL x TSC456 scFv-Fc-scFv TRI129
source                  1..759
                        mol_type = protein
                        organism = synthetic construct
SEQUENCE: 130
EVQLLESGGG LVQPGGSLRL SCAASGFTFS SYGMSWVRQA PGKGLEGVSA ISGSGGSTYY  60
ADSVKGRFTI SRDNSKNTLY LQMNSLRAED TAVYYCAKEK LRYFDWLSDA FDIWGQGTMV  120
TVSSGGGGSG GGGSGGGGSG GGGSDIVMTQ SPDSLAVSLG ERATINCKSS HSVLYSSNNK  180
NYLAWYQQKP GQPPKLLIYW ASTRESGVPD RFSGSGSGTD FTLTISSLQA EDVAVYYCQQ  240
YYSTPPTTFG GGTKVEIKSS SEPKSSDKTH TCPPCPAPEA AGAPSVFLFP PKPKDTLMIS  300
RTPEVTCVVV DVSHEDPEVK FNWYVDGVEV HNAKTKPREE QYNSTYRVVS VLTVLHQDWL  360
NGKEYKCAVS NKALPAPIEK TISKAKGQPR EPQVYTLPPS RDELTKNQVS LTCLVKGFYP  420
SDIAVEWESN GQPENNYKTT PPVLDSDGSF FLYSKLTVDK SRWQQGNVFS CSVMHEALHN  480
HYTQKSLSLS PGSGGGGSGG GGSGGGGSPS QVQLVQSGPE VKKPGSSVKV SCKASGYTFS  540
RSTMHWVRQA PGQGLEWIGY INPSSAYTNY NQKFKDRVTI TADKSTSTAY MELSSLRSED  600
TAVYYCARPQ VHYDYNGFPY WGQGTLVTVS SGGGGSGGGG SGGGGSGGGG SDIQMTQSPS  660
TLSASVGDRV TMTCSASSSV SYMNWYQQKP GKAPKRWIYD SSKLASGVPS RFSGSGSGTD  720
YTLTISSLQP DDFATYYCQQ WSRNPPTFGG GTKVEIKRS                          759

SEQ ID NO: 131          moltype = DNA  length = 2334
FEATURE                 Location/Qualifiers
misc_feature            1..2334
                        note = OMT1 VLVH x TSC456 scFv-Fc-scFv TRI130
source                  1..2334
                        mol_type = other DNA
                        organism = synthetic construct
SEQUENCE: 131
atggaagcac cagcgcagct tctcttcctc ctgctactct ggctcccaga taccaccggt  60
gacatcgtga tgacccagtc tccagactcc ctggctgtgt ctctgggcga gagggccacc  120
atcaactgca agtccagcca cagtgtttta tacagctcca acaataagaa ctacttagct  180
tggtaccagc agaaaccagg acagcctcct aagctgctca tttactgggc atctacccgg  240
gaatccgggg tccctgaccg attcagtggc agcgggtctg ggacagattt cactctcacc  300
atcagcagcc tgcaggctga agatgtggca gtttattact gtcagcaata ttatagtact  360
cctccgacca ctttcggcgg agggaccaag gtggagatca aaggtggagg cggttcaggc  420
ggaggtggat ccggcggtgg cggctccggt ggcggcggat ctgaggtgca gctgttggag  480
tctgggggag gcttggtaca gcctgggggg tccctgagac tctcctgtgc agcctctgga  540
ttcaccttta gcagctatgg catgagctgg gtccgccagg ctccagggaa ggggctggag  600
ggggtctcag ctattagtgg tagtggtggt agcacatact acgcagactc cgtgaagggc  660
cggttcacca tctccagaga caattccaag aacacgctgt atctgcaaat gaacagcctg  720
agagccgagg acacggccgt atattactgt gcgaaagaaa agttacgata ttttgactgg  780
ttatccgatg cttttgatat ctggggccaa gggacaatgg tcaccgtctc ctcgagtgag  840
cccaaatctt ctgacaaaac tcacacatgc ccaccgtgcc cagcacctga agccgcgggt  900
gcaccgtcag tcttcctctt ccccccaaaa cccaaggaca ccctcatgat ctcccggacc  960
cctgaggtca catgcgtggt ggtggacgtg agccacgaag accctgaggt caagttcaac  1020
tggtacgtgg acggcgtgga ggtgcataat gccaagacaa agccgcggga ggagcagtac  1080
aacagcacgt accgtgtggt cagcgtcctc accgtcctgc accaggactg gctgaatggc  1140
aaggaataca agtgcgcggt ctccaacaaa gccctcccag cccccatcga gaaaaccatc  1200
tccaaagcca aagggcagcc ccgagaacca caggtgtaca ccctgccccc atcccgggat  1260
gagctgacca agaaccaggt cagcctgacc tgcctggtca aaggcttcta tccaagcgac  1320
atcgccgtgg agtgggagag caatgggcag ccggagaaca actacaagac cacgcctccc  1380
gtgctggact ccgacggctc cttcttcctc tacagcaagc tcaccgtgga caagagcagg  1440
tggcagcagg ggaacgtctt ctcatgctcc gtgatgcatg aggctctgca caaccactac  1500
acgcagaaga gcctctccct gtctccgggt tccggaggag gggggttcagg tgggggaggt  1560
tctggcggcg ggggaagccc ttcacaggtg caactggtgc agagtggacc cgaggttaaa  1620
aaaccagggt cctccgttaa ggttagctgc aaagcctctg gctacacatt ttccaggagt  1680
acaatgcact gggtgaggca ggctcctgga cagggactcg agtggatcgg gtatatcaac  1740
ccatctagcg cctataccaa ttacaaccaa aagtttaagg accgagttac cattaccgct  1800
gacaaatcca ccagtacagc ttatatggag ctgtcatctc ttaggtccga ggacactgct  1860
gtttattact gcgctcgtcc tcaggttcac tatgactata atggttttcc ctactggggt  1920
cagggaaccc tggtgactgt ctcttctggc ggtggaggca gcggtggggg tgggtctgga  1980
ggcggtggca gtggcggcgg aggctctgat attcagatga ctcagtctcc tagcactctc  2040
```

```
agcgccagcg tgggggatcg tgtgacaatg acttgctccg ctagcagtag tgtgtcttac  2100
atgaattggt atcagcagaa gcccgggaaa gcacctaagc gctggatcta tgactcttcc  2160
aagctggcaa gtggtgtccc ctcacggttc tctggctcag gttctggtac tgactatact  2220
ttgactatct cctccctcca gcccgatgat ttcgctacct attattgtca gcagtggagc  2280
cgtaacccac ccactttcgg aggcggtacc aaagtggaga tcaagaggtc ataa        2334

SEQ ID NO: 132         moltype = AA  length = 757
FEATURE                Location/Qualifiers
REGION                 1..757
                       note = OMT1 VLVH x TSC456 scFv-Fc-scFv TRI130
source                 1..757
                       mol_type = protein
                       organism = synthetic construct
SEQUENCE: 132
DIVMTQSPDS LAVSLGERAT INCKSSHSVL YSSNNKNYLA WYQQKPGQPP KLLIYWASTR  60
ESGVPDRFSG SGSGTDFTLT ISSLQAEDVA VYYCQQYYST PPTTFGGGTK VEIKGGGGSG  120
GGGSGGGGSG GGGSEVQLLE SGGGLVQPGG SLRLSCAASG FTFSSYGMSW VRQAPGKGLE  180
GVSAISGSGG STYYADSVKG RFTISRDNSK NTLYLQMNSL RAEDTAVYYC AKEKLRYFDW  240
LSDAFDIWGQ GTMVTVSSSE PKSSDKTHTC PPCPAPEAAG APSVFLFPPK PKDTLMISRT  300
PEVTCVVVDV SHEDPEVKFN WYVDGVEVHN AKTKPREEQY NSTYRVVSVL TVLHQDWLNG  360
KEYKCAVSNK ALPAPIEKTI SKAKGQPREP QVYTLPPSRD ELTKNQVSLT CLVKGFYPSD  420
IAVEWESNGQ PENNYKTTPP VLDSDGSFFL YSKLTVDKSR WQQGNVFSCS VMHEALHNHY  480
TQKSLSLSPG SGGGGSGGGG SGGGGSPSQV QLVQSGPEVK KPGSSVKVSC KASGYTFSRS  540
TMHWVRQAPG QGLEWIGYIN PSSAYTNYNQ KFKDRVTITA DKSTSTAYME LSSLRSEDTA  600
VYYCARPQVH YDYNGFPYWG QGTLVTVSSG GGGSGGGGSG GGGSGGGGSD IQMTQSPSTL  660
SASVGDRVTM TCSASSSVSY MNWYQQKPGK APKRWIYDSS KLASGVPSRF SGSGSGTDYT  720
LTISSLQPDD FATYYCQQWS RNPPTFGGGT KVEIKRS                          757

SEQ ID NO: 133         moltype = DNA  length = 2313
FEATURE                Location/Qualifiers
misc_feature           1..2313
                       note = DB8 VHVL x TSC456 scFv-Fc-scFv TRI123
source                 1..2313
                       mol_type = other DNA
                       organism = synthetic construct
SEQUENCE: 133
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata catcttcacc gactactata tgcactgggt gcgtcaggcc  180
cctggacaag ggcttgagtg gatgggatgg atgagcccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc gagagatgcg  360
gcggattacg gtgactacgt tgcttttgat atctggggcc aagggacaat ggtcaccgtc  420
tcttcaggcg gcggcggcag cggcggcggc ggcagcggcg gcggaggctc cggcggcggc  480
ggcagcgaca tccagatgac ccagtctcca tcctccctgt ctgcatctgt aggagacaga  540
gtcaccatca cttgccgggc aagtcagagc attagcagct atctgaattg gtatcagcag  600
aaaccaggga aagcccctaa gctcctgatc tatgctgcat ccagtttgca aagtggggtc  660
ccatcaaggt tcagtggcag tggatctggg acagatttca ctctcaccat cagcagtctg  720
caacctgaag attttgcaac ttactactgt caacagagtt acagtacccc tctcactttc  780
ggcggaggta ccaaggtgga gatcaaatcc tcgagtgagc ccaaatcttc tgacaaaact  840
cacacatgcc caccgtgccc agcacctgaa gccgcgggtg caccgtcagt cttcctcttc  900
cccccaaaac ccaaggacac cctcatgatc tcccggaccc ctgaggtcac atgcgtggtg  960
gtggacgtga gccacgaaga ccctgaggtc aagttcaact ggtacgtgga cggcgtggag  1020
gtgcataatg ccaagacaaa gccgcgggag gagcagtaca acagcacgta ccgtgtggtc  1080
agcgtcctca ccgtcctgca ccaggactgg ctgaatggca aggaatacaa gtgcgcggtc  1140
tccaacaaag ccctcccagc ccccatcgag aaaaccatct ccaaagccaa agggcagccc  1200
cgagaaccac aggtgtacac cctgccccca tcccgggatg agctgaccaa gaaccaggtc  1260
agcctgacct gcctggtcaa aggcttctat ccaagcgaca tcgccgtgga gtgggagagc  1320
aatgggcagc cggagaacaa ctacaagacc acgcctcccg tgctggactc cgacggctcc  1380
ttcttcctct acagcaagct caccgtggac aagagcaggt ggcagcaggg gaacgtcttc  1440
tcatgctccg tgatgcatga ggctctgcac aaccactaca cgcagaagag cctctccctg  1500
tctccgggtt ccggaggagg gggttcaggt gggggaggtt ctggcggcgg gggaagccct  1560
tcacaggtgc aactggtgca gagtggaccc gaggttaaaa aaccagggtc ctccgttaag  1620
gttagctgca aagcctctgg ctacacattt tccaggagta caatgcactg ggtgaggcag  1680
gctcctggac agggactcga gtggatcggg tatatcaacc catctagcgc ctataccaat  1740
tacaaccaaa agtttaagga ccgagttacc attaccgctg acaaatccac cagtacagct  1800
tatatggagc tgtcatctct taggtccgag gacactgctg tttattactg cgctcgtcct  1860
caggttcact atgactataa tggttttccc tactggggtc agggaaccct ggtgactgtc  1920
tcttctggcg gtggaggcag cggtgggggt gggtctggag gcggtggcag tggcggcgga  1980
ggctctgata ttcagatgac tcagtctcct agcactctca gcgccagcgt gggggatcgt  2040
gtgacaatga cttgctccgc tagcagtagt gtgtcttaca tgaattggta tcagcagaag  2100
cccgggaaag cacctaagcg ctggatctat gactcttcca agctggcaag tggtgtcccc  2160
tcacggttct ctggctcagg ttctggtact gactatactt tgactatctc ctccctccag  2220
cccgatgatt tcgctaccta ttattgtcag cagtggagcc gtaacccacc cactttcgga  2280
ggcggtacca aagtggagat caagaggtca taa                              2313

SEQ ID NO: 134         moltype = AA  length = 750
FEATURE                Location/Qualifiers
REGION                 1..750
```

```
                        note = DB8 VHVL x TSC456 scFv-Fc-scFv TRI123
source                  1..750
                        mol_type = protein
                        organism = synthetic construct
SEQUENCE: 134
QVQLVQSGAE VKKPGASVKV SCKASGYIFT DYYMHWVRQA PGQGLEWMGW MSPNSGNTGY  60
AQKFQGRVTM TRDTSTSTVY MELSSLRSED TAVYYCARDA ADYGDYVAFD IWGQGTMVTV  120
SSGGGGSGGG GSGGGGSGGG GSDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIKS SSEPKSSDKT HTCPPCPAPE AAGAPSVFLF PPKPKDTLMI SRTPEVTCVV  300
VDVSHEDPEV KFNWYVDGVE VHNAKTKPRE EQYNSTYRVV SVLTVLHQDW LNGKEYKCAV  360
SNKALPAPIE KTISKAKGQP REPQVYTLPP SRDELTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGSGGGGSG GGGSGGGGSP SQVQLVQSGP EVKKPGSSVK VSCKASGYTF SRSTMHWVRQ  540
APGQGLEWIG YINPSSAYTN YNQKFKDRVT ITADKSTSTA YMELSSLRSE DTAVYYCARP  600
QVHYDYNGFP YWGQGTLVTV SSGGGGSGGG GSGGGGSGGG GSDIQMTQSP STLSASVGDR  660
VTMTCSASSS VSYMNWYQQK PGKAPKRWIY DSSKLASGVP SRFSGSGSGT DYTLTISSLQ  720
PDDFATYYCQ QWSRNPPTFG GGTKVEIKRS                                   750

SEQ ID NO: 135          moltype = DNA  length = 2307
FEATURE                 Location/Qualifiers
misc_feature            1..2307
                        note = DB8 VLVH x TSC456 scFv-Fc-scFv TRI124
source                  1..2307
                        mol_type = other DNA
                        organism = synthetic construct
SEQUENCE: 135
atggaagcac cagcgcagct tctcttcctc ctgctactct ggctcccaga taccaccggt  60
gacatccaga tgacccagtc tccatcctcc ctgtctgcat ctgtaggaga cagagtcacc  120
atcacttgcc gggcaagtca gagcattagc agctatctga attggtatca gcagaaacca  180
gggaaagccc ctaagctcct gatctatgct gcatccagtt tgcaaagtgg ggtcccatca  240
aggttcagtg gcagtggatc tgggacagat ttcactctca ccatcagcag tctgcaacct  300
gaagattttg caacttacta ctgtcaacag agttacagta cccctctcac tttcggcgga  360
ggtaccaagg tggagatcaa aggcggcggc ggcagcggcg gcggcggcag cggcggcgga  420
ggctccggcg gcggcggcag ccaggtgcag ctggtgcagt ctggggctga ggtgaagaag  480
cctggggcct cagtgaaggt ttcctgcaag gcatctggat acatcttcac cgactactat  540
atgcactggg tgcgtcaggc ccctggacaa gggcttgagt ggatgggatg gatgagccct  600
aacagtggta acacaggcta tgcacagaag ttccagggcc gtgtcaccat gacccgcgac  660
acgtccacga gcacagtcta catggagctg agcagcctgc gttctgagga cacggccgtg  720
tattactgtg cgagagatgc ggcggattac ggtgactacg ttgcttttga tatctggggc  780
caagggacaa tggtcaccgt ctcctcgagt gagcccaaat cttctgacaa aactcacaca  840
tgcccaccgt gcccagcacc tgaagccgcg ggtgcaccgt cagtcttcct cttcccccca  900
aaacccaagg acaccctcat gatctcccgg acccctgagg tcacatgcgt ggtggtggac  960
gtgagccacg aagaccctga ggtcaagttc aactggtacg tggacggcgt ggaggtgcat  1020
aatgccaaga caaagccgcg ggaggagcag tacaacagca cgtaccgtgt ggtcagcgtc  1080
ctcaccgtcc tgcaccagga ctggctgaat ggcaaggaat acaagtgcgc ggtctccaac  1140
aaagccctcc cagcccccat cgagaaaacc atctccaaag ccaaagggca gccccgagaa  1200
ccacaggtgt acaccctgcc cccatcccgg gatgagctga ccaagaacca ggtcagcctg  1260
acctgcctgg tcaaaggctt ctatccaagc gacatcgccg tggagtggga gagcaatggg  1320
cagccggaga acaactacaa gaccacgcct cccgtgctgg actccgacgg ctccttcttc  1380
ctctacagca agctcaccgt ggacaagagc aggtggcagc aggggaacgt cttctcatgc  1440
tccgtgatgc atgaggctct gcacaaccac tacacgcaga agagcctctc cctgtctccg  1500
ggttccggag gagggggttc aggtggggga ggttctggcg gcgggggaag cccttcacag  1560
gtgcaactgg tgcagagtgg acccgaggtt aaaaaaccag ggtcctccgt taaggttagc  1620
tgcaaagcct ctggctacac attttccagg agtacaatgc actgggtgag gcaggctcct  1680
ggacagggac tcgagtggat cggtatatc aacccatcta gcgcctatac caattacaac  1740
caaaagttta aggaccgagt taccattacc gctgacaaat ccaccagtac agcttatatg  1800
gagctgtcat ctcttaggtc cgaggacact gctgtttatt actgcgctcg tcctcaggtt  1860
cactatgact ataatggttt tccctactgg ggtcagggaa ccctggtgac tgtctcttct  1920
ggcggtggag gcagcggtgg gggtgggtct ggaggcggtg gcagtggcgg cggaggctct  1980
gatattcaga tgactcagtc tcctagcact ctcagcgcca gcgtgggga tcgtgtgaca  2040
atgacttgct ccgctagcag tagtgtgtct tacatgaatt ggtatcagca gaagcccggg  2100
aaagcaccta agcgctggat ctatgactct tccaagctgg caagtggtgt cccctcacgg  2160
ttctctggct caggttctgg tactgactat actttgacta tctcctccct ccagcccgat  2220
gatttcgcta cctattattg tcagcagtgg agccgtaacc cacccacttt cggaggcggt  2280
accaaagtgg agatcaagag gtcataa                                      2307

SEQ ID NO: 136          moltype = AA  length = 748
FEATURE                 Location/Qualifiers
REGION                  1..748
                        note = DB8 VLVH x TSC456 scFv-Fc-scFv TRI124
source                  1..748
                        mol_type = protein
                        organism = synthetic construct
SEQUENCE: 136
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIKGGG GSGGGGSGGG  120
GSGGGGSQVQ LVQSGAEVKK PGASVKVSCK ASGYIFTDYY MHWVRQAPGQ GLEWMGWMSP  180
NSGNTGYAQK FQGRVTMTRD TSTSTVYMEL SSLRSEDTAV YYCARDAADY GDYVAFDIWG  240
```

```
QGTMVTVSSS EPKSSDKTHT CPPCPAPEAA GAPSVFLFPP KPKDTLMISR TPEVTCVVVD  300
VSHEDPEVKF NWYVDGVEVH NAKTKPREEQ YNSTYRVVSV LTVLHQDWLN GKEYKCAVSN  360
KALPAPIEKT ISKAKGQPRE PQVYTLPPSR DELTKNQVSL TCLVKGFYPS DIAVEWESNG  420
QPENNYKTTP PVLDSDGSFF LYSKLTVDKS RWQQGNVFSC SVMHEALHNH YTQKSLSLSP  480
GSGGGGSGGG GSGGGGSPSQ VQLVQSGPEV KKPGSSVKVS CKASGYTFSR STMHWVRQAP  540
GQGLEWIGYI NPSSAYTNYN QKFKDRVTIT ADKSTSTAYM ELSSLRSEDT AVYYCARPQV  600
HYDYNGFPYW GQGTLVTVSS GGGGSGGGGS GGGGSGGGGS DIQMTQSPST LSASVGDRVT  660
MTCSASSSVS YMNWYQQKPG KAPKRWIYDS SKLASGVPSR FSGSGSGTDY TLTISSLQPD  720
DFATYYCQQW SRNPPTFGGG TKVEIKRS                                     748

SEQ ID NO: 137          moltype = DNA  length = 2313
FEATURE                 Location/Qualifiers
misc_feature            1..2313
                        note = DB8 VHVL x TSC456 scFv-Fc-scFv TRI137
source                  1..2313
                        mol_type = other DNA
                        organism = synthetic construct
SEQUENCE: 137
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata catcttcacc gactactata tgcactgggt gcgtcaggcc  180
cctggacaag ggcttgagtg gatgggatgg atgagcccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc gagagatgcg  360
gcggattacg gtgactacgt tgcttttgat atctggggcc aagggacaat ggtcaccgtc  420
tcttcaggtg gaggcggttc aggcggaggt ggatccggcg gtggcggctc cggtggcggc  480
ggatctgaca tccagatgac ccagtctcca tcctccctgt ctgcatctgt aggagacaga  540
gtcaccatca cttgccgggc aagtcagagc attagcagct atctgaattg gtatcagcag  600
aaaccaggga aagcccctaa gctcctgatc tatgctgcat ccagtttgca aagtggggtc  660
ccatcaaggt tcagtggcag tggatctggg acagatttca ctctcaccat cagcagtctg  720
caacctgaag attttgcaac ttactactgt caacagagtt acagtacccc tctcactttc  780
ggcggaggta ccaaggtgga gatcaaatcc tcgagtgagc ccaaatcttc tgacaaaact  840
cacacatgcc caccgtgccc agcacctgaa gccgcgggtg caccgtcagt cttcctcttc  900
cccccaaaac ccaaggacac cctcatgatc tcccggaccc ctgaggtcac atgcgtggtg  960
gtggacgtga gccacgaaga ccctgaggtc aagttcaact ggtacgtgga cggcgtggag  1020
gtgcataatg ccaagacaaa gccgcgggag gagcagtaca acagcacgta ccgtgtggtc  1080
agcgtcctca ccgtcctgca ccaggactgg ctgaatggca aggaatacaa gtgcgcggtc  1140
tccaacaaag ccctcccagc ccccatcgag aaaaccatct ccaaagccaa agggcagccc  1200
cgagaaccac aggtgtacac cctgccccca tcccgggatg agctgaccaa gaaccaggtc  1260
agcctgacct gcctggtcaa aggcttctat ccaagcgaca tcgccgtgga gtgggagagc  1320
aatgggcagc cggagaacaa ctacaagacc acgcctcccg tgctggactc cgacggctcc  1380
ttcttcctct acagcaagct caccgtggac aagagcaggt ggcagcaggg gaacgtcttc  1440
tcatgctccg tgatgcatga ggctctgcac aaccactaca cgcagaagag cctctccctg  1500
tctccgggtt ccggaggagg gggttcaggt gggggaggtt ctggcggcgg gggaagccct  1560
tcacaggtgc aactggtgca gagtggaccc gaggttaaaa aaccagggtc ctccgttaag  1620
gttagctgca aagcctctgg ctacacattt tccaggagta caatgcactg ggtgaggcag  1680
gctcctggac agggactcga gtggatcggg tatatcaacc catctagcgc ctataccaat  1740
tacaaccaaa agtttaagga ccgagttacc attaccgctg acaaatccac cagtacagct  1800
tatatggagc tgtcatctct taggtccgag gacactgctg tttattactg cgctcgtcct  1860
caggttcact atgactataa tggttttccc tactggggtc agggaaccct ggtgactgtc  1920
tcttctggcg gtggaggcag cggtgggggt gggtctggag gcggtggcag tggcggcgga  1980
ggctctgata ttcagatgac tcagtctcct agcactctca gcgccagcgt gggggatcgt  2040
gtgacaatga cttgctccgc tagcagtagt gtgtcttaca tgaattggta tcagcagaag  2100
cccgggaaag cacctaagcg ctggatctat gactcttcca agctggcaag tggtgtcccc  2160
tcacggttct ctggctcagg ttctggtact gactatactt tgactatctc ctccctccag  2220
cccgatgatt tcgctaccta ttattgtcag cagtggagcc gtaacccacc cactttcgga  2280
ggcggtacca aagtggagat caagaggtca tga                               2313

SEQ ID NO: 138          moltype = AA  length = 750
FEATURE                 Location/Qualifiers
REGION                  1..750
                        note = DB8 VHVL x TSC456 scFv-Fc-scFv TRI137
source                  1..750
                        mol_type = protein
                        organism = synthetic construct
SEQUENCE: 138
QVQLVQSGAE VKKPGASVKV SCKASGYIFT DYYMHWVRQA PGQGLEWMGW MSPNSGNTGY  60
AQKFQGRVTM TRDTSTSTVY MELSSLRSED TAVYYCARDA ADYGDYVAFD IWGQGTMVTV  120
SSGGGGSGGG GSGGGGSGGG GSDIQMTQSP SSLSASVGDR VTITCRASQS ISSYLNWYQQ  180
KPGKAPKLLI YAASSLQSGV PSRFSGSGSG TDFTLTISSL QPEDFATYYC QQSYSTPLTF  240
GGGTKVEIKS SSEPKSSDKT HTCPPCPAPE AAGAPSVFLF PPKPKDTLMI SRTPEVTCVV  300
VDVSHEDPEV KFNWYVDGVE VHNAKTKPRE EQYNSTYRVV SVLTVLHQDW LNGKEYKCAV  360
SNKALPAPIE KTISKAKGQP REPQVYTLPP SRDELTKNQV SLTCLVKGFY PSDIAVEWES  420
NGQPENNYKT TPPVLDSDGS FFLYSKLTVD KSRWQQGNVF SCSVMHEALH NHYTQKSLSL  480
SPGSGGGGSG GGGSGGGGSP SQVQLVQSGP EVKKPGSSVK VSCKASGYTF SRSTMHWVRQ  540
APGQGLEWIG YINPSSAYTN YNQKFKDRVT ITADKSTSTA YMELSSLRSE DTAVYYCARP  600
QVHYDYNGFP YWGQGTLVTV SSGGGGSGGG GSGGGGSGGG GSDIQMTQSP STLSASVGDR  660
VTMTCSASSS VSYMNWYQQK PGKAPKRWIY DSSKLASGVP SRFSGSGSGT DYTLTISSLQ  720
PDDFATYYCQ QWSRNPPTFG GGTKVEIKRS                                   750
```

```
SEQ ID NO: 139          moltype = DNA  length = 2304
FEATURE                 Location/Qualifiers
misc_feature            1..2304
                        note = DB60 VHVL x TSC456 scFv-Fc-scFv TRI125
source                  1..2304
                        mol_type = other DNA
                        organism = synthetic construct
SEQUENCE: 139
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata caccttcacc agctactata tgcactgggt gcgtcaggcc  180
cctggacaag ggcttgagtg gatggggtgg atcaacccta acagtggtga cacaagctat  240
gcacagaagt tccagggccg tgtcaccatg acccgcgaca cgtccacgag cacagtctac  300
atggagctga gcagcctgcg ttctgaggac acggccgtgt attactgtgc gcaggatagt  360
agtggttccg gggcttttga tatctggggc caagggacaa tggtcaccgt ctcttcaggc  420
ggcggcggca gcggcggcgg cggcagcggc ggcggaggct ccggcggcgg cggcagcgac  480
atccagatga cccagtctcc atcctccctg tctgcatctg taggagacag agtcaccatc  540
acttgccggg caagtcagag cattagcagc tatctgaatt ggtatcagca gaaaccaggg  600
aaagccccta agctcctgat ctatgctgca tccagtttgc aaagtggggt cccatcaagg  660
ttcagtggca gtggatctgg gacagatttc actctcacca tcagcagtct gcaacctgaa  720
gattttgcaa cttactactg tcaacagagt tacagtaccc ctctcacttt cggcggaggt  780
accaaggtgg agatcaaatc ctcgagtgag cccaaatctt ctgacaaaac tcacacatgc  840
ccaccgtgcc cagcacctga agccgcgggt gcaccgtcag tcttcctctt ccccccaaaa  900
cccaaggaca ccctcatgat ctcccggacc cctgaggtca catgcgtggt ggtggacgtg  960
agccacgaag accctgaggt caagttcaac tggtacgtgg acggcgtgga ggtgcataat  1020
gccaagacaa agccgcggga ggagcagtac aacagcacgt accgtgtggt cagcgtcctc  1080
accgtcctgc accaggactg gctgaatggc aaggaataca agtgcgcggt ctccaacaaa  1140
gccctcccag cccccatcga gaaaaccatc tccaaagcca aagggcagcc ccgagaacca  1200
caggtgtaca ccctgccccc atcccgggat gagctgacca agaaccaggt cagcctgacc  1260
tgcctggtca aaggcttcta tccaagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
tccggaggag gggttcagg tgggggaggt tctggcggcg gggaagccc ttcacaggtg  1560
caactggtgc agagtggacc cgaggttaaa aaaccagggt cctccgttaa ggttagctgc  1620
aaagcctctg gctacacatt ttccaggagt acaatgcact gggtgaggca ggctcctgga  1680
cagggactcg agtggatcgg gtatatcaac ccatctagcg cctataccaa ttacaaccaa  1740
aagtttaagg accgagttac cattaccgct gacaaatcca ccagtacagc ttatatggag  1800
ctgtcatctc ttaggtccga ggacactgct gtttattact gcgctcgtcc tcaggttcac  1860
tatgactata atggttttcc ctactggggt cagggaaccc tggtgactgt ctcttctggc  1920
ggtggaggca gcggtggggg tggtctgga ggcggtggca gtggcggcgg aggctctgat  1980
attcagatga ctcagtctcc tagcactctc agcgccagcg tgggggatcg tgtgacaatg  2040
acttgctccg ctagcagtag tgtgtcttac atgaattggt atcagcagaa gcccgggaaa  2100
gcacctaagc gctggatcta tgactcttcc aagctggcaa gtggtgtccc ctcacggttc  2160
tctggctcag gttctggtac tgactatact ttgactatct cctccctcca gcccgatgat  2220
ttcgctacct attattgtca gcagtggagc cgtaacccac ccactttcgg aggcggtacc  2280
aaagtggaga tcaagaggtc ataa                                        2304

SEQ ID NO: 140          moltype = AA  length = 747
FEATURE                 Location/Qualifiers
REGION                  1..747
                        note = DB60 VHVL x TSC456 scFv-Fc-scFv TRI125
source                  1..747
                        mol_type = protein
                        organism = synthetic construct
SEQUENCE: 140
QVQLVQSGAE VKKPGASVKV SCKASGYTFT SYYMHWVRQA PGQGLEWMGW INPNSGDTSY  60
AQKFQGRVTM TRDTSTSTVY MELSSLRSED TAVYYCAQDS SGSGAFDIWG QGTMVTVSSG  120
GGGSGGGGSG GGGSGGGGSD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIKSSSE PKSSDKTHTC PPCPAPEAAG APSVFLFPPK PKDTLMISRT PEVTCVVVDV  300
SHEDPEVKFN WYVDGVEVHN AKTKPREEQY NSTYRVVSVL TVLHQDWLNG KEYKCAVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
SGGGGSGGGG SGGGGSPSQV QLVQSGPEVK KPGSSVKVSC KASGYTFSRS TMHWVRQAPG  540
QGLEWIGYIN PSSAYTNYNQ KFKDRVTITA DKSTSTAYME LSSLRSEDTA VYYCARPQVH  600
YDYNGFPYWG QGTLVTVSSG GGGSGGGGSG GGGSGGGGSD IQMTQSPSTL SASVGDRVTM  660
TCSASSSVSY MNWYQQKPGK APKRWIYDSS KLASGVPSRF SGSGSGTDYT LTISSLQPDD  720
FATYYCQQWS RNPPTFGGGT KVEIKRS                                     747

SEQ ID NO: 141          moltype = DNA  length = 2316
FEATURE                 Location/Qualifiers
misc_feature            1..2316
                        note = DB65 VHVL x TSC456 scFv-Fc-scFv TRI126
source                  1..2316
                        mol_type = other DNA
                        organism = synthetic construct
SEQUENCE: 141
```

```
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata caccttcacc ggctactata tgcactgggt gcgtcaggcc  180
cctggacaag ggcttgagtg gatgggatgg atgaacccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc gaaagaggaa  360
ccgatttttg gagtggttat ggatgctttt gatatctggg gccaagggac aatggtcacc  420
gtctcctcag gcggcggcgg cagcggcggc ggcggcagcg gcggcggagg ctccggcggc  480
ggcggcagcg acatccagat gacccagtct ccatcctccc tgtctgcatc tgtaggagac  540
agagtcacca tcacttgccg ggcaagtcag agcattagca gctatctgaa ttggtatcag  600
cagaaaccag ggaaagcccc taagctcctg atctatgctg catccagttt gcaaagtggg  660
gtcccatcaa ggttcagtgg cagtggatct gggacagatt tcactctcac catcagcagt  720
ctgcaacctg aagattttgc aacttactac tgtcaacaga gttacagtac ccctctcact  780
ttcggcggag gtaccaaggt ggagatcaaa tcctcgagtg agcccaaatc ttctgacaaa  840
actcacacat gcccaccgtg cccagcacct gaagccgcgg gtgcaccgtc agtcttcctc  900
ttccccccaa aacccaagga caccctcatg atctcccgga cccctgaggt cacatgcgtg  960
gtggtggacg tgagccacga agaccctgag gtcaagttca actggtacgt ggacggcgtg  1020
gaggtgcata atgccaagac aaagccgcgg gaggagcagt acaacagcac gtaccgtgtg  1080
gtcagcgtcc tcaccgtcct gcaccaggac tggctgaatg gcaaggaata caagtgcgcg  1140
gtctccaaca aagccctccc agcccccatc gagaaaacca tctccaaagc caaagggcag  1200
ccccgagaac cacaggtgta caccctgccc ccatcccggg atgagctgac caagaaccag  1260
gtcagcctga cctgcctggt caaaggcttc tatccaagcg acatcgccgt ggagtgggag  1320
agcaatgggc agccggagaa caactacaag accacgcctc ccgtgctgga ctccgacggc  1380
tccttcttcc tctacagcaa gctcaccgtg gacaagagca ggtggcagca ggggaacgtc  1440
ttctcatgct ccgtgatgca tgaggctctg cacaaccact acacgcagaa gagcctctcc  1500
ctgtctccgg gttccggagg aggggggttca ggtgggggag gttctggcgg cgggggaagc  1560
ccttcacagg tgcaactggt gcagagtgga cccgaggtta aaaaaccagg gtcctccgtt  1620
aaggttagct gcaaagcctc tggctacaca ttttccagga gtacaatgca ctgggtgagg  1680
caggctcctg gacagggact cgagtggatc gggtatatca acccatctag cgcctatacc  1740
aattacaacc aaaagtttaa ggaccgagtt accattaccg ctgacaaatc caccagtaca  1800
gcttatatgg agctgtcatc tcttaggtcc gaggacactg ctgtttatta ctgcgctcgt  1860
cctcaggttc actatgacta taatggtttt ccctactggg gtcagggaac cctggtgact  1920
gtctcttctg gcggtggagg cagcggtggg ggtgggtctg gaggcggtgg cagtggcggc  1980
ggaggctctg atattcagat gactcagtct cctagcactc tcagcgccag cgtgggggat  2040
cgtgtgacaa tgacttgctc cgctagcagt agtgtgtctt acatgaattg gtatcagcag  2100
aagcccggga aagcacctaa gcgctggatc tatgactctt ccaagctggc aagtggtgtc  2160
ccctcacggt tctctggctc aggttctggt actgactata ctttgactat ctcctccctc  2220
cagcccgatg atttcgctac ctattattgt cagcagtgga gccgtaaccc acccactttc  2280
ggaggcggta ccaaagtgga gatcaagagg tcataa                            2316

SEQ ID NO: 142          moltype = AA  length = 751
FEATURE                 Location/Qualifiers
REGION                  1..751
                        note = DB65 VHVL x TSC456 scFv-Fc-scFv TRI126
source                  1..751
                        mol_type = protein
                        organism = synthetic construct
SEQUENCE: 142
QVQLVQSGAE VKKPGASVKV SCKASGYTFT GYYMHWVRQA PGQGLEWMGW MNPNSGNTGY  60
AQKFQGRVTM TRDTSTSTVY MELSSLRSED TAVYYCAKEE PIFGVVMDAF DIWGQGTMVT  120
VSSGGGGSGG GGSGGGGSGG GGSDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGGGTKVEIK SSSEPKSSDK THTCPPCPAP EAAGAPSVFL FPPKPKDTLM ISRTPEVTCV  300
VVDVSHEDPE VKFNWYVDGV EVHNAKTKPR EEQYNSTYRV VSVLTVLHQD WLNGKEYKCA  360
VSNKALPAPI EKTISKAKGQ PREPQVYTLP PSRDELTKNQ VSLTCLVKGF YPSDIAVEWE  420
SNGQPENNYK TTPPVLDSDG SFFLYSKLTV DKSRWQQGNV FSCSVMHEAL HNHYTQKSLS  480
LSPGSGGGGS GGGGSGGGGS PSQVQLVQSG PEVKKPGSSV KVSCKASGYT FSRSTMHWVR  540
QAPGQGLEWI GYINPSSAYT NYNQKFKDRV TITADKSTST AYMELSSLRS EDTAVYYCAR  600
PQVHYDYNGF PYWGQGTLVT VSSGGGGSGG GGSGGGGSGG GGSDIQMTQS PSTLSASVGD  660
RVTMTCSASS SVSYMNWYQQ KPGKAPKRWI YDSSKLASGV PSRFSGSGSG TDYTLTISSL  720
QPDDFATYYC QQWSRNPPTF GGGTKVEIKR S                                 751

SEQ ID NO: 143          moltype = DNA  length = 2304
FEATURE                 Location/Qualifiers
misc_feature            1..2304
                        note = DB82 VLVH x TSC456 scFv-Fc-scFv TRI127
source                  1..2304
                        mol_type = other DNA
                        organism = synthetic construct
SEQUENCE: 143
atggaagcac cagcgcagct tctcttcctc ctgctactct ggctcccaga taccaccggt  60
gacatccaga tgacccagtc tccatcctcc ctgtctgcat ctgtaggaga ccgcgtcacc  120
atcacttgcc gggcaagtca gaccataaac aactatttga actggtatca gcagaaacca  180
gggaaagccc ctaagctcct gatctattct gcatctactt tgcaaagtgg ggtcccatca  240
cgtttcagtg gcagtggatc tgggacagat ttcactctca ccatcagcag tctgcaacct  300
gaagattttg caacttacta ctgtcaccag agttacactt cacctctcac tttcggcgga  360
ggtaccaagg tggagatcaa aggcggcggc ggcagcggcg gcggcggcag cggcggcgga  420
ggctccggcg gcggcggcag cgaggtgcag ctggtggagt ctgggggagg cttggtacag  480
cctggggggt ccctgcgcct ctcctgtgca gcctctggat tcacctttag cagctatgcc  540
```

-continued

```
atgagctggg tccgccaggc tccagggaag ggcctggagt gggtctcagt tattagtgcc  600
aatagtgctg gtctaggcca tgcggactct gtgaagggcc ggttcaccat ctcccgcgac  660
aattccaaga acacgctgta tctgcaaatg aacagcctgc gcgccgagga cacggccgta  720
tattactgtg cgagagtggg ctatagcagc tcggctgatg cttttgatat ctggggccaa  780
gggacaatgg tcaccgtctc ctcgagtgag cccaaatctt ctgacaaaac tcacacatgc  840
ccaccgtgcc cagcacctga agccgcgggt gcaccgtcag tcttcctctt ccccccaaaa  900
cccaaggaca ccctcatgat ctcccggacc cctgaggtca catgcgtggt ggtggacgtg  960
agccacgaag accctgaggt caagttcaac tggtacgtgg acggcgtgga ggtgcataat  1020
gccaagacaa agccgcggga ggagcagtac aacagcacgt accgtgtggt cagcgtcctc  1080
accgtcctgc accaggactg gctgaatggc aaggaataca agtgcgcggt ctccaacaaa  1140
gccctcccag cccccatcga gaaaaccatc tccaaagcca aagggcagcc ccgagaacca  1200
caggtgtaca ccctgccccc atcccgggat gagctgacca agaaccaggt cagcctgacc  1260
tgcctggtca aaggcttcta tccaagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
tccggaggag gggggttcagg tgggggaggt tctggcggcg gggggaagccc ttcacaggtg  1560
caactggtgc agagtggacc cgaggttaaa aaaccagggt cctccgttaa ggttagctgc  1620
aaagcctctg gctacacatt ttccaggagt acaatgcact gggtgaggca ggctcctgga  1680
cagggactcg agtggatcgg gtatatcaac ccatctagcg cctataccaa ttacaaccaa  1740
aagtttaagg accgagttac cattaccgct gacaaatcca ccagtacagc ttatatggag  1800
ctgtcatctc ttaggtccga ggacactgct gtttattact gcgctcgtcc tcaggttcac  1860
tatgactata atggttttcc ctactggggt cagggaaccc tggtgactgt ctcttctggc  1920
ggtggaggca gcggtggggg tgggtctgga ggcggtggca gtggcggcgg aggctctgat  1980
attcagatga ctcagtctcc tagcactctc agcgccagcg tgggggatcg tgtgacaatg  2040
acttgctccg ctagcagtag tgtgtcttac atgaattggt atcagcagaa gcccgggaaa  2100
gcacctaagc gctggatcta tgactcttcc aagctggcaa gtggtgtccc ctcacggttc  2160
tctggctcag gttctggtac tgactatact ttgactatct cctccctcca gcccgatgat  2220
ttcgctacct attattgtca gcagtggagc cgtaacccac ccactttcgg aggcggtacc  2280
aaagtggaga tcaagaggtc ataa                                         2304
```

```
SEQ ID NO: 144         moltype = AA  length = 747
FEATURE                Location/Qualifiers
REGION                 1..747
                       note = DB82 VLVH x TSC456 scFv-Fc-scFv TRI127
source                 1..747
                       mol_type = protein
                       organism = synthetic construct
SEQUENCE: 144
DIQMTQSPSS LSASVGDRVT ITCRASQTIN NYLNWYQQKP GKAPKLLIYS ASTLQSGVPS  60
RFSGSGSGTD FTLTISSLQP EDFATYYCHQ SYTSPLTFGG GTKVEIKGGG GSGGGGSGGG  120
GSGGGGSEVQ LVESGGGLVQ PGGSLRLSCA ASGFTFSSYA MSWVRQAPGK GLEWVSVISA  180
NSAGLGHADS VKGRFTISRD NSKNTLYLQM NSLRAEDTAV YYCARVGYSS SADAFDIWGQ  240
GTMVTVSSSE PKSSDKTHTC PPCPAPEAAG APSVFLFPPK PKDTLMISRT PEVTCVVVDV  300
SHEDPEVKFN WYVDGVEVHN AKTKPREEQY NSTYRVVSVL TVLHQDWLNG KEYKCAVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
SGGGGSGGGG SGGGGSPSQV QLVQSGPEVK KPGSSVKVSC KASGYTFSRS TMHWVRQAPG  540
QGLEWIGYIN PSSAYTNYNQ KFKDRVTITA DKSTSTAYME LSSLRSEDTA VYYCARPQVH  600
YDYNGFPYWG QGTLVTVSSG GGGSGGGGSG GGGSGGGGSD IQMTQSPSTL SASVGDRVTM  660
TCSASSSVSY MNWYQQKPGK APKRWIYDSS KLASGVPSRF SGSGSGTDYT LTISSLQPDD  720
FATYYCQQWS RNPPTFGGGT KVEIKRS                                      747
```

```
SEQ ID NO: 145         moltype = DNA  length = 2337
FEATURE                Location/Qualifiers
misc_feature           1..2337
                       note = DB83 VHVL x TSC456 scFv-Fc-scFv TRI134
source                 1..2337
                       mol_type = other DNA
                       organism = synthetic construct
SEQUENCE: 145
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata caccttcact agctatgcta tgcattgggt gcgtcaggcc  180
cctggacaag ggcttgagtg gatgggactt gttgatcctg aagatggtga aacaatatat  240
gcagagaagt tccagggccg tgtcaccatg acccgcgaca cgtccacgag cacagtctac  300
atggagctga gcagcctgcg ttctgaggac acggccgtgt attactgtgc gagacgaacg  360
tattactatg atagtagtgg ttcccgttat gcttttgata tctggggcca agggaccacg  420
gtcaccgtct cttcaggcgg cggcggcagc ggcggcggcg gcagcggcgg cggaggctcc  480
ggcggcggcg gcagcgatgt tgtgatgact cagtctccac tctccctgcc cgtcacccct  540
ggagagccgg cctccatctc ctgcaggtct agtcagagcc tcctgcatag taatggagac  600
aactatttgg attggtacct gcagaagcca gggcagtctc cacagctcct gatctatttg  660
ggttctaatc gggcctccgg ggtccctgac cgtttcagtg gcagtggatc aggcacagat  720
tttacactga aaatcagccg tgtggaggct gaggatgttg gggtttatta ctgcatgcaa  780
gctacacact ggccactcac tttcggccct ggtaccaaag tggatatcaa atcctcgagt  840
gagcccaaat cttctgacaa aactcacaca tgcccaccgt gcccagcacc tgaagccgcg  900
ggtgcaccgt cagtcttcct cttcccccca aaacccaagg acaccctcat gatctcccgg  960
acccctgagg tcacatgcgt ggtggtggac gtgagccacg aagaccctga ggtcaagttc  1020
aactggtacg tggacggcgt ggaggtgcat aatgccaaga caaagccgcg ggaggagcag  1080
```

```
tacaacagca cgtaccgtgt ggtcagcgtc ctcaccgtcc tgcaccagga ctggctgaat  1140
ggcaaggaat acaagtgcgc ggtctccaac aaagccctcc cagcccccat cgagaaaacc  1200
atctccaaag ccaaagggca gccccgagaa ccacaggtgt acaccctgcc cccatcccgg  1260
gatgagctga ccaagaacca ggtcagcctg acctgcctgg tcaaaggctt ctatccaagc  1320
gacatcgccg tggagtggga gagcaatggg cagccggaga acaactacaa gaccacgcct  1380
cccgtgctgg actccgacgg ctccttcttc ctctacagca agctcaccgt ggacaagagc  1440
aggtggcagc aggggaacgt cttctcatgc tccgtgatgc atgaggctct gcacaaccac  1500
tacacgcaga agagcctctc cctgtctccg ggttccggag gaggggggttc aggtggggga  1560
ggttctggcg gcgggggaag cccttcacag gtgcaactgg tgcagagtgg acccgaggtt  1620
aaaaaaccag ggtcctccgt taaggttagc tgcaaagcct ctggctacac attttccagg  1680
agtacaatgc actgggtgag gcaggctcct ggacagggac tcgagtggat cgggtatatc  1740
aacccatcta gcgcctatac caattacaac caaaagttta aggaccgagt taccattacc  1800
gctgacaaat ccaccagtac agcttatatg gagctgtcat ctcttaggtc cgaggacact  1860
gctgtttatt actgcgctcg tcctcaggtt cactatgact ataatggttt tccctactgg  1920
ggtcagggaa ccctggtgac tgtctcttct ggcggtggag gcagcggtgg gggtgggtct  1980
ggaggcggtg gcagtggcgg cggaggctct gatattcaga tgactcagtc tcctagcact  2040
ctcagcgcca gcgtggggga tcgtgtgaca atgacttgct ccgctagcag tagtgtgtct  2100
tacatgaatt ggtatcagca gaagcccggg aaagcaccta agcgctggat ctatgactct  2160
tccaagctgg caagtggtgt cccctcacgg ttctctggct caggttctgg tactgactat  2220
actttgacta tctcctccct ccagcccgat gatttcgcta cctattattg tcagcagtgg  2280
agccgtaacc cacccacttt cggaggcggt accaaagtgg agatcaagag gtcataa     2337

SEQ ID NO: 146          moltype = AA  length = 758
FEATURE                 Location/Qualifiers
REGION                  1..758
                        note = DB83 VHVL x TSC456 scFv-Fc-scFv TRI134
source                  1..758
                        mol_type = protein
                        organism = synthetic construct
SEQUENCE: 146
QVQLVQSGAE VKKPGASVKV SCKASGYTFT SYAMHWVRQA PGQGLEWMGL VDPEDGETIY  60
AEKFQGRVTM TRDTSTSTVY MELSSLRSED TAVYYCARRT YYYDSSGSRY AFDIWGQGTT  120
VTVSSGGGGS GGGGSGGGGS GGGGSDVVMT QSPLSLPVTP GEPASISCRS SQSLLHSNGD  180
NYLDWYLQKP GQSPQLLIYL GSNRASGVPD RFSGSGSGTD FTLKISRVEA EDVGVYYCMQ  240
ATHWPLTFGP GTKVDIKSSS EPKSSDKTHT CPPCPAPEAA GAPSVFLFPP KPKDTLMISR  300
TPEVTCVVVD VSHEDPEVKF NWYVDGVEVH NAKTKPREEQ YNSTYRVVSV LTVLHQDWLN  360
GKEYKCAVSN KALPAPIEKT ISKAKGQPRE PQVYTLPPSR DELTKNQVSL TCLVKGFYPS  420
DIAVEWESNG QPENNYKTTP PVLDSDGSFF LYSKLTVDKS RWQQGNVFSC SVMHEALHNH  480
YTQKSLSLSP GSGGGGSGGG GSGGGGSPSQ VQLVQSGPEV KKPGSSVKVS CKASGYTFSR  540
STMHWVRQAP GQGLEWIGYI NPSSAYTNYN QKFKDRVTIT ADKSTSTAYM ELSSLRSEDT  600
AVYYCARPQV HYDYNGFPYW GQGTLVTVSS GGGGSGGGGS GGGGSGGGGS DIQMTQSPST  660
LSASVGDRVT MTCSASSSVS YMNWYQQKPG KAPKRWIYDS SKLASGVPSR FSGSGSGTDY  720
TLTISSLQPD DFATYYCQQW SRNPPTFGGG TKVEIKRS                         758

SEQ ID NO: 147          moltype = DNA  length = 2307
FEATURE                 Location/Qualifiers
misc_feature            1..2307
                        note = DB86 VHVL x TSC456 scFv-Fc-scFv TRI128
source                  1..2307
                        mol_type = other DNA
                        organism = synthetic construct
SEQUENCE: 147
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata tatgttcagt ggccattctg cacactgggt gcgtcaggcc  180
cctggacaag ggcttgagtg gatgggatgg atgaacccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc gagagatagc  360
agtggctggt acgatgtctt tgactactgg ggccagggga ccctggtcac cgtctcctca  420
ggtggaggcg gttcaggcgg aggtggatcc ggcggtggcg gctccggtgg cggcggatct  480
gacatccaga tgacccagtc tccatcctcc ctgtctgcat ctgtaggaga ccgcgtcacc  540
atcacttgcc gggcaagtca gggcatcaga aatgatttag gttggtatca gcagaaacca  600
gggaaagccc ctaagctcct gatctatgct gcatccactt tgcaatcagg ggtcccatca  660
cgtttcagtg gcagtggatc tgggacagat ttcactctca ccatcagcag tctgcaacct  720
gaagatttg caacttacta ctgtcaacag agttacggtg cccccctcac tttcggcgga  780
ggtaccaagg tggagatcaa atcctcgagt gagcccaaat cttctgacaa aactcacaca  840
tgcccaccgt gcccagcacc tgaagccgcg ggtgcaccgt cagtcttcct cttcccccca  900
aaacccaagg acaccctcat gatctcccgg acccctgagg tcacatgcgt ggtggtggac  960
gtgagccacg aagaccctga ggtcaagttc aactggtacg tggacggcgt ggaggtgcat  1020
aatgccaaga caaagccgcg ggaggagcag tacaacagca cgtaccgtgt ggtcagcgtc  1080
ctcaccgtcc tgcaccagga ctggctgaat ggcaaggaat acaagtgcgc ggtctccaac  1140
aaagccctcc cagcccccat cgagaaaacc atctccaaag ccaaagggca gccccgagaa  1200
ccacaggtgt acaccctgcc cccatcccgg gatgagctga ccaagaacca ggtcagcctg  1260
acctgcctgg tcaaaggctt ctatccaagc gacatcgccg tggagtggga gagcaatggg  1320
cagccggaga acaactacaa gaccacgcct cccgtgctgg actccgacgg ctccttcttc  1380
ctctacagca agctcaccgt ggacaagagc aggtggcagc aggggaacgt cttctcatgc  1440
tccgtgatgc atgaggctct gcacaaccac tacacgcaga agagcctctc cctgtctccg  1500
ggttccggag gaggggggttc aggtggggga ggttctggcg gcgggggaag cccttcacag  1560
gtgcaactgg tgcagagtgg acccgaggtt aaaaaaccag ggtcctccgt taaggttagc  1620
```

```
tgcaaagcct ctggctacac attttccagg agtacaatgc actgggtgag gcaggctcct  1680
ggacagggac tcgagtggat cgggtatatc aacccatcta gcgcctatac caattacaac  1740
caaaagttta aggaccgagt taccattacc gctgacaaat ccaccagtac agcttatatg  1800
gagctgtcat ctcttaggtc cgaggacact gctgtttatt actgcgctcg tcctcaggtt  1860
cactatgact ataatggttt tccctactgg ggtcagggaa ccctggtgac tgtctcttct  1920
ggcggtggag gcagcggtgg gggtgggtct ggaggcggtg gcagtggcgg cggaggctct  1980
gatattcaga tgactcagtc tcctagcact ctcagcgcca gcgtggggga tcgtgtgaca  2040
atgacttgct ccgctagcag tagtgtgtct tacatgaatt ggtatcagca gaagcccggg  2100
aaagcaccta agcgctggat ctatgactct tccaagctgg caagtggtgt cccctcacgg  2160
ttctctggct caggttctgg tactgactat actttgacta tctcctccct ccagcccgat  2220
gatttcgcta cctattattg tcagcagtgg agccgtaacc cacccacttt cggaggcggt  2280
accaaagtgg agatcaagag gtcataa                                     2307
```

```
SEQ ID NO: 148          moltype = AA  length = 748
FEATURE                 Location/Qualifiers
REGION                  1..748
                        note = DB86 VHVL x TSC456 scFv-Fc-scFv TRI128
source                  1..748
                        mol_type = protein
                        organism = synthetic construct
SEQUENCE: 148
QVQLVQSGAE VKKPGASVKV SCKASGYMFS GHSAHWVRQA PGQGLEWMGW MNPNSGNTGY  60
AQKFQGRVTM TRDTSTSTVY MELSSLRSED TAVYYCARDS SGWYDVFDYW GQGTLVTVSS  120
GGGGSGGGGS GGGGSGGGGS DIQMTQSPSS LSASVGDRVT ITCRASQGIR NDLGWYQQKP  180
GKAPKLLIYA ASTLQSGVPS RFSGSGSGTD FTLTISSLQP EDFATYYCQQ SYGAPLTFGG  240
GTKVEIKSSS EPKSSDKTHT CPPCPAPEAA GAPSVFLFPP KPKDTLMISR TPEVTCVVVD  300
VSHEDPEVKF NWYVDGVEVH NAKTKPREEQ YNSTYRVVSV LTVLHQDWLN GKEYKCAVSN  360
KALPAPIEKT ISKAKGQPRE PQVYTLPPSR DELTKNQVSL TCLVKGFYPS DIAVEWESNG  420
QPENNYKTTP PVLDSDGSFF LYSKLTVDKS RWQQGNVFSC SVMHEALHNH YTQKSLSLSP  480
GSGGGGSGGG GSGGGGSPSQ VQLVQSGPEV KKPGSSVKVS CKASGYTFSR STMHWVRQAP  540
GQGLEWIGYI NPSSAYTNYN QKFKDRVTIT ADKSTSTAYM ELSSLRSEDT AVYYCARPQV  600
HYDYNGFPYW GQGTLVTVSS GGGGSGGGGS GGGGSGGGGS DIQMTQSPST LSASVGDRVT  660
MTCSASSSVS YMNWYQQKPG KAPKRWIYDS SKLASGVPSR FSGSGSGTDY TLTISSLQPD  720
DFATYYCQQW SRNPPTFGGG TKVEIKRS                                    748
```

```
SEQ ID NO: 149          moltype = DNA  length = 2325
FEATURE                 Location/Qualifiers
misc_feature            1..2325
                        note = DB280 VHVL x TSC456 scFv-Fc-scFv TRI131
source                  1..2325
                        mol_type = other DNA
                        organism = synthetic construct
SEQUENCE: 149
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata cagcctcaac ttatactata tgcactgggt gcgtcaggcc  180
cctggacaag ggcttgagtg gatgggatgg atgaacccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc gagcctcgat  360
tgtagtggtg gtagctgcta ctccgaatat gatgcttttg atatctgggg ccaagggacc  420
acggtcaccg tctcctcagg cggcggcggc agcggcggcg gcggcagcgg cggcggaggc  480
tccggcggcg gcggcagcga catccagatg acccagtctc catcctccct gtctgcatct  540
gtaggagaca gagtcaccat cacttgccgg gcaagtcaga gcattagcag ctatctgaat  600
tggtatcagc agaaaccagg gaaagcccct aagctcctga tctatgctgc atccagtttg  660
caaagtgggg tcccatcaag gttcagtggc agtggatctg ggacagattt cactctcacc  720
atcagcagtc tgcaacctga agattttgca acttactact gtcaacagag ttacagtacc  780
cctctcactt tcggcggagg taccaaggtg gagatcaaat cctcgagtga gcccaaatct  840
tctgacaaaa ctcacacatg cccaccgtgc ccagcacctg aagccgcggg tgcaccgtca  900
gtcttcctct tccccccaaa acccaaggac accctcatga tctcccggac ccctgaggtc  960
acatgcgtgg tggtggacgt gagccacgaa gaccctgagg tcaagttcaa ctggtacgtg  1020
gacggcgtgg aggtgcataa tgccaagaca aagccgcggg aggagcagta caacagcacg  1080
taccgtgtgg tcagcgtcct caccgtcctg caccaggact ggctgaatgg caaggaatac  1140
aagtgcgcgg tctccaacaa agccctccca gcccccatcg agaaaaccat ctccaaagcc  1200
aaagggcagc cccgagaacc acaggtgtac accctgcccc catcccggga tgagctgacc  1260
aagaaccagg tcagcctgac ctgcctggtc aaaggcttct atccaagcga catcgccgtg  1320
gagtgggaga gcaatgggca gccggagaac aactacaaga ccacgcctcc cgtgctggac  1380
tccgacggct ccttcttcct ctacagcaag ctcaccgtgg acaagagcag gtggcagcag  1440
gggaacgtct tctcatgctc cgtgatgcat gaggctctgc acaaccacta cacgcagaag  1500
agcctctccc tgtctccggg ttccggagga gggggttcag gtgggggagg ttctggcggc  1560
gggggaagcc cttcacaggt gcaactggtg cagagtggac ccgaggttaa aaaaccaggg  1620
tcctccgtta aggttagctg caaagcctct ggctacacat tttccaggag tacaatgcac  1680
tgggtgaggc aggctcctgg acagggactc gagtggatcg ggtatatcaa cccatctagc  1740
gcctatacca attacaacca aaagtttaag gaccgagtta ccattaccgc tgacaaatcc  1800
accagtacag cttatatgga gctgtcatct cttaggtccg aggacactgc tgtttattac  1860
tgcgctcgtc ctcaggttca ctatgactat aatggtttcc cctactgggg tcagggaacc  1920
ctggtgactg tctcttctgg cggtggaggc agcggtgggg gtgggtctgg aggcggtggc  1980
agtggcggcg gaggctctga tattcagatg actcagtctc ctagcactct cagcgccagc  2040
gtgggggatc gtgtgacaat gacttgctcc gctagcagta gtgtgtctta catgaattgg  2100
tatcagcaga agcccgggaa agcacctaag cgctggatct atgactcttc caagctggca  2160
```

```
agtggtgtcc cctcacggtt ctctggctca ggttctggta ctgactatac tttgactatc  2220
tcctccctcc agcccgatga tttcgctacc tattattgtc agcagtggag ccgtaaccca  2280
cccactttcg gaggcggtac caaagtggag atcaagaggt cataa                  2325

SEQ ID NO: 150         moltype = AA  length = 754
FEATURE                Location/Qualifiers
REGION                 1..754
                       note = DB280 VHVL x TSC456 scFv-Fc-scFv TRI131
source                 1..754
                       mol_type = protein
                       organism = synthetic construct
SEQUENCE: 150
QVQLVQSGAE VKKPGASVKV SCKASGYSLN LYYMHWVRQA PGQGLEWMGW MNPNSGNTGY  60
AQKFQGRVTM TRDTSTSTVY MELSSLRSED TAVYYCASLD CSGGSCYSEY DAFDIWGQGT  120
TVTVSSGGGG SGGGGSGGGG SGGGGSDIQM TQSPSSLSAS VGDRVTITCR ASQSISSYLN  180
WYQQKPGKAP KLLIYAASSL QSGVPSRFSG SGSGTDFTLT ISSLQPEDFA TYYCQQSYST  240
PLTFGGGTKV EIKSSSEPKS SDKTHTCPPC PAPEAAGAPS VFLFPPKPKD TLMISRTPEV  300
TCVVVDVSHE DPEVKFNWYV DGVEVHNAKT KPREEQYNST YRVVSVLTVL HQDWLNGKEY  360
KCAVSNKALP APIEKTISKA KGQPREPQVY TLPPSRDELT KNQVSLTCLV KGFYPSDIAV  420
EWESNGQPEN NYKTTPPVLD SDGSFFLYSK LTVDKSRWQQ GNVFSCSVMH EALHNHYTQK  480
SLSLSPGSGG GGSGGGGSGG GGSPSQVQLV QSGPEVKKPG SSVKVSCKAS GYTFSRSTMH  540
WVRQAPGQGL EWIGYINPSS AYTNYNQKFK DRVTITADKS TSTAYMELSS LRSEDTAVYY  600
CARPQVHYDY NGFPYWGQGT LVTVSSGGGG SGGGGSGGGG SGGGGSDIQM TQSPSTLSAS  660
VGDRVTMTCS ASSSVSYMNW YQQKPGKAPK RWIYDSSKLA SGVPSRFSGS GSGTDYTLTI  720
SSLQPDDFAT YYCQQWSRNP PTFGGGTKVE IKRS                              754

SEQ ID NO: 151         moltype = DNA  length = 2304
FEATURE                Location/Qualifiers
misc_feature           1..2304
                       note = DB331 VHVL x TSC456 scFv-Fc-scFv TRI132
source                 1..2304
                       mol_type = other DNA
                       organism = synthetic construct
SEQUENCE: 151
atggaagcac cagcgcagct tctcttcctc ctgctactct ggctcccaga taccaccggt  60
caggtgcagc tggtgcagtc tggggctgag gtgaagaagc ctggggcctc agtgaaggtt  120
tcctgcaagg catctggata caccttcacc agctactata tgcactgggt gcgtcaggcc  180
cctggacaag ggcttgagtg gatgggatgg atgaacccta acagtggtaa cacaggctat  240
gcacagaagt tccagggccg tgtcaccatg acccgcgaca cgtccacgag cacagtctac  300
atggagctga gcagcctgcg ttctgaggac acggccgtgt attactgtgc aacagatctc  360
gcgggggaag ccttgttcga cccctggggc cagggcaccc tggtcaccgt ctcctcaggc  420
ggcggcggca gcggcggcgg cggcagcggc ggcggaggct ccggcggcgg cggcagcgac  480
atccagatga cccagtctcc atcctccctg tctgcatctg taggagacag agtcaccatc  540
acttgccggg caagtcagag cattagcagc tatctgaatt ggtatcagca gaaaccaggg  600
aaagccccta agctcctgat ctatgctgca tccagtttgc aaagtggggt cccatcaagg  660
ttcagtggca gtggatctgg gacagatttc actctcacca tcagcagtct gcaacctgaa  720
gattttgcaa cttactactg tcaacagagt tacagtaccc ctctcacttt cggcggaggt  780
accaaggtgg agatcaaatc ctcgagtgag cccaaatctt ctgacaaaac tcacacatgc  840
ccaccgtgcc cagcacctga agccgcgggt gcaccgtcag tcttcctctt ccccccaaaa  900
cccaaggaca ccctcatgat ctcccggacc cctgaggtca catgcgtggt ggtggacgtg  960
agccacgaag accctgaggt caagttcaac tggtacgtgg acggcgtgga ggtgcataat  1020
gccaagacaa agccgcggga ggagcagtac aacagcacgt accgtgtggt cagcgtcctc  1080
accgtcctgc accaggactg gctgaatggc aaggaataca agtgcgcggt ctccaacaaa  1140
gccctcccag cccccatcga gaaaaccatc tccaaagcca aagggcagcc ccgagaacca  1200
caggtgtaca ccctgccccc atcccgggat gagctgacca agaaccaggt cagcctgacc  1260
tgcctggtca aaggcttcta tccaagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
tccggaggag gggttcagg tgggggaggt tctggcggcg ggggaagccc ttcacaggtg  1560
caactggtgc agagtggacc cgaggttaaa aaaccagggt cctccgttaa ggttagctgc  1620
aaagcctctg gctacacatt ttccaggagt acaatgcact gggtgaggca ggctcctgga  1680
cagggactcg agtggatcgg gtatatcaac ccatctagcg cctataccaa ttacaaccaa  1740
aagtttaagg accgagttac cattaccgct gacaaatcca ccagtacagc ttatatggag  1800
ctgtcatctc ttaggtccga ggacactgct gtttattact gcgctcgtcc tcaggttcac  1860
tatgactata atggttttcc ctactggggt cagggaaccc tggtgactgt ctcttctggc  1920
ggtggaggca gcggtggggg tgggtctgga ggcggtggca gtggcggcgg aggctctgat  1980
attcagatga ctcagtctcc tagcactctc agcgccagcg tgggggatcg tgtgacaatg  2040
acttgctccg ctagcagtag tgtgtcttac atgaattggt atcagcagaa gcccgggaaa  2100
gcacctaagc gctggatcta tgactcttcc aagctggcaa gtggtgtccc ctcacggttc  2160
tctggctcag gttctggtac tgactatact ttgactatct cctccctcca gcccgatgat  2220
ttcgctacct attattgtca gcagtggagc cgtaacccac ccactttcgg aggcggtacc  2280
aaagtggaga tcaagaggtc ataa                                         2304

SEQ ID NO: 152         moltype = AA  length = 747
FEATURE                Location/Qualifiers
REGION                 1..747
                       note = DB331 VHVL x TSC456 scFv-Fc-scFv TRI132
source                 1..747
```

```
                         mol_type = protein
                         organism = synthetic construct
SEQUENCE: 152
QVQLVQSGAE VKKPGASVKV SCKASGYTFT SYYMHWVRQA PGQGLEWMGW MNPNSGNTGY  60
AQKFQGRVTM TRDTSTSTVY MELSSLRSED TAVYYCATDL AGEALFDPWG QGTLVTVSSG  120
GGGSGGGGSG GGGSGGGGSD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIKSSSE PKSSDKTHTC PPCPAPEAAG APSVFLFPPK PKDTLMISRT PEVTCVVVDV  300
SHEDPEVKFN WYVDGVEVHN AKTKPREEQY NSTYRVVSVL TVLHQDWLNG KEYKCAVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
SGGGGSGGGG SGGGGSPSQV QLVQSGPEVK KPGSSVKVSC KASGYTFSRS TMHWVRQAPG  540
QGLEWIGYIN PSSAYTNYNQ KFKDRVTITA DKSTSTAYME LSSLRSEDTA VYYCARPQVH  600
YDYNGFPYWG QGTLVTVSSG GGGSGGGGSG GGGSGGGGSD IQMTQSPSTL SASVGDRVTM  660
TCSASSSVSY MNWYQQKPGK APKRWIYDSS KLASGVPSRF SGSGSGTDYT LTISSLQPDD  720
FATYYCQQWS RNPPTFGGGT KVEIKRS                                     747

SEQ ID NO: 153           moltype = DNA  length = 2298
FEATURE                  Location/Qualifiers
misc_feature             1..2298
                         note = DB415 VHVL x TSC456 scFv-Fc-scFv TRI138
source                   1..2298
                         mol_type = other DNA
                         organism = synthetic construct
SEQUENCE: 153
atggaagcac cagcgcagct tctcttcctc ctgctactct ggctcccaga taccaccggt  60
gaggtgcagc tggtggagtc tgggggaggc ttggtacagc ctggggggtc cctgcgcctc  120
tcctgtgcag cctctggaat caccttcagt agttatggca tgcattgggt ccgccaggct  180
ccagggaagg ggctggagtg ggtctcaggt attagttgga atagtggtaa cagagtctat  240
gtggactctg tgaagggccg gttcaccatc tcccgcgaca attccaagaa cacgctgtat  300
ctgcaaatga acagcctgcg cgccgaggac acggccgtat attactgtgc gagagatact  360
aatgatgctt ttgatatctg gggccaaggg accacggtca ccgtctcctc aggtggaggc  420
ggttcaggcg gaggtggatc cggcggtggc ggctccggtg gcggcggatc tgacatccag  480
atgacccagt ctccatcctc cctgtctgca tctgtaggag acagagtcac catcacttgc  540
cgggcaagtc agagcattag cagctatctg aattggtatc agcagaaacc agggaaagcc  600
cctaagctcc tgatctatgc tgcatccagt ttgcaaagtg gggtcccatc aaggttcagt  660
ggcagtggat ctgggacaga tttcactctc accatcagca gtctgcaacc tgaagatttt  720
gcaacttact actgtcaaca gagttacagt accccctctca ctttcggcgg aggtaccaag  780
gtggagatca aatcctcgag tgagcccaaa tcttctgaca aaactcacac atgcccaccg  840
tgcccagcac ctgaagccgc gggtgcaccg tcagtcttcc tcttcccccc aaaacccaag  900
gacaccctca tgatctcccg gacccctgag gtcacatgcg tggtggtgga cgtgagccac  960
gaagaccctg aggtcaagtt caactggtac gtggacggcg tggaggtgca taatgccaag  1020
acaaagccgc gggaggagca gtacaacagc acgtaccgtg tggtcagcgt cctcaccgtc  1080
ctgcaccagg actggctgaa tggcaaggaa tacaagtgcg cggtctccaa caaagccctc  1140
ccagccccca tcgagaaaac catctccaaa gccaaagggc agccccgaga accacaggtg  1200
tacaccctgc ccccatcccg ggatgagctg accaagaacc aggtcagcct gacctgcctg  1260
gtcaaaggct tctatccaag cgacatcgcc gtggagtggg agagcaatgg gcagccggag  1320
aacaactaca agaccacgcc tcccgtgctg gactccgacg gctccttctt cctctacagc  1380
aagctcaccg tggacaagag caggtggcag caggggaacg tcttctcatg ctccgtgatg  1440
catgaggctc tgcacaacca ctacacgcag aagagcctct ccctgtctcc gggttccgga  1500
ggagggggtt caggtggggg aggttctggc ggcgggggaa gcccttcaca ggtgcaactg  1560
gtgcagagtg gacccgaggt taaaaaacca gggtcctccg ttaaggttag ctgcaaagcc  1620
tctggctaca cattttccag gagtacaatg cactgggtga ggcaggctcc tggacaggga  1680
ctggagtgga tcgggtatat caacccatct agcgcctata ccaattacaa ccaaaagttt  1740
aaggaccgag ttaccattac cgctgacaaa tccaccagta cagcttatat ggagctgtca  1800
tctcttaggt ccgaggacac tgctgtttat tactgcgctc gtcctcaggt tcactatgac  1860
tataatggtt ttccctactg gggtcaggga accctggtga ctgtctcttc tggcggtgga  1920
ggcagcggtg ggggtgggtc tggaggcggt ggcagtggcg gcggaggctc tgatattcag  1980
atgactcagt ctcctagcac tctcagcgcc agcgtggggg atcgtgtgac aatgacttgc  2040
tccgctagca gtagtgtgtc ttacatgaat tggtatcagc agaagcccgg gaaagcacct  2100
aagcgctgga tctatgactc ttccaagctg gcaagtggtg tcccctcacg gttctctggc  2160
tcaggttctg gtactgacta tactttgact atctcctccc tccagcccga tgatttcgct  2220
acctattatt gtcagcagtg gagccgtaac ccacccactt tcggaggcgg taccaaagtg  2280
gagatcaaga ggtcatga                                               2298

SEQ ID NO: 154           moltype = AA  length = 745
FEATURE                  Location/Qualifiers
REGION                   1..745
                         note = DB415 VHVL x TSC456 scFv-Fc-scFv TRI138
source                   1..745
                         mol_type = protein
                         organism = synthetic construct
SEQUENCE: 154
EVQLVESGGG LVQPGGSLRL SCAASGITFS SYGMHWVRQA PGKGLEWVSG ISWNSGNRVY  60
VDSVKGRFTI SRDNSKNTLY LQMNSLRAED TAVYYCARDT NDAFDIWGQG TTVTVSSGGG  120
GSGGGGSGGG GSGGGGSDIQ MTQSPSSLSA SVGDRVTITC RASQSISSYL NWYQQKPGKA  180
PKLLIYAASS LQSGVPSRFS GSGSGTDFTL TISSLQPEDF ATYYCQQSYS TPLTFGGGTK  240
VEIKSSSEPK SSDKTHTCPP CPAPEAAGAP SVFLFPPKPK DTLMISRTPE VTCVVVDVSH  300
EDPEVKFNWY VDGVEVHNAK TKPREEQYNS TYRVVSVLTV LHQDWLNGKE YKCAVSNKAL  360
```

```
PAPIEKTISK AKGQPREPQV YTLPPSRDEL TKNQVSLTCL VKGFYPSDIA VEWESNGQPE  420
NNYKTTPPVL DSDGSFFLYS KLTVDKSRWQ QGNVFSCSVM HEALHNHYTQ KSLSLSPGSG  480
GGGSGGGGSG GGGSPSQVQL VQSGPEVKKP GSSVKVSCKA SGYTFSRSTM HWVRQAPGQG  540
LEWIGYINPS SAYTNYNQKF KDRVTITADK STSTAYMELS SLRSEDTAVY YCARPQVHYD  600
YNGFPYWGQG TLVTVSSGGG GSGGGGSGGG GSGGGGSDIQ MTQSPSTLSA SVGDRVTMTC  660
SASSSVSYMN WYQQKPGKAP KRWIYDSSKL ASGVPSRFSG SGSGTDYTLT ISSLQPDDFA  720
TYYCQQWSRN PPTFGGGTKV EIKRS                                         745

SEQ ID NO: 155          moltype = DNA  length = 2304
FEATURE                 Location/Qualifiers
misc_feature            1..2304
                        note = DB435 VHVL x TSC456 scFv-Fc-scFv TRI139
source                  1..2304
                        mol_type = other DNA
                        organism = synthetic construct
SEQUENCE: 155
atggaagcac cagcgcagct tctcttcctc ctgctactct ggctcccaga taccaccggt  60
caggtgcagc tggtgcagtc tggggctgag gtgaagaagc ctgggggcctc agtgaaggtt  120
tcctgcaagg catctggagg caccttcagc agctatgcta tcagctgggt gcgtcaggcc  180
cctggacaag ggcttgagtg gatgggctgg atcacccctc acaatggtaa cataaagtat  240
gcacgggagt tccagggccg tgtcaccatg acccgcgaca cgtccacgag cacagtctac  300
atggagctga gcagcctgcg ttctgaggac acggccgtgt attactgtgc gaaagatctg  360
aactggaacg cagcctttga ctactggggc caggggaccc tggtcaccgt ctcctcaggt  420
ggaggcggtt caggcggagg tggatccggc ggtggcggct ccggtggcgg cggatctgac  480
atccagatga cccagtctcc atcctccctg tctgcatctg taggagacag agtcaccatc  540
acttgccggg caagtcagag cattagcagc tatctgaatt ggtatcagca gaaaccaggg  600
aaagccccta agctcctgat ctatgctgca tccagtttgc aaagtggggt cccatcaagg  660
ttcagtggca gtggatctgg gacagatttc actctcacca tcagcagtct gcaacctgaa  720
gattttgcaa cttactactg tcaacagagt tacagtaccc ctctcacttt cggcggaggt  780
accaaggtgg agatcaaatc ctcgagtgag cccaaatctt ctgacaaaac tcacacatgc  840
ccaccgtgcc cagcacctga agccgcgggt gcaccgtcag tcttcctctt ccccccaaaa  900
cccaaggaca ccctcatgat ctcccggacc cctgaggtca catgcgtggt ggtggacgtg  960
agccacgaag accctgaggt caagttcaac tggtacgtgg acggcgtgga ggtgcataat  1020
gccaagacaa agccgcggga ggagcagtac aacagcacgt accgtgtggt cagcgtcctc  1080
accgtcctgc accaggactg gctgaatggc aaggaataca agtgcgcggt ctccaacaaa  1140
gccctcccag cccccatcga gaaaaccatc tccaaagcca aagggcagcc ccgagaacca  1200
caggtgtaca ccctgccccc atcccgggat gagctgacca agaaccaggt cagcctgacc  1260
tgcctggtca aaggcttcta tccaagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
tccggaggag gggttcagg tgggggaggt tctggcggcg ggggaagccc ttcacaggtg  1560
caactggtgc agagtggacc cgaggttaaa aaaccagggt cctccgttaa ggttagctgc  1620
aaagcctctg gctacacatt ttccaggagt acaatgcact gggtgaggca ggctcctgga  1680
cagggactgg agtggatcgg gtatatcaac ccatctagcg cctataccaa ttacaaccaa  1740
aagtttaagg accgagttac cattaccgct gacaaatcca ccagtacagc ttatatggag  1800
ctgtcatctc ttaggtccga ggacactgct gtttattact gcgctcgtcc tcaggttcac  1860
tatgactata atggttttcc ctactggggt cagggaaccc tggtgactgt ctcttctggc  1920
ggtggaggca gcggtggggg tgggtctgga ggcggtggca gtggcggcgg aggctctgat  1980
attcagatga ctcagtctcc tagcactctc agcgccagcg tgggggatcg tgtgacaatg  2040
acttgctccg ctagcagtag tgtgtcttac atgaattggt atcagcagaa gcccgggaaa  2100
gcacctaagc gctggatcta tgactcttcc aagctggcaa gtggtgtccc ctcacggttc  2160
tctggctcag gttctggtac tgactatact ttgactatct cctccctcca gcccgatgat  2220
ttcgctacct attattgtca gcagtggagc cgtaacccac ccactttcgg aggcggtacc  2280
aaagtggaga tcaagaggtc atga                                          2304

SEQ ID NO: 156          moltype = AA  length = 747
FEATURE                 Location/Qualifiers
REGION                  1..747
                        note = DB435 VHVL x TSC456 scFv-Fc-scFv TRI139
source                  1..747
                        mol_type = protein
                        organism = synthetic construct
SEQUENCE: 156
QVQLVQSGAE VKKPGASVKV SCKASGGTFS SYAISWVRQA PGQGLEWMGW ITPHNGNIKY  60
AREFQGRVTM TRDTSTSTVY MELSSLRSED TAVYYCAKDL NWNAAFDYWG QGTLVTVSSG  120
GGGSGGGGSG GGGSGGGGSD IQMTQSPSSL SASVGDRVTI TCRASQSISS YLNWYQQKPG  180
KAPKLLIYAA SSLQSGVPSR FSGSGSGTDF TLTISSLQPE DFATYYCQQS YSTPLTFGGG  240
TKVEIKSSSE PKSSDKTHTC PPCPAPEAAG APSVFLFPPK PKDTLMISRT PEVTCVVVDV  300
SHEDPEVKFN WYVDGVEVHN AKTKPREEQY NSTYRVVSVL TVLHQDWLNG KEYKCAVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
SGGGGSGGGG SGGGGSPSQV QLVQSGPEVK KPGSSVKVSC KASGYTFSRS TMHWVRQAPG  540
QGLEWIGYIN PSSAYTNYNQ KFKDRVTITA DKSTSTAYME LSSLRSEDTA VYYCARPQVH  600
YDYNGFPYWG QGTLVTVSSG GGGSGGGGSG GGGSGGGGSD IQMTQSPSTL SASVGDRVTM  660
TCSASSSVSY MNWYQQKPGK APKRWIYDSS KLASGVPSRF SGSGSGTDYT LTISSLQPDD  720
FATYYCQQWS RNPPTFGGGT KVEIKRS                                       747

SEQ ID NO: 157          moltype = AA  length = 108
```

```
FEATURE                Location/Qualifiers
REGION                 1..108
                       note = TSC455 variable light domain
source                 1..108
                       mol_type = protein
                       organism = synthetic construct
SEQUENCE: 157
DIQMTQSPST LSASVGDRVT MTCSASSSVS YMNWYQQKPG KAPKRWIYDS SKLASGVPSR  60
FSGSGSGTEY TLTISSLQPD DFATYYCQQW SRNPPTFGGG TKVEIKRS               108

SEQ ID NO: 158         moltype = AA  length = 108
FEATURE                Location/Qualifiers
REGION                 1..108
                       note = TSC456 variable light domain
source                 1..108
                       mol_type = protein
                       organism = synthetic construct
SEQUENCE: 158
DIQMTQSPST LSASVGDRVT MTCSASSSVS YMNWYQQKPG KAPKRWIYDS SKLASGVPSR  60
FSGSGSGTDY TLTISSLQPD DFATYYCQQW SRNPPTFGGG TKVEIKRS               108

SEQ ID NO: 159         moltype = AA  length = 121
FEATURE                Location/Qualifiers
REGION                 1..121
                       note = TSC455 and TSC456 variable heavy domain
source                 1..121
                       mol_type = protein
                       organism = synthetic construct
SEQUENCE: 159
QVQLVQSGPE VKKPGSSVKV SCKASGYTFS RSTMHWVRQA PGQGLEWIGY INPSSAYTNY  60
NQKFKDRVTI TADKSTSTAY MELSSLRSED TAVYYCARPQ VHYDYNGFPY WGQGTLVTVS  120
S                                                                  121

SEQ ID NO: 160         moltype = AA  length = 107
FEATURE                Location/Qualifiers
REGION                 1..107
                       note = DRA222 variable light domain
source                 1..107
                       mol_type = protein
                       organism = synthetic construct
SEQUENCE: 160
DIQMTQSPSS LSASVGDRVT MTCSASSSVS YMNWYQQKPG KAPKRWIYDS SKLASGVPAR  60
FSGSGSGTDY TLTISSLQPE DFATYYCQQW SRNPPTFGGG TKLQITS                107

SEQ ID NO: 161         moltype = AA  length = 121
FEATURE                Location/Qualifiers
REGION                 1..121
                       note = DRA222 variable heavy domain
source                 1..121
                       mol_type = protein
                       organism = synthetic construct
SEQUENCE: 161
QVQLVESGGG VVQPGRSLRL SCKASGYTFT RSTMHWVRQA PGQGLEWIGY INPSSAYTNY  60
NQKFKDRFTI SADKSKSTAF LQMDSLRPED TGVYFCARPQ VHYDYNGFPY WGQGTPVTVS  120
S                                                                  121

SEQ ID NO: 162         moltype = AA  length = 10
FEATURE                Location/Qualifiers
REGION                 1..10
                       note = Cris7 and DRA222 VL CDR1 (Kabat)
source                 1..10
                       mol_type = protein
                       organism = synthetic construct
SEQUENCE: 162
SASSSVSYMN                                                         10

SEQ ID NO: 163         moltype = AA  length = 7
FEATURE                Location/Qualifiers
REGION                 1..7
                       note = Cris7 and DRA222 VL CDR2 (Kabat)
source                 1..7
                       mol_type = protein
                       organism = synthetic construct
SEQUENCE: 163
DSSKLAS                                                            7

SEQ ID NO: 164         moltype = AA  length = 9
FEATURE                Location/Qualifiers
REGION                 1..9
```

```
                        note = Cris7 and DRA222 VL CDR3 (Kabat)
source                  1..9
                        mol_type = protein
                        organism = synthetic construct
SEQUENCE: 164
QQWSRNPPT                                                                9

SEQ ID NO: 165          moltype = AA  length = 5
FEATURE                 Location/Qualifiers
REGION                  1..5
                        note = Cris7 and DRA222 VH CDR1 (Kabat)
source                  1..5
                        mol_type = protein
                        organism = synthetic construct
SEQUENCE: 165
RSTMH                                                                    5

SEQ ID NO: 166          moltype = AA  length = 16
FEATURE                 Location/Qualifiers
REGION                  1..16
                        note = Cris7 and DRA222 VH CDR2 (Kabat)
source                  1..16
                        mol_type = protein
                        organism = synthetic construct
SEQUENCE: 166
YINPSSAYTN YNQKFK                                                        16

SEQ ID NO: 167          moltype = AA  length = 11
FEATURE                 Location/Qualifiers
REGION                  1..11
                        note = Cris7 and DRA222 VH CDR3 (Kabat)
source                  1..11
                        mol_type = protein
                        organism = synthetic construct
SEQUENCE: 167
QVHYDYNGFP Y                                                             11

SEQ ID NO: 168          moltype = AA  length = 7
FEATURE                 Location/Qualifiers
REGION                  1..7
                        note = Cris7 and DRA222 VL CDR1 (IMGT)
source                  1..7
                        mol_type = protein
                        organism = synthetic construct
SEQUENCE: 168
ASSSVSY                                                                  7

SEQ ID NO: 169          moltype =   length =
SEQUENCE: 169
000

SEQ ID NO: 170          moltype = AA  length = 9
FEATURE                 Location/Qualifiers
REGION                  1..9
                        note = Cris7 and DRA222 VL CDR3 (IMGT)
source                  1..9
                        mol_type = protein
                        organism = synthetic construct
SEQUENCE: 170
QQWSRNPPT                                                                9

SEQ ID NO: 171          moltype = AA  length = 8
FEATURE                 Location/Qualifiers
REGION                  1..8
                        note = Cris7 and DRA222 VH CDR1 (IMGT)
source                  1..8
                        mol_type = protein
                        organism = synthetic construct
SEQUENCE: 171
GYTFTRST                                                                 8

SEQ ID NO: 172          moltype = AA  length = 8
FEATURE                 Location/Qualifiers
REGION                  1..8
                        note = Cris7 and DRA222 VH CDR2 (IMGT)
source                  1..8
                        mol_type = protein
                        organism = synthetic construct
SEQUENCE: 172
```

```
INPSSAYT                                                8

SEQ ID NO: 173          moltype = AA  length = 9
FEATURE                 Location/Qualifiers
REGION                  1..9
                        note = Cris7 and DRA222 VH CDR3 (IMGT)
source                  1..9
                        mol_type = protein
                        organism = synthetic construct
SEQUENCE: 173
QQWSRNPPT                                               9

SEQ ID NO: 174          moltype = AA  length = 5
FEATURE                 Location/Qualifiers
REGION                  1..5
                        note = I2C VH CDR1 (Kabat)
source                  1..5
                        mol_type = protein
                        organism = synthetic construct
SEQUENCE: 174
KYAMN                                                   5

SEQ ID NO: 175          moltype = AA  length = 19
FEATURE                 Location/Qualifiers
REGION                  1..19
                        note = I2C VH CDR2 (Kabat)
source                  1..19
                        mol_type = protein
                        organism = synthetic construct
SEQUENCE: 175
RIRSKYNNYA TYYADSVKD                                    19

SEQ ID NO: 176          moltype = AA  length = 14
FEATURE                 Location/Qualifiers
REGION                  1..14
                        note = I2C VH CDR3 (Kabat)
source                  1..14
                        mol_type = protein
                        organism = synthetic construct
SEQUENCE: 176
HGNFGNSYIS YWAY                                         14

SEQ ID NO: 177          moltype =   length =
SEQUENCE: 177
000

SEQ ID NO: 178          moltype = AA  length = 9
FEATURE                 Location/Qualifiers
REGION                  1..9
                        note = I2C VL CDR3 (IMGT)
source                  1..9
                        mol_type = protein
                        organism = synthetic construct
SEQUENCE: 178
VLWYSNRWV                                               9

SEQ ID NO: 179          moltype = AA  length = 8
FEATURE                 Location/Qualifiers
REGION                  1..8
                        note = I2C VH CDR1 (IMGT)
source                  1..8
                        mol_type = protein
                        organism = synthetic construct
SEQUENCE: 179
GFTFNKYA                                                8

SEQ ID NO: 180          moltype = AA  length = 10
FEATURE                 Location/Qualifiers
REGION                  1..10
                        note = I2C VH CDR2 (IMGT)
source                  1..10
                        mol_type = protein
                        organism = synthetic construct
SEQUENCE: 180
IRSKYNNYAT                                              10

SEQ ID NO: 181          moltype = AA  length = 16
FEATURE                 Location/Qualifiers
REGION                  1..16
```

```
                        note = I2C VH CDR3 (IMGT)
source                  1..16
                        mol_type = protein
                        organism = synthetic construct
SEQUENCE: 181
VRHGNFGNSY ISYWAY                                              16

SEQ ID NO: 182          moltype = AA  length = 10
FEATURE                 Location/Qualifiers
REGION                  1..10
                        note = HuM291 VL CDR1 (Kabat)
source                  1..10
                        mol_type = protein
                        organism = synthetic construct
SEQUENCE: 182
SASSSVSYMN                                                     10

SEQ ID NO: 183          moltype = AA  length = 7
FEATURE                 Location/Qualifiers
REGION                  1..7
                        note = HuM291 VL CDR2 (Kabat)
source                  1..7
                        mol_type = protein
                        organism = synthetic construct
SEQUENCE: 183
DTSKLAS                                                        7

SEQ ID NO: 184          moltype = AA  length = 9
FEATURE                 Location/Qualifiers
REGION                  1..9
                        note = HuM291 VL CDR3 (Kabat)
source                  1..9
                        mol_type = protein
                        organism = synthetic construct
SEQUENCE: 184
QQWSSNPPT                                                      9

SEQ ID NO: 185          moltype = AA  length = 5
FEATURE                 Location/Qualifiers
REGION                  1..5
                        note = HuM291 VH CDR1 (Kabat)
source                  1..5
                        mol_type = protein
                        organism = synthetic construct
SEQUENCE: 185
SYTMH                                                          5

SEQ ID NO: 186          moltype = AA  length = 17
FEATURE                 Location/Qualifiers
REGION                  1..17
                        note = HuM291 VH CDR2 (Kabat)
source                  1..17
                        mol_type = protein
                        organism = synthetic construct
SEQUENCE: 186
YINPRSGYTH YNQKLKD                                             17

SEQ ID NO: 187          moltype = AA  length = 11
FEATURE                 Location/Qualifiers
REGION                  1..11
                        note = HuM291 VH CDR3 (Kabat)
source                  1..11
                        mol_type = protein
                        organism = synthetic construct
SEQUENCE: 187
SAYYDYDGFA Y                                                   11

SEQ ID NO: 188          moltype = AA  length = 7
FEATURE                 Location/Qualifiers
REGION                  1..7
                        note = HuM291 VL CDR1 (IMGT)
source                  1..7
                        mol_type = protein
                        organism = synthetic construct
SEQUENCE: 188
ASSSVSY                                                        7

SEQ ID NO: 189          moltype =   length =
SEQUENCE: 189
```

```
000

SEQ ID NO: 190         moltype = AA  length = 9
FEATURE                Location/Qualifiers
REGION                 1..9
                       note = HuM291 VL CDR3 (IMGT)
source                 1..9
                       mol_type = protein
                       organism = synthetic construct
SEQUENCE: 190
QQWSSNPPT                                                  9

SEQ ID NO: 191         moltype = AA  length = 8
FEATURE                Location/Qualifiers
REGION                 1..8
                       note = HuM291 VH CDR1 (IMGT)
source                 1..8
                       mol_type = protein
                       organism = synthetic construct
SEQUENCE: 191
GYTFISYT                                                   8

SEQ ID NO: 192         moltype = AA  length = 8
FEATURE                Location/Qualifiers
REGION                 1..8
                       note = HuM291 VH CDR2 (IMGT)
source                 1..8
                       mol_type = protein
                       organism = synthetic construct
SEQUENCE: 192
INPRSGYT                                                   8

SEQ ID NO: 193         moltype = AA  length = 13
FEATURE                Location/Qualifiers
REGION                 1..13
                       note = HuM291 VH CDR3 (IMGT)
source                 1..13
                       mol_type = protein
                       organism = synthetic construct
SEQUENCE: 193
ARSAYYDYDG FAY                                             13

SEQ ID NO: 194         moltype = DNA  length = 339
FEATURE                Location/Qualifiers
source                 1..339
                       mol_type = other DNA
                       organism = Mus sp.
SEQUENCE: 194
gacatcatga tgtcccagtc cccctcctcc ctggccgtgt ccgtgggcga gaagttcacc  60
atgacctgca agtcctccca gtccctgttc ttcggctcca cccagaagaa ctacctggcc  120
tggtaccagc agaagcccgg ccagtccccc aagctgctga tctactgggc ctccacccgg  180
gagtccggcg tgcccgaccg gttcaccggc tccggctccg gcaccgactt caccctggcc  240
atctcctccg tgatgcccga ggacctggcc gtgtactact gccagcagta ctacaactac  300
ccctggacct tcggcggcgg caccaagctg gagatcaag                        339

SEQ ID NO: 195         moltype = AA  length = 113
FEATURE                Location/Qualifiers
source                 1..113
                       mol_type = protein
                       organism = Mus sp.
SEQUENCE: 195
DIMMSQSPSS LAVSVGEKFT MTCKSSQSLF FGSTQKNYLA WYQQKPGQSP KLLIYWASTR  60
ESGVPDRFTG SGSGTDFTLA ISSVMPEDLA VYYCQQYYNY PWTFGGGTKL EIK         113

SEQ ID NO: 196         moltype = DNA  length = 345
FEATURE                Location/Qualifiers
source                 1..345
                       mol_type = other DNA
                       organism = Mus sp.
SEQUENCE: 196
cagctgcagg agtccggccc cggcctggtg aagccctccc agtccctgtc cctgacctgc  60
tccgtgaccg actactccat cacctccggc tactactgga actggattcg gcagttcccc  120
ggcaacaagc tggagtggat gggctacatc tcctacgacg gctccaacaa ctacaacccc  180
tccctgaaga accggatctc catcacccgg gacacctcca agaaccagtt cttcctgaag  240
ctgtcctccg tgaccaccga ggacaccgcc acctactact gctcccgggg cgagggcttc  300
tacttcgact cctggggcca gggcaccacc ctgaccgtgt cctcg                  345

SEQ ID NO: 197         moltype = AA  length = 116
FEATURE                Location/Qualifiers
```

```
source                  1..116
                        mol_type = protein
                        organism = Mus sp.
SEQUENCE: 197
VQLQESGPGL VKPSQSLSLT CSVTDYSITS GYYWNWIRQF PGNKLEWMGY ISYDGSNNYN  60
PSLKNRISIT RDTSKNQFFL KLSSVTTEDT ATYYCSRGEG FYFDSWGQGT TLTVSS      116

SEQ ID NO: 198          moltype = AA  length = 20
FEATURE                 Location/Qualifiers
REGION                  1..20
                        note = secretory signal sequence
source                  1..20
                        mol_type = protein
                        organism = synthetic construct
SEQUENCE: 198
MEAPAQLLFL LLLWLPDTTG                                              20

SEQ ID NO: 199          moltype = DNA  length = 1074
FEATURE                 Location/Qualifiers
misc_feature            1..1074
                        note = human CD123 ectodomain, with Avi-3xFLAG-His affinity
                         tag TRI032
source                  1..1074
                        mol_type = other DNA
                        organism = synthetic construct
SEQUENCE: 199
atggaagcac cagcgcagct tctcttcctc ctgctactct ggctcccaga taccaccggt  60
aaggaggacc ccaaccccc catcaccaac ctgaggatga aggccaaggc ccagcagctg  120
acctgggacc tgaacaggaa cgtgacagac atcgaatgcg tgaaggatgc cgactacagc  180
atgcccgccg tgaacaactc ctactgccag ttcggcgcca tcagcctgtg cgaggtgaca  240
aactacaccg tgagagtggc caacccccc ttcagcacct ggatcctgtt tcccgagaac  300
agcggcaaac cctgggctgg cgctgagaac ctgacctgct ggatccacga cgtggacttt  360
ctgtcctgca gctgggctgt gggacccgga gctcctgccg atgtgcagta cgacctgtac  420
ctgaatgtgg ccaacagaag acagcagtac gagtgcctgc attacaagac cgacgcccag  480
ggaaccagga tcggctgcag gtttgatgac atcagcaggc tgtcctccgg cagccagtcc  540
agccacatcc tggtgagagg cagatccgcc gccttcggca ttccctgcac agacaagttc  600
gtcgtcttca gccagatcga gattctgacc cccccaaca tgaccgccaa gtgtaacaag  660
acccacagct tcatgcactg gaagatgagg agccacttca acaggaagtt caggtacgag  720
ctccagatcc agaagaggat gcagcccgtg atcaccgagc aggtgaggga caggacatcc  780
ttccagctgc tgaatcccgg cacatacacc gtgcagatca gggccaggga aagggtgtac  840
gagttcctgt ccgcctggag cacccccag aggttcgagt gtgaccagga ggagggagcc  900
aataccaggg cctggagatc ctcgagtctc aacgatattt ttgaagccca aaaaattgag  960
tggcatgaag attacaagga cgatgacgac aaagactata aggacgacga cgataaggat  1020
tacaaggatg acgatgataa gcaccatcat catcaccatc accaccacca ctga        1074

SEQ ID NO: 200          moltype = AA  length = 337
FEATURE                 Location/Qualifiers
REGION                  1..337
                        note = human CD123 ectodomain, with Avi-3xFLAG-His affinity
                         tag TRI032
source                  1..337
                        mol_type = protein
                        organism = synthetic construct
SEQUENCE: 200
KEDPNPPITN LRMKAKAQQL TWDLNRNVTD IECVKDADYS MPAVNNSYCQ FGAISLCEVT  60
NYTVRVANPP FSTWILFPEN SGKPWAGAEN LTCWIHDVDF LSCSWAVGPG APADVQYDLY  120
LNVANRRQQY ECLHYKTDAQ GTRIGCRFDD ISRLSSGSQS SHILVRGRSA AFGIPCTDKF  180
VVFSQIEILT PPNMTAKCNK THSFMHWKMR SHFNRKFRYE LQIQKRMQPV ITEQVRDRTS  240
FQLLNPGTYT VQIRARERVY EFLSAWSTPQ RFECDQEEGA NTRAWRSSSL NDIFEAQKIE  300
WHEDYKDDDD KDYKDDDDKD YKDDDDKHHH HHHHHHH                            337

SEQ ID NO: 201          moltype = DNA  length = 996
FEATURE                 Location/Qualifiers
source                  1..996
                        mol_type = other DNA
                        organism = Homo sapiens
SEQUENCE: 201
atggtcctcc tttggctcac gctgctcctg atcgccctgc cctgtctcct gcaaacgaag  60
gaaggtggga agccttgggc aggtgcggag aatctgacct gctggattca tgacgtggat  120
ttcttgagct gcagctgggc ggtaggcccg ggggccccg cggacgtcca gtacgacctg  180
tacttgaacg ttgccaacag gcgtcaacag tacgagtgtc ttcactacaa aacggatgct  240
cagggaacac gtatcgggtg tcgtttcgat gacatctctc gactctccag cggttctcaa  300
agttcccaca tcctggtgcg gggcaggagc gcagccttcg gtatcccctg cacagataag  360
tttgtcgtct tttcacagat tgagatatta actccaccca acatgactgc aaagtgtaat  420
aagacacatt cctttatgca ctggaaaatg agaagtcatt tcaatcgcaa atttcgctat  480
gagcttcaga tacaaaagag aatgcagcct gtaatcacag aacaggtcag agacagaacc  540
tccttccagc tactcaatcc tggaacgtac acagtacaaa taagagcccg ggaaagagtg  600
tatgaattct tgagcgcctg gagcaccccc cagcgcttcg agtgcgacca ggaggagggc  660
gcaaacacac gtgcctggcg gacgtcgctg ctgatcgcgc tggggacgct gctggccctg  720
```

```
gtctgtgtct tcgtgatctg cagaaggtat ctggtgatgc agagactctt tccccgcatc  780
cctcacatga aagaccccat cggtgacagc ttccaaaacg acaagctggt ggtctgggag  840
gcgggcaaag ccggcctgga ggagtgtctg gtgactgaag tacaggtcgt gcagaaaact  900
acgcgtacgc ggccgctcga gcagaaactc atctcagaag aggatctggc agcaaatgat  960
atcctggatt acaaggatga cgacgataag gtttaa                          996

SEQ ID NO: 202         moltype = AA  length = 310
FEATURE                Location/Qualifiers
source                 1..310
                       mol_type = protein
                       organism = Homo sapiens
SEQUENCE: 202
GGKPWAGAEN LTCWIHDVDF LSCSWAVGPG APADVQYDLY LNVANRRQQY ECLHYKTDAQ  60
GTRIGCRFDD ISRLSSGSQS SHILVRGRSA AFGIPCTDKF VVFSQIEILT PPNMTAKCNK  120
THSFMHWKMR SHFNRKFRYE LQIQKRMQPV ITEQVRDRTS FQLLNPGTYT VQIRARERVY  180
EFLSAWSTPQ RFECDQEEGA NTRAWRTSLL IALGTLLALV CVFVICRRYL VMQRLFPRIP  240
HMKDPIGDSF QNDKLVVWEA GKAGLEECLV TEVQVVQKTT RTRPLEQKLI SEEDLAANDI  300
LDYKDDDDKV                                                        310

SEQ ID NO: 203         moltype = DNA  length = 1140
FEATURE                Location/Qualifiers
source                 1..1140
                       mol_type = other DNA
                       organism = Homo sapiens
SEQUENCE: 203
atggaagccc ccgcccagct gctcttcctg ctgctcctgt ggctgcctga caccaccggc  60
aaggaagacc ccaatgcccc catcaggaac ctgagaatga aggagaaggc ccagcagctc  120
atgtgggatc tgaacaggaa cgtgaccgac gtggagtgta tcaagggcac cgactactcc  180
atgcccgcca tgaataacag ctattgccag ttcggcgcca tcagcctgtg cgaggtcacc  240
aactacaccg tgagagtggc cagccccccc ttctccacct ggattctgtt ccctgagaac  300
agcggcaccc ctagggctgg cgctgagaat ctgacatgct gggtccatga cgtggacttc  360
ctgagctgca gctgggtggt gggacctgct gctcccgctg acgtgcagta cgatctgtat  420
ctgaacaacc ccaactccca cgagcagtac aggtgcctgc actacaagac agacgctaga  480
ggcacccaga tcggctgcag gttcgatgat atcgcccctc tgagcagggg atcccagagc  540
tcccatatcc tggtgagggg caggtccgcc gctgtgagca ttccttgcac cgacaagttc  600
gtcttcttca gccagatcga gaggctgacc cccccctaaca tgacaggcga gtgcaacgag  660
acccacagct tcatgcactg gaagatgaag agccatttca acaggaaatt caggtacgaa  720
ctgaggattc agaagagaat gcagcccgtg aggacagagc aggtgaggga tacaaccagc  780
ttccagctgc ccaatcctgg cacctatacc gtgcagatca gggctagaga gaccgtgtac  840
gagtttctgt ccgcctggag cacccccag aggtttgaat gtgaccagga ggagggagcc  900
tccagcaggg cttggagaac cagcctcctc atcgccctgg gcacactgct ggctctgctg  960
tgtgtgttcc tgatctgcag aaggtacctg gtgatgcaga ggctcttccc taggattccc  1020
cacatgaagg accccatcgg cgacaccttc cagcaggaca aactggtggt gtgggaagcc  1080
ggaaaggccg gcctggagga atgcctcgtg tccgaggtgc aggtggtgga gaagacctaa  1140

SEQ ID NO: 204         moltype = AA  length = 359
FEATURE                Location/Qualifiers
source                 1..359
                       mol_type = protein
                       organism = Homo sapiens
SEQUENCE: 204
KEDPNAPIRN LRMKEKAQQL MWDLNRNVTD VECIKGTDYS MPAMNNSYCQ FGAISLCEVT  60
NYTVRVASPP FSTWILFPEN SGTPRAGAEN LTCWVHDVDF LSCSWVVGPA APADVQYDLY  120
LNNPNSHEQY RCLHYKTDAR GTQIGCRFDD IAPLSRGSQS SHILVRGRSA AVSIPCTDKF  180
VFFSQIERLT PPNMTGECNE THSFMHWKMK SHFNRKFRYE LRIQKRMQPV RTEQVRDTTS  240
FQLPNPGTYT VQIRARETVY EFLSAWSTPQ RFECDQEEGA SSRAWRTSLL IALGTLLALL  300
CVFLICRRYL VMQRLFPRIP HMKDPIGDTF QQDKLVVWEA GKAGLEECLV SEVQVVEKT   359

SEQ ID NO: 205         moltype = DNA  length = 1713
FEATURE                Location/Qualifiers
source                 1..1713
                       mol_type = other DNA
                       organism = Homo sapiens
SEQUENCE: 205
gtcaggttca tggttacgaa gctgctgacc ccaggatccc agcccgtggg agagaagggg  60
gtctctgaca gcccccaccc ctccccactg ccagatcctt attgggtctg agtttcaggg  120
gtggggcccc agctggaggt tataaaacag ctcaatcggg gagtacaacc ttcggtttct  180
cttcggggaa agctgctttc agcgcacacg ggaagatatc agaaacatcc taggatcagg  240
acaccccaga tcttctcaac tggaaccacg aaggctgttt cttccacaca gtactttgat  300
ctccatttaa gcaggcacct ctgtcctgcg ttccggagct gcgttcccga tggtcctcct  360
ttggctcacg ctgctcctga tcgccctgcc ctgtctcctg caaacgaagg aagatccaaa  420
cccaccaatc acgaacctaa ggatgaaagc aaaggctcag cagttgacct gggaccttaa  480
cagaaatgtg accgatatcg agtgtgttaa agacgccgac tattctatgc cggcagtgaa  540
caatagctat tgccagtttg gagcaatttc cttatgtgaa gtgaccaact acaccgtccg  600
agtggccaac ccaccattct ccacgtggat cctcttccct gagaacagtg ggaagccttg  660
ggcaggtgcg gagaatctga cctgctggat tcatgacgtg gatttcttga gctgcagctg  720
ggcggtaggc ccgggggccc ccgcggacgt ccagtacgac ctgtacttga acgttgccaa  780
caggcgtcaa cagtacgagt gtcttcacta caaaacggat gctcagggaa cacgtatcgg  840
gtgtcgtttc gatgacatct ctcgactctc cagcggttct caaagttccc acatcctggt  900
```

```
gcggggcagg agcgcagcct tcggtatccc ctgcacagat aagtttgtcg tcttttcaca  960
gattgagata ttaactccac ccaacatgac tgcaaagtgt aataagacac attcctttat  1020
gcactggaaa atgagaagtc atttcaatcg caaatttcgc tatgagcttc agatacaaaa  1080
gagaatgcag cctgtaatca cagaacaggt cagagacaga acctccttcc agctactcaa  1140
tcctggaacg tacacagtac aaataagagc ccgggaaaga gtgtatgaat tcttgagcgc  1200
ctggagcacc ccccagcgct tcgagtgcga ccaggaggag ggcgcaaaca cacgtgcctg  1260
gcggacgtcg ctgctgatcg cgctggggac gctgctggcc ctggtctgtg tcttcgtgat  1320
ctgcagaagg tatctggtga tgcagagact ctttccccgc atccctcaca tgaaagaccc  1380
catcggtgac agcttccaaa acgacaagct ggtggtctgg gaggcgggca aagccggcct  1440
ggaggagtgt ctggtgactg aagtacaggt cgtgcagaaa acttgagact ggggttcagg  1500
gcttgtgggg gtctgcctca atctccctgg ccgggccagg cgcctgcaca gactggctgc  1560
tggacctgcg cacgcagccc aggaatggac attcctaacg ggtggtgggc atgggagatg  1620
cctgtgtaat ttcgtccgaa gctgccagga agaagaacag aactttgtgt gtttatttca  1680
tgataaagtg attttttttt ttttaaccca aaa                               1713

SEQ ID NO: 206         moltype = AA  length = 378
FEATURE                Location/Qualifiers
source                 1..378
                       mol_type = protein
                       organism = Homo sapiens
SEQUENCE: 206
MVLLWLTLLL IALPCLLQTK EDPNPPITNL RMKAKAQQLT WDLNRNVTDI ECVKDADYSM  60
PAVNNSYCQF GAISLCEVTN YTVRVANPPF STWILFPENS GKPWAGAENL TCWIHDVDFL  120
SCSWAVGPGA PADVQYDLYL NVANRRQQYE CLHYKTDAQG TRIGCRFDDI SRLSSGSQSS  180
HILVRGRSAA FGIPCTDKFV VFSQIEILTP PNMTAKCNKT HSFMHWKMRS HFNRKFRYEL  240
QIQKRMQPVI TEQVRDRTSF QLLNPGTYTV QIRARERVYE FLSAWSTPQR FECDQEEGAN  300
TRAWRTSLLI ALGTLLALVC VFVICRRYLV MQRLFPRIPH MKDPIGDSFQ NDKLVVWEAG  360
KAGLEECLVT EVQVVQKT                                                378

SEQ ID NO: 207         moltype = DNA  length = 1479
FEATURE                Location/Qualifiers
source                 1..1479
                       mol_type = other DNA
                       organism = Homo sapiens
SEQUENCE: 207
gtcaggttca tggttacgaa gctgctgacc ccaggatccc agcccgtggg agagaagggg  60
gtctctgaca gcccccaccc ctccccactg ccagatcctt attgggtctg agtttcaggg  120
gtggggcccc agctggaggt tataaaacag ctcaatcggg gagtacaacc ttcggtttct  180
cttcggggaa agctgctttc agcgcacacg ggaagatatc agaaacatcc taggatcagg  240
acaccccaga tcttctcaac tggaaccacg aaggctgttt cttccacaca gtactttgat  300
ctccatttaa gcaggcacct ctgtcctgcg ttccggagct gcgttcccga tggtcctcct  360
ttggctcacg ctgctcctga tcgccctgcc ctgtctcctg caaacgaagg aaggtgggaa  420
gccttgggca ggtgcggaga atctgacctg ctggattcat gacgtggatt tcttgagctg  480
cagctgggcg gtaggcccgg gggcccccgc ggacgtccag tacgacctgt acttgaacgt  540
tgccaacagg cgtcaacagt acgagtgtct tcactacaaa acggatgctc agggaacacg  600
tatcgggtgt cgtttcgatg acatctctcg actctccagc ggttctcaaa gttcccacat  660
cctggtgcgg ggcaggagcg cagccttcgg tatcccctgc acagataagt ttgtcgtctt  720
ttcacagatt gagatattaa ctccacccaa catgactgca aagtgtaata agacacattc  780
ctttatgcac tggaaaatga gaagtcattt caatcgcaaa tttcgctatg agcttcagat  840
acaaaagaga atgcagcctg taatcacaga acaggtcaga gacagaacct ccttccagct  900
actcaatcct ggaacgtaca cagtacaaat aagagcccgg gaaagagtgt atgaattctt  960
gagcgcctgg agcacccccc agcgcttcga gtgcgaccag gaggagggcg caaacacacg  1020
tgcctggcgg acgtcgctgc tgatcgcgct ggggacgctg ctggccctgg tctgtgtctt  1080
cgtgatctgc agaaggtatc tggtgatgca gagactcttt ccccgcatcc ctcacatgaa  1140
agaccccatc ggtgacagct tccaaaacga caagctggtg gtctgggagg cgggcaaagc  1200
cggcctggag gagtgtctgg tgactgaagt acaggtcgtg cagaaaactt gagactgggg  1260
ttcagggctt gtgggggtct gcctcaatct ccctggccgg gccaggcgcc tgcacagact  1320
ggctgctgga cctgcgcacg cagcccagga atggacattc ctaacgggtg gtgggcatgg  1380
gagatgcctg tgtaatttcg tccgaagctg ccaggaagaa gaacagaact ttgtgtgttt  1440
atttcatgat aaagtgattt tttttttttt aacccaaaa                         1479

SEQ ID NO: 208         moltype = AA  length = 300
FEATURE                Location/Qualifiers
source                 1..300
                       mol_type = protein
                       organism = Homo sapiens
SEQUENCE: 208
MVLLWLTLLL IALPCLLQTK EGGKPWAGAE NLTCWIHDVD FLSCSWAVGP GAPADVQYDL  60
YLNVANRRQQ YECLHYKTDA QGTRIGCRFD DISRLSSGSQ SSHILVRGRS AAFGIPCTDK  120
FVVFSQIEIL TPPNMTAKCN KTHSFMHWKM RSHFNRKFRY ELQIQKRMQP VITEQVRDRT  180
SFQLLNPGTY TVQIRARERV YEFLSAWSTP QRFECDQEEG ANTRAWRTSL LIALGTLLAL  240
VCVFVICRRY LVMQRLFPRI PHMKDPIGDS FQNDKLVVWE AGKAGLEECL VTEVQVVQKT  300

SEQ ID NO: 209         moltype = AA  length = 107
FEATURE                Location/Qualifiers
REGION                 1..107
                       note = CRIS-7 monoclonal antibody VL amino acid sequence
source                 1..107
                       mol_type = protein
```

```
                          organism = synthetic construct
SEQUENCE: 209
QVVLTQSPAI MSAFPGEKVT MTCSASSSVS YMNWYQQKSG TSPKRWIYDS SKLASGVPAR  60
FSGSGSGTSY SLTISSMETE DAATYYCQQW SRNPPTFGGG TKLQITR                107

SEQ ID NO: 210            moltype = AA  length = 121
FEATURE                   Location/Qualifiers
REGION                    1..121
                          note = CRIS-7 monoclonal antibody VH amino acid sequence
source                    1..121
                          mol_type = protein
                          organism = synthetic construct
SEQUENCE: 210
QVQLQQSGAE LARPGASVKM SCKASGYTFT RSTMHWVKQR PGQGLEWIGY INPSSAYTNY  60
NQKFKDKATL TADKSSSTAY MQLSSLTSED SAVYYCASPQ VHYDYNGFPY WGQGTLVTVS  120
A                                                                  121

SEQ ID NO: 211            moltype = AA  length = 106
FEATURE                   Location/Qualifiers
REGION                    1..106
                          note = HuM291 VL amino acid sequence
source                    1..106
                          mol_type = protein
                          organism = synthetic construct
SEQUENCE: 211
DIQMTQSPSS LSASVGDRVT ITCSASSSVS YMNWYQQKPG KAPKRLIYDT SKLASGVPSR  60
FSGSGSGTDF TLTISSLQPE DFATYYCQQW SSNPPTFGGG TKVEIK                 106

SEQ ID NO: 212            moltype = AA  length = 120
FEATURE                   Location/Qualifiers
REGION                    1..120
                          note = HuM291 VH amino acid sequence
source                    1..120
                          mol_type = protein
                          organism = synthetic construct
SEQUENCE: 212
QVQLVQSGAE VKKPGASVKV SCKASGYTFI SYTMHWVRQA PGQGLEWMGY INPRSGYTHY  60
NQKLKDKATL TADKSASTAY MELSSLRSED TAVYYCARSA YYDYDGFAYW GQGTLVTVSS  120

SEQ ID NO: 213            moltype = AA  length = 15
FEATURE                   Location/Qualifiers
REGION                    1..15
                          note = peptide linker
source                    1..15
                          mol_type = protein
                          organism = synthetic construct
SEQUENCE: 213
GGGGSGGGGS GGGGS                                                   15

SEQ ID NO: 214            moltype = AA  length = 25
FEATURE                   Location/Qualifiers
REGION                    1..25
                          note = peptide linker
VARIANT                   6..25
                          note = Residues at positions 6-25 may be absent
source                    1..25
                          mol_type = protein
                          organism = synthetic construct
SEQUENCE: 214
GGGGSGGGGS GGGGSGGGGS GGGGS                                        25

SEQ ID NO: 215            moltype = AA  length = 15
FEATURE                   Location/Qualifiers
REGION                    1..15
                          note = sss(s)-hIgG1 hinge
source                    1..15
                          mol_type = protein
                          organism = synthetic construct
SEQUENCE: 215
EPKSSDKTHT SPPSS                                                   15

SEQ ID NO: 216            moltype = AA  length = 15
FEATURE                   Location/Qualifiers
REGION                    1..15
                          note = csc(s)-hIgG1 hinge
source                    1..15
                          mol_type = protein
                          organism = synthetic construct
SEQUENCE: 216
```

```
EPKSCDKTHT SPPCS                                                   15

SEQ ID NO: 217          moltype = AA  length = 15
FEATURE                 Location/Qualifiers
REGION                  1..15
                        note = ssc(s)-hIgG1 hinge
source                  1..15
                        mol_type = protein
                        organism = synthetic construct
SEQUENCE: 217
EPKSSDKTHT SPPCS                                                   15

SEQ ID NO: 218          moltype = AA  length = 15
FEATURE                 Location/Qualifiers
REGION                  1..15
                        note = scc(s)-hIgG1 hinge
source                  1..15
                        mol_type = protein
                        organism = synthetic construct
SEQUENCE: 218
EPKSSDKTHT CPPCS                                                   15

SEQ ID NO: 219          moltype = AA  length = 15
FEATURE                 Location/Qualifiers
REGION                  1..15
                        note = css(s)-hIgG1 hinge
source                  1..15
                        mol_type = protein
                        organism = synthetic construct
SEQUENCE: 219
EPKSCDKTHT SPPSS                                                   15

SEQ ID NO: 220          moltype = AA  length = 15
FEATURE                 Location/Qualifiers
REGION                  1..15
                        note = scs(s)-hIgG1 hinge
source                  1..15
                        mol_type = protein
                        organism = synthetic construct
SEQUENCE: 220
EPKSSDKTHT CPPSS                                                   15

SEQ ID NO: 221          moltype = AA  length = 15
FEATURE                 Location/Qualifiers
REGION                  1..15
                        note = ccc(s)-hIgG1 hinge
source                  1..15
                        mol_type = protein
                        organism = synthetic construct
SEQUENCE: 221
EPKSCDKTHT SPPCS                                                   15

SEQ ID NO: 222          moltype = AA  length = 15
FEATURE                 Location/Qualifiers
REGION                  1..15
                        note = ccc(p)-hIgG1 hinge
source                  1..15
                        mol_type = protein
                        organism = synthetic construct
SEQUENCE: 222
EPKSCDKTHT SPPCP                                                   15

SEQ ID NO: 223          moltype = AA  length = 15
FEATURE                 Location/Qualifiers
REGION                  1..15
                        note = sss(p)-hIgG1 hinge
source                  1..15
                        mol_type = protein
                        organism = synthetic construct
SEQUENCE: 223
EPKSSDKTHT SPPSP                                                   15

SEQ ID NO: 224          moltype = AA  length = 15
FEATURE                 Location/Qualifiers
REGION                  1..15
                        note = csc(p)-hIgG1 hinge
source                  1..15
                        mol_type = protein
                        organism = synthetic construct
```

```
SEQUENCE: 224
EPKSCDKTHT SPPCP                                                  15

SEQ ID NO: 225          moltype = AA  length = 15
FEATURE                 Location/Qualifiers
REGION                  1..15
                        note = ssc(p)-hIgG1 hinge
source                  1..15
                        mol_type = protein
                        organism = synthetic construct
SEQUENCE: 225
EPKSSDKTHT SPPCP                                                  15

SEQ ID NO: 226          moltype = AA  length = 15
FEATURE                 Location/Qualifiers
REGION                  1..15
                        note = scc(p)-hIgG1 hinge
source                  1..15
                        mol_type = protein
                        organism = synthetic construct
SEQUENCE: 226
EPKSSDKTHT CPPCP                                                  15

SEQ ID NO: 227          moltype = AA  length = 15
FEATURE                 Location/Qualifiers
REGION                  1..15
                        note = css(p)-hIgG1 hinge
source                  1..15
                        mol_type = protein
                        organism = synthetic construct
SEQUENCE: 227
EPKSCDKTHT SPPSP                                                  15

SEQ ID NO: 228          moltype = AA  length = 15
FEATURE                 Location/Qualifiers
REGION                  1..15
                        note = scs(p)-hIgG1 hinge
source                  1..15
                        mol_type = protein
                        organism = synthetic construct
SEQUENCE: 228
EPKSSDKTHT CPPSP                                                  15

SEQ ID NO: 229          moltype = AA  length = 6
FEATURE                 Location/Qualifiers
REGION                  1..6
                        note = Scppcp linker
source                  1..6
                        mol_type = protein
                        organism = synthetic construct
SEQUENCE: 229
SCPPCP                                                            6

SEQ ID NO: 230          moltype = AA  length = 20
FEATURE                 Location/Qualifiers
REGION                  1..20
                        note = STD1 linker
source                  1..20
                        mol_type = protein
                        organism = synthetic construct
SEQUENCE: 230
NYGGGGSGGG GSGGGGSGNS                                             20

SEQ ID NO: 231          moltype = AA  length = 38
FEATURE                 Location/Qualifiers
REGION                  1..38
                        note = STD2 linker
source                  1..38
                        mol_type = protein
                        organism = synthetic construct
SEQUENCE: 231
NYGGGGSGGG GSGGGGSGNY GGGGSGGGGS GGGGSGNS                         38

SEQ ID NO: 232          moltype =   length =
SEQUENCE: 232
000

SEQ ID NO: 233          moltype = AA  length = 8
FEATURE                 Location/Qualifiers
```

```
REGION                 1..8
                       note = H2 linker
source                 1..8
                       mol_type = protein
                       organism = synthetic construct
SEQUENCE: 233
GGGGSGNS                                                                  8

SEQ ID NO: 234         moltype = AA  length = 10
FEATURE                Location/Qualifiers
REGION                 1..10
                       note = H3 linker
source                 1..10
                       mol_type = protein
                       organism = synthetic construct
SEQUENCE: 234
NYGGGGSGNS                                                                10

SEQ ID NO: 235         moltype = AA  length = 13
FEATURE                Location/Qualifiers
REGION                 1..13
                       note = H4 linker
source                 1..13
                       mol_type = protein
                       organism = synthetic construct
SEQUENCE: 235
GGGGSGGGGS GNS                                                            13

SEQ ID NO: 236         moltype = AA  length = 15
FEATURE                Location/Qualifiers
REGION                 1..15
                       note = H5 linker
source                 1..15
                       mol_type = protein
                       organism = synthetic construct
SEQUENCE: 236
NYGGGGSGGG GSGNS                                                          15

SEQ ID NO: 237         moltype = AA  length = 18
FEATURE                Location/Qualifiers
REGION                 1..18
                       note = H6 linker
source                 1..18
                       mol_type = protein
                       organism = synthetic construct
SEQUENCE: 237
GGGGSGGGGS GGGGSGNS                                                       18

SEQ ID NO: 238         moltype = AA  length = 8
FEATURE                Location/Qualifiers
REGION                 1..8
                       note = H7 linker
source                 1..8
                       mol_type = protein
                       organism = synthetic construct
SEQUENCE: 238
GCPPCPNS                                                                  8

SEQ ID NO: 239         moltype = AA  length = 15
FEATURE                Location/Qualifiers
REGION                 1..15
                       note = (G4S)3 linker
source                 1..15
                       mol_type = protein
                       organism = synthetic construct
SEQUENCE: 239
GGGGSGGGGS GGGGS                                                          15

SEQ ID NO: 240         moltype = AA  length = 16
FEATURE                Location/Qualifiers
REGION                 1..16
                       note = H105 linker
source                 1..16
                       mol_type = protein
                       organism = synthetic construct
SEQUENCE: 240
SGGGGSGGGG SGGGGS                                                         16

SEQ ID NO: 241         moltype = AA  length = 20
```

```
FEATURE                Location/Qualifiers
REGION                 1..20
                       note = (G4S)4 linker
source                 1..20
                       mol_type = protein
                       organism = synthetic construct
SEQUENCE: 241
GGGGSGGGGS GGGGSGGGGS                                                      20

SEQ ID NO: 242         moltype = AA  length = 21
FEATURE                Location/Qualifiers
REGION                 1..21
                       note = H75 (NKG2A quadruple mutant) linker
source                 1..21
                       mol_type = protein
                       organism = synthetic construct
SEQUENCE: 242
QRHNNSSLNT GTQMAGHSPN S                                                    21

SEQ ID NO: 243         moltype = AA  length = 16
FEATURE                Location/Qualifiers
REGION                 1..16
                       note = H83 (NKG2A derived) linker
source                 1..16
                       mol_type = protein
                       organism = synthetic construct
SEQUENCE: 243
SSLNTGTQMA GHSPNS                                                          16

SEQ ID NO: 244         moltype = AA  length = 18
FEATURE                Location/Qualifiers
REGION                 1..18
                       note = H106 (NKG2A derived) linker
source                 1..18
                       mol_type = protein
                       organism = synthetic construct
SEQUENCE: 244
QRHNNSSLNT GTQMAGHS                                                        18

SEQ ID NO: 245         moltype = AA  length = 14
FEATURE                Location/Qualifiers
REGION                 1..14
                       note = H81 (NKG2D derived) linker
source                 1..14
                       mol_type = protein
                       organism = synthetic construct
SEQUENCE: 245
EVQIPLTESY SPNS                                                            14

SEQ ID NO: 246         moltype = AA  length = 20
FEATURE                Location/Qualifiers
REGION                 1..20
                       note = H91 (NKG2D derived) linker
source                 1..20
                       mol_type = protein
                       organism = synthetic construct
SEQUENCE: 246
NSLANQEVQI PLTESYSPNS                                                      20

SEQ ID NO: 247         moltype = AA  length = 19
FEATURE                Location/Qualifiers
REGION                 1..19
                       note = H94 linker
source                 1..19
                       mol_type = protein
                       organism = synthetic construct
SEQUENCE: 247
SGGGGSGGGG SGGGGSPNS                                                       19

SEQ ID NO: 248         moltype = AA  length = 19
FEATURE                Location/Qualifiers
REGION                 1..19
                       note = H111 linker
source                 1..19
                       mol_type = protein
                       organism = synthetic construct
SEQUENCE: 248
SGGGGSGGGG SGGGGSPGS                                                       19
```

```
SEQ ID NO: 249          moltype = AA  length = 15
FEATURE                 Location/Qualifiers
REGION                  1..15
                        note = H16 linker
source                  1..15
                        mol_type = protein
                        organism = synthetic construct
SEQUENCE: 249
LSVKADFLTP SIGNS                                                    15

SEQ ID NO: 250          moltype = AA  length = 20
FEATURE                 Location/Qualifiers
REGION                  1..20
                        note = H17 linker
source                  1..20
                        mol_type = protein
                        organism = synthetic construct
SEQUENCE: 250
LSVKADFLTP SISCPPCPNS                                               20

SEQ ID NO: 251          moltype = AA  length = 15
FEATURE                 Location/Qualifiers
REGION                  1..15
                        note = H18 linker
source                  1..15
                        mol_type = protein
                        organism = synthetic construct
SEQUENCE: 251
LSVLANFSQP EIGNS                                                    15

SEQ ID NO: 252          moltype = AA  length = 20
FEATURE                 Location/Qualifiers
REGION                  1..20
                        note = H19 linker
source                  1..20
                        mol_type = protein
                        organism = synthetic construct
SEQUENCE: 252
LSVLANFSQP EISCPPCPNS                                               20

SEQ ID NO: 253          moltype = AA  length = 15
FEATURE                 Location/Qualifiers
REGION                  1..15
                        note = H20 linker
source                  1..15
                        mol_type = protein
                        organism = synthetic construct
SEQUENCE: 253
LKIQERVSKP KISNS                                                    15

SEQ ID NO: 254          moltype = AA  length = 20
FEATURE                 Location/Qualifiers
REGION                  1..20
                        note = H21 linker
source                  1..20
                        mol_type = protein
                        organism = synthetic construct
SEQUENCE: 254
LKIQERVSKP KISCPPCPNS                                               20

SEQ ID NO: 255          moltype = AA  length = 15
FEATURE                 Location/Qualifiers
REGION                  1..15
                        note = H22 linker
source                  1..15
                        mol_type = protein
                        organism = synthetic construct
SEQUENCE: 255
LNVSERPFPP HIQNS                                                    15

SEQ ID NO: 256          moltype = AA  length = 21
FEATURE                 Location/Qualifiers
REGION                  1..21
                        note = H23 linker
source                  1..21
                        mol_type = protein
                        organism = synthetic construct
SEQUENCE: 256
LDVSERPFPP HIQSCPPCPN S                                             21
```

```
SEQ ID NO: 257          moltype = AA  length = 15
FEATURE                 Location/Qualifiers
REGION                  1..15
                        note = H24 linker
source                  1..15
                        mol_type = protein
                        organism = synthetic construct
SEQUENCE: 257
REQLAEVTLS LKANS                                                   15

SEQ ID NO: 258          moltype = AA  length = 20
FEATURE                 Location/Qualifiers
REGION                  1..20
                        note = H25 linker
source                  1..20
                        mol_type = protein
                        organism = synthetic construct
SEQUENCE: 258
REQLAEVTLS LKACPPCPNS                                              20

SEQ ID NO: 259          moltype = AA  length = 15
FEATURE                 Location/Qualifiers
REGION                  1..15
                        note = H26 linker
source                  1..15
                        mol_type = protein
                        organism = synthetic construct
SEQUENCE: 259
RIHQMNSELS VLANS                                                   15

SEQ ID NO: 260          moltype = AA  length = 20
FEATURE                 Location/Qualifiers
REGION                  1..20
                        note = H27 linker
source                  1..20
                        mol_type = protein
                        organism = synthetic construct
SEQUENCE: 260
RIHQMNSELS VLACPPCPNS                                              20

SEQ ID NO: 261          moltype = AA  length = 15
FEATURE                 Location/Qualifiers
REGION                  1..15
                        note = H28 linker
source                  1..15
                        mol_type = protein
                        organism = synthetic construct
SEQUENCE: 261
DTKGKNVLEK IFSNS                                                   15

SEQ ID NO: 262          moltype = AA  length = 15
FEATURE                 Location/Qualifiers
REGION                  1..15
                        note = H30 linker
source                  1..15
                        mol_type = protein
                        organism = synthetic construct
SEQUENCE: 262
LPPETQESQE VTLNS                                                   15

SEQ ID NO: 263          moltype = AA  length = 15
FEATURE                 Location/Qualifiers
REGION                  1..15
                        note = H32 linker
source                  1..15
                        mol_type = protein
                        organism = synthetic construct
SEQUENCE: 263
RIHLNVSERP FPPNS                                                   15

SEQ ID NO: 264          moltype = AA  length = 20
FEATURE                 Location/Qualifiers
REGION                  1..20
                        note = H33 linker
source                  1..20
                        mol_type = protein
                        organism = synthetic construct
SEQUENCE: 264
```

```
RIHLNVSERP FPPCPPCPNS                                          20

SEQ ID NO: 265          moltype = AA  length = 13
FEATURE                 Location/Qualifiers
REGION                  1..13
                        note = H36 linker
source                  1..13
                        mol_type = protein
                        organism = synthetic construct
SEQUENCE: 265
GCPPCPGGGG SNS                                                 13

SEQ ID NO: 266          moltype = AA  length = 9
FEATURE                 Location/Qualifiers
REGION                  1..9
                        note = H40 linker
source                  1..9
                        mol_type = protein
                        organism = synthetic construct
SEQUENCE: 266
GCPPCPANS                                                      9

SEQ ID NO: 267          moltype = AA  length = 9
FEATURE                 Location/Qualifiers
REGION                  1..9
                        note = H41 linker
source                  1..9
                        mol_type = protein
                        organism = synthetic construct
SEQUENCE: 267
GCPPCPANS                                                      9

SEQ ID NO: 268          moltype = AA  length = 8
FEATURE                 Location/Qualifiers
REGION                  1..8
                        note = H42 linker
source                  1..8
                        mol_type = protein
                        organism = synthetic construct
SEQUENCE: 268
GCPPCPNS                                                       8

SEQ ID NO: 269          moltype = AA  length = 13
FEATURE                 Location/Qualifiers
REGION                  1..13
                        note = H44 linker
source                  1..13
                        mol_type = protein
                        organism = synthetic construct
SEQUENCE: 269
GGGASCPPCP GNS                                                 13

SEQ ID NO: 270          moltype = AA  length = 13
FEATURE                 Location/Qualifiers
REGION                  1..13
                        note = H45 linker
source                  1..13
                        mol_type = protein
                        organism = synthetic construct
SEQUENCE: 270
GGGASCPPCA GNS                                                 13

SEQ ID NO: 271          moltype = AA  length = 12
FEATURE                 Location/Qualifiers
REGION                  1..12
                        note = H46 linker
source                  1..12
                        mol_type = protein
                        organism = synthetic construct
SEQUENCE: 271
GGGASCPPCA NS                                                  12

SEQ ID NO: 272          moltype = AA  length = 15
FEATURE                 Location/Qualifiers
REGION                  1..15
                        note = H47 linker
source                  1..15
                        mol_type = protein
                        organism = synthetic construct
```

```
SEQUENCE: 272
LSVKADFLTP SIGNS                                                    15

SEQ ID NO: 273          moltype = AA  length = 11
FEATURE                 Location/Qualifiers
REGION                  1..11
                        note = H48 linker
source                  1..11
                        mol_type = protein
                        organism = synthetic construct
SEQUENCE: 273
ADFLTPSIGN S                                                        11

SEQ ID NO: 274          moltype = AA  length = 15
FEATURE                 Location/Qualifiers
REGION                  1..15
                        note = H50 linker
source                  1..15
                        mol_type = protein
                        organism = synthetic construct
SEQUENCE: 274
LSVLANFSQP EIGNS                                                    15

SEQ ID NO: 275          moltype = AA  length = 15
FEATURE                 Location/Qualifiers
REGION                  1..15
                        note = H51 linker
source                  1..15
                        mol_type = protein
                        organism = synthetic construct
SEQUENCE: 275
LSVLANFSQP EIGNS                                                    15

SEQ ID NO: 276          moltype = AA  length = 11
FEATURE                 Location/Qualifiers
REGION                  1..11
                        note = H52 linker
source                  1..11
                        mol_type = protein
                        organism = synthetic construct
SEQUENCE: 276
SQPEIVPISN S                                                        11

SEQ ID NO: 277          moltype = AA  length = 16
FEATURE                 Location/Qualifiers
REGION                  1..16
                        note = H53 linker
source                  1..16
                        mol_type = protein
                        organism = synthetic construct
SEQUENCE: 277
SQPEIVPISC PPCPNS                                                   16

SEQ ID NO: 278          moltype = AA  length = 19
FEATURE                 Location/Qualifiers
REGION                  1..19
                        note = H54 linker
source                  1..19
                        mol_type = protein
                        organism = synthetic construct
SEQUENCE: 278
SVLANFSQPE ISCPPCPNS                                                19

SEQ ID NO: 279          moltype = AA  length = 15
FEATURE                 Location/Qualifiers
REGION                  1..15
                        note = H55 linker
source                  1..15
                        mol_type = protein
                        organism = synthetic construct
SEQUENCE: 279
RIHQMNSELS VLANS                                                    15

SEQ ID NO: 280          moltype = AA  length = 12
FEATURE                 Location/Qualifiers
REGION                  1..12
                        note = H56 linker
source                  1..12
                        mol_type = protein
```

```
                        organism = synthetic construct
SEQUENCE: 280
QMNSELSVLA NS                                                12

SEQ ID NO: 281          moltype = AA  length = 10
FEATURE                 Location/Qualifiers
REGION                  1..10
                        note = H57 linker
source                  1..10
                        mol_type = protein
                        organism = synthetic construct
SEQUENCE: 281
VSERPFPPNS                                                   10

SEQ ID NO: 282          moltype = AA  length = 15
FEATURE                 Location/Qualifiers
REGION                  1..15
                        note = H58 linker
source                  1..15
                        mol_type = protein
                        organism = synthetic construct
SEQUENCE: 282
KPFFTCGSAD TCPNS                                             15

SEQ ID NO: 283          moltype = AA  length = 15
FEATURE                 Location/Qualifiers
REGION                  1..15
                        note = H59 linker
source                  1..15
                        mol_type = protein
                        organism = synthetic construct
SEQUENCE: 283
KPFFTCGSAD TCPNS                                             15

SEQ ID NO: 284          moltype = AA  length = 15
FEATURE                 Location/Qualifiers
REGION                  1..15
                        note = H60 linker
source                  1..15
                        mol_type = protein
                        organism = synthetic construct
SEQUENCE: 284
QYNCPGQYTF SMPNS                                             15

SEQ ID NO: 285          moltype = AA  length = 21
FEATURE                 Location/Qualifiers
REGION                  1..21
                        note = H61 linker
source                  1..21
                        mol_type = protein
                        organism = synthetic construct
SEQUENCE: 285
EPAFTPGPNI ELQKDSDCPN S                                      21

SEQ ID NO: 286          moltype = AA  length = 21
FEATURE                 Location/Qualifiers
REGION                  1..21
                        note = H62 linker
source                  1..21
                        mol_type = protein
                        organism = synthetic construct
SEQUENCE: 286
QRHNNSSLNT RTQKARHCPN S                                      21

SEQ ID NO: 287          moltype = AA  length = 20
FEATURE                 Location/Qualifiers
REGION                  1..20
                        note = H63 linker
source                  1..20
                        mol_type = protein
                        organism = synthetic construct
SEQUENCE: 287
NSLFNQEVQI PLTESYCPNS                                        20

SEQ ID NO: 288          moltype = AA  length = 17
FEATURE                 Location/Qualifiers
REGION                  1..17
                        note = H114 linker
source                  1..17
```

```
                        mol_type = protein
                        organism = synthetic construct
SEQUENCE: 288
GGGGSGGGGS GGGGSPS                                             17

SEQ ID NO: 289          moltype = AA  length = 14
FEATURE                 Location/Qualifiers
REGION                  1..14
                        note = CD3-binding domain LCDR1
source                  1..14
                        mol_type = protein
                        organism = synthetic construct
SEQUENCE: 289
GSSTGAVTSG YYPN                                                14

SEQ ID NO: 290          moltype = AA  length = 14
FEATURE                 Location/Qualifiers
REGION                  1..14
                        note = CD3-binding domain LCDR1
source                  1..14
                        mol_type = protein
                        organism = synthetic construct
SEQUENCE: 290
RSSTGAVTSG YYPN                                                14

SEQ ID NO: 291          moltype = AA  length = 14
FEATURE                 Location/Qualifiers
REGION                  1..14
                        note = CD3-binding domain LCDR1
source                  1..14
                        mol_type = protein
                        organism = synthetic construct
SEQUENCE: 291
GSSTGAVTSG NYPN                                                14

SEQ ID NO: 292          moltype = AA  length = 7
FEATURE                 Location/Qualifiers
REGION                  1..7
                        note = CD3-binding domain LCDR2
source                  1..7
                        mol_type = protein
                        organism = synthetic construct
SEQUENCE: 292
GTKFLAP                                                        7

SEQ ID NO: 293          moltype = AA  length = 7
FEATURE                 Location/Qualifiers
REGION                  1..7
                        note = CD3-binding domain LCDR2
source                  1..7
                        mol_type = protein
                        organism = synthetic construct
SEQUENCE: 293
ATDMRPS                                                        7

SEQ ID NO: 294          moltype = AA  length = 7
FEATURE                 Location/Qualifiers
REGION                  1..7
                        note = CD3-binding domain LCDR2
source                  1..7
                        mol_type = protein
                        organism = synthetic construct
SEQUENCE: 294
GTKFLAP                                                        7

SEQ ID NO: 295          moltype = AA  length = 9
FEATURE                 Location/Qualifiers
REGION                  1..9
                        note = CD3-binding domain LCDR3
source                  1..9
                        mol_type = protein
                        organism = synthetic construct
SEQUENCE: 295
ALWYSNRWV                                                      9

SEQ ID NO: 296          moltype = AA  length = 9
FEATURE                 Location/Qualifiers
REGION                  1..9
                        note = CD3-binding domain LCDR3
```

```
source                  1..9
                        mol_type = protein
                        organism = synthetic construct
SEQUENCE: 296
ALWYSNRWV                                                                9

SEQ ID NO: 297          moltype = AA  length = 9
FEATURE                 Location/Qualifiers
REGION                  1..9
                        note = CD3-binding domain LCDR3
source                  1..9
                        mol_type = protein
                        organism = synthetic construct
SEQUENCE: 297
VLWYSNRWV                                                                9

SEQ ID NO: 298          moltype = AA  length = 5
FEATURE                 Location/Qualifiers
REGION                  1..5
                        note = CD3-binding domain HCDR1
source                  1..5
                        mol_type = protein
                        organism = synthetic construct
SEQUENCE: 298
IYAMN                                                                    5

SEQ ID NO: 299          moltype = AA  length = 5
FEATURE                 Location/Qualifiers
REGION                  1..5
                        note = CD3-binding domain HCDR1
source                  1..5
                        mol_type = protein
                        organism = synthetic construct
SEQUENCE: 299
KYAMN                                                                    5

SEQ ID NO: 300          moltype = AA  length = 5
FEATURE                 Location/Qualifiers
REGION                  1..5
                        note = CD3-binding domain HCDR1
source                  1..5
                        mol_type = protein
                        organism = synthetic construct
SEQUENCE: 300
SYAMN                                                                    5

SEQ ID NO: 301          moltype = AA  length = 19
FEATURE                 Location/Qualifiers
REGION                  1..19
                        note = CD3-binding domain HCDR2
source                  1..19
                        mol_type = protein
                        organism = synthetic construct
SEQUENCE: 301
RIRSKYNNYA TYYADSVKS                                                     19

SEQ ID NO: 302          moltype = AA  length = 19
FEATURE                 Location/Qualifiers
REGION                  1..19
                        note = CD3-binding domain HCDR2
source                  1..19
                        mol_type = protein
                        organism = synthetic construct
SEQUENCE: 302
RIRSKYNNYA TYYADSVKD                                                     19

SEQ ID NO: 303          moltype = AA  length = 19
FEATURE                 Location/Qualifiers
REGION                  1..19
                        note = CD3-binding domain HCDR2
source                  1..19
                        mol_type = protein
                        organism = synthetic construct
SEQUENCE: 303
RIRSKYNNYA TYYADSVKG                                                     19

SEQ ID NO: 304          moltype = AA  length = 14
FEATURE                 Location/Qualifiers
REGION                  1..14
```

```
                         note = CD3-binding domain HCDR3
source                   1..14
                         mol_type = protein
                         organism = synthetic construct
SEQUENCE: 304
HGNFGNSYVS FFAY                                                  14

SEQ ID NO: 305           moltype = AA  length = 14
FEATURE                  Location/Qualifiers
REGION                   1..14
                         note = CD3-binding domain HCDR3
source                   1..14
                         mol_type = protein
                         organism = synthetic construct
SEQUENCE: 305
HGNFGNSYIS YWAY                                                  14

SEQ ID NO: 306           moltype = AA  length = 14
FEATURE                  Location/Qualifiers
REGION                   1..14
                         note = CD3-binding domain HCDR3
source                   1..14
                         mol_type = protein
                         organism = synthetic construct
SEQUENCE: 306
HGNFGNSYLS FWAY                                                  14

SEQ ID NO: 307           moltype = AA  length = 14
FEATURE                  Location/Qualifiers
REGION                   1..14
                         note = I2C VL CDR1 (Kabat)
source                   1..14
                         mol_type = protein
                         organism = synthetic construct
SEQUENCE: 307
GSSTGAVTSG NYPN                                                  14

SEQ ID NO: 308           moltype = AA  length = 7
FEATURE                  Location/Qualifiers
REGION                   1..7
                         note = I2C VL CDR2 (Kabat)
source                   1..7
                         mol_type = protein
                         organism = synthetic construct
SEQUENCE: 308
GTKFLAP                                                          7

SEQ ID NO: 309           moltype = AA  length = 9
FEATURE                  Location/Qualifiers
REGION                   1..9
                         note = I2C VL CDR3 (Kabat)
source                   1..9
                         mol_type = protein
                         organism = synthetic construct
SEQUENCE: 309
VLWYSNRWV                                                        9

SEQ ID NO: 310           moltype = AA  length = 9
FEATURE                  Location/Qualifiers
REGION                   1..9
                         note = I2C VL CDR1 (IMGT)
source                   1..9
                         mol_type = protein
                         organism = synthetic construct
SEQUENCE: 310
TGAVTSGNY                                                        9

SEQ ID NO: 311           moltype = AA  length = 251
FEATURE                  Location/Qualifiers
REGION                   1..251
                         note = TSC455 (anti-CD3) TSC394 F87Y scFv
source                   1..251
                         mol_type = protein
                         organism = synthetic construct
SEQUENCE: 311
QVQLVQSGPE VKKPGSSVKV SCKASGYTFS RSTMHWVRQA PGQGLEWIGY INPSSAYTNY  60
NQKFKDRVTI TADKSTSTAY MELSSLRSED TAVYYCARPQ VHYDYNGFPY WGQGTLVTVS  120
SGGGGSGGGG SGGGGSGGGG SDIQMTQSPS TLSASVGDRV TMTCSASSSV SYMNWYQQKP  180
GKAPKRWIYD SSKLASGVPS RFSGSGSGTE YTLTISSLQP DDFATYYCQQ WSRNPPTFGG  240
```

-continued

```
GTKVEIKRSS S                                                        251

SEQ ID NO: 312          moltype = AA  length = 251
FEATURE                 Location/Qualifiers
REGION                  1..251
                        note = TSC456 (anti-CD3) TSC394 E86D F87Y scFv
source                  1..251
                        mol_type = protein
                        organism = synthetic construct
SEQUENCE: 312
QVQLVQSGPE VKKPGSSVKV SCKASGYTFS RSTMHWVRQA PGQGLEWIGY INPSSAYTNY  60
NQKFKDRVTI TADKSTSTAY MELSSLRSED TAVYYCARPQ VHYDYNGFPY WGQGTLVTVS  120
SGGGGSGGGG SGGGGSGGGG SDIQMTQSPS TLSASVGDRV TMTCSASSSV SYMNWYQQKP  180
GKAPKRWIYD SSKLASGVPS RFSGSGSGTD YTLTISSLQP DDFATYYCQQ WSRNPPTFGG  240
GTKVEIKRSS S                                                        251

SEQ ID NO: 313          moltype = AA  length = 247
FEATURE                 Location/Qualifiers
REGION                  1..247
                        note = DRA222 (anti-CD3) scFv
source                  1..247
                        mol_type = protein
                        organism = synthetic construct
SEQUENCE: 313
QVQLVESGGG VVQPGRSLRL SCKASGYTFT RSTMHWVRQA PGQGLEWIGY INPSSAYTNY  60
NQKFKDRFTI SADKSKSTAF LQMDSLRPED TGVYFCARPQ VHYDYNGFPY WGQGTPVTVS  120
SGGGGSGGGG SGGGGSAQDI QMTQSPSSLS ASVGDRVTMT CSASSSVSYM NWYQQKPGKA  180
PKRWIYDSSK LASGVPARFS GSGSGTDYTL TISSLQPEDF ATYYCQQWSR NPPTFGGGTK  240
LQITSSS                                                             247

SEQ ID NO: 314          moltype = AA  length = 35
FEATURE                 Location/Qualifiers
REGION                  1..35
                        note = peptide linker
VARIANT                 6..35
                        note = Residues at positions 6-35 may be absent
source                  1..35
                        mol_type = protein
                        organism = synthetic construct
SEQUENCE: 314
GGGGSGGGGS GGGGSGGGGS GGGGSGGGGS GGGGS                              35

SEQ ID NO: 315          moltype = AA  length = 5
FEATURE                 Location/Qualifiers
REGION                  1..5
                        note = peptide linker
source                  1..5
                        mol_type = protein
                        organism = synthetic construct
SEQUENCE: 315
GGGGS                                                               5

SEQ ID NO: 316          moltype = AA  length = 22
FEATURE                 Location/Qualifiers
REGION                  1..22
                        note = peptide linker
source                  1..22
                        mol_type = protein
                        organism = synthetic construct
SEQUENCE: 316
GGGGSGGGGS GGGGSGGGGS PS                                            22
```